(12) United States Patent
Lang et al.

(10) Patent No.: US 6,462,024 B1
(45) Date of Patent: Oct. 8, 2002

(54) USE OF INHIBITORS OF THE SODIUM-HYDROGEN EXCHANGER FOR THE PRODUCTION OF A MEDICAMENT FOR DECREASING UNDESIRED EFFECTS OF SUBSTRATES OF THE HEART

(75) Inventors: Hans Jochen Lang, Hofheim; Hartmut Rütten, Kronberg; Holger Heitsch, Mainz-Kastel; Wolfgang Linz, Mainz; Bernward Schölkens, Kelkheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 68 days.

(21) Appl. No.: 09/614,122

(22) Filed: Jul. 11, 2000

Related U.S. Application Data

(63) Continuation of application No. 09/397,727, filed on Sep. 17, 1999, now abandoned, which is a continuation of application No. 09/146,941, filed on Sep. 3, 1998, now abandoned.

(30) Foreign Application Priority Data

Sep. 4, 1997 (DE) .......................................... 197 38 604

(51) Int. Cl.$^7$ ................................................. A61K 31/70
(52) U.S. Cl. ........................... 514/29; 514/34; 514/183; 514/212; 514/237.8; 514/255; 514/275; 514/303; 514/311; 514/313; 514/316; 514/331; 514/400; 514/415; 514/427; 514/455
(58) Field of Search ............................ 514/29, 34, 183, 514/212, 237.8, 255, 275, 303, 311, 316, 400, 331, 415, 410, 427, 455

(56) References Cited

U.S. PATENT DOCUMENTS

| | | |
|---|---|---|
| 5,292,755 A | 3/1994 | Englert et al. |
| 5,364,868 A | 11/1994 | Englert et al. |

*Primary Examiner*—James H. Reamer
(74) *Attorney, Agent, or Firm*—Finnegan, Henderson, Farabow, Garrett, & Dunner, LLP

(57) ABSTRACT

Inhibitors of the sodium-hydrogen exchanger are used for the production of a medicament for decreasing the undesired effects in human and in veterinary medicine which originate from substances which cause damage to the heart when administered acutely or chronically.

20 Claims, No Drawings

USE OF INHIBITORS OF THE SODIUM-HYDROGEN EXCHANGER FOR THE PRODUCTION OF A MEDICAMENT FOR DECREASING UNDESIRED EFFECTS OF SUBSTRATES OF THE HEART

This is a continuation of patent application Ser. No. 09/397,727, filed Sep. 17, 1999, abandoned which is a continuation of patent application Ser. No. 09/146,941 filed Sep. 3, 1998, abandoned which are incorporated herein by reference.

The use of inhibitors of the sodium-hydrogen exchanger for the production of a medicament for decreasing undesired effects of substances on the heart.

The present invention relates to the use of inhibitors of the sodium-hydrogen exchanger for decreasing functional impairment of the heart in human and veterinary medicine, such as can be caused, for example, by animal and plant cardiotoxins, by pharmaceuticals having a cardiotoxic component or by pharmaceuticals having undesired side effects on the heart and can cause health disorders due to chronic or acute absorption into the body.

Inhibitors of the sodium/hydrogen exchanger (NHE) have been characterized in recent years in numerous preclinical studies as substances which in the case of restricted circulation of the heart are suitable in a superior manner to protect endangered heart tissue from death. The protection of the heart tissue by NHE inhibitors includes all expressions of the damage caused by inadequate circulation, starting with cardiac arrhythmias via hypercontraction of the heart muscle and temporary loss of function up to death of the heart tissue and permanent damage associated therewith.

1. (see 1. Scholz W, Albus U, Lang H-J, Linz W, Martorana P A, Englert H C, Schölkens B A: Hoe 694, a new Na+/H+ exchange inhibitor and its effects in cardiac ischemia. Br J Pharmacol 1993; 109:562–568;
2. Scholz W, Albus U, Counillon L T, Gögelein H, Lang H-J, Linz W, Weichert A, Schölkens B A: Protective effects of HOE 642, a selective sodium-hydrogen exchange subtype 1 inhibitor, on cardiac ischaemia and reperfusion. Cardiovasc Res 1995;29:260–268;
3. Scholz W, Albus U: Potential of selective sodium-hydrogen exchange inhibitors in cardiovascular therapy, Cardiovasc Res 1995;29: 184–188
4. Karmazyn M: Editorial: Sodium-Hydrogen Exchange Inhibition—A Superior Cardioprotective Strategy. J Thorac Cardiovasc Surg 1996;112: 776–777)
5a. Verdonck F, Bielen F, Ver Donck L: Preferential block of the veratridine-induced, noninactivating $Na^{30}$ current by R56865 in single cardiac Purkinje cells. Eur J Pharmacol 1991;203: 371–378;
5b. Kehrbach et al., U.S. Pat. No. 5,547,967;
6. Walker M J A, Curtis M J, Hearse D J, Campbell R W F, Janse M J, Yellon D M, Cobbe S M, Cokes S J, Harness J B, Harron D W G, Higgins S J, Julian D G, Lab M J, Manning A S, Northover B J, Parratt J R, Riemersma R A, Rieva E, Russell D G, Sheridan D J, Winslow E, Woodward B: The Lambeth convention: Guidelines for the study of arrhythmias in ischemia, infarction and reperfusion. Cardiovasc. Res 1988; 22:447–455.

The mechanism of action of the NHE inhibitors is that they decrease the increased influx of sodium ions which arises in inadequately supplied tissues due to activation of the NHE as a result of intracellular acidification. By means of this, the situation of sodium overloading of the tissue is delayed. Since in the heart tissue sodium and calcium ion transport are coupled with one another, the life-threatening calcium overloading of the heart cells is thus prevented.

The action of the NHE inhibitors was directed as described above toward the abolition and reduction of damage which takes place due to ischemia, i.e. essentially due to absence or lack of oxygen—and nutrient supply of the heart.

It was therefore surprising that by means of NHE inhibitors such damage which is caused by the presence of substances having cardiotoxic potential can also be inhibited or prevented. What is involved here can be natural and synthetic toxins having a cardiotoxic component, such as snake venoms, fish toxins, sting toxins of marine jellyfish, spider or scorpion toxins etc.

The administration of NHE inhibitors is of importance in the treatment of acute and chronic disorders of which the therapy used until now is restricted by the cardiotoxicity of the medicaments used. Combined administration can be carried out here in the form of separate substances or of a fixed combination preparation. Pharmaceutical indications of this type, whose use is characterized by cardiotoxic side effects, involve the combined administration of NHE inhibitors with thyroid hormones, such as thyroxine and triiodothyronine. They also involve the combined administration of NHE inhibitors with anticholesterolemic pharmaceuticals, which derive chemically and pharmacologically from thyroid hormones, such as, for example, thyropropic acid. A logical consequence of this is the use of NHE inhibitors for the treatment of hyperthyroidism, in which the high levels of the secreted thyroid hormones lead, as is known, to heart damage.

The administration of NHE inhibitors is of particular importance in cancer therapy, in which medicaments are employed which have a marked cardiotoxic potential. Thus the dosage of a number of tumor therapeutics is limited by their cardiotoxic action and thus the success of an effective and relatively long-lasting cancer therapy is greatly restricted by the cardiac side effects. The mechanism of action of a number of cardiotoxic cancer preparations is explained, inter alia, in that peroxides and highly reactive oxygen species such as peroxide radical anions, which have a cytotoxic action and thus display at least part of their cytostatica action, are formed by some cancer medicaments. This cytotoxicity is relatively nonspecific and not directed solely toward the tumor tissue, but detrimentally affects other organs, in particular the heart tissue. It is attempted in some clinics to eliminate the cytotoxic component of the reactive oxygen species on the heart by parallel administration of antioxidants such as vitamins or probucol by radical capture. However, it is also taken into consideration that due to the nonspecific distribution of the antioxidants in the body the desired cytotoxic oxygen species in the cancerous tissue are also trapped and thus the action of the cancerostatics, additionally to the development of resistance of the tumor, is weakened. The advantage of the protective action of the NHE inhibitors relative to the antioxidants consists in their specific strong protective action, which is largely restricted to the heart, such that tumor tissue which is foreign to the heart remains unaffected by the protective action of the NHE inhibitors and thus the cytotoxic action of the tumor agents comes fully to bear. Moreover, the cardiotoxic action of the cytostatics is largely abolished by the NHE inhibitors, so that the cytostatics can be administered in considerably higher doses. Thus the cytostatic therapy can be carried out considerably more successfully. Cytostatics of this type having a cardiotoxic component, which can be administered particularly favorably together with NHE inhibitors or in a fixed combination, include, in particular, quinone-like therapeutics, such as, for example, anthracycline and anthraquinone-like chemotherapeutics, in particular adriamycin (doxorubicin), 4'-epidoxorubicin, daunorubicin, carubicin, aclarubicin, dactinomycin, mitoxantrone, ametantrone, bisanthrene, amsacrine, nitacrine, mitomycin etc.

The administration of NHE inhibitors is also of particular importance in the reduction of disorders of the cardiac function, such as can occur as side effects of therapeutics for the treatment of infections. In this case, therapeutics against protozoa, fungi, bacteria and viruses can be involved. It is known that infections with bacteria and viruses, in particular by Chlamydia, lead to severe heart complications and an increased incidence of cardiac infarct. An optimal treatment of infections of this type with antibiotics should therefore be free of cardiac side effects in order to keep the stress on the endangered heart as small as possible. It therefore represents a great therapeutic advance that cardiac functional disorders, such as can occur, for example, as side effects during treatment with macrolide and ketolide antibiotics, can be decreased or abolished by NHE inhibitors having a cardioprotective component, such as, for example, by cariporide and its pharmacologically tolerable salts.

The active compounds which are known and identified as NHE inhibitors are guanidine derivatives, preferably acylguanidines, inter alia such as described in the following publications and patent disclosures: Edward J. Cragoe, Jr., "DIURETICS, Chemistry, Pharmacology and Medicine", J. WILEY & Sons (1983), 303–341, additionally compounds of the following formulae:

I. (HOE 89/F 288-U.S. Pat. No. 5,292,755)
a) benzoylguanidines of the formula I

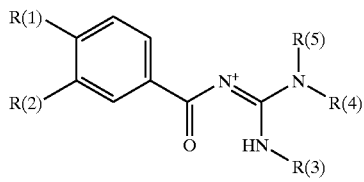

in which:
R(1) or R(2) is R(6)—S(O)$_n$— or R(7)R(8)N—O$_2$S—;
and the other substituent R(1) or R(2) in each case is H, F, Cl, Br, (C$_1$–C$_4$)-alkyl, (C$_1$–C$_4$)-alkoxy or phenoxy, which is unsubstituted or substituted by 1–3 substituents selected from the group consisting of fluorine, chorine, methyl and methoxy;
or the other substituent R(1) or R(2) in each case is R(6)—S(O)$_n$ or R(7)R(8)N—;
n is zero, 1 or 2;
R(6) is (C$_1$–C$_6$)-alkyl, ((C$_5$–C$_7$)-cycloalkyl, cyclopentylmethyl, cyclohexylmethyl or phenyl, which is unsubstituted or substituted by 1–3 substituents selected from the group consisting of fluorine, chlorine, methyl and methoxy,
R(7) and R(8) identically or differently are H or (C$_1$–C$_6$)-alkyl;
or
R(7) is phenyl-(CH$_2$)$_m$;
m is 1–4;
or
R(7) is phenyl, which is unsubstituted or substituted by 1–2 substituents selected from the group consisting of fluorine, chlorine, methyl and methoxy;
or
R(7) and R(8) together are a straight-chain or branched (C$_4$–C$_6$)-chain, where the chain can additionally be interrupted by O, S or NR(9);
R(9) is H or methyl;
or
R(7) and R(8) together with the nitrogen atom to which they are bonded, are a dihydroindole, tetrahydroquinoline or tetrahydroisoquinoline system;
R(3), R(4) and R(5) independently of one another are H or (C$_1$–C$_2$)-alkyl,
or
R(3) and R(4) together are a (C$_2$–C$_4$)-alkylene chain;
or
R(4) and R(5) together are a (C$_4$–C$_7$)-alkylene chain;
and their pharmaceutically tolerable salts;
(HOE 92/F 034-U.S. Pat. No. 5,373,924)
b) benzoylguanidines of the formula I

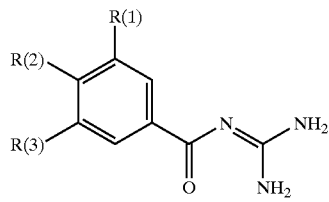

in which:
R(1) is R(4)—SO$_m$ or R(5)R(6)N—SO$_2$—;
m is zero, 1 or 2;
R(4) and R(5) are C$_1$–C$_8$-alkyl, C$_3$–C$_6$-alkenyl or —C$_n$H$_{2n}$—R(7);
n is zero, 1, 2, 3 or 4;
R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);
R(8) and R(9) are H or C$_1$–C$_4$-alkyl;
or
R(5) is H;
R(6) is H or C$_1$–C$_4$-alkyl,
or
R(5) and R(6) together are 4 or 5 methylene groups, of which one CH$_2$ group can be replaced by an O, S, NH, N—CH$_3$ or N-benzyl;
R(2) is hydrogen, F, Cl, Br, (C$_1$–C$_4$)-alkyl—, O—(CH$_2$)$_m$C$_p$F$_{2p+1}$ or —X—R(10);
m is zero or 1;
p is 1, 2 or 3;
X is O, S or NR(11);
R(10) H, C$_1$–C$_6$-alkyl, C$_5$–C$_7$-cycloalkyl, cyclohexymethyl, cyclopentylmethyl or —C$_n$H$_{2n}$—R(12);
n is zero, 1, 2, 3or 4;
R(12) is phenyl, which is unsubstituted or substituted by 1–3 substituents selected from the group consisting of F, Cl, CF$_3$ methyl, methoxy and NR(8)R(9);
R(8) and R(9) are H or C$_1$–C$_4$-alkyl;
R(11) is hydrogen or C$_1$–C$_4$-alkyl;
or
R(10) and R(11) together are 4 or 5 methylene groups, of which one CH$_2$ group can be replaced by O, S, NH, N—CH$_3$ or N-benzyl;
R(3) is-defined as R(1), or is C$_1$–C$_6$-alkyl, nitro, cyano, trifluoromethyl, F, Cl, Br, I or —X—R(10);
X is O, S or NR(11);
R(10) is H, $C_1$–$C_6$-alkyl, $C_5$–$C_7$-cycloalkyl, cyclohexylmethyl, cyclopentylmethyl or —$C_nH_{2n}$—R(12);
n is zero to 4;
R(12) is phenyl, which is unsubstituted or substituted by 1–3 substituents selected from the group consisting of F, Cl, $CF_3$, methyl, methoxy and NR(8)R(9);
R(8) and R(9) are H or $C_1$–$C_4$-alkyl;
R(11) is $C_1$–$C_4$-alkyl,
or
R(10) and R(11) together are 4 or 5 methylene groups, of which one $CH_2$ group can be replaced by O, S, NH, N—$CH_3$ or
and their pharmaceutically tolerable salts;
(HOE 92/F 035 EP-Offendegungsschrift 556 673)
c) ortho-substituted benzoylguanidines of the formula I

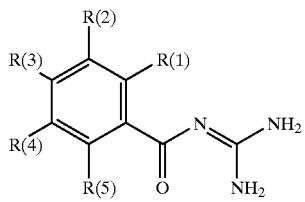

in which:
R(1) is F, Cl, Br, I, $C_1$–$C_6$-alkyl or —X—R(6);
X is O, S, NR(7) or Y ZO;
Y is O or NR(7);
Z is C or SO;
R(6) is H, $C_1$–$C_6$-alkyl, ($C_5$–$C_7$-cycloalkyl, cyclohexylmethyl, cyclopentylmethyl, —$(CH_2)_m$ $C_pF_{2p+1}$ or —$C_nH_{2n}$—R(8);
m is zero or 1;
p is 1–3;
n is zero to 4;
R(8) is phenyl, which is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
R(7) is H or $C_1$–$C_3$-alkyl;
or
R(6) and R(7) together are 4 or 5 methylene groups, of which one $CH_2$ group can be replaced by O, S, NH, N—$CH_3$ or N-benzyl;
R(3) is H or —X—R(6);
X is O, S, NR(7) or Y—ZO;
R(7) is H or $C_1$–$C_3$-alkyl;
Y is O or NR(7); where Y is bonded to the phenyl radical of the formula I,
Z is C or SO;
R(6) is H, $C_1$–$C_6$-alkyl, ($C_5$–$C_7$-cycloalkyl, cyclohexylmethyl, cyclopentylmethyl, —$(CH_2)_m$ $C_pF_{2p+1}$ or —$C_nH_{2n}$—R(8);
m is zero or 1;
p is 1–3;
n is zero to 4;
R(8) is phenyl, which is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
or
R(6) and R(7) together are 4 or 5 methylene groups, of which one $CH_2$ group can be replaced by O, S, NH, N—$CH_3$ or N-benzyl;

R(2) and R(4) identically or differently are R(11)—$SO_q$— or R(12)R(13)N—$SO_2$—;
q is zero–2;
R(11) is $C_1$–$C_4$-alkyl, which is unsubstituted or carries phenyl as a substituent, where phenyl is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
R(12) and R(13) are defined as R(6) and R(7);
or
one of the two radicals R(2) or R(4) is hydrogen or is defined as R(4);
R(5) is H, methyl, F, Cl or methoxy,
and their pharmaceutically tolerable salts;
(HOE 92/F 036-U.S. Pat. No. 5,346,868)
d) benzoylguanidines of the formula I

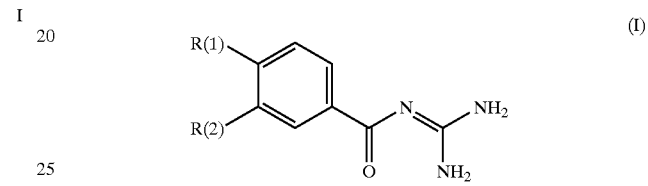

in which:
R(1) or R(2) is an amino group —NT(3)R(4);
R(3) and R(4) identically or differently are H, $C_1$–$C_6$-alkyl or $C_3$–$C_7$-cycloalkyl;
or
R(3) is phenyl—$(CH_2)_p$—;
p is 0, 1, 2, 3 or 4;
or
R(3) is phenyl, where the phenyl in each case is unsubstituted or carries one to two substituents selected from the group consisting of fluorine, chlorine, methyl and methoxy;
or
R(3) and R(4) together can be a straight-chain or branched $C_4$–$C_7$-methylene chain, where one —$CH_2$— member of the Methylene chain can be replaced by oxygen, S or NR(5);
R(5) is H or lower alkyl;
the other substituent R(1) or R(2) in each case is H, F, Cl, $C_1$–$C_4$-alkyl, $C_1$–$C_4$-alkoxy, $CF_3$, $C_mF_{2m+1}$—$CH_2$—, benzyl or phenoxy, where the respective phenyl radical is unsubstituted or carries one to two substituents selected from the group consisting of methyl, methoxy, fluorine and chlorine;
m is 1, 2 or 3;
and their pharmaceutically tolerable salts;
(92/F 197 K-NZ 248 013)
e) benzoylguanidines of the formula I

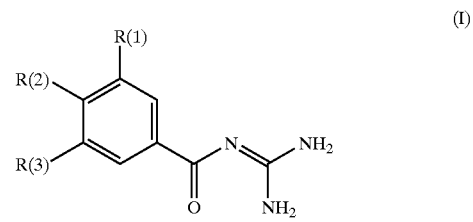

in which:

R(1) is R(4)—SO$_m$ or R(5)R(6)N—SO$_2$—;
 m is zero, 1 or 2;
  R(4) and R(5) are C$_1$–C$_8$-alkyl, C$_3$–C$_6$-alkenyl or —C$_n$H$_{2n}$—R(7);
   n is zero, 1, 2, 3 or 4;
   R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);
    R(8) and R(9) are H or C$_1$–C$_4$-alkyl;
or
 R(5) is H;
 R(6) is H or C$_1$–C$_4$-alkyl:
or
 R(5) and R(6) together are 4 or 5 methylene groups, of which one CH$_2$ group can be replaced by an O, S, NH, N—CH$_3$ or N-benzyl;
R(2) is hydrogen, straight-chain or branched (C$_5$–C$_6$)-alkyl, —CR(13)=CHR(12) or —C≡CR(12);
 R(12) is phenyl, which is unsubstituted or substituted by 1–3 substituents selected from the group consisting of F, Cl, CF$_3$, methyl, methoxy and NR(14)R(15);
  R(14) and R(15) are H or (C$_1$–C$_4$)-alkyl;
or
 R(12) is (C$_1$–C$_9$)-heteroaryl, which is unsubstituted or substituted as phenyl,
or
 R(12) is (C$_1$–C$_6$)-alkyl, which is unsubstituted or substituted by 1–3 OH,
or
 R(12) is (C$_3$–C$_8$)-cycloalkyl;
 R(13) is hydrogen or methyl,
or
 R(12) is (C$_3$–C$_8$)-cycloalkyl, (C$_3$–C$_8$)-cycloalkyl-(C$_1$–C$_4$)-alkyl, phenyl, C6H$_5$—(C$_1$–C$_4$)-alkyl, naphthyl, biphenylyl, 1,1-diphenyl-(C$_1$–C$_4$)-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;
R(3) is defined as R(2); and where the aromatic substituents R(2) and R(3) are unsubstituted or substituted by 1–3 substituents from the groups F, CI, CF$_3$, (C$_1$–C$_4$)-alkyl or —alkoxy, or NR(10)R(11) with R(10) and R(11) being H or (C$_1$–C$_4$)-alkyl;
and their pharmaceutically tolerable salts;
(HOE 92/F 303 K-EP-Offendegungsschrift 589 336, NZ 248 703)

f) benzoylguanidines of the formula I

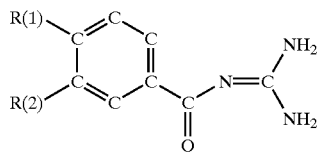

in which:
R(1) or R(2) is or R(3)—S(O$_n$—or R(4)R(5)N—SO$_2$—
the other substituent R(1) or R(2) in each case is H, OH, F, Cl, Br, I, C$_1$–C$_4$-alkyl, C$_1$–C$_4$-alkoxy, benzyloxy or phenoxy, which is unsubstituted or carries one to three substituents selected from the group consisting of fluorine, chlorine, methyl, methoxy, hydroxyl and benzyloxy,
R(3)—S(O)$_n$, —NR(4)R(5) or 3,4-dehydropipeddine
 R(3) is C$_1$–C$_6$-alkyl, C$_5$–C$_7$-cycloalkyl, cyclopentylmethyl, cyclohexylmethyl or phenyl, which is unsubstituted or substituted by one to three substituents selected from the group consisting of fluorine, chlorine, methyl and methoxy;
 P R(4) and R(5) identically or differently, are H or C$_1$–C$_6$-alkyl;
or
 R(4) is phenyl-(CH$_2$)$_m$—;
  m is 1, 2, 3 or 4;
or
 R(4) is phenyl, which is unsubstituted or carries one to two substituents selected from the group consisting of fluorine, chlorine, methyl and methoxy;
or
 R(4) and R(5) together are a straight-chain or branched C$_4$–C$_7$-chain, where the chain can additionally be interrupted by O, S or NR(6),
 R(6) is H or methyl;
or
 R(4) and R(5) together with the nitrogen atom to which they are bonded, are a dihydroindole, tetrahydroquinoline or tetrahydroisoquinoline system;
  n is zero, 1 or 2;
and their pharmaceutically tolerable salts;
(92/F 304-U.S. Pat. No. 5,416,094)

g) isoquinolines of the formula I

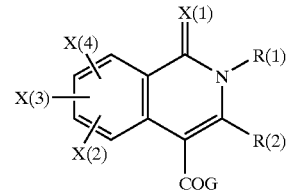

in which:
R(1) is hydrogen, alkyl, cycloalkyl, arylalkyl, alkenyl, substituted aminoalkyl or an aryl or heteroaryl ring; where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl,
R(2) is hydrogen, halogen, alkyl or aryl; which is unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl,
G is —N=C{[NR(3)R(4)][(NR(5)R(6)]}
X(2), X(3) and X(4) independently of one another are hydrogen, halogen, nitro, amino, alkyl, sulfonamide, mono(lower alkyl)amino, di(lower alkyl)amino, lower alkyl, benzyloxy, hydroxyl;
X(1) is hydrogen, oxygen, sulfur or NR(7);
 R(7) is hydrogen, alkyl, cycloalkyl, arylalkyl, alkenyl, substituted aminoalkyl or an aryl or a heteroaryl ring; which rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl and trifluoromethyl;

in which substituents each alkyl chain or alkenyl chain can be interrupted by oxygen, sulfur or NR(8);

R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl and trifluoromethyl;

and their pharmaceutically acceptable salts;

(92/F 404-EP 602 522, NZ 250 438)

h) compounds of the formula I

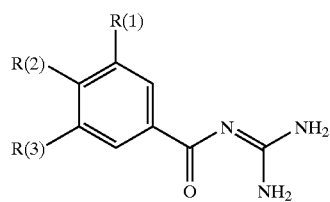

(I)

in which:

R(1) is hydrogen, F, Cl, Br, I, —$NO_2$, —C≡N, —$CF_3$, R(4)—$SO_m$ or R(5)R(6)N—$SO_2$—;

m is zero, 1 or 2;

R(4) and R(5) are ($C_1$–$C_8$)-alkyl, ($C_3$–$C_6$)-alkenyl, —$C_nH_{2n}$—R(7) or $CF_3$;

n is zero, 1, 2, 3 or 4;

R(7) is ($C_3$–$C_7$)-cycloalkyl or phenyl, which is not substituted or is substituted by 1–3 substituents selected from the group consisting of F, Cl, $CF_3$, methyl, methoxy and NR(8)R(9);

R(8) and R(9) are H or $C_1$–$C_4$-alkyl;

or

R(5) is H;

R(6) is H or ($C_1$–$C_4$)-alkyl;

or

R(5) and R(6) together are 4 or 5 methylene groups, of which one $CH_2$ group can be replaced by oxygen, S, NH, N—$CH_3$ or N-benzyl;

R(2) is —SR(10), —OR(10), —NHR(10), —NH(10)R(11), —CHR(10)R(12), —[CR(12)R(13)OR(13')], —{C—[$CH_2$—OR(13')]R(12) (R(13)} or —[CR(18)R(17)]$_p$—(CO)—[CR(19)R(20)]$_q$—R(14); R(10) and R(11) identically or differently are —[CHR(16)]$_s$—($CH_2$)$_p$—(CHOH)$_q$ —($CH_2$)$_r$—(CHOH)$_t$—R(21) or —($CH_2$)$_p$—O—($CH_2$—$CH_2$O)$_q$—R(21), R(21) is hydrogen, methyl, p, q, r identically or differently are zero, 1, 2, 3 or 4;

s is zero or 1;

t is 1, 2, 3 or 4;

R(12) and R(13) identically or differently are hydrogen, ($C_1$–$C_6$)-alkyl or, together with the carbon atom carrying them, are a ($C_3$–$C_8$)-cycloalkyl, R(13') is hydrogen or ($C_1$–$C_4$)-alkyl;

R(14) is H, ($C_1$–$C_6$)-alkyl, ($C_3$–$C_8$)-cycloalkyl or —$C_aH_{2a}$—R(15);

a is zero, 1, 2, 3 or 4;

R(15) is phenyl, which is unsubstituted or substituted by 1–3 substituents selected from the group consist ing of F, Cl, $CF_3$, methyl, methoxy and NR(8)R(9);

R(8) and R(9) are H or ($C_1$–$C_4$)-alkyl;

or

R(15) is ($C_1$–$C_9$)-heteroaryl, which is unsubstituted or substituted as phenyl, or R(15) is ($C_1$–$C_9$)-alkyl, which is unsubstituted or substituted by 1–3 OH;

R(16), R(17), R(18), R(19) and R(20) are hydrogen or ($C_1$–$C_3$)-alkyl;

R(3) is defined as R(1), or

R(3) is ($C_1$–$C_6$)-alkyl or —X—R(22);

X is oxygen, S or NR(16);

R(16) is H or ($C_1$–$C_3$)-alkyl;

or

R(22) and R(16) together are 4 or 5 methylene groups, of which one $CH_2$ group can be replaced by oxygen, S, NH, N—$CH_3$ or N-benzyl;

R(22) is defined as R(14);

and their pharmaceutically tolerable salts;

(HOE 92/F 405-EP 602 523, NZ 250 437)

i) benzoylguanidines of the formula I

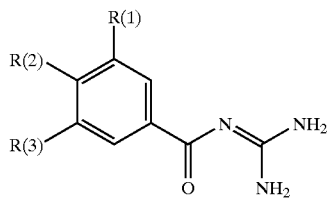

(I)

in which:

R(1) is hydrogen, F, Cl, Br, I, —$NO_2$, —C≡N, R(16)—$C_pH_{2p}$—$O_q$, R(4)—$SO_m$ or R(5)R(6)N—$SO_2$—;

m is zero, 1 or 2;

p is zero or 1;

q is zero, 1, 2 or 3;

R(16) is $C_rF_{2r+1}$;

r is 1, 2 or 3;

R(4) and R(5) are ($C_1$–$C_8$)-alkyl, ($C_3$–$C_6$)-alkenyl, —$C_nH_{2n}$—R(7) or $CF_3$;

n is zero, 1, 2, 3 or 4;

R(7) is ($C_3$–$C_7$)-cycloalkyl or phenyl, which is not substituted or is substituted by 1–3 substituents selected from the group consisting of F, Cl, $CF_3$, methyl, methoxy and NR(8)R(9);

R(8) and R(9) are H or $C_1$–$C_4$-alkyl;

or

R(5) is H;

R(6) is H or ($C_1$–$C_4$)-alkyl;

or

R(5) and R(6) together are 4 or 5 methylene groups, of which one $CH_2$ group can be replaced by oxygen, S, NH, N—$CH_3$ or N-benzyl, R(2) is ($C_1$–$C_9$)-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

or
R(2) is —SR(10), —OR(10), —NH(10)R(11), —CR(10)R(11)R(12);
R(10) is —$C_aH_{2a}$—($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(11) and R(12) independently of one another are defined as R(10) or are hydrogen or ($C_1$–$C_4$)-alkyl;
R(3) is defined as R(1), or is ($C_1$–$C_6$)-alkyl or —X—R(13);
X is oxygen, S, or NR(14);
R(14) is H or ($C_1$–$C_3$)-alkyl;
R(13) is H, ($C_1$–$C_6$)-alkyl, ($C_3$–$C_8$)-cycloalkyl or —$C_bH_{2b}$—R(15);
b is zero, 1, 2, 3 or 4;
or
R(13) and R(14) together are 4 or 5 methylene groups, of which one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(8)R(9);
R(8) and R(9) are H or ($C_1$–$C_4$)-alkyl;
and their pharmaceutically tolerable salts;
(HOE 92/F 411-NZ 250 450, EP 603 650)
k) benzoylguanidines of the formula I

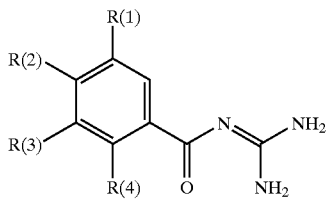

in which:
one of the substituents R(1), R(2), R(3) or R(4) is an amino group —NH(5)[$C_nH_{2n}$—R(6)];
R(5) is hydrogen or $C_{(1-6)}$-alkyl;
n is zero, 1, 2, 3 or 4;
R(6) is H or $C_{(1-4)}$-alkyl;
in which one $CH_2$ group can be replaced by 1 sulfur atom or a group NR(7);
R(7) is hydrogen, methyl or ethyl;
or
R(6) is $C_{3-8}$-cycloalkyl or phenyl, which is unsubstituted or carries 1, 2 or 3 substituents selected from the group consisting of F, Cl, Br, methyl, methoxy, —NH(8)R(9);
R(8) and R(9) are H, methyl or ethyl;
or
R(5) and R(6) together with the nitrogen atom are a 5-, 6- or 7-membered ring, in which 1 carbon atom can be replaced by oxygen, S or NR(10);
R(10) is H, $C_{(1-3)}$-alkyl or benzyl;
and the other substituents R(1), R(2), R(3), R(4) in each case are:
hydrogen, F, Cl, Br, I, CN, $CF_3$, $NO_2$, $CF_3$—O—, $C_mF_{2m+1}$—$CH_2$—O— or R(11)—$C_qH_{2q}$—$X_p$—;
m is 1, 2 or 3;
q is zero, 1, 2, 3 or 4;
p is zero or 1;

X is oxygen or NR(12);
R(12) is H or $C_{(1-3)}$—alkyl;
R(11) is hydrogen, $C_{(1-6)}$-alkyl, $C_{(3-8)}$-cycloalkyl or phenyl, which is unsubstituted or substituted by 1, 2 or 3 substituents selected from the group consisting of F, Cl, $CH_3$, $CH_3$—O— and NR(13)R(14);
R(13), R(14) are H, methyl or ethyl;
and their pharmaceutically tolerable salts;
(HOE 92/E 422-EP 604 852)
l) benzoylguanidines of the formula I

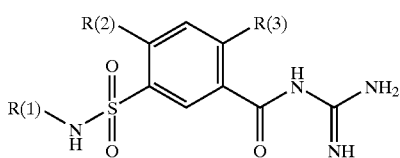

in which:
R(1) is R(4)R(5)N—C(X)—;
X is oxygen, S or N—R(6);
R(4) and R(5) identically or differently, are H, ($C_1$–$C_8$)-alkyl, ($C_3$–$C_6$)-alkenyl or —$C_nH_{2n}$—R(7);
n is zero, 1, 2, 3 or 4;
R(7) is ($C_5$–$C_7$)-cycloalkyl or phenyl, which is unsubstituted or substituted by 1–3 substituents selected from the group consisting of F, Cl, $CF_3$, methoxy and ($C_1$–$C_4$)-alkyl;
or
R(4) and R(5) together are 4 or 5 methylene groups, of which one $CH_2$ group can be replaced by oxygen, S, NH, N—$CH_3$ or N-benzyl;
R(6) is defined as R(4) or is amidine;
R(2) is H, F, Cl, Br, I, ($C_1$–$C_8$)-alkyl, 1-alkenyl or 1-alkynyl, ($C_3$–$C_8$)-cycloalkyl, ($C_3$–$C_8$)-cycloalkyl-($C_1$–$C_4$)-alkyl, phenyl, C6H5—($C_1$–$C_4$)-alkyl, naphthyl, biphenylyl, 1,1-diphenyl-($C_1$–$C_4$)-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);
W is oxygen, S or NR(9);
R(8) is H, ($C_1$–$C_6$)-alkyl, ($C_5$–$C_7$)-cycloalkyl, cyclohexylmethyl, cyclopentylmethyl, —$(CH_2)_mC_pF_{2p+1}$ or —$C_qH_{2q}$—R(10);
m is zero or 1;
p is 1, 2 or 3;
q is zero, 1, 2, 3 or 4;
R(10) is phenyl, which is unsubstituted or substituted by 1–3 substituents selected from the group consisting of F, Cl, $CF_3$, methyl, methoxy and NR(11)R(12);
R(11) and R(12) are H or ($C_1$–$C_4$)-alkyl;
R(9) is H or ($C_1$–$C_3$)-alkyl;
or
R(8) and R(9) together are 4 or 5 methylene groups, of which one $CH_2$ group can be replaced by oxygen, S, NH, N—$CH_3$ or N-benzyl;
R(3) is H, F, Cl, Br, I, ($C_1$–$C_6$)-alkyl or —W—R(8) as defined for R(2), and their pharmaceutically acceptable salts;

(93/F 054-NZ 250 919, EP-Offendegungsschrift 612 723)
m) benzoylguanidines of the formula I

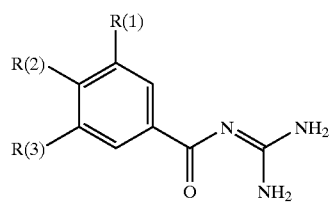

in which:
R(1), R(2), R(3) are hydrogen, F, Cl, Br, I or $(C_1-C_{12})$-alkyl;
one of the substituents R(1), R(2) or R(3) is $N_3$, CN, OH or $(C_1-C_{10})$-alkyloxy, if at least one of the remaining substituents R(1), R(2) or R(3) is a sufficiently lipophilic alkyl radical having 3 to 12 carbon atoms;
or
one of the substituents R(1), R(2) and R(3) is R(4)—$C_nH_{2n}$—$O_m$—;
m is zero or 1;
n is zero, 1, 2 or 3;
R(4) is $C_pF_{2P+1}$;
p is 1, 2 or 3, if n is zero or 1;
or
R(4) is $(C_3-C_{12})$-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or $(C_1-C_4)$-alkyl;
or one of the substituents R(1), R(2) and R(3) is —C≡CR(5) or —C[R(6)]=CR(5);
R(5) is phenyl, which is unsubstituted or substituted by 1–3 substituents selected from the group consisting of F, Cl, $CF_3$, methyl, methoxy, hydroxyl, amino, methylamino and dimethylamino, $(C_1-C_9)$-heteroaryl, which is unsubstituted or substituted as phenyl,
or
R(5) is $(C_1-C_6)$-alkyl, which is unsubstituted or substituted by 1–3 OH;
or
R(5) is $(C_3-C_8)$-cycloalkyl,
R(6) is hydrogen or methyl;
and their pharmacologically acceptable salts;
(93/F 153-EP-Offenlegungsschrift 627 413, NZ 260 660)
o) benzoylguanidines of the formula I

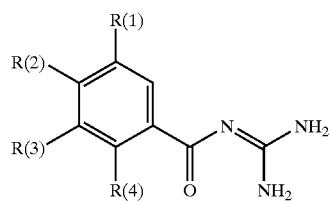

in which:
R(1) is hydrogen, F, Cl, Br, I, —$NO_2$, —C≡N, $X_o$—$(CH_2)_q$—$CF_3$, R(5)—$SO_m$, R(6)—CO— or R(6)R(7)N—$SO_2$—, where
X is oxygen, S or NR(14);
m is zero, 1 or 2;
o is zero or 1;
p is zero, 1 or 2;
q is zero, 1, 2, 3, 4, 5 or 6;
R(5) and R(6) are $(C_1-C_8)$-alkyl, $(C_3-C_6)$-alkenyl, —$C_nH_{2n}$—R(8) or $CF_3$;
n is zero, 1, 2, 3 or 4;
R(8) is $(C_3-C_7)$-cycloalkyl or phenyl, which is not substituted or is substituted by 1–3 substituents selected from the group consisting of F, Cl, $CF_3$, methyl, methoxy and NR(9)R(10);
R(9) and R(10) are H or $C_1-C_4$-alkyl;
or
R(6) is H;
R(7) is H or $(C_1-C_4)$-alkyl;
or
R(6) and R(7) together are 4 or 5 methylene groups, of which one $CH_2$ group can be replaced by oxygen, S, NH, N—$CH_3$ or N-benzyl;

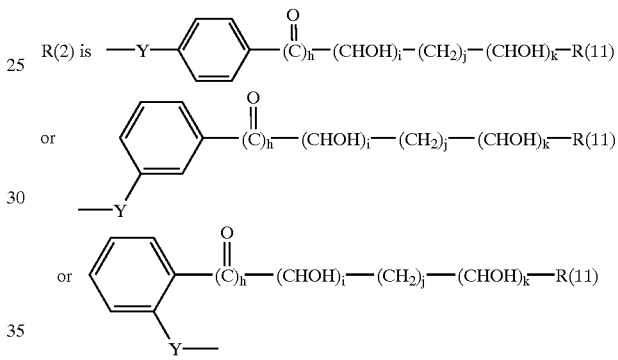

Y is oxygen, —S— or —NH(12)—;
R(11) and R(12) are hydrogen or $(C_1-C_3)$-alkyl;
h is zero or 1;
i, j and k independently are zero, 1, 2, 3 or 4;
but where h, i and k are not simultaneously zero,
R(3) is defined as R(1), or is $(C_1-C_8)$-alkyl or —X—R(13);
X is oxygen, S or NR(14);
R(14) is H or $(C_1-C_3)$-alkyl;
R(13) is H, $(C_1-C_6)$-alkyl, $(C_3-C_8)$-cycloalkyl or —$C_bH_{2b}$—R(15);
b is zero, 1, 2, 3 or 4;
or
R(13) and R(14) together are 4 or 5 methylene groups, where one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(9)R(10);
R(9) and R(10) are H or $(C_1-C_4)$-alkyl;
R(4) is hydrogen, —OR(16) or —NR(16)R(17);
R(16) and R(17) independently are hydrogen or $(C_1-C_3)$-alkyl;
and their pharmaceutically tolerable salts;
(HOE 93/F 154-EP-Offenlegungsschrift 628 543, NZ 260 681)

p) benzoylguanidines of the formula I

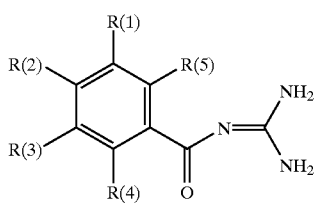

in which:

R(1) is R(6)—CO or R(7)R(8)N—CO;
R(6) is $(C_1-C_8)$-alkyl, $(C_1-C_8)$-perfluoroalkyl, $(C_3-C_8)$-alkenyl or —$C_nH_{2n}$—R(9);
n is zero, 1, 2, 3 or 4;
R(9) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11);
R(10) and R(11) are H, $(C_1-C_4)$-alkyl or $(C_1-C_4)$-perfluoroalkyl;
R(7) is H, $(C_1-C_8)$-alkyl, $(C_1-C_8)$-perfluoroalkyl, $(C_3-C_8)$-alkenyl or —$C_nH_{2n}$—R(12);
n is zero, 1, 2, 3 or 4;
R(12) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
R(13) and R(14) are H, $(C_1-C_4)$-alkyl or $(C_1-C_4)$-perfluoroalkyl;
R(8) is H, $(C_1-C_4)$-alkyl or $(C_1-C_4)$-perfluoroalkyl;
or
R(7) and R(8) together are 4 or 5 methylene groups, of which one $CH_2$ group can be replaced by oxygen, S, NH, N—$CH_3$ or N-benzyl;
R(2) is defined as R(1), or is H, F, Cl, Br, I, CN, $NO_2$, $(C_1-C_8)$-alkyl, $(C_1-C_8)$-perfluoroalkyl, $(C_3-C_8)$-alkenyl or —$C_nH_{2n}$R(15);
n is zero, 1, 2, 3, 4;
R(15) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
R(16) and R(17) are H, $(C_1-C_4)$-alkyl or $(C_1-C_4)$-perfluoroalkyl;
or
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;
R(2) is SR(18), —OR(18), —NR(18)R(19), —CR(18)R(19)R(20);
R(18) is —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(19) and R(20) independently of one another are defined as R(18) or are hydrogen, $(C_1-C_4)$-alkyl or $(C_1-C_4)$-perfluoroalkyl;

or
R(2) is R(21)—$SO_m$ or R(22)R(23)N—$SO_2$—;
m is 1 or 2;
R(21) is $(C_1-C_8)$-alkyl, $(C_1-C_8)$-perfluoroalkyl, $(C_3-C_8)$-alkenyl, —$C_nH_{2n}$—R(24),
n is zero, 1, 2, 3 or 4;
R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
R(27) and R(28) are H, $(C_1-C_4)$-alkyl or $(C_1-C_4)$-perfluoroalkyl;
R(22) is H, $(C_1-C_8)$-alkyl, $(C_1-C_8)$-perfluoroalkyl, $(C_3-C_8)$-alkenyl, —$C_nH_{2n}$—R(29);
n is zero, 1, 2, 3 or 4;
R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
R(30) and R(31) are H, $(C_1-C_4)$-alkyl or $(C_1-C_4)$-perfluoroalkyl;
R(23) is H, $(C_1-C_4)$-alkyl or $(C_1-C_4)$-perfluoroalkyl;
or
R(22) and R(23) together are 4 or 5 methylene groups, of which one $CH_2$ group can be replaced by oxygen, S, NH, N—$CH_3$ or N-benzyl;
or
R(2) is R(33)X—;
X is oxygen, S, NR(34), (D=O)A—, NR(34)C=$MN^{(*)}$R(35)—;
M is oxygen or S;
A is oxygen or NR(34);
D is C or SO;
R(33) is $(C_1-C_8)$-alkyl, $(C_3-C_8)$-alkenyl, $(CH_2)_bC_dF_{2d+1}$, —$C_nH_{2n}$—R(36),
b is zero of 1;
d is 1, 2, 3, 4, 5, 6 or 7;
n is zero, 1, 2, 3 or 4;
R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
R(37) and R(38) are H, $(C_1-C_4)$-alkyl or $(C_1-C_4)$-perfluoroalkyl;
R(34) is H, $(C_1-C_4)$-alkyl or $(C_1-C_4)$-perfluoroalkyl;
R(35) is defined as R(33);
or
R(33) and R(34) together are 4 or 5 methylene groups, or which one $CH_2$ group can be replaced by oxygen, S, NH, N—$CH_3$ or N-benzyl; where A and $N^{(*)}$ are bonded to the phenyl nucleus of the benzoylguanidine parent structure;
or
R(2) is —SR(40), —OR(40), —NHR(40), —NR(40)R(41), —CHR(40)R(42), —C[R(42)R(43)OH], —C≡CR(45), —CR(46)=CHR(45), —[CR(47)R(48)]$_u$—(CO)—[CR49)R(50)]$_v$—R(44);
R(40), R(41) identically or differently are —$(CH_2)_p$—$(CHOH)_q$—$(CH_2)_r$—$(CHOH)_r$—R(51) or —$(CH_2)_p$—O—$(CH_2—CH_2O)_q$—R(51);
R(51) is hydrogen or methyl;
u is 1, 2, 3 or 4;

v is zero, 1, 2, 3 or 4;
p, q, r identically or differently are zero, 1, 2, 3 or 4;
t is 1, 2, 3 or 4;
R(42) and R(43) identically or differently are hydrogen or $(C_1-C_6)$-alkyl;
or
R(42) and R(43) together with the carbon atom carrying them form a $(C_3-C_8)$-cycloalkyl;
R(44) is H, $(C_1-C_6)$-alkyl, $(C_3-C_8)$-cycloalkyl or $-C_eH_{2e}-R(45)$;
e is zero, 1, 2, 3 or 4;
R(45) is phenyl, which is unsubstituted or substituted 1–3 substituents from the group consisting of F, Cl, $CF_3$, methyl, methoxy and NR(52)R(53) where R(52) and R(53) are H or $(C_1-C_4)$-alkyl, or
R(45) is $(C_1-C_9)$-heteroaryl, which is unsubstituted or substituted as phenyl;
or
R(45) is $(C_1-C_6)$-alkyl, which is unsubstituted or substituted by 1–3 OH;
R(46), R(47), R(48), R(49) and R(50) are hydrogen or methyl;
or
R(2) is R(55)—NH—SO$_2$—;
R(55) is R(56)R(57)N—(C=Y)—;
Y is oxygen, S or N—R(58);
R(56) and R(57) identically or differently are H, $(C_1-C_8)$-alkyl, $(C_3-C_6)$-alkenyl or $-C_fH_{2f}-R(59)$;
f is zero, 1, 2, 3 or 4;
R(59) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl;
of
R(56) and R(57) together are 4 or 5 methylene groups, of which one CH$_2$ group can be replaced by oxygen, S, NH, N—CH$_3$ or N-benzyl;
R(58) is defined as R(56) or is amidine;
R(3), R(4) and R(5) independently of one another are defined as R(1) or R(2);
and their pharmaceutically tolerable salts;
(HOE 93/F 220-EP-Offenlegungsschrift 640 593, NZ 264 117)
q) benzoylguanidines of the formula I

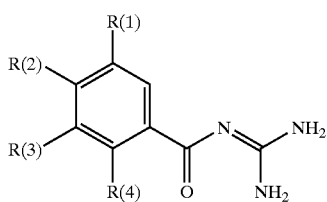

in which:
R(1) is hydrogen, F, Cl, Br, I, —NO$_2$, —C≡N, —X$_o$—(CH$_2$)$_p$—(CF$_2$)$_q$—CF$_3$, R(5)—SO$_m$—, R(6)—CO—, R(6)R(7)N—CO— or R(6)R(7)N—SO$_2$—;
X is oxygen, —S— or NR(14);
m is zero, 1 or 2;
o is zero or 1;
p is zero, 1 or 2;
q is zero, 1, 2, 3, 4, 5 or 6;
R(5) and R(6) are $(C_1-C_8)$-alkyl, $(C_3-C_6)$-alkenyl, $-C_nH_{2n}-R(8)$ or $CF_3$;

n is zero, 1, 2, 3 or 4;
R(8) is $(C_3-C_7)$-cycloalkyl, phenyl, which is not substituted or is substituted by 1 to 3 substituents selected from the group consisting of F, Cl, $CF_3$, methyl, methoxy and NR(9)R(10);
R(9) and R(10) are H or $(C_1-C_4)$-alkyl;
or
R(6) is hydrogen;
R(7) is hydrogen or $(C_1-C_4)$-alkyl;
or
R(6) and R(7) together are 4 or 5 methylene groups, of which one CH$_2$ group can be replaced by oxygen, S, NH, N—CH$_3$ or N-benzyl;
R(2) is

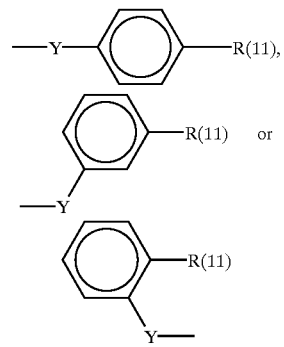

R(11) is $(C_1-C_9)$-heteroaryl, which is linked via C or N and which is unsubstituted or substituted by 1 to 3 substituents selected from the group consisting of F, Cl, $CF_3$, $CH_3$, methoxy, hydroxyl, amino, methylamino, dimethylamino and benzyl;
Y is oxygen, —S— or NR(12);
R(12) is H or $(C_1-C_4)$-alkyl;
R(3) is defined as R(1); or
R(3) is $(C_1-C_6)$-alkyl or —X—R(13);
X is oxygen, —S— or NR(14);
R(14) is H or $(C_1-C_3)$-alkyl;
R(13) is H, $(C_1-C_6)$-alkyl, $(C_3-C_8)$-cycloalkyl or $-C_bH_{2b}-R(15)$;
b is zero, 1, 2, 3 or 4; or
R(13) and R(14) together are 4 or 5 methylene groups, of which one CH$_2$ group can be replaced by oxygen, S, NH, N—CH$_3$ or N-benzyl;
R(15) is phenyl, which is unsubstituted or substituted by 1–3 substituents selected from the group consisting of F, Cl, $CF_3$, methyl, methoxy and NR(9)R(10);
R(9) and R(10) are H or $(C_1-C_4)$-alkyl;
R(4) is hydrogen, —OR(16), —NR(16)R(17) or $C_rF_{2r+1}$;
R(16) and R(17) independently are hydrogen or $(C_1-C_3)$-alkyl;
r is 1, 2, 3 or 4;
and their pharmaceutically tolerable salts;

(HOE 93/F 223 K-EP 639 573, NZ 264 130)

r) benzo-fused 5-membered ring heterocycles of the formula I s) benzoylguanidines of the formula I

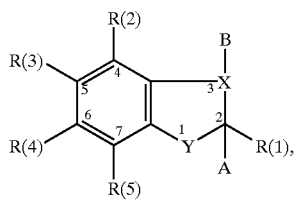

(I)

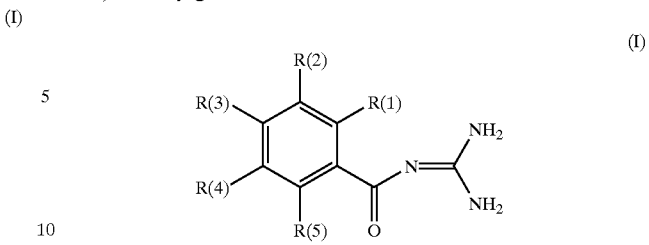

(I)

in which:
X is N or CR(6);
Y is oxygen, S or NR(7);
A, B together are a bond or
A, B are both hydrogen, if X is simultaneously CR(6) and Y is NR(7); one of the substituents R(1) to R(6) is a —CO—N=C(NH$_2$)$_2$ group;
the other substituents R(1) to R(6) in each case are hydrogen, F, Cl, Br, I or (C$_1$–C$_6$)-alkyl;
up to two of the other substituents R(1) to R(6) are CN, NO$_2$, N$_3$, (C$_1$–C$_4$)-alkyloxy or CF$_3$;
up to one of the other substituents is R(8)—C$_n$H$_{2n}$—Z—;
n is zero to 10; where the alkylene chain —C$_n$H$_{2n}$— is straight-chain or branched and where one carbon atom can be replaced by an oxygen or sulfur atom or by a nitrogen atom;
R(8) is hydrogen, (C$_2$–C$_6$)-alkenyl or (C$_3$–C$_{10}$)-cycloalkyl, which is unsubstituted or substituted by 1 to 4 methyl groups or an OH group, or can contain an ethylene group —CH=CH—, and in which one methylene group can be replaced by an oxygen or sulfur atom or by a nitrogen atom;
or
R(8) is phenyl, which is unsubstituted or substituted by 1 to 3 substituents selected from the group consisting of F, Cl, Br, I, CF$_3$, CH$_3$—S(O)$_s$— or R(9)—W$_y$—;
s is zero, 1 or 2;
R(9) is H, methyl, ethyl,
W is oxygen or NR(10);
R(10) is H or methyl;
y is zero or 1;
or
R(8) is C$_m$F$_{2m+1}$;
m is 1 to 3;
or
R(8) is 1- or 2-naphthyl, pyridyl, quinolyl or isoquinolyl;
Z is —CO—, —CH$_2$— or —[CR(11)(OH)]$_q$—;
q is 1, 2 or 3;
R(11) is H or methyl or
Z is oxygen or —NR(12)—;
R(12) is H or methyl; or
Z is —S(O)$_s$—;
s is zero, 1 or 2; or
Z is —SO$_2$—NR(13)—;
R(13) is H or (C$_1$–C$_4$)-alkyl;
R(7) is hydrogen, (C$_1$–C$_{10}$)-alkyl, (C$_2$–C$_{10}$)-alkenyl or R(8)—C$_n$H$_{2n}$—;
and their pharmaceutically tolerable salts;
(HOE 93/F 236-EP-Offenlegungsschrift 638 548, NZ 264 216)

in which:
R(1), R(3) or R(4) is —NR(6)C=XNR(7)R(8);
X is oxygen or S;
R(6) is hydrogen, (C$_1$–C$_8$)-alkyl, (C$_1$–C$_8$)-perfluoroalkyl, (C$_3$–C$_8$)-alkenyl or —C$_n$H$_{2n}$—R(9);
n is zero, 1, 2, 3 or 4;
R(9) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11);
R(10) and R(11) are H, (C$_1$–C$_4$)-alkyl or (C$_1$–C$_4$)-perfluoroalkyl;
R(7) is hydrogen, (C$_1$–C$_8$)-alkyl, (C$_1$–C$_8$)-perfluoroalkyl, (C$_3$–C$_8$)-alkenyl or —C$_o$H$_{2o}$—R(12);
o is zero, 1, 2, 3 or 4;
R(12) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);
R(13) and R(14) are H, (C$_1$–C$_4$)-alkyl or (C$_1$–C$_4$)-perfluoroalkyl
R(8) is defined as R(7);
or
R(7) and R(8) together are 4 or 5 methylene groups, of which one CH$_2$ group can be replaced by oxygen, S, NH, N—CH$_3$ or N-benzyl;
the remaining substituents R(2), R(3), R(4), R(5) or R(1), R(2), R(4), R(5) or R(1), R(2), R(3), R(5) in each case independently of one another are hydrogen, F, Cl, Br, I, —O$_{ta}$(C$_1$–C$_8$)-alkyl, —O$_{tb}$(C$_3$–C$_8$)-alkenyl, —O$_{tc}$(CH$_2$)$_b$C$_d$F$_{2d+1}$, —O$_{td}$C$_p$H$_{2p}$R(18),
or up to 2 groups CN, NO$_2$, NR(16)R(17),
b is zero or 1;
d is 1, 2, 3, 4, 5, 6 or 7;
ta is zero or 1;
tb is zero or 1;
tc is zero or 1;
td is zero or 1;
p is zero, 1, 2, 3 or 4;
R(18) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(19) R(20);
R(19) and R(20) are hydrogen or (C$_1$–C$_4$)-alkyl or (C$_1$–C$_4$)-perfluoroalkyl;
R(16) is hydrogen, (C$_1$–C$_8$)-alkyl, (C$_1$–C$_8$)-perfluoroalkyl, (C$_3$–C$_8$)-alkenyl, —C$_q$H$_{2q}$—R(21),
q is zero, 1, 2, 3 or 4;
R(21) is (C$_3$–C$_8$)-cycloalkyl, phenyl, biphenylyl or naphthyl, where the aromatics are not substituted or are substituted by 1–3 substituents from the group F, Cl, CF$_3$, methyl, methoxy or NR(22)R(23), R(22) and R(23) are hydrogen, (C$_1$–C$_4$)-alkyl or (C$_1$–C$_4$)-perfluoroalkyl;

R(17) is hydrogen, (C$_1$–C$_8$)-alkyl, (C$_1$–C$_8$)-perfluoroalkyl, (C$_3$–C$_8$)-alkenyl, —C$_r$H$_{2r}$—R(24);

r is zero, 1, 2, 3 or 4;

R(24) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(25)R(26);

R(25) and R(26) are hydrogen, (C$_1$–C$_4$)-alkyl or (C$_1$–C$_4$)-perfluoroalkyl;

or

R(16) and R(17) together are 4 or 5 methylene groups, of which one CH$_2$ group can be replaced by oxygen, S, NH, N—CH$_3$ or N-benzyl;

and their pharmaceutically tolerable salts;

(HOE 93/F 249-EP-Offenlegungsschrift 640 587, NZ 264 282)

t) diacyl-substituted guanidines of the formula I

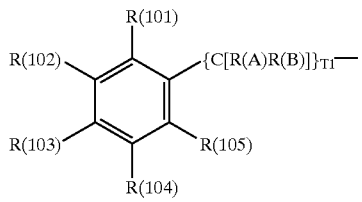

in which:
X(1) and X(2) are

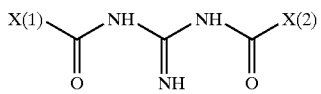

T1 is zero, 1, 2, 3 or 4;

R(A) and R(B) independently of one another are hydrogen, F, Cl, Br, I, CN, OR(106), (C$_1$–C$_8$)-alkyl, (C$_3$–C$_8$)-cycloalkyl, O$_{zk}$(CH$_1$)$_{zl}$C$_{zm}$F$_{2zm+1}$, NR(107)R(108), phenyl or benzyl, where the aromatics are not substituted or are substituted by 1–3 substituents selected from the group consisting of F, Cl, CF$_3$, methyl, methoxy and NR(109)R(110); R(109) and R(110) are hydrogen, (C$_1$–C$_4$)-alkyl or (C$_1$–C$_4$)-perfluoroalkyl;

zl is zero, 1, 2, 3 or 4;

zk is zero or 1;

zm is 1, 2, 3, 4, 5, 6, 7 or 8;

R(106) is hydrogen, (C$_1$–C$_8$)-alkyl, (C$_1$–C$_8$)-perfluoroalkyl, (C$_3$–C$_8$)-alkenyl, (C$_3$–C$_8$)-cycloalkyl, phenyl or benzyl, where the aromatics are not substituted or are substituted by 1–3 substituents selected from the group consisting of F, Cl, CF$_3$, methyl, methoxy and NR(111)R(112);

R(111) and R(112) are hydrogen, (C$_1$–C$_4$)-alkyl or (C$_1$–C$_4$)-perfluoroalkyl;

R(107) and R(108) independently of one another are defined as R(106), or

R(107) and R(108) together are 4 or 5 methylene groups, of which one CH$_2$ group can be replaced by oxygen, S, NH, N—CH$_3$ or N-benzyl;

X(1) and X(2) are

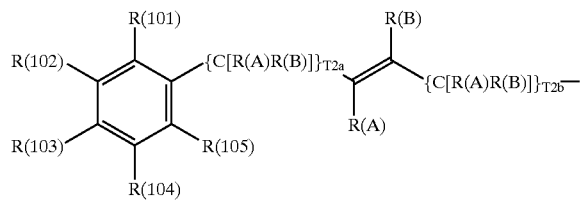

T2a and T2b independently of one another are zero, 1 or 2; where the double bond can have the (E)- or (Z)-configuration;

or

X(1) and X(2) are

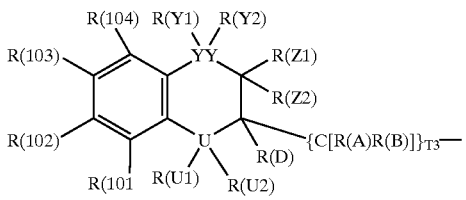

T3 is zero, 1 or 2;

U, YY and Z independently of one another are C or N, where U, YY, Z can carry the following number of substituents:

| U, YY or Z | Bonded in the ring to a double bond | Number of permitted substituents |
| --- | --- | --- |
| C | yes | 1 |
| C | no | 2 |
| N | yes | 0 |
| N | no | 1 |

R(D) is hydrogen, (C$_1$–C$_8$)-alkyl or (C$_1$–C$_8$)-perfluoroalkyl, R(U1), R(U2), R(Y1), R(Y2), R(Z1), R(Z2) independently of one another are hydrogen, F, Cl, Br, I, CN, OR(114), (C$_1$–C$_8$)-alkyl, (C$_3$–C$_8$)-cycloalkyl, O$_{zka}$(CH$_2$)$_{zla}$C$_{zma}$F$_{2zma+1}$, NR(115)R(116), phenyl or benzyl, where the aromatics are not substituted or are substituted by 1–3 substituents selected from the group consisting of F, Cl, CF$_3$, methyl, methoxy, NR(117)R(118), R(117) and R(118) are hydrogen, (C$_1$–C$_4$)-alkyl or (C$_1$–C$_4$)-perfluoroalkyl, zka is zero or 1;

zla is zero, 1, 2, 3 or 4;

zma is 1, 2, 3, 4, 5, 6, 7 or 8;

R(114) is hydrogen, (C$_1$–C$_8$)-alkyl, (C$_1$–C$_8$)-perfluoroalkyl, (C$_3$–C$_8$)-alkenyl, (C$_3$–C$_8$)-cycloalkyl, phenyl or benzyl, where the aromatics are not substituted or are substituted by 1–3 substituents selected from the group consisting of F, Cl, CF$_3$, methyl, methoxy and NR(119)R(120);

R(119) and R(120) are hydrogen, (C$_1$–C$_4$)-alkyl or (C$_1$–C$_4$)-perfluoroalkyl;

R(115) and R(116) independently of one another are defined as R(114);

or

R(115) and R(116) together are 4 or 5 methylene groups, of which one CH$_2$ group can be replaced by oxygen, S, NH, N—CH$_3$ or N-benzyl;

but where the constitution of U is nitrogen (N), YY is nitrogen (N) and Z is carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zpa}F_{2zpa+1})$, R(110a)—$SO_{zbm}$, R(110b)R(110c)N—CO, R(111a)—CO— or R(112a)R(113a)N—$SO_2$—, where the perfluoroalkyl group is straight-chain or branched, X is oxygen, S or NR(114a);
  R(114a) is H or $(C_1-C_3)$-alkyl;
zoa is zero or 1;
zbm is zero, 1 or 2;
zpa is zero, 1, 2, 3 or 4;
zqa is 1, 2, 3, 4, 5, 6, 7 or 8;
R(110a), R(110b), R(111a) and R(112a) independently of one another are $(C_1-C_8)$-alkyl, $(C_3-C_8)$-alkenyl, —$C_{zn}H_{2zn}$—R(115a) or $(C_1-C_8)$-perfluoroalkyl;
  zn is zero, 1, 2, 3 or 4;
  R(115a) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);
    R(116a) and R(117a) are hydrogen, $(C_1-C_4)$-perfluoroalkyl or $(C_1-C_4)$-alkyl;
or
R(110b), R(111a) and R(112a) are hydrogen;
R(110c) and R(113a) independently are hydrogen, $(C_1-C_4)$-perfluoroalkyl or $(C_1-C_4)$-alkyl;
or
R(110b) and R(110c) and R(112a) and R(113a) together are 4 or 5 methylene groups, of which one $CH_2$ group can be replaced by oxygen, sulfur, NH, N—$CH_3$ or N-benzyl;
or
R(101), R(102), R(103), R(104), R(105) independently of one another are $(C_1-C_8)$-alkyl, —$C_{zal}H_{2zal}$R(118a) or $(C_3-C_8)$-alkenyl,
  zal is zero, 1, 2, 3 or 4;
  R(118a) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a)R(119b);
    R(119a) and R(119b) are hydrogen, $(C_1-C_4)$-alkyl or $(C_1-C_4)$-perfluoroalkyl;
or
R(101), R(102), R(103), R(104), R(105) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino and dimethylamino;
or
R(101), R(102), R(103), R(104), R(105) independently of one another are —C≡C—R(193);
  R(193) is phenyl which is not substituted or is substituted by 1–3 substituents from the group consisting of F, Cl, $CF_3$, methyl, methoxy or NR(194)R(195);
  R(194) and R(195) are hydrogen or $CH_3$;
or
R(101), R(102), R(103), R(104), R(105) independently of one another are
  —Y-para-$C_6H_4$—$(CO)_{zh}$—$(CHOH)_{zi}$—$(CH_2)_{zj}$—$(CHOH)_{zk}$—R(123), —Y-meta-$C_6H_4$—$(CO)_{zad}$—$(CHOH)_{zae}$—$(CH_2)_{zaf}$—$(CHOH)_{zag}$—R(124)
or
—Y-ortho-$C_6H_4$—$(CO)_{zah}$—$(CHOH)_{zao}$—$(CH_2)_{zap}$—$(CHOH)_{zak}$—R(125);
Y is oxygen, —S— or —NR(122d)—;
zh, zad, zah independently are zero or 1;
zi, zj, zk, zae, zaf, zag, zao, zap and zak independently are zero, 1, 2, 3 or 4;
but where in each case
  zh, zi and zk are not simultaneously zero,
  zad, zae and zag are not simultaneously zero, and
  zah, zao and zak are not simultaneously zero,
R(123), R(124) R(125) and R(122d) independently are hydrogen or $(C_1-C_3)$-alkyl;
or
R(101), R(102), R(103), R(104) and R(105) independently of one another are SR(129), —OR(130), —NR(131)R(132) or —CR(133)R(134)R(135);
  R(129), R(130), R(131) and R(133) independently are —$C_{zab}H_{2zab}$—$(C_1-C_9)$-heteroaryl, which is unsubstituted or substituted by 1–3 substituents from the group consisting of F, Cl, $CF_3$, $CH_3$, methoxy, hydroxyl, amino, methylamino and dimethylamino;
  zab is zero, 1 or 2;
  R(132), R(134) and R(135) independently are defined as R(129) or are hydrogen, $(C_1-C_4)$-alkyl or $(C_1-C_4)$-perfluoroalkyl;
or
R(101), R(102), R(103), R(104) and R(105) independently of one another are —W-para-$(C_6H_4)$—R(196), —W-meta-$(C_6H_4)$-R(197) or —W-ortho-$(C_6H_4)$-R(198);
  R(196), R(197) and R(198) independently of one another are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino and benzyl;
  W is oxygen, S or NR(136)—;
  R(136) is hydrogen or $(C_1-C_4)$-alkyl;
or
R(101), R(102), R(103), R(104) and R(105) independently of one another are R(146)X(1a)—;
  X(1a) is oxygen, S, NR(147), (D=O)A—, NR(148)C=MN$^{(*)}$R(149)—;
  M is oxygen or sulfur;
  A is oxygen or NR(150);
  D is C or SO;
  R(146) is $(C_1-C_8)$-alkyl, $(C_3-C_8)$-alkenyl, $(CH_2)_{zbz}C_{zdz}F_{2zdz+1}$ or —$C_{zxa}H_{2zxa}$—R(151);
  zbz is zero of 1;
  zdz is 1, 2, 3, 4, 5, 6 or 7;
  zxa is zero, 1, 2, 3 or 4;
  R(151) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy and NR(152)R(153);
    R(152) and R(153) are hydrogen, $(C_1-C_4)$-alkyl or $(C_1-C_4)$-perfluoroalkyl;
  R(147), R(148) and R(150) independently are hydrogen, $(C_1-C_4)$-alkyl, $(C_1-C_4)$-perfluoroalkyl;
  R(149) is defined as R(146),
or
R(146) and R(147), or R(146) and R(148) together are 4 or 5 methylene groups, of which one $CH_2$ group can be replaced by oxygen, sulfur, NH, N—$CH_3$ or N-benzyl;

where A and N$^{(*)}$ are bonded to the phenyl nucleus of the alkanoyl parent structure;

or

R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or R(164), R(165), R(166), R(167), R(169) identically or differently are —(CH$_2$)$_{zy}$—(CHOH)$_{zz}$—(CH$_2$)$_{zaa}$—(CHOH)$_{zt}$—R(171) or —(CH$_2$)$_{zab}$—O—(CH$_2$—CH$_2$O)$_{zac}$—R(172);

R(171) and R(172) are hydrogen or methyl;

zu is 1, 2, 3 or 4;

zv is zero, 1, 2, 3, or 4;

zy, zz, zaa, zab, zac identically or differently are zero, 1, 2, 3 or 4;

zt is 1, 2, 3 or 4;

R(168), R(170), R(154), R(155) identically or differently are hydrogen or (C$_1$–C$_6$)-alkyl, or R(169) and R(170), or R(154) and R(155) together with the carbon atom carrying them are a (C$_3$–C$_8$)-cycloalkyl;

R(163) is hydrogen, (C$_1$–C$_6$)-alkyl, (C$_3$–C$_8$)-cycloalkyl or —C$_{zeb}$H$_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, CF$_3$, methyl, methoxy and NR(174)R(175);

R(174) and R(175) are hydrogen or (C$_1$–C$_4$)-alkyl;

or

R(156), R(157) and R(173) independently are (C$_1$–C$_9$)-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—SO$_2$—;

R(176) is R(177)R(178)N-(C=Y')—;

Y' is oxygen, S or N—R(179);

R(177) and R(178) identically or differently are hydrogen, (C$_1$–C$_8$)-alkyl, (C$_3$–C$_6$)-alkenyl or —C$_{zfa}$H$_{2xfa}$—R(180); zfa is zero, 1, 2, 3 or 4;

R(180) is (C$_5$–C$_7$)-cycloalkyl or phenyl, which is unsubstituted or substituted by 1–3 substituents selected from the group consisting of F, Cl, CF$_3$, methoxy or (C$_1$–C$_4$)-alkyl;

or

R(177) and R(178) together are 4 or 5 methylene groups, of which one CH$_2$ group can be replaced by oxygen, sulfur, NH, N—CH$_3$ or N-benzyl;

R(179) is defined as R(177) or is amidine, or

R(101), R(102), R(103), R(104), R(105) independently of one another are NR(184a)R(185), OR(184b), SR(184c) or —C$_{znx}$H$_{2znx}$—R(184d);

znx is zero, 1, 2, 3 or 4;

R(184d) is (C$_3$–C$_7$)-cycloalkyl or phenyl, which is not substituted or substituted by 1–3 substituents from the group consisting of F, Cl, CF$_3$, methyl, methoxy an NR(116k)R(117k);

R(116k) and R(117k) are hydrogen or C$_1$–C$_4$-alkyl;

R(184a), R(184b), R(184c), R(185) independently of one another are hydrogen, (C$_1$–C$_8$)-alkyl, (C$_1$–C$_8$)-perfluoroalkyl or (CH$_2$)$_{zao}$—R(184g);

zao is zero, 1, 2, 3 or 4;

R(184g) is (C$_3$–C$_7$)-cycloalkyl or phenyl, which is not substituted or substituted by 1–3 substituents from the group consisting of F, Cl, CF$_3$, methyl, methoxy and NR(184u)R(184v);

R(184u) and R(184v) are hydrogen or C$_1$–C$_4$-alkyl;

or

R(184a) and R(185) together are 4 and 5 methylene groups, of which one CH$_2$ group can be replaced by oxygen, sulfur, NH, N—CH$_3$ or N-benzyl;

and their pharmaceutically tolerable salts;

(HOE 93/F 254-EP-Offenlegungsschrift 640 588, NZ 264 307)

u) benzoylguanidines of the formula I

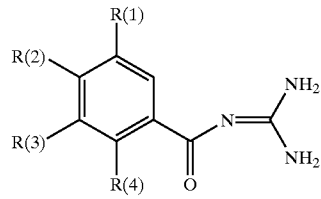

in which:

R(1) is H, F, Cl, Br, I, CN, NO$_2$, (C$_1$–C$_8$)-alkyl, (C$_3$–C$_8$)-cycloalkyl or X$_a$—(CH$_2$)$_b$—(CF$_2$)$_c$—CF$_3$;

X is oxygen, S or NR(5);

a is zero or 1;

b is a zero, 1 or 2;

c is zero, 1, 2 or 3;

R(5) is H, (C$_1$–C$_4$)-alkyl or —C$_d$H$_{2d}$R(6);

d is zero, 1, 2, 3 or 4;

R(6) is (C$_3$–C$_8$)-cycloalkyl, phenyl, biphenylyl or naphthyl, where the aromatics are not substituted or are substituted by 1 to 3 substituents selected from the group consisting of F, Cl, CF$_3$, methyl, methoxy and NR(7)R(8);

R(7) and R(8) independently are H or (C$_1$–C$_4$)-alkyl;

or

R(1) is —SR(10), —OR(10) or —CR(10)R(11)R(12);

R(10) is —C$_1$H$_{21}$—(C$_3$–C$_8$)-cycloalkyl, —(C$_1$–C$_9$)-heteroaryl or phenyl, where the aromatic systems are unsubstituted or substituted by one to 3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10) or are hydrogen or (C$_1$–C$_4$)-alkyl;

or

R(1) is phenyl, naphthyl, biphenylyl or (C$_1$–C$_9$)-heteroaryl, the latter linked via C or N, and which are unsubstituted or substituted by 1 to 3 substituents selected from the group consisting of F, Cl, CF$_3$, CH$_3$, methoxy, hydroxyl, amino, methylamino and dimethylamino;

or

R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)]$_l$;

R(13) and R(14) identically or differently are —(CH$_2$)$_g$—(CHOH)$_h$—(CH$_2$)$_i$—(CHOH)$_j$—R(17), R(17) is hydrogen or methyl;

—(CH$_2$)$_g$—O—(CH$_2$—CH$_2$O)$_h$—R(24), g, h, i identically or differently are zero, 1, 2, 3 or 4;

j is 1, 2, 3 or 4;

R(15) and R(16) identically or differently are hydrogen, $(C_1-C_6)$-alkyl or together with the carbon atom carrying them are a $(C_3-C_8)$-cycloalkyl;

R(18) is phenyl, which is unsubstituted or substituted by 1 to 3 substituents selected from the group consisting of F, Cl, $CF_3$, methyl, methoxy and NR(25)R(26)

R(25) and R(26) are H or $(C_1-C_4)$-alkyl;

or

R(18) is $(C_1-C_9)$-heteroaryl, which is unsubstituted or substituted as phenyl;

or

R(18) is $(C_1-C_6)$-alkyl, which is unsubstituted or substituted by 1 to 3 OH;

or

R(18) is $(C_3-C_8)$-cycloalkyl;

R(19), R(20), R(21), R(22) and R(23) are hydrogen or methyl;

k is zero, 1, 2, 3 or 4;

l is zero, 1, 2, 3 or 4;

R(24) is H, $(C_1-C_6)$-alkyl, $(C_3-C_8)$-cycloalkyl or —$C_mH_{2m}$—R(18);

m is 1, 2, 3 or 4;

R(2) and R(3) independently of one another are defined as R(1);

R(4) is $(C_1-C_3)$-alkyl, F, Cl, Br, l, CN or —$(CH_2)_n$—$(CF_2)_o$—$CF_3$;

n is zero or 1;

o is zero, 1 or 2;

and their pharmaceutically tolerable salts;

(HOE 93/F 436-EP-Offenlegungsschrift 659 748, NZ 270 264)

v) acylguanidines of the formula I

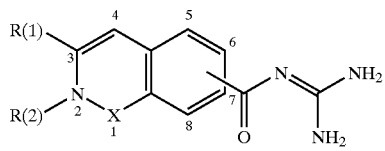

(I)

in which:

X is carbonyl, sulfonyl,

R(1) is H, $(C_1-C_8)$-alkyl, unsubstituted or substituted by hydroxyl, $(C_3-C_8)$-cycloalkyl, phenyl, which is unsubstituted or substituted by 1–3 substituents from the group F, Cl, $CF_3$, $CH_3$, methoxy, hydroxyl, amino, methylamino or dimethylamino, R(2) is H, $(C_1-C_4)$-alkyl, and their pharmaceutically tolerable salts;

(HOE 94/F 014 K-EP-Offenlegungsschrift 666 252, NZ 270 370)

w) phenyl-substituted alkycarboxylic acid guanidides, carrying perfluoroalkyl groups, of the formula I

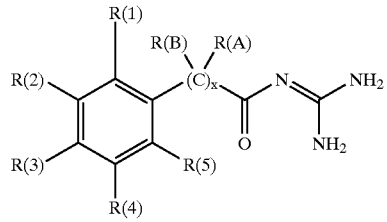

(I)

in which:

R(A) is hydrogen, F, Cl, Br, l, CN, OR(6), $(C_1-C_8)$-alkyl, $(C_3-C_8)$-cycloalkyl, $O_r(CH_2)_aC_bF_{2b+1}$ or NR(7)R(8);

r is zero or 1;

a is zero, 1, 2, 3 or 4;

b is 1, 2, 3, 4, 5, 6, 7 or 8;

R(6) is hydrogen, $(C_1-C_8)$-alkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(9)R(10);

R(6) and R(10) are H, $(C_1-C_4)$-alkyl or $(C_1-C_4)$-perfluoroalkyl;

R(7) and R(8) independently of one another are defined as R(6);

R(B) independently is defined as R(A);

X is 1, 2, or 3;

R(1) is hydrogen, $(C_1-C_8)$-alkyl, $(C_3-C_8)$-cycloalkyl, —$O_t(CH_2)_dC_eF_{2e+1}$, F, Cl, Br, l or CN;

t is zero or 1;

d is zero, 1, 2, 3 or 4;

e is 1, 2, 3, 4, 5, 6, 7 or 8;

R(2),R(3), R(4) and R(5) independently of one another are defined as R(1); but with the condition that at least one of the substituents R(1), R(2), R(3), R(4), R(5), R(A) and R(B) is an —$O_t(CH_2)_dC_eF_{2e+1}$ or an $O_r(CH_2)_aC_bF_{2b+1}$ group, and their pharmaceutically tolerable salts;

(HOE 94/F 094-EP-Offenlegungsschrift 676 395, NZ 270 894)

x) heteroaroylguanidines of the formula I

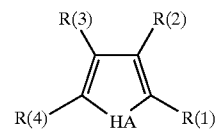

I in which:

HA is $SO_m$, O or NR(5);

m is zero, 1 or 2;

R(5) is hydrogen, $(C_1-C_8)$-alkyl or —$C_{am}H_{2am}$R(81);

am is zero, 1 or 2;

R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);

R(82) and R(83) Is H or $CH_3$;

or

R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

one of the two substituents R(1) and R(2) is —CO—N═C(NH$_2$)$_2$;

and the other in each case is hydrogen, F, Cl, Br, I, (C$_1$–C$_3$)-alkyl, —OR(6), C$_r$F$_{2r+1}$, —CO—N═C(NH$_2$)$_2$ or —NR(6)R(7);

R(6) and R(7) independently are hydrogen or (C$_1$–C$_3$)-alkyl;

r is 1, 2, 3 or 4;

R(3) and R(4) independently of one another are hydrogen, F, Cl, Br, I, —C≡N, X—(CH$_2$)$_p$—(C$_q$—F$_{2q+1}$), R(8)—SO$_{bm}$, R(9)R(10)N—CO, R(11)—CO— or R(12)R(13)N—SO$_2$—, where the perfluoroalkyl group is straight-chain or branched, X is oxygen, S or NR(14);
R(14) is H or (C$_1$–C$_3$)-alkyl;

bm is zero, 1 or 2;

p is zero, 1 or 2;

q is zero, 1, 2, 3, 4, 5 or 6;

R(8), R(9), R(11) and R(12) independently are (C$_1$–C$_8$)-alkyl, (C$_3$–C$_6$)-alkenyl, —C$_n$H$_{2n}$—R(15), CF$_3$;
n is zero, 1, 2, 3 or 4;
R(15) is (C$_3$–C$_7$)-cycloalkyl or phenyl; which is not substituted or is substituted by 1–3 substituents selected from the group consisting of F, Cl, CF$_3$, methyl, methoxy, or NR(16)R(17);
R($_{16}$) and R(17) are H or C$_1$–C$_4$-alkyl;

or

R(9), R(11) and R(12) are H;
R(10) and R(13) independently are H or (C$_1$–C$_4$)-alkyl;

or

R(9) and R(10), and R(12) and R(13) together are 4 or 5 methylene groups, of which one CH$_2$ group can be replaced by oxygen, S, NH, N—CH$_3$ or N-benzyl, or R(3) and R(4) independently of one another are (C$_1$–C$_8$)-alkyl or —C$_{al}$H$_{2al}$R(18);
al is zero, 1 or 2;
R(18) is (C$_3$–C$_8$)-cycloalkyl or phenyl; which is not substituted or is substituted by 1–3 substitutents selected from the group consisting of F, Cl, CF$_3$, methyl, methoxy and NR(19)R(20);
R(19) and R(20) are H or CH$_3$;

or

R(3) and R(4) independently of one another are (C$_1$–C$_9$)-heteroaryl, which is linked via C or N and which is unsubstituted or substituted by 1–3 substituents selected from the group consisting of F, Cl, CF$_3$, CH$_3$, methoxy, hydroxyl, amino, methylamino and dimethylamino;

or

R(3) and R(4) independently of one another are

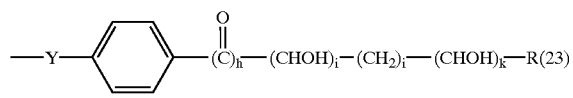

or

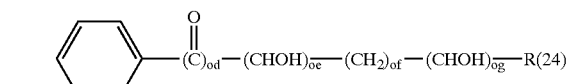

or

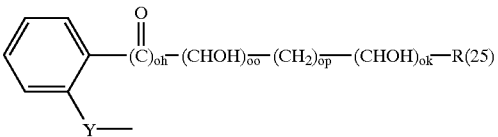

Y is oxygen, —S— or —NR(22)—;

h, ad, ah independently are zero or 1;

i, j, k, ae, af, ag, ao, ap and ak independently are zero, 1, 2, 3, 4, but where in each case
h, i and k are not simultaneously zero,
ad, ae and ag are not simultaneously zero,
ah, ao and ak are not simultaneously zero, R(23), R(24) R(25) and R(22) independently are hydrogen or (C$_1$–C$_3$)-alkyl;

or

R(3) and R(4) independently are hydrogen, F, Cl, Br, I, CN, (C$_1$–C$_8$)-alkyl, (C$_1$–C$_8$)-perfluoroalkyl, (C$_3$–C$_8$)-alkenyl or —C$_g$H$_{2g}$R(26);

g is zero, 1, 2, 3 or 4;

R(26) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(27)R(28);
R(27) and R(28) are H, (C$_1$–C$_4$)-alkyl or (C$_1$–C$_4$)-pefluoroalkyl;

or

R(3) and R(4) independently of one another are SR(29), —OR(30); —NR(31)R(32) or —CR(33)R(34)R(35);
R(29), R(30), R(31) and R(33) independently of one another are —C$_a$H$_{2a}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
a is zero, 1 or 2;
R(32), R(34) and R(35) independently of one another are defined as R(29) or are hydrogen, (C$_1$–C$_4$)-alkyl or (C$_1$–C$_4$)-perfluoroalkyl;

or

R(3) and R(4) independently of one another are

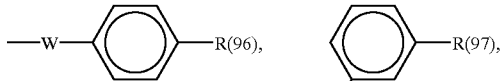

or

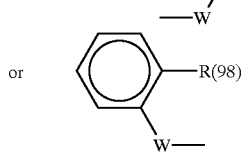

R(96), R(97) and R(98) independently are (C$_1$–C$_9$)-heteroaryl, which is linked via C or N and which is unsubstituted or substituted by 1 to 3 substituents selected from the group consisting of F, Cl, CF$_3$, CH$_3$, methoxy, hydroxyl, amino, methylamino, dimethylamino or benzyl;

W is oxygen, S or NR(36)—;
R(36) is H or $(C_1-C_4)$-alkyl;

or

R(3) and R(4) independently of one another are R(37)—$SO_{cm}$ or R(38)R(39)N—$SO_2$—;

cm is 1 or 2;

R(37) is $(C_1-C_8)$-alkyl, $(C_1-C_8)$-perfluoroalkyl, $(C_3-C_8)$-alkenyl or —$C_sH_{2s}$R(40);

s is zero, 1, 2, 3 or 4;

R(40) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(41)R(42);

R(41) and R(42) are H, $(C_1-C_4)$-alkyl or $(C_1-C_4)$-perfluoroalkyl;

R(38) is H, $(C_1-C_8)$-alkyl, $(C_1-C_8)$-perfluoroalkyl, $(C_3-C_8)$-alkenyl or —$C_wH_{2w}$—R(43);

w is zero, 1, 2, 3 or 4;

R(43) is $(C_3-C_8)$-cycloalkyl, phenyl, biphenylyl or naphthyl, where the aromatics are not substituted or are substituted by 1–3 substituents selected from the group conssisting of F, Cl, $CF_3$, methyl, methoxy and NR(44)R(45);

R(44) and R(45) are H, $(C_1-C_4)$-alkyl or $(C_1-C_4)$-perfluoroalkyl;

R(39) is H, $(C_1-C_4)$-alkyl or $(C_1-C_4)$-perfluoroalkyl;

or

R(38) and R(39) together are 4 or 5 methylene groups, which one $CH_2$ group can be replaced by oxygen, S, NH, N—$CH_3$ or N-benzyl;

or

R(3) and R(4) independently of one another are R(46)X(1)—;

X(1) is oxygen, S, NR(47), (D=O)A—, NR(48)C=MN$^{(*)}$R(49)—,

M is oxygen or S;

A is oxygen or NR(50);

D is C or SO;

R(46) is $(C_1-C_8)$-alkyl, $(C_3-C_8)$-alkenyl, $(CH_2)_bC_dF_{2d+1}$ or —$C_xH_{2x}$—R(51);

b is zero or 1;

d is 1, 2, 3, 4, 5, 6 or 7;

x is zero, 1, 2, 3 or 4;

R(51) is $(C_1-C_8)$-cycloalkyl, phenyl, biphenylyl or naphthyl, where the aromatics are nhot substituted or are substituted by 1–3 substituents selected from the group consisting of F, Cl, $CF_3$, methyl, methoxy and NR(52)R(53);

R(52) and R(53) are H, $(C_1-C_4)$-alkyl or $(C_1-C_4)$-perfluoroalkyl;

R(47), R(48) and R(50) independently are hydrogen, $(C_1-C_4)$-alkyl or $(C_1-c_4)$-perfluoroalkyl;

R(49) is defined as R(46);

or

R(46) and R(47), or R(46) and R(48) together are 4 or 5 methylene groups, of which one $CH_2$ group can be replaced by oxygen, S, NH, N—$CH_3$ or N-benzyl, where A and N$^{(*)}$ are bonded to the phenyl nucleus of the benzoylguanidine parent structure;

or

R(3) and R(4) independently of one another are —SR(64), —OR(65), —NHR(66), —NR(67)R(68), —CHR(69)R(70), —C(OH)R(54)R(55), —C≡CR(56), —CR(58)=CHR(57), —[CR(59)R(60)]$_u$—(CO)—[CR(61)R(62)]$_v$—R(63);

R(64), R(65), R(66), R(67) and R(69) identically or differently are —$(CH_2)_y$—$(CHOH)_z$—$(CH_2)_{22}$—$(CH_2OH)_t$—R(71) or —$(CH_2)_{ab}$—O—$(CH_2$—$CH_2O)_{ac}$—R(72), R(71) and R(72) are hydrogen or methyl;

u is 1, 2, 3 or 4;

v is zero, 1, 2, 3 or 4;

y, z, aa identically or differently are zero, 1, 2, 3 or 4;

t is 1, 2, 3 or 4;

R(68), R(70), R(54), and R(55) identically or differently are hydrogen, $(C_1-C_6)$-alkyl;

or

R(69) and R(70), or R(54) and R(55) together with the carbon atom carrying them are a $(C_3-C_8)$-cycloalkyl;

R(63) is H, $(C_1-C_6)$-alkyl, $(C_3-C_8)$-cycloalkyl or —$C_eH_{2e}$—R(73);

e is zero, 1, 2, 3 or 4;

R(56), R(57) and R(73) independently are phenyl, which are unsubstituted or substituted by 1–3 substituents selected from the group consisting of F, Cl, $CF_3$, methyl, methoxy and NR(74)R(75);

R(74) and R(75) are H or $(C_1-C_4)$-alkyl;

or

R(56), R(57) and R(73) independently are $(C_1-C_9)$-heteroaryl, which is unsubstituted or substitued as phenyl;

R(58), R(59), R(60), R(61) and R(62) are hydrogen or methyl, or

R(3) and R(4) independently of one another are R(76)—NH—$S_2$—;

R(76) is R(77)R(78)N—(C=Y')—;

Y' is oxygen, S or N—R(79);

R(77) and R(78) identically or differently are H, $(C_1-C_8)$-alkyl, $(C_3-C_6)$-alkenyl, —$C_1H_{2f}$—R(80);

f is zero, 1, 2, 3 or 4;

R(80) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl;

or

R(77) and R(78) together are 4 or 5 methylene groups, of which one $CH_2$ group can be replaced by oxygen, S, NH, N—$CH_3$ or N-benzyl, R(79) is defined as R(77) or is amidine;

or

R(3) and R(4) independently of one another are NR(84)R(85);

R(84) and R(85) independently of one another are H, $(C_1-C_4)$-alkyl, or together are 4 or 5 methylene groups, of which one $CH_2$ group can be replaced by oxygen, S, NH, N—$CH_3$ or N-benzyl; or of which one or two $CH_2$ groups can be replaced by CH—$C_{dm}H_{2dm+1}$, and their pharmaceutically tolerable salts;

(HOE 94/F 123-EP-Offenlegungsschrift 682 017, NZ 272 058)

y) bicyclic heteroaroylguanidines of the formula I

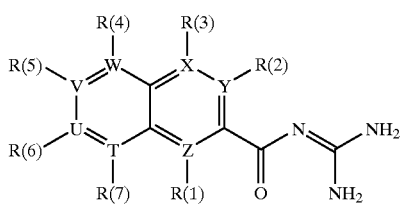

in which:
T, U, V, W, X, Y and Z independently of one another are nitrogen or carbon; but with the restriction that X and Z are not simultaneously nitrogen, and that, T, U, V, W, X, Y and Z carry no substituents if they are nitrogen, and that no more than four of them are simultaneously nitrogen, R(1) and R(2) independently of one another are hydrogen, F, Cl, Br, l, $(C_1-C_3)$-alkyl, $(C_1-C_3)$-perfluoroalkyl, OR(8), NR(8)R(9) or $C(=O)N=C(NH_2)_2$;

R(8) and R(9) independently of one another are hydrogen or $(C_1-C_3)$-alkyl, or R(8) and R(9) together are 4 or 5 methylene groups, of which one $CH_2$ group can be replaced by oxygen, S, NH, N—$CH_3$ or N-benzyl;

R(3), R(4), R(5), R(6) and R(7) independently of one another are hydrogen, F, Cl, Br, l, —C≡N, $X_k$—$(CH_2)_p$—$(C_qF_{2q+1})$, R(10a)—$SO_{bm}$, R(10b)R(10c)N—CO, R(11)—CO— or R(12)R(13)N—$SO_2$—, where the perfluoroalkyl group is straight-chain or branched;

X is oxygen, S or NR(14);
R(14) is H or $(C_1-C_3)$-alkyl;
bm is zero, 1 or 2;
p is zero, 1 or 2;
k is zero or 1;
q 1, 2, 3, 4, 5 or 6;

R(10a), R(10b), R(11) and R(12) independently of one another are $(C_1-C_8)$-alkyl; $(C_3-C_6)$-alkenyl, —$C_nH_{2n}$—R(15) or $(C_1-C_8)$-perfluoroalkyl;
n is zero, 1, 2, 3 or 4;

R(15) is $(C_3-C_7)$-cycloalkyl or phenyl, which is not substituted or is substituted by 1-3 substituents selected from the group consisting of F, Cl, $CF_3$, methyl, methoxy and NR(16)R(17);
R(16) and R(17) are H or $C_1-C_4$-alkyl;

or

R(10b), R(11) and R(12) are hydrogen;
R(10c) and R(13) independently are hydrogen or $(C_1-C_4)$-alkyl;

or

R(10b) and R(10c) and R(12) and R(13) together are 4 or 5 methylene groups, of which one $CH_2$ group can be replaced by oxygen, sulfur, NH, N—$CH_3$ or N-benzyl;

or

R(3), R(4), R(5), R(6) and R(7) independently of one another are $(C_1-C_8)$-alkyl, —$C_{al}H_{2al}$R(18) or $(C_3-C_8)$-alkenyl;
al is zero, 1 or 2;

R(18) is $(C_3-C_8)$-cycloalkyl, phenyl, biphenylyl or naphthyl, where the aromatics are not substituted or are substituted by 1-3 substituents selected from the group consisting of F, Cl, $CF_3$, methyl, methoxy and NR(19a)R(19b);

R(19a) and R(19b) are hydrogen, $(C_1-C_4)$-alkyl or $(C_1-C_4)$-perfluoroalkyl;

or

R(3), R(4), R(5), R(6) and R(7) independently of one another are $(C_1-C_9)$-heteroaryl, which is linked via C or N and with is unsubstituted or substituted by 1-3 substituents from the group consisting of F, Cl, $CF_3$, $CH_3$, methoxy, hydroxyl, amino, methylamino or dimethylamino;

or

R(3), R(4), R(5), R(6) and R(7) independently of one another are

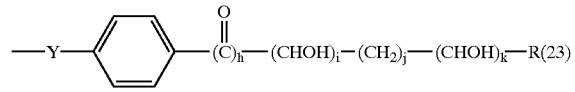

or

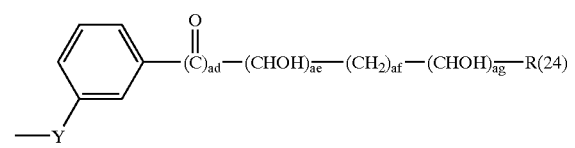

or

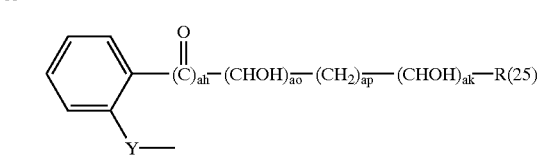

Y is oxygen, —S— or —NR(22)—;
h, ad, ah independently of one another are zero or 1;
i, j, k, ae, af, ag, ao, ap and ak independently of one another are zero, 1, 2, 3 or 4;
but where in each case h, i and k are not simultaneously zero, ad, ae and ag are not simultaneously zero, and ah, ao and ak are not simultaneously zero, R(23), R(24) R(25) and R(22) independently of one another are hydrogen or $(C_1-C_3)$-alkyl;

or

R(3), R(4), R(5), R(6) and R(7) independently of one another are SR(29), —OR(30), —NR(31)R(32) or —CR(33)R(34)R(35);

R(29), R(30), R(31) and R(33) independently of one another are —$C_aH_{2a}$—$(C_1-C_9)$-heteroaryl, which is unsubstituted or substituted by 1-3 substituents selected from the group consisting of F, Cl, $CF_3$, $CH_3$, methoxy, hydroxyl, amino, methylamino and dimethylamino;
a is zero, 1 or 2;

R(32), R(34) and R(35) independently of one another are defined as R(29) or are hydrogen, $(C_1-C_4)$-alkyl or $(C_1-C_4)$-perfluoroalkyl;

or

R(3), R(4), R(5), R(6) and R(7) independently of one another are

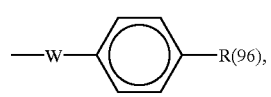 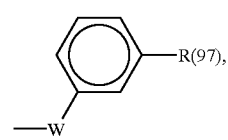

or 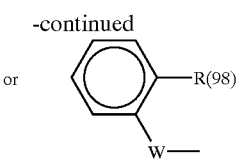

R(96), R(97) and R(98) independently of one another are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—;
R(36) is H or $(C_1-C_4)$-alkyl;

or

R(3), R(4), R(5), R(6) and R(7) independently of one another are R(46)X(1)—;

X(1) is oxygen, S, NR(47), (D=O)A— or NR(48)C=MN$^{(*)}$R(49)—;

M is oxygen or sulfur;
A is oxygen or NR(50);
D is C or SO;
R(46) is $(C_1-C_8)$-alkyl, $(C_3-C_8)$-alkenyl, $(CH_2)_bC_dF_{2d+1}$ or —$C_{2x}H_x$—R(51);
b is zero or 1;
d is 1, 2, 3, 4, 5, 6 or 7;
x is zero, 1, 2, 3 or 4;
R(51) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);
R(52) and R(53) are hydrogen, $(C_1-C_4)$-alkyl or $(C_1-C_4)$-perfluoroalkyl;
R(47), R(48) and R(50) independently are hydrogen, $(C_1-C_4)$-alkyl or $(C_1-C_4)$-perfluoroalkyl;
R(49) is defined as R(46);

or

R(46) and R(47), or R(46) and R(48) together are 4 or 5 methylene groups, of which one $CH_2$ groups can be replaced by oxygen, sulfur, NH, N—$CH_3$ or N-benzyl;
where A and N$^{(*)}$ are bonded to the phenyl necleus of the heteroaroylguanidine parent structure;

or

R(3), R(4), R(5), R(6) and R(7) independently of one another are —SR(64), —OR(65), —NHR(66), —NR(67)R(68), —CHR(69)R(70) or —CR(54)R(55)OH, —C≡CR(56), —CR(58)=CR(57) or —[CR(59)R(60)]$_u$—CO—[CR(61)R(62)]$_v$—R(63);
R(64), R(65), R(66), R(67) and R(69) indentically or differently are —$(CH_2)_y$—$(CHOH)_z$—$(CH_2)_{aa}$—$(CHOH)_t$—R(71) or —$(CH_2)_{ab}$—O—$(CH_2-CH_2O)_{ac}$—R(72);
R(71) and R(72) independently of one another are hydrogen or methyl;
u is 1, 2, 3 or 4;
v is zero, 1, 2, 3 or 4;
y, z, aa identically or differently are zero, 1, 2, 3 or 4;
t is 1, 2, 3 or 4;
R(68), R(70), R(54) and R(55) identically or differently are hydrogen or $(C_1-C_6)$-alkyl;

or

R(69) and R(70), or R(54) and R(55) together with the carbon atom carrying them are $(C_3-C_8)$-cycloalkyl;

R(63) is hydrogen, $(C_1-C_6)$-alkyl, $(C_3-C_8)$-cycloalkyl or —$C_eH_{2e}$—R(73);
e is zero, 1, 2, 3 or 4;
R(56), R(57) and R(73) independently are phenyl, which is unsubstituted or substituted by 1–3 substituents selected from the group consisting of F, Cl, $CF_3$, methyl, methoxy and NR(74)R(75);
R(74) and R(75) are hydrogen or $(C_1-C_4)$-alkyl;

or

R(56), R(57) and R(73) independently are $(C_1-C_9)$-heteroaryl, which is unsubstituted or substituted as phenyl;
R(58), R(59), R(60), R(61) and R(62) are hydrogen or methyl;

or

R(3), R(4), R(5), R(6) and R(7) independently of one another are R(76)—NH—$SO_2$—;
R(76) is R(77)R(78)N—(C=Y')—;
Y' is oxygen, S or N—R(79);
R(77) and R(78) identically or differently are hydrogen, $(C_1-C_8)$-alkyl, $(C_3-C_6)$-alkenyl or —$CH_fH_{2f}$—R(80);
f is zero, 1, 2, 3 or 4;
R(80) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl;

or

R(77) and R(78) together are 4 or 5 methylene groups, of which one $CH_2$ group can be replaced by oxygen, sulfur, NH, N—$CH_3$ or N-benzyl;
R(79) is defined as R(77) or is amidine;

or

R(3), R(4), R(5), R(6) and R(7) independently of one another are NR(84a)R(85), OR(84b), SR(84c) or —$C_nH_{2n}$—R(84d);
n is zero, 1, 2, 3 or 4;
R(84d) is $(C_3-C_7)$-cycloalkyl or phenyl, which is not substituted or is substituted by 1–3 substituents from the group consisting of F, Cl, $CF_3$, methyl, methoxy and NR(16)R(17);
R(16) and R(17) are hydrogen or $C_1-C_4$-alkyl;
R(84a), R(84b), R(84c) and R(85) independently of one another are hydrogen, $(C_1-C_8)$-alkyl, $(C_1-C_8)$-perfluoroalkyl or $(CH_2)_{ax}$—R(84g);
ax is zero, 1, 2, 3 or 4;
R(84g) is $(C_3-C_7)$-cycloalkyl or phenyl, which is not substituted or is substituted by 1–3 substituents selected from the group consisting of F, Cl, $CF_3$, methyl, methoxy and NR(84u) and R(84v);
R(84) and R(84) are hydrogen or $C_1-C_4$-alkyl;

or

R(84a) and R(85) together are 4 or 5 methylene groups, of which one $CH_2$ group can be replaced by oxygen, sulfur, NH, N—$CH_3$ or N-benzyl, and their pharmaceutically tolerable salts;

(HOE 94/F 134-EP-Offenlegungsschrift 686 627, NZ 272 103)

z) benzoylguanidines of the formula I

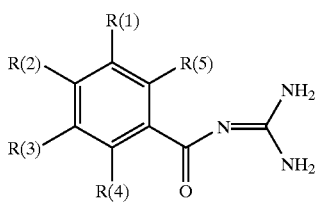

in which:
R(1) is R(6)—SO$_m$;
  m is zero, 1 or 2;
  R(6) is perfluoralkyl having 1, 2, 3, 4, 5 or 6 carbon atoms, which is straigh-chain or branched;
R(2) and R(3) independently of one another are hydrogen, F, Cl, Br, l, alkyl having 1, 2, 3 and 4 carbon atoms, alkoxy having 1, 2, 3 or 4 carbon atoms or phenoxy, which is unsubstituted or substituted by 1–3 substituents selected from the group consisting of F, Cl, methyl and methoxy;
or
R(2) and R(3) independently of one another are pyrrol-1-yl, pyrrol-2-yl or pyrrol-3-yl, which is not substituted or is substituted by 1 to 4 substituents selected from the group consisting of F, Cl, Br, l, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, CF$_3$, methyl and methoxy;
R(4) and R(5) independently of one another are hydrogen, alkyl having 1, 2 or 3 carbon atoms, F, Cl, Br, l, CN, OR(7), NR(8)R(9) or —CH$_2$)$_n$—(CF$_2$)$_o$—CF$_3$;
  R(7), R(8) and R(9) independently of one another are hydrogen or alkyl having 1, 2, 3 or 4 carbon atoms;
  n is zero or 1;
  o is zero, 1 or 2;
and their pharmacologically acceptable salts;
(HOE 94/F 168-EP-Offenlegungsschrift 690 048, NZ 272 373)

aa) Phenyl-substituted alkenylcarboxylic acid guanidides, carrying perfluoroalkyl groups, of the formula I

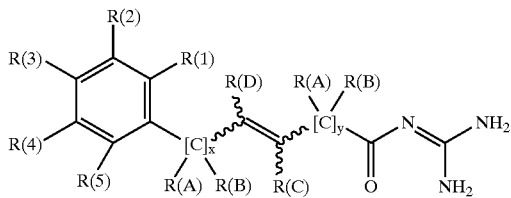

in which:
R(A) is hydrogen, F, Cl, Br, l, CN, OH, OR(6), (C$_1$–C$_8$)-alkyl, O$_r$(CH$_2$)$_a$C$_b$F$_{2b+1}$, (C$_3$–C$_8$)-cycloalkyl or NR(7)R(8);
  r is zero or 1;
  a is zero, 1, 2, 3 or 4;
  b is zero, 1, 2, 3, 4, 5, 6, 7 or 8;
  R(6) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl; where the aromatics are not substituted or are substituted by 1–3 substituents from the group consisting of F, Cl, CF$_3$, methyl, methoxy and NR(9) and R(10);
  R(9) and R(10) are H, (C$_1$–C$_4$)-alkyl or (C$_1$–C$_4$)-perfluoroalkyl;
  R(7) and R(8) independently of one another are defined as R(6);
or
  R(7) and R(8) together are 4 or 5 methylene groups, of which one CH$_2$ group can be replaced by oxygen, sulfur, NH, N—CH$_3$ or N-benzyl;
R(B) independently is defined as R(A);
x is zero, 1 or 2;
y is zero, 1 or 2;
R(C) is hydrogen, F, Cl, Br, I, CN, OR(12), (C$_1$–C$_8$)-alkyl, O$_p$(CH$_2$)$_f$C$_g$F$_{2g+1}$ or (C$_3$–C$_8$)-cycloalkyl;
  p is zero or 1;
  f is zero, 1, 2, 3 or 4;
  g is 1, 2, 3, 4, 5, 6, 7 or 8;
  R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl; where the aromatics phenyl or benzyl are not substituted or are substituted by 1–3 substituents from the group consisting of F, Cl, CF$_3$, methyl, methoxy and NR(13)R(14);
  R(13) and R(14) independently of one another are H, (C$_1$–C$_4$)-alkyl or (C$_1$–C$_4$)-perfluoroalkyl;
R(D) independently is defined as R(C),
R(1) is hydrogen, (C$_1$–C$_8$)-alkyl, —O$_t$)CH$_2$)$_d$C$_e$F$_{2e+1}$, (C$_3$–C$_8$)-cycloalkyl, F, Cl, Br, I or CN;
  t is zero or 1;
  d is zero, 1, 2, 3 or 4;
  e is 1, 2, 3, 4, 5, 6, 7 or 8;
R(2), R(3), R(4) and R(5) independently of one another are defined as R(1); but with the condition that at least one of the substituents R(A), R(B), R(C), R(D), R(1), R(2), R(4) or R(5) is a O$_r$(CH$_2$)$_a$C$_b$F$_{2b+1}$, O$_p$(CH$_2$)$_f$C$_g$F$_{2g+1}$ or O$_t$(CH$_2$)$_d$C$_e$F$_{2e+1}$ group and R(3) is not a O$_t$(CH$_2$)$_d$C$_e$F$_{2e+1}$ group;
and their pharmaceutically tolerable salts;
(HOE 94/F 182-EP-Offenlegungsschrift 690 048, NZ 272 449)

ab) ortho-amino-substituted benzoylguanidines of the formula I

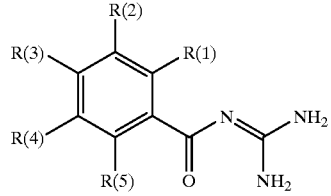

in which:
R(1) is NR(50)R(6),
  R(50) and R(6) independently of one another are hydrogen, (C$_1$–C$_8$)-alkyl or (C$_1$–C$_8$)-perfluoroalkyl;
R(2), R(3), R(4) and R(5) independently of one another are R(10)—SO$_a$—, R(11)R(12)N—CO—, R(13)—CO— or R(14)R(15)N—SO$_2$—;
  a is zero, 1 or 2,
  R(10), R(11), R(12), R(13), R(14) and R(15) independently of one another are (C$_1$–C$_8$)-alkyl, (C$_1$–C$_8$)-perfluoroalkyl, (C$_3$–C$_6$)-alkenyl or —C$_{ab}$H$_{2ab}$—R(16);
  ab is zero, 1, 2, 3 or 4;
  R(16) is (C$_3$–C$_7$)-cycloalkyl, phenyl, which is not substituted or is substituted by 1–3 substituents selected from the group consisting of F, Cl, $CF_3$, methyl, methoxy and NR(17)R(18);
R(17) and R(18) independently of one another are H, $CF_3$ or $(C_1-C_4)$-alkyl;
or
R(11), R(12), and also R(14) and R(15) together are 4 or 5 methylene groups, of which one $CH_2$ group can be replaced by oxygen, S, NH, N—$CH_3$ or N-benzyl;
or
R(11), R(12), R(14) and R(15) independently of one another are hydrogen;
or
R(2), R(3), R(4) and R(5) independently of one another are SR(21), —OR(22), —NR(23)R(24) or —CR(25)R(26)R(27);
R(21), R(22), R(23) and R(25) independently of one another are —$C_bH_{2b}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
b is zero, 1 or 2;
R(24), R(26) and R(27) independently of one another are hydrogen, $(C_1-C_4)$-alkyl or $(C_1-C_4)$-perfluoroalkyl;
or
R(2), R(3), R(4) and R(5) independently of one another are hydrogen, F, Cl, Br, I, CN, —$(Xa)_{dg}$—$C_{da}H_{2da+1}$, —$(Xb)_{dh}$—$C_{de}F_{2de+1}$, $(C_3-C_8)$-alkenyl or —$C_{df}H_{2df}R(30)$;
(Xa) is O, S or NR(33);
R(33) is H, $(C_1-C_4)$-alkyl or $(C_1-C_4)$-perfluoroalkyl;
dg is zero or 1;
(Xb) is O, S or NR(34);
R(34) is H, $(C_1-C_4)$-alkyl or $(C_1-C_4)$-perfluoroalkyl;
dh is zero or 1;
da is zero, 1, 2, 3, 4, 5, 6, 7, 8;
db is zero, 1, 2, 3, 4;
de is zero, 1, 2, 3, 4, 5, 6, 7;
df is zero, 1, 2, 3, 4;
R(30) is $(C_3-C_8)$-cycloalkyl, phenyl, biphenylyl or naphthyl, where the aromatics phenyl, biophenylyl or naphthyl are not substituted or are substituted by 1–3 substituents selected from the group consisting of F, Cl, $CF_3$, methyl, methoxy and NR(31)R(32);
R(31) and R(32) are H, $(C_1-C_4)$-alkyl or $(C_1-C_4)$-perfluoroalkyl;
or
R(2), R(3), R(4) and R(5) independently of one another are NR(40)R(41) or —(Xe)—$(CH_2)_{eb}$R(45);
R(40) and R(41) independently of one another are hydrogen, $(C_1-C_8)$-alkyl, $(C_1-C_8)$-perfluoroalkyl or $(CH_2)_e$—R(42);
e is zero, 1, 2, 3 or 4;
R(42) is $(C_3-C_7)$-cycloalkyl, phenyl, which is not substituted or is substituted by 1–3 substituents selected from the group consisting of F, Cl, $CF_3$, methyl, methoxy and NR(43)R(44);
R(43) and R(44) independently of one another are H, $CF_3$ or $(C_1-C_4)$-alkyl;
or
R(40) and R(41) together are 4 or 5 methylene groups, of which one $CH_2$ group can be replaced by oxygen, sulfur, NH, N—$CH_3$ or N-benzyl;
(Xe) is O, S or NR(47);

R(47) is H, $(C_1-C_4)$-alkyl or $(C_1-C_4)$-perfluoroalkyl;
eb is zero, 1, 2, 3 or 4;
R(45) is $(C_3-C_7)$-cycloalkyl, phenyl, which is not substituted or is substituted by 1–3 substituents selected from the group consisting of F, Cl, $CF_3$, methyl, methoxy, NR(50)R(51) and —(Xfa)—$(CH_2)_{ed}$—(Xfb)R(46);
Xfa is $CH_2$, O, S or NR(48);
Xfb is O, S or NR(49);
ed is 1, 2, 3 or 4;
R(46) is H, $(C_1-C_4)$-alkyl or $(C_1-C_4)$-perfluoroalkyl;
(R48), R(49), R(50) and R(51) independently of one another are H or $(C_1-C_4)$-alkyl or $(C_1-C_4)$-perfluoroalkyl;
where R(3) and R(4), however, cannot be hydrogen, and their pharmaceutically tolerable salts;
(HOE 94/F 265-NZ 272 946, EP-Offenlegungsschrift 700 904)

ac) benzoylguanidines of the formula I in which:
one of the three substituents R(1), R(2) and R(3) is $(C_1-C_9)$-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino;
or
one of the three substituents R(1), R(2) and R(3) is —SR(10), —OR(10), —NR(10)R(11) or —CR(10)R(11)R(12);
R(10) is —$C_aH_{2a}$—$(C_1-C_9)$-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(11) and R(12) independently of one another are defined as R(10), are hydrogen or $(C_1-C_4)$-alkyl;
and the other substituents R(1), R(2) and R(3) in each case independently of one another are $(C_1-C_8)$-alkyl, $(C_2-C_8)$-alkenyl or —$C_mH_{2m}$R(14);
m is zero, 1 or 2;
R(14) is $(C_3-C_8)$-cycloalkyl or phenyl, which is not substituted or is substituted by 1–3 substituents selected from the group consisting of F, Cl, $CF_3$, methyl, methoxy and NR(15)R(16),
R(15) and R(16) are hydrogen or $CH_3$;
or
the other substituents R(1), R(2) and R(3) in each case independently of one another are hydrogen, F, Cl, Br, I, —C≡N, X—$(CH_2)_p$—$(C_qF_{2q+1})$, R(22)—$SO_u$, R(23)R(24)N—CO, R(25)—CO— or R(26)R(27)N—$SO_2$—, where the perfluoroalkyl group is straight-chain or branched;
X is a bond, oxygen, S or NR(28);
u is zero, 1 or 2;

p is zero, 1 or 2;
q is zero, 1, 2, 3, 4, 5 or 6;
R(22), R(23), R(25) and R(26) independently are ($C_1$–$C_8$)-alkyl, ($C_2$–$C_6$)-alkenyl, —$C_nH_{2n}$—R(29) or $CF_3$;
n is zero, 1, 2, 3 or 4;
R(28) is hydrogen or ($C_1$–$C_3$)-alkyl;
R(29) is ($C_3$–$C_7$)-cycloalkyl or phenyl; which is not substituted or is substituted by 1–3 substituents selected from the group consisting of F, Cl, $CF_3$, methyl, methoxy and NR(30)R(31);
R(30) and R(31) are hydrogen or $C_1$–$C_4$-alkyl,
or
R(23), R(25) and R(26) are also hydrogen;
R(24) and R(27) independently of one another are hydrogen or ($C_1$–$C_4$)-aklyl;
or
R(23) and R(24), and also R(26) and R(27) together are 4 or 5 methylene groups, of which one $CH_2$ group can be replaced by oxygen, S, NH, N—$CH_3$ or N-benzyl;
or
the other substituents R(1), R(2) and R(3) in each case independently of one another are OR(35) or NR(35)R(36);
R(35) and R(36) independently of one another are hydrogen or ($C_1$–$C_6$)-alkyl;
or
R(35) and R(36) together are 4–7 methylene groups, of which one $CH_2$ group can be replaced by oxygen, S, NH, N—$CH_3$ or N-benzyl,
R(4) and R(5) independently of one another are hydrogen, ($C_1$–$C_4$)-alkyl, F, Cl, —OR(32), —NR(33)R(34) or $C_rF_{2r+1}$;
R(32), R(33) and R(34) independently of one another are hydrogen or ($C_1$–$C_3$)-alkyl;
r is 1, 2, 3 or 4;
and their pharmaceutically tolerable salts;
(HOE 94/F 266-EP-Offenlegungsschrift 702 001, NZ 272 948)
ad) benzoylguanidines of the formula I

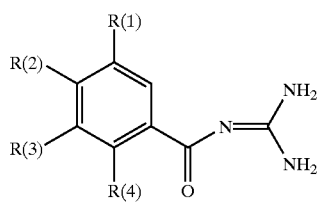

in which:
R(1) is hydrogen, F, Cl, Br, I, CN, $NO_2$, OH, ($C_1$–$C_8$)-alkyl, ($C_3$–$C_8$)-cycloalkyl, $O_a$—$(CH_2)_b$—$(CF_2)_c$—$CF_3$;
a is zero or 1;
b is zero, 1 or 2;
c is zero, 1, 2 or 3;
or
R(1) is R(5)—$SO_m$ or R(6)R(7)N—$SO_2$—
m is zero, 1 or 2;
R(5) and R(6) independently of one another are ($C_1$–$C_8$)-alkyl, ($C_3$–$C_6$)-alkenyl, $CF_3$ or —$C_nH_{2n}$—R(8);
n is zero, 1, 2, 3 or 4;
R(7) is hydrogen or ($C_1$–$C_4$)-alkyl;
R(8) is ($C_3$–$C_7$)-cycloalkyl or phenyl, which is not substituted or is substituted by 1–3 substituents selected from the group consisting of F, Cl, $CF_3$, methyl, methoxy and NR(9)R(10);
R(9) and R(10) independently of one another are hydrogen or ($C_1$–$C_4$)-alkyl;
or
R(6) is H;
or R(6) and R(7) together are 4 or 5 methylene groups, of which one $CH_2$ group can be replaced by oxygen, S, NH, N—$CH_3$ or N-benzyl,
or
R(1) is —SR(11), —OR(11) or —CR(11)R(12)R(13);
R(11) is —$C_pH_{2p}$—($C_3$–$C_8$)-cycloalkyl, —($C_1$–$C_9$)-heteroaryl or phenyl, where the aromatic systems are unsubstituted or substituted by 1–3 substituents selected from the group consisting of F, Cl, $CF_3$, $CH_3$, methoxy, hydroxyl, amino, methylamino and dimethylamino;
R(12), R(13) independently of one another are defined as R(11) or are hydrogen or ($C_1$–$C_4$)-alkyl;
p is zero, 1 or 2;
or
R(1) is phenyl, naphthyl, biphenylyl or ($C_1$–$C_9$)-heteroaryl, the latter linked via C or N, which are unsubstituted or substituted by 1–3 substituents selected from the group consisting of F, Cl, $CF_3$, $CH_3$, methoxy, hydroxyl, amino, methylamino and dimethylamino;
R(2) is —$CF_2$R(14), —CF[R(15)][R(16)], —CF[$(CF_2)_q$—$CF_3$][R(15)], —C[$(C_2)_r$—$CF_3$]=CR(15)R(16);
R(14) is ($C_1$–$C_4$)-alkyl or ($C_3$–$C_6$)-cycloalkyl;
R(15) and R(16) independently of one another are hydrogen or ($C_1$–$C_4$)-alkyl;
q is zero, 1 or 2;
r is zero, 1 or 2;
R(3) is defined as R(1);
R(4) is hydrogen, ($C_1$–$C_3$)-alkyl, F, Cl, Br, I, CN, —$(CH_2)_s$—$(CF_2)_t$—$CF_3$;
s is zero or 1;
t is zero, 1 or 2;
and their pharmaceutically tolerable salts;
(HOE 94/F267-EP-Offenlegungsschrift 700 899, NZ 272 947)
ae) benzoylguanidines of the formula I

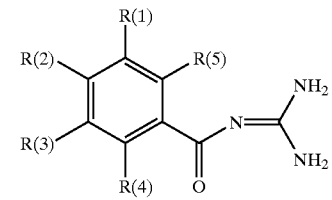

in which:
one of the three substituents R(1), R(2) and R(3) is —Y—4-[$(CH_2)_k$—CHR(7)—(C=O)R(8)]-phenyl, —Y—3-[$(CH_2)_k$—CHR(7)—(C=O)R(8)]-phenyl or —Y—2-[$(CH_2)_k$—CHR(7)—(C=O)R(8)]-phenyl, where the phenyl in each case is unsubstituted or substituted by 1–2 substituents from the group F, Cl, —$CF_3$, methyl, hydroxyl, methoxy, or —NR(37)R(38);
R(37) and R(38) independently of one another are hydrogen or —$CH_3$;
Y is a bond, oxygen, —S— or —NR(9);
R(9) is hydrogen or —($C_1$–$C_4$)-alkyl;

R(7) is —OR(10) or —NR(10)R(11);
  R(10) and R(11) independently of one another are hydrogen, —($C_1$–$C_8$)-alkyl, —($C_1$–$C_8$)-alkanoyl, —($C_1$–$C_8$)-alkoxycarbonyl, benzyl, benzyloxycarbonyl;
  or
  R(10) is trityl;
R(8) is —OR(12) or —NR(12)R(13);
  R(12) and R(13) independently of one another are hydrogen, —($C_1$–$C_8$)-alkyl or benzyl;
  k is zero, 1, 2, 3 or 4;
and the other radicals R(1), R(2) and R(3) in each case independently of one another are —($C_1$–$C_8$)-alkyl, —($C_2$–$C_8$)-alkenyl or —($CH_2$)$_m$R(14);
  m is zero, 1 or 2;
  R(14) is —($C_3$–$C_8$)-cycloalkyl or phenyl, which is not substituted or is substituted by 1–3 substituents selected from the group consisting of F, Cl, —$CF_3$, methyl, methoxy and —NR(15)R(16);
  R(15) and R(16) are hydrogen or —$CH_3$;
or
the other radicals R(1), R(2) and R(3) in each case independently of one another are R(18)R(19)N—(C=Y')—NH—$SO_2$—;
  Y' is oxygen, —S— or —N—R(20);
  R(18) and R(19) independently of one another are hydrogen, —($C_1$–$C_8$)-alkyl, —($C_3$–$C_6$)-alkenyl or —($CH_2$)$_t$—R(21);
  t is zero, 1, 2, 3 or 4;
  R(21) is —($C_5$–$C_7$)-cycloalkyl or phenyl, which is unsubstituted or substituted by 1–3 substituents selected from the group consisting of F, Cl, —$CF_3$, methoxy and —($C_1$–$C_4$)-alkyl;
  or
  R(18) and R(19) together are 4 or 5 methylene groups, of which one $CH_2$ group can be replaced by oxygen, —S—, —NH—, —N—$CH_3$ or —N—benzyl;
  R(20) is defined as R(18) or is amidine;
or
the other radicals R(1), R(2) and R(3) in each case independently of one another are hydrogen, F, Cl, Br, I, —C≡N, X—($CH_2$)$_p$—($C_qF_{2q+1}$), R(22)—$SO_u$—, R(23)R(24)N—CO—, R(25)—CO— or R(26)R(27)N—$SO_2$—, where the perfluoroalkyl group is straight-chain or branched;
  X is a bond, oxygen, —S— or —NR(28);
  u is zero, 1 or 2;
  p is zero, 1 or 2;
  q is 1, 2, 3, 4, 5 or 6;
  R(22), R(23), R(25) and R(26) independently of one another are —($C_1$–$C_8$)-alkyl, —($C_3$–$C_6$)-alkenyl, —($CH_2$)$_n$—R(29) or —$CF_3$;
  n is zero, 1, 2, 3 or 4;
  R(28) is hydrogen or —($C_1$–$C_3$)-alkyl;
  R(29) is —($C_3$–$C_7$)-cycloalkyl or phenyl, which is not substituted or is substituted by 1–3 substituents selected from the group consisting of F, Cl, —$CF_3$, methyl, methoxy and —NR(30)R(31);
  R(30) and R(31) are hydrogen or —($C_1$–$C_4$)-alkyl;
or
R(23), R(25) and R(26) are hydrogen;
R(24) and R(27) independently of one another are hydrogen or —($C_1$–$C_4$)-alkyl;
or
R(23) and R(24), and also R(26) and R(27) together are 4 or 5 methylene groups, of which one $CH_2$ group can be replaced by oxygen, —S—, —NH—, —N—$CH_3$ or —N-benzyl;

or
the other radicals R(1), R(2) and R(3) in each case independently of one another are —OR(35) or —NR(35)R(36);
  R(35) and R(36) independently of one another are hydrogen or —($C_1$–$C_6$)-alkyl;
  or
  R(35) and R(36) together are 4–7 methylene groups, of which one $CH_2$ group can be replaced by oxygen, —S—, —NH—, —N—$CH_3$ or —N-benzyl;
R(4) and R(5) independently of one another are hydrogen, —($C_1$–$C_4$)-alkyl, F, Cl, —OR(32), —NR(33)R(34) or —$C_rF_{2r+1}$;
  R(32), R(33) and R(34) independently of one another are hydrogen or —($C_1$–$C_3$)-alkyl;
  r is 1, 2, 3 or 4;
and their pharmaceutically tolerable salts;
(HOE 94/F 352-EP-Offenlegungsschrift 713 684, NZ 280 517)
  af) benzoylguanidines of the formula I

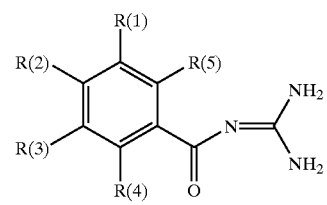

in which:
R(1) is R(6)—CO or R(7)R(8)N—CO;
  R(6) is ($C_1$–$C_8$)-alkyl, ($C_1$–$C_8$)-perfluoroalkyl, ($C_3$–$C_8$)-alkenyl or —$C_nH_{2n}$—R(9),
  n is zero, 1, 2, 3 or 4;
  R(9) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11),
  R(10) and R(11) are H, ($C_1$–$C_4$)-alkyl or ($C_1$–$C_4$)-perfluoroalkyl;
  R(7) is H, ($C_1$–$C_8$)-alkyl, ($C_1$–$C_8$)-perfluoroalkyl, ($C_3$–$C_8$)-alkenyl or —$C_nH_{2n}$—R(12);
  n is zero, 1, 2, 3 or 4;
  R(12) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
  R(13) and R(14) are H, ($C_1$–$C_4$)-alkyl or ($C_1$–$C_4$)-perfluoroalkyl;
  R(8) is H, ($C_1$–$C_4$)-alkyl or ($C_1$–$C_4$)-perfluoroalkyl;
  or
  R(7) and R(8) together are 4 or 5 methylene groups, of which one $CH_2$ group can be replaced by oxygen, S, NH, N—$CH_3$ or N-benzyl;
R(2) is defined as R(1), or is H, OH, F, Cl, Br, I, CN, $NO_2$, ($C_1$–$C_8$)-alkyl, ($C_1$–$C_8$)-perfluoroalkyl, ($C_3$–$C_8$)-alkenyl or —$C_nH_{2n}$R(15);
  n is zero, 1, 2, 3 or 4;
  R(15) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);

R(16) and R(17) are H, $(C_1-C_4)$-alkyl or $(C_1-C_4)$-perfluoroalkyl;

or

R(2) is $(C_1-C_8)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

or

R(2) is SR(18), —OR(18), —NR(18)R(19) or —CR(18)R(19)R(20);

R(18) -is $C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino, dimethylamino;

a is zero, 1 or 2;

R(19) and R(20) independently of one another are defined as R(18) or are hydrogen, $(C_1-C_4)$-alkyl or $(C_1-C_4)$-perfluoroalkyl;

or

R(2) is R(21)—$SO_m$ or R(22)R(23)N—$SO_2$—;

m is 1 or 2;

R(21) is $(C_1-C_8)$-alkyl, $(C_1-C_8)$-perfluoroalkyl, $(C_3-C_8)$-alkenyl or —$C_nH_{2n}$—R(24);

n is zero, 1, 2, 3 or 4;

R(24) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, $(C_1-C_4)$-alkyl or $(C_1-C_4)$-perfluoroalkyl;

R(22) is H, $(C_1-C_8)$-alkyl, $(C_1-C_8)$-perfluoroalkyl, $(C_3-C_8)$-alkenyl or —$C_nH_{2n}$—R(29);

n is zero, 1, 2, 3 or 4;

R(29) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);

R(30) and R(31) are H, $(C_1-C_4)$-alkyl or $(C_1-C_4)$-perfluoroalkyl;

R(23) is hydrogen, $(C_1-C_4)$-alkyl or $(C_1-C_4)$-perfluoroalkyl; or

R(22) and R(23) together are 4 or 5 methylene groups, of which one $CH_2$ group can be replaced by oxygen, S, NH, N—$CH_3$ or N-benzyl;

or

R(2) is R(33)X—;

X is oxygen, S, NR(34), (D=O)A— or NR(34)C=MN$^{(*)}$R(35)—;

M is oxygen or S;

A is oxygen or NR(34);

D is C or SO;

R(33) is $(C_1-C_8)$-alkyl, $(C_3-C_8)$-alkenyl, $(CH_2)_b$$C_dF_{2d+1}$ or —$C_nH_{2n}$—R(36);

b is zero or 1;

d is 1, 2, 3, 4, 5, 6 or 7;

n is zero, 1, 2, 3, or 4;

R(36) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);

R(37) and R(38) are H, $(C_1-C_4)$-alkyl or $(C_1-C_4)$-perfluoroalkyl;

R(34) is hydrogen, $(C_1-C_4)$-alkyl or $(C_1-C_4)$-perfluoroalkyl;

R(35) is defined as R(33); or

R(33) and R(34) together are 4 or 5 methylene groups, of which one $CH_2$ group can be replaced by oxygen, S, NH, N—$CH_3$ or N-benzyl;

where A and $N^{(*)}$ are bonded to the phenyl nucleus of the benzoylguanidine parent structure;

or

R(2) is —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$—R(44);

R(40) and R(41) independently of one another are —$(CH_2)_p$—$(CHOH)_q$—$(CH_2)_r$—$(CHOH)_t$—R(51) or —$(CH_2)_p$—O—$(CH_2$—$CH_2$—O)$_q$—R(51);

R(51) is hydrogen or methyl;

u is 1, 2, 3 or 4;

v is zero, 1, 2, 3 or 4;

p, q and r independently of one another are zero, 1, 2, 3 or 4;

t is 1, 2, 3 or 4;

R(42) and R(43) idependently of one another are hydrogen or $(C_1-C_6)$-alkyl; or R(42) and R(43) together with the carbon atom carrying them are a $(C_3-C_8)$-cycloalkyl;

R(44) is hydrogen, $(C_1-C_6)$-alkyl, $(C_3-C_8)$-cycloalkyl, —$C_eH_{2e}$—R(45);

e is zero, 1, 2, 3 or 4;

R(45) is phenyl, which is unsubstituted or substituted by 1–3 substituents selected from the group consisting of F, Cl, $CF_3$, methyl, methoxy and NR(52)R(53);

R(52) and R(53) are H or $(C_1-C_4)$-alkyl; or

R(45) is $(C_1-C_9)$-heteroaryl, which is unsubstituted or substituted as phenyl; or R(45) is $(C_1-C_6)$-alkyl, which is unsubstituted or substituted by 1–3 OH;

R(46), R(47), R(48), R(49) and R(50) independently of one another are hydrogen or methyl; or R(2) is R(55)—NH—$SO_2$—;

R(55) is R(56)R(57)N—(C=Y)—;

Y is oxygen, S or N—R(58);

R(56) and R(57) independently of one another are hydrogen, $(C_1-C_8)$-alkyl, $(C_3-C_8)$-alkenyl or —$C_fH_{2f}$R(59);

f is zero, 1, 2, 3 or 4;

R(59) is $(C_5-C_7)$-cycloalkyl, phenyl, which is unsubstituted or substituted by 1–3 substituents selected from the group consisting of F, Cl, $CF_3$, methoxy and $(C_1-C_4)$-alkyl; or R(56) and R(57) together are 4 or 5 methylene groups, of which one $CH_2$ group can be replaced by oxygen, S, NH, N—$CH_3$ or N-benzyl;

R(58) is defined as R(56) or is amidine;

R(3), R(4) and R(5) are idependently of one another defined as R(1) or R(2), but where at least one of the substituents R(2), R(3), R(4) and R(5) must be OH:

and their pharmaceutically tolerable salts;

(HOE 95/F 007 K-EP-Offenlegungsschrift 723 956, NZ 280 887)

ag) benzoylguanidines of the formula I

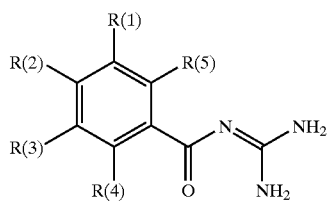

in which:
one of the three substiuents R(1), R(2) and R(3) is R(6)-A-B-D;
R(6) is a basic protonatable radical, i.e. an amino group —NR(7)R(8), an amidino group R(7)R(8)N—C[=N—R(9)]— or a guanidino group

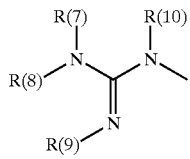

R(7), R(8), R(9) and R(10) independently of one another are hydrogen or alkyl having 1, 2, 3 or 4 carbon atoms;
or
R(7) and R(8) together are $C_aH_{2a}$;
a is 4, 5, 6 or 7;
where if a=5, 6 or 7 a methylene group of the group $C_1H_{2a}$ can be replaced by a heteratom group O, $SO_m$ or NR(11),
or
R(8) and R(9) or R(9) and R(10) or R(7) and R(10) are a group $C_aH_{2a}$;
a is 2, 3, 4 or 5;
where if a=3, 4 or 5 a methylene gruop of the group $C_aH_{2a}$ can be replaced by a heteratom group O, $SO_m$ or NR(11);
m is zero, 1 or 2;
R(11) is hydrogen or methyl;
or
R(6) is a basic heteroaromatic ring system having 1–9 carbon atoms;
A is $C_bH_{2b}$;
b is 1, 2, 3, 4, 5, 6, 7, 8, 9 or 10;
where in the group $C_bH_{2b}$ one or two methylene groups can be replaced by one of the groupings selected from the group consisting of —O—, —CO—, —CH[OR(20)]—, —$SO_m$—, —NR(20)—, —NR(20)—CO—, —NR(20)—CO—NH, —NR(20)—CO—NH—$SO_2$—

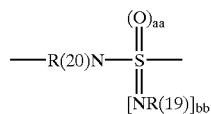

and —$SO_{aa}[NR(19)]_{bb}$—;
and where in the group $C_bH_{2b}$ a methylene group can be replaced by —CH—R(99), where R(99) together with R(7) forms a pyrrolidine or piperidine ring;

aa is 1 or 2;
bb is 0 or 1;
aa+bb=2;
R(19) is hydrogen or alkyl having 1, 2, 3 or 4 carbon atoms;
R(20) is hydrogen or methyl;
B is a phenylene or naphthylene radical

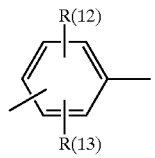 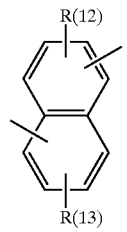

R(12) and R(13) independently of one another are hydrogen, methyl, F, Cl, Br, I, $CF_3$ or —$SO_w$—R(14);
R(14) is methyl or NR(15)R(16);
R(15) and R(16) independently of one another are hydrogen or alkly having 1, 2, 3 or 4 carbon atoms;
w is zero, 1 or 2;
D is —$C_dH_{2d}$—$X_f$—;
d is zero, 1, 2, 3 or 4;
X is —O—, —CO—, —CH[OR(21)]—, —$SO_m$— or —NR(21);
f is zero or 1;
R(21) is hydrogen or methyl;
m is zero, 1 or 2;
and hte other substituents R(1) and R(2) and R(3) in each case independently of one another are hydrogen, F, Cl, Br, I, —CN, —($C_1$–$C_8$)-alkyl, —($C_2$–$C_8$)-alkenyl, —NR(35)R(36) or R(17)—$C_gH_{2g}$—$Z_h$—;
g is zero, 1, 2, 3 or 4;
h is zero or 1;
R(35) and R(36) independently of one another are hydrogen or alkyl having 1, 2, 3, 4, 5 or 6 carbon atoms;
or
R(35) and R(36) together are 4–7 methylene groups, of which one $CH_2$ group can be replaced by oxygen, —S—, —NH—, —$NCH_3$ or —N-benzyl;
Z is —O—, —CO—, —$SO_v$—, —NR(18)—,—NR(18)—CO—, —NR(18)—CO—NH— or —NR(18)—$SO_2$—;
R(18) is hydrogen or methyl;
v is zero, 1 or 2;
R(17) is hydrogen, cycloalkyl having 3, 5 or 6 carbon atoms or $C_kF_{2k+1}$;
k is 1, 2 or 3,
or
R(17) is pyrrol-1-yl, pyrrol-2-yl or pyrrol-3-yl, which is not subustituted or is substituted by 1–4 substituents selected from the gruop consisting of F, Cl, Br, I, —CN, ($C_2$–$C_8$)-alkanoyl, ($C_2$–$C_8$)-alkoxycarbonyl, formyl, carboxyl, —$CF_3$, methyl and methoxy;
or
R(17) -is ($C_3$–$C_8$)-cycloalkyl or phenyl, which is not substituted or is sustituted by 1–3 substituents selected from the group consisting of F and Cl, —$CF_3$, methyl, hydroxyl, methoxy, —NR(37)R(38), $CH_3SO_2$— and $H_2NO_2S$—;

R(37) and R(38) are hydrogen or —CH₃;
R(4) and R(5) independently of one another are hydrogen, alkyl having 1, 2, 3 or 4 carbon atoms, F, Cl, —OR(32), —NR(33)R(34) or —C$_r$F$_{2r+1}$;
R(32), R(33) and R(34) independently of one another are hydrogen or alkyl having 1, 2 or 3 carbon atoms;
r is 1, 2, 3 or 4;
and their pharmacologically tolerable salts;
(HOE 95/F 072-EP-Offenlegungsschrift 738 712, NZ 286 380)
ah) indenoylguanidines of the formula I

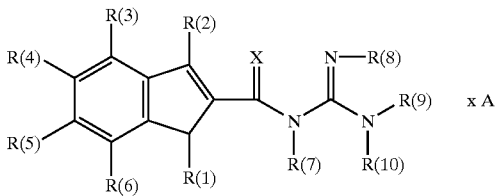

in which:
R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O—C(=O)-alkyl having, 1, 2, 3 or 4 carbon atoms or C$_m$H$_{2m}$—NR(12)R(13);
R(12) and R(13) independently of one another are hydrogen or alkyl having 1, 2, 3 or 4 carbon atoms;
m is zero, 1, 2, 3 or 4;
NH—C(=O)—NH₂, C(=O)—O—alkyl having 1, 2, 3 or 4 carbon atoms, C(=O)—NH₂, C(=O)—NH-alkyl having 1, 2, 3 or 4 carbon atoms, C(=O)—N(alkyl)₂ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, C₁–C₄-alkyl-substituted aryl, C₁–C₄-alkylheteroaryl, C₁–C₄-alkenylheteroaryl, aminoalkylaryl having 1, 2, 3 or 4 carbon atoms in the alkyl group, substituted aryl, heteroaryl and substituted heteroaryl;
R(3), R(4), R(5) and R(6) indepedently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, O—C(=O)—C₁–C₄-alkylaryl, O—C(=O)—NH—C₁–C₄-alkyl, O—C(=O)—N(C₁–C₄-alkyl)₂, NO₂, CN, CF₃, NH₂, NH—C(=O)—C₁–C₄-alkyl, NH—C(=O)—NH₂, COOH, C(=O)—O—C₁–C₄-alkyl, C(=O)—NH₂, C(=O)—NH—C₁–C₄-alkyl, C(=O)—N(C₁–C₄-alkyl)₂, C₁–C₄—COOH, C₁–C₄-alkyl-C(=O)—O—C₁–C₄)-alkyl), SO₃H, SO₂-alkyl, SO₂-alkylaryl, SO₂—N-(alkyl)₂, SO₂—N(alkyl)(alkylaryl), C(=O)—R(11), C₁–C₁₀-alkyl-C(=O)—R(11), C₂–C₁₀alkenyl-C(=O)—R(11), C₂–C₁₀-alkynyl-C(=O)—R(11), NH—C(=O)—C-C₁₀-alkyl-C(=O)—R(11), O—C₁–C₁₁-alkyl-C(=O)—R(11);
R(11) is C₁–C₄-alkyl, C₁–C₄-alkynyl, aryl, substituted aryl, NH₂, NH—C₁–C₄-alkyl, N—(C₁–C₄-alkyl)₂, SO₃H, SO₂-alkyl, SO₂-alkylaryl, SO₂—N-(alkyl)₂, SO₂-N(alkyl)(alkylaryl);

X is O, S or NH;
R(7), R(8), R(9) and R(10) independently of one another are hydrogen, alkyl, cycloalkyl, aryl, alkylaryl;
or
R(8) and R(9) together are part of a 5, 6 or 7-membered heterocyclic ring;
A is absent or is a nontoxic organic or inorganic acid;
(HOE 95/F 109-EP 748 795, NZ 286 583)
ai) benzyloxycarbonylguanidines of the formula I

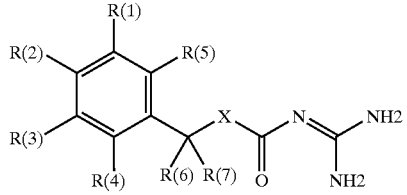

in which:
R(1), R(2) and R(3) independently of one another are —Y—[4—R(8)-phenyl], —Y—[3—R(8)-phenyl] or —Y—[2—R(8)-phenyl], where the phenyl is in each case unsubstituted or substituted by 1–2 substituents from the group consisting of F, Cl, —CF₃, methyl, hydroxyl, methoxy and —NR(96)R(97);
R(96) and R(97) independently of one another are hydrogen or —CH₃;
Y is a bond, CH₂, oxygen, —S— or —NR(9);
R(9) is hydrogen or alkyl having 1, 2, 3 or 4 carbon atoms;
R(8) is SO$_a$[NR(98)]$_b$NR(99)R(10);
a is 1 or 2;
b is 0 or 1;
a+b=2;
R(98), R(99) and R(10) independently of one another are hydrogen, —(C₁–C₈)-alkyl, benzyl, —(C₂–C₈) alkylene-NR(11)R(12), (C₂–C₈)-alkylene-NR(13)-(C₂–C₈)-alkylene-NR(27)R(38) or (C₀–C₈)-alkylene-CR(39)R(40)CR(41)R(42)(C₀–C₈)-alkylene-NR(43)R(44);
R(11), R(12), R(13), R(37), R(38), R(43) and R(44) independently of one another are hydrogen, —(C₁—C₈)-alkyl or benzyl;
R(39), R(40), R(41) and R(42) independently of one another are hydrogen, —(C₁–C₈)-alkyl or —(C₀–C₃)-alkylenephenyl, where the phenyl is not substituted or is substituted by 1–3 substituents selected from the group consisting of F, Cl, —CF₃, methyl and methoxy;
or
R(99) and R(10) together are 4–6 methylene groups, of which one CH₂ group can be replaced by oxygen, —S—, —NH—, —N—CH₃ or —N-benzyl;
or
R(8) is SO$_a$[NR(98)]$_b$NR(95)—C[=N—R(94)]—NR(93)R(92); R(92), R(93), R(94) and R(95) independently of one another are hydrogen or alkyl having 1, 2, 3 or 4 carbon atoms;
or
R(1), R(2) and R(3) independently of one another are pyrrol-1-yl, pyrrol-2-ol or pyrrol-3-yl, which is not substituted or is substituted by 1–4 substituents selected from the group consisting of F, Cl, Br, I, —CN, (C₂–C₈)-alkanoyl, (C₂–C₈)-alkoxycarbonyl, formyl, carboxyl, —CF₃, methyl, methoxy;

or

R(1), R(2) and R(3) independently of one another are hydrogen, —($C_1$–$C_8$)-alkyl, —($C_2$–$C_8$)-alkenyl or —$(CH_2)_m$R(14);
  m is zero, 1 or 2;
    R(14) is —($C_3$–$C_8$)-cycloalkyl or phenyl, which is not substituted or is substituted by 1–3 substituents selected from the group consisting of F and —Cl, —$CF_3$, methyl, methoxy and —NR(15)R(16);
    R(15) and R(16) are hydrogen or —$CH_3$;

or

R(1), R(2) and R(3) independently of one another are —Q-4-[$(CH_2)_k$—CHR(17)-(C=O)R(20)]-phenyl, —Q-3-$(CH_2)_k$—CHR(17)-(C=O)R(20)]-phenyl or —Q-2-[$(CH_2)_k$—CHR(17)-(C=O)R(20)]-phenyl, where the phenyl in each case is unsubstituted or substituted by 1–2 substituents from the group F, Cl, —$CF_3$, methyl, hydroxy, methoxy and —NR(35)R(36);
    R(35) and R(36) independently of one another are hydrogen or —$CH_3$;
  Q is a bond, oxygen, —S— or —NR(18);
    R(18) is hydrogen or —($C_1$–$C_4$)-alkyl;
  R(17) is —OR(21) or —NR(21)R(22);
    R(21) and R(22) independently of one another are hydrogen, —($C_1$–$C_8$)-alkyl, —($C_1$–$C_8$)-alkanoyl, —($C_1$–$C_8$)-alkoxycarbonyl, benzyl, benzyloxycarbonyl;
    R(21) is trityl;
  R(20) is —OR(23) or —NR(23)R(24);
    R(23), R(24) independently of one another are hydrogen, —($C_1$–$C_8$)-alkyl or benzyl;
  k is zero, 1, 2, 3 or 4;

or

R(1), R(2) and R(3) independently of one another are ($C_1$–$C_9$)-heteroaryl, which is linked via C or N and which is unsubstituted or substituted by 1–3 substituents from the group F, Cl, $CF_3$, $CH_3$, methoxy, hydroxyl, amino, methylamino and dimethylamino;

or

R(1), R(2) and R(3) are —SR(25), —OR(25), —NR(25)R(26), —CR(25)R(26)R(27);
    R(25) is —$C_fH_{2f}$—($C_1$–$C_9$)-heteroaryl, which is unsubstituted or substituted by 1–3 substituents from the group F, Cl, $CF_3$, $CH_3$, methoxy, hydroxyl, amino, methylamino and dimethylamino;
    f is zero, 1 or 2;
    R(26) and R(27) independently of one another are defined as R(25) or are hydrogen or ($C_1$–$C_4$)-alkyl, or R(1), R(2) and R(3) independently of one another are ($C_1$–$C_9$)-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino;

or

R(1), R(2) and R(3) independently of one another are —SR(28), —OR(28), —NR(28)R(29) or —CR(28)R(29)R(30);
    R(28) is —$C_gH_{2g}$—($C_1$–$C_9$)-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;
    g is zero, 1 or 2;
    R(29), R(30) independently of one another are defined as R(28), hydrogen or ($C_1$–$C_4$)-alkyl;

or

R(1), R(2) and R(3) independently of one another are hydrogen, F, Cl, Br, I, —C≡N, T—$(CH_2)_h$—($C_iF_{2i+1}$), R(31)$SO_l$—, R(32)R(33)N—CO—, R(34)—CO— or R(45)R(46)N—$SO_2$, where the perfluoroalkyl group is straight-chain or branched;
  T is a bond, oxygen, —S— or —NR(47);
  l is zero, 1 or 2;
  h is zero, 1 or 2;
  i is 1, 2, 3, 4, 5 or 6;
  R(31), R(32), R(34) and R(45) independently of one another are —($C_1$–$C_8$)-alkyl, —($C_3$–$C_6$)-alkenyl, $(CH_2)_n$R(48) or —$CF_3$;
    n is zero, 1, 2, 3 or 4;
    R(47) is hydrogen or alkyl with 1, 2 or 3 carbon atoms;
    R(48) is —($C_3$–$C_7$)-cycloalkyl or phenyl, which is not substituted or is substituted by 1–3 substituents selected from the group consisting of F, Cl, —$CF_3$, methyl, methoxy and —NR(49)R(50);
    R(49) and R(50) are hydrogen or alkyl having 1, 2, 3 or 4 carbon atoms;

or

R(32), R(34) and R(35) are hydrogen;
R(33) and R(46) independently of one another are hydrogen or alkyl having 1, 2, 3 or 4 carbon atoms;

or

R(32) and R(33), and R(45) and R(46) together are 5 or 6 methylene groups, of which one $CH_2$ group can be replaced by oxygen, —S—, —NH—, —$NCH_3$ or —N-benzyl;

or

R(1), R(2) and R(3) independently of one another are R(51)—A—G—D—;
  R(51) is a basic protonatable radical, i.e. an amino group —NR(52)R(53), an amidino group R(52)R(53)N—C[=N—R(54)]— or a guanidino group R(52)R(53)N—C[=N—R(54)]—NR(55)—;
  R(52), R(53), R(54) and R(55) independently of one another are hydrogen or alkyl having 1, 2, 3 or 4 carbon atoms;

or

R(52) and R(53) are a group $C_\alpha H_{2\alpha}$;
  α is 4, 5, 6 or 7;
  where if α=5, 6 or 7 a carbon atom of the group $C_\alpha H_{2\alpha}$ can be replaced by a heteroatom group O, $SO_d$ or NR(56), or R(53) and R(54) or R(54) and R(55) or R(52) and R(55) are a group $C_Y H_{2Y}$;
  Y is 2, 3, 4 or 5;
  where if Y=3, 4 or 5 a carbon atom of the group $C_Y H_{2Y}$ can be replaced by a heteroatom group O, $SO_d$ or NR(56);
  d is zero, 1 or 2;
  R(56) is hydrogen or methyl;

or

R(51) is a basic heteroaromatic ring system having 1–9 carbon atoms;
A is a group $C_e H_{2e}$;
  e is zero, 1, 2, 3, 4, 5, 6, 7, 8, 9 or 10;
  where in the group $C_e H_{2e}$ a carbon atom can be replaced by one of the groupings —O—, —CO—, —CH[OR(57)]—, —SO$_r$—, —NR(57)—, —NR(57)—CO—, —NR(57)—CO—NH—, —NR(57)—CO—NH—SO$_2$— or —NR(57)—SO$_2$—;
r is zero, 1 or 2;
G is a phenylene radical

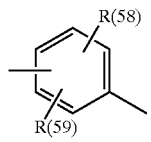

R(58) and R(59) independently of one another are hydrogen, methyl, methoxy, F, Cl, Br, I, CF$_3$ or —SO$_s$—R(60);
R(60) is methyl or NR(61)R(62);
R(61) and R(62) independently of one another are hydrogen or alkyl having 1, 2, 3 or 4 carbon atoms;
D is —C$_v$H$_{2v}$—E$_w$—;
v is zero, 1, 2, 3 or 4;
E is —O—, —CO—, —CH[OR(63)]—, —SO$_{aa}$— or —NR(63)—;
w is zero or 1;
aa is zero, 1 or 2 R(63) is hydrogen or methyl, or R(1), R(2) and R(3) independently of one another are —CF$_2$R(64), —CF[R(65)][R(66)], —CF[(CF$_2$)$_q$—CF$_3$][R(65)], —C[(CF$_2$)$_p$—CF$_3$]=CR(65)R(66);
R(64) is alkyl having 1, 2, 3 or 4 carbon atoms or cycloalkyl having 3, 4, 5, 6 or 7 carbon atoms;
R(65) and R(66) independently of one another are hydrogen or alkyl having 1, 2, 3 or 4 carbon atoms;
q is zero, 1 or 2;
p is zero, 1 or 2;

or

R(1), R(2) and R(3) independently of one another are —OR(67) or —NR(67)R(68);
R(67) and R(68) independently of one another are hydrogen or alkyl having 1, 2, 3, 4, 5 or 6 carbon atoms;
or
R(67) and R(68) together are 4, 5, 6 or 7 methylene groups, of which one CH$_2$ group can be replaced by oxygen, —S—, SO$_2$, —NH—, —NCH$_3$ or —N-benzyl;
R(4) and R(5) independently of one another are hydrogen, alkyl having 1, 2, 3 or 4 carbon atoms, F, Cl, —OR(69), —NR(70)R(71) or —C$_z$F$_{2z+1}$;
R(69), R(70) and R(71) independently of one another are hydrogen or alkyl having 1, 2 or 3 carbon atoms;
z is 1, 2, 3 or 4;
R(6) and R(7) independently of one another are hydrogen or alkyl having 1, 2, 3 or 4 carbon atoms;
X is oxygen or NR(72);
R(72) is hydrogen or alkyl having 1, 2, 3 or 4 carbon atoms;
and their pharmaceutically tolerable salts;
(HOE 95/F 115-EP 744 397, NZ 286 622)
ak) alkenylcarboxylic acid guanidides, carrying fluorophenyl groups, of the formula I

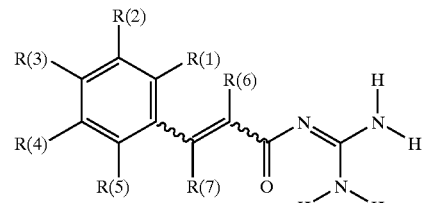

in which:
R(6) is hydrogen, (C$_1$–C$_8$)-alkyl, (C$_3$–C$_8$)-cycloalkyl or phenyl, where the phenyl group is not substituted or is substituted by 1–3 substituents selected from the group consisting of F, Cl, CF$_3$, methyl, methoxy, and NR(9)R(10);
R(9) and R(10) are hydrogen, (C$_1$–C$_4$)-alkyl or (C$_1$–C$_4$)-perfluoroalkyl;
R(7) independently is defined as R(6);
R(1), R(2), R(3), R(4) and R(5) independently of one another are hydrogen or F; where, however, at least one of the radicals R(1), R(2), R(3), R(4) and R(5) must be fluorine;
and their pharmaceutically tolerable salts;
(HOE 95/F 167-NZ 299 015)
al) benzoylguanidines of the formula I

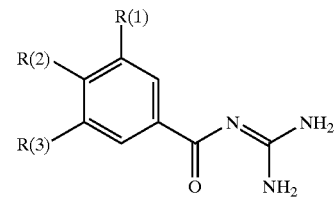

in which:
R(1) is R(4)—SO$_m$ or R(5)R(6)N—SO$_2$—;
m is 1 or 2;
R(4) and R(5) independently of one another are alkyl having 1, 2, 3, 4, 5, 6, 7 or 8 carbon atoms, alkenyl having 3, 4, 5 or 6 carbon atoms, CF$_3$ or —C$_n$H$_{2n}$—R(7);
n is zero, 1, 2, 3 or 4;
R(6) is H or alkyl having 1, 2, 3 or 4 carbon atoms;
R(7) is cycloalkyl having 3, 4, 5, 6, 7 or 8 carbon atoms or phenyl, which is not substituted or is substituted by 1 3 substituents selected from the group consisting of F, Cl, CF$_3$, methyl, methoxy and NR(8)R(9);
R(8) and R(9) are H or alkyl having 1, 2, 3 or 4 carbon atoms;
or
R(5) is also hydrogen;
or
R(5) and R(6) together are 4 or 5 methylene groups, of which a CH$_2$ group can be replaced by oxygen, S, NH, N—CH$_3$ or N-benzyl;
or
R(1) is —O$_p$—(CH$_2$)$_q$—(CF$_2$)$_r$—CF$_3$;
p is zero or 1;
q is zero, 1 or 2;
r is zero, 1 or 2 or 3;
or
R(1) is —SR(10), —OR(10) or —CR(10)R(11)R(12);

R(10), R(11) and R(12) independently of one another are hydrogen, alkyl having 1, 2, 3, 4, 5, 6, 7 or 8 carbon atoms, —$C_sH_{2s}$—($C_3$–$C_8$)-cycloalkyl or an aromatic system selected from the group consisting of pyridyl, pyrrolyl, quinolyl, isoquinolyl, imidazolyl or phenyl;

s is zero, 1 or 2; where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is —$(CH_2)_u$—$(CF_2)_t$—$CF_3$;

t is zero, 1, 2 or 3;

u is zero or 1;

R(3) is hydrogen or independently is defined as R(1);

and their pharmaceutically tolerable salts;

(HOE 95/F 173-NZ 299 052)

am) substituted cinnamic acid guanidides of the formula I

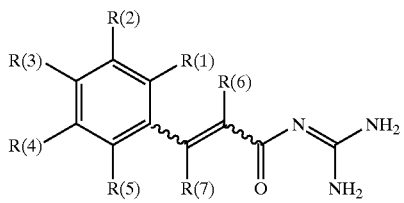

I in which:

at least one of the substituents R(1), R(2), R(3), R(4) and R(5) is —$X_a$—$Y_b$—$L_n$—U;

X is CR(16)R(17), O, S or NR(18);

R(16), R(17) and R(18) independently of one another are H, alkyl having 1, 2, 3 or 4 carbon atoms or perfluoroalkyl having 1, 2, 3 or 4 carbon atoms;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group;

T is NR(20), O, S or phenylene, where the phenylene is not substituted or is substituted by 1–3 substituents selected from the group consisting of F, Cl, $CF_3$, methyl, methoxy and NR(21)R(22);

R(20), R(21) and R(22) independently of one another are H, alkyl having 1, 2, 3 or 4 carbon atoms or perfluoroalkyl having 1, 2, 3 or 4 carbon atoms;

b is zero or 1;

L is O, S, NR(23) or $C_kH_{2k}$;

k is 1, 2, 3, 4, 5, 6, 7, 8;

n is zero or 1;

U is NR(24)R(25) or an N-containing heterocycle having 1, 2, 3, 4, 5, 6, 7, 8 or 9 carbon atoms;

R(24) and R(25) independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;

or

R(24) and R(25) together are 4 or 5 methylene groups, of which one $CH_2$ group can be replaced by oxygen, S, NH, N—$CH_3$ or N-benzyl;

where the N-containing heterocycles are N- or C-bridged and are not substituted or are substituted by 1–3 substituents selected from the group consisting of F, Cl, $CF_3$, methyl, methoxy and NR(27)R (28);

R(23), R(27) and R(28) independently of one another are H, alkyl having 1, 2, 3 or 4 carbon atoms or perfluoroalkyl having 1, 2, 3 or 4 carbon atoms;

and the other substituents R(1), R(2), R(3), R(4) and R(5) in each case independently of one another are H, F, Cl, Br, I, CN, —$O_n$—$C_mH_{2m+1}$, —$O_p$—$(CH_2)_s$—$S_qF_{2q+1}$ or —$C_rH_{2r}R(10)$;

n is zero or 1;

m is zero 1, 2, 3, 4, 5, 6, 7 or 8;

p is zero or 1;

q is 1, 2, 3, 4, 5, 6, 7 or 8;

s is zero, 1, 2, 3 or 4;

r is zero, 1, 2, 3 or 4;

R(10) is cycloalkyl having 3, 4, 5, 6, 7 or 8 carbon atoms, or phenyl, where the phenyl is not substituted or is substituted by 1–3 substituents selected from the group consisting of F, Cl, $CF_3$, methyl, methoxy and NR(11) R(12);

R(11) and R(12) independently of one another are H, alkyl having 1, 2, 3 or 4 carbon atoms or perfluoroalkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;

(HOE 95/F 220-NZ 299 052)

an) benzoylguanidines of the formula I

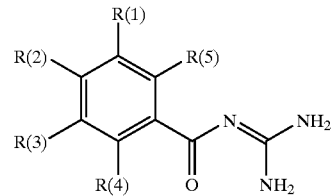

I in which:

at least one of the substituents R(1), R(2) and R(3) is R(6)—C(OH)$_2$—;

R(6) is perfluoroalkyl having 1, 2 or 3 carbon atoms, which is straight-chain or branched;

and the other substituents R(1), R(2) and R(3) independently of one another are hydrogen, OH, F, Cl, Br, I, alkyl having 1, 2, 3, 4, 5 or 6 carbon atoms, cycloalkyl with 3, 4, 5 or 6 carbon atoms, alkoxy having 1, 2, 3 or 4 carbon atoms or phenoxy, which is unsubstituted or is substituted by 1–3 substituents selected from the group consisting of F, Cl, methyl and methoxy;

or the other substituents R(1), R(2) and R(3) independently of one another are alkyl-SO$_x$, —CR(7)=CR(8)R(9) or —C≡CR(9);

x is zero, 1 or 2;

R(7) is hydrogen or methyl;

R(8) and R(9) independently of one another are hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents selected from the group consisting of F, Cl, CF$_3$, methyl and methoxy;

or the other substituents R(1), R(2) and R(3) independently of one another are phenyl, C$_6$H$_5$-(C$_1$-C$_4$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$-(C$_1$-C$_4$)-alkyl, naphthyl, biphenylyl, quinolinyl, isoquinolinyl and imidazolyl are unsubstituted or are substituted by 1–3 substituents selected from the group consisting of F, Cl, CF$_3$, CH$_3$methoxy, hydroxyl, amino, methylamino and dimethylamino;

or the other substituents R(1), R(2) and R(3) independently of one another are SR(10), —OR(10), —CR(10)R(11)R(12);
- R(10) is —C$_f$H$_{2f}$—(C$_3$-C$_8$)-cycloalkyl, quinolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, CF$_3$, CH$_3$, methoxy, hydroxyl, amino, methylamino and dimethylamino;
- f is zero, 1 or 2;
- R(11) and R(12) independently of one another are defined as R(10), hydrogen or alkyl having 1, 2, 3 or 4 carbon atoms;

R(4) and R(5) independently of one another are hydrogen, alkyl having 1, 2 or 3 carbon atoms, F, Cl, Br, I, CN, OR(13), NR(14)R(15), —(CH$_2$)$_n$—(CF$_2$)$_o$—CF$_3$;

R(13), R(14) and R(15) independently of one another are hydrogen or alkyl having 1, 2, 3 or 4 carbon atoms;

n is zero or 1;

o is zero, 1 or 2;

and their pharmaceutically acceptable salts;

(HOE 95/F 253-NZ 299 682)

ao) sulfonimidamides of the formula I

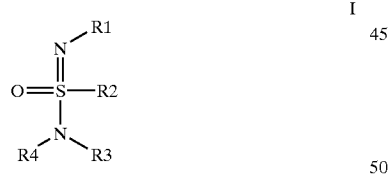

in which:

at least one of the three substituents R(1), R(2) and R(3) is a benzoylguanidine,

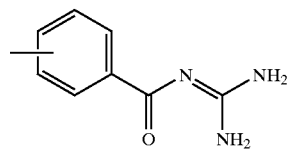

which is unsubstituted or substituted in the phenyl moiety by 1–4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22)SO$_2$—, R(23)R(24)N—CO—, R(25)—CO—, R(26)R(27)N—SO$_2$, —OR(35), —SR(35) or —NR(35)R(36);

m is zero, 1 or 2;

R(14) is —(C$_3$-C$_8$)-cycloalkyl or phenyl, which is not substituted or is substituted by 1–3 substituents selected from the group consisting of F and Cl, —CF$_3$, methyl, methoxy and —NR(15)R(16);
- R(15) and R(16) independently of one another are hydrogen or —CH$_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;

n is zero, 1, 2, 3 or 4;

R(29) is —(C$_3$-C$_7$)-cycloalkyl or phenyl, which is not substituted or is substituted by 1–3 substituents selected from the group consisting of F, Cl, —CF$_3$, methyl, methoxy and —NR(30)R(31);
- R(30) and R(31) are hydrogen or alkyl having 1, 2, 3 or 4 carbon atoms;

or

R(23), R(25) and R(26) are hydrogen;

R(24) and R(27) independently of one another are hydrogen or alkyl having 1, 2, 3 or 4 carbon atoms;

or

R(23) and R(24), and also R(256) and R(27) together are 5 or 6 methylene groups, of which one CH$_2$ group can be replaced by oxygen, —S—, —NH—, —NCH$_3$ or —N-benzyl;

R(35) and R(36) independently of one another are hydrogen or alkyl having 1, 2, 3, 4, 5, or 6 carbon atoms;

or

R(35) and R(36) together are 4–7 methylene groups, of which one CH$_2$ group can be replaced by oxygen, —S—, —NH—, —NCH$_3$ or —N-benzyl;

or

R(35) is phenyl, which is not substituted or is substituted by 1–3 substituents selected from the group consisting of F, Cl, —CF$_3$, methyl, methoxy, SO$_2$R(5), SO$_2$NR(6)R(7) and —NR(32)R(33);
- (R5) is alkyl having 1, 2, 3, 4, 5 or 6 carbon atoms
- R(6) and R(7) independently of one another are hydrogen or alkyl having 1, 2, 3 or 4 carbon atoms;
- R(32) and R(33) independently of one another are hydrogen or alkyl having 1, 2, 3 or 4 carbon atoms;

R(35) is C$_1$-C$_9$-heteroaryl, which is unsubstituted or substituted by 1–3 substituents selected from the group consisting of F, Cl, CF$_3$, CH$_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, (CH$_2$)$_p$R(10)

p is zero, 1, 2, 3, or 4;

R(10) is phenyl, which is not substituted or is substituted by 1–3 substituents selected from the group consisting of F, Cl, —CF$_3$, methyl, methoxy, —SO$_2$NR(17)R(8) and —SO$_2$R(9);
- R(17) and R(8) independently of one another are hydrogen or alkyl having 1, 2, 3 or 4 carbon atoms;
- R(9) is alkyl having 1, 2, 3 or 4 carbon atoms;

or the other radicals R(1) and R(3) in each case are hydrogen,
R(4) is hydrogen or alkyl having 1, 2, 3, or 4 carbon atoms;
and their pharmaceutically tolerable salts;

(HOE 95/F 265-NZ 299 739)

ap) benzoylguanidines of the formula I

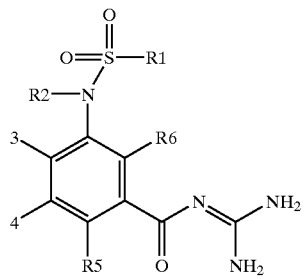

in which:
R(1) is alkyl having 1, 2, 3, 4, 5, 6, 7 or 8 carbon atoms or NR(7)R(8); R(7) and R(8) independently of one another are hydrogen or alkyl having 1, 2, 3, 4, 5, 6, 7 or 8 carbon atoms;
R(2) is hydrogen, alkyl having 1, 2, 3, 4, 5, 6, 7 or 8 carbon atoms or —SO$_2$R(9);
R(9) independently is defined as R(1);
R(3) is hydrogen, —SR(25), —OR(25), —NR(25)R(26) or —CR(25)R(26)R(27);
  R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$methoxy, hydroxyl, amino, methylamino and dimethylamino;
  or
  R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
  R(26) and R(27) independently of one another are defined as R(25) or are hydrogen or alkyl having 1, 2, 3, 4, 5, 6, 7 or 8 carbon atoms;
R(4) is hydrogen, F, Cl, Br, I, OH, —C≡N, CF$_3$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
  R(14) is —(C$_3$—C$_8$)-cycloalkyl or phenyl, which is not substituted or is substituted by 1–3 substituents selected from the group consisting of F and Cl, —CF$_3$, methyl, methoxy and —NR(14(R(16);
    R(15) and R(16) independently of one another are hydrogen or —CH$_3$;
R(5) and R(6) independently of one another are hydrogen, alkyl having 1, 2, 3 or 4 carbon atoms, F, Cl, —OR(32), —NR(33)R(34) or CF$_3$;
  R(32), R(33) and R(34) independently of one another are hydrogen or alkyl having 1, 2, 3 or 4 carbon atoms;
and their pharmaceutically tolerable salts;

(HOE 95/F 269 K)

aq) benzenedicarboxylic acid diguanidides of the formula I

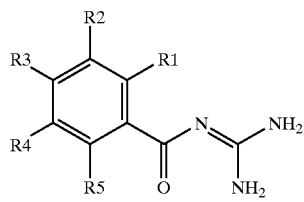

in which:
one of the radicals R(1), R(2), R(3) and R(4) is —CO—N═C(NH$_2$)$_2$;
and the other radicals R(1), R(2), R(3) and R(4) in each case are:
R(1) is hydrogen, alkyl having 1, 2, 3 or 4 carbon atoms, F, Cl, Br, I, —OR(32), —NR(33)R(34) or CF$_3$;
  R(32), R(33) and R(34) independently of one another are hydrogen or alkyl having 1, 2, 3 or 4 carbon atoms;
R(2) and R(4) independently of one another are hydrogen, F, Cl, Br, I, OH, —CN, CF$_3$, —CO—N═C(NH$_{22}$), alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero 1 or 2;
  R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16); R(15) and R(16) are hydrogen or —CH$_3$;
or
R(2) and R(4) independently of one another are pyrrol-1-yl, pyrrol-2-yl or pyrrol-3-yl, not which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy;
or
R(2) and R(4) independently of one another are R(22)—SO$_2$—, R(23)R(24)N—CO—, R(28)—CO— or R(29)R(30)N—SO$_2$;
  R(22) and R(28) independently of one another are methyl or —CF$_3$;
  R(23), R(24), R(29) and R(30) independently of one another are hydrogen or methyl;
or
R(2) and R(4) independently of one another are —OR(35) or —NR(35)R(36);
  R(35) and R(36) independently of one another are hydrogen or alkyl having 1, 2, 3, 4, 5 or 6 carbon atoms;
  or
  R(35) and R(36) together are 4–7 methylene groups, of which one CH$_2$ group can be replaced by oxygen, —S—, —NH—, —NCH$_3$ or —N-benzyl;
R(3) is hydrogen, —SR(25), —OR(25), —NR(25)R(26), —CR(25)R(26)R(27);
  R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino;
  or
  R(25) is —(C$_1$–C$_9$)-heteroaryl, which is unsubstituted or substituted by 1–3 substituents selected from the group consisting of F, Cl, CF₃, CH₃, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(5) is alkyl having 1, 2, 3 or 4 carbon atoms, F, Cl, Br, I, X—(CH₂)ᵧ—CF₃ or phenyl, which is not substituted or is substituted by 1–3 substituents selected from the group consisting of F and Cl, —CF₃methyl, methoxy and —NR(6)R(7);

R(6) and R(7) independently of one another are hydrogen or —CH₃;

X is a bond or oxygen;

y is zero, 1 or 2;

and their pharmaceutically tolerable salts;

(HOE 95/F 269 BK)

ar) benzenedicarboxylic acid diguanidides of the formula I

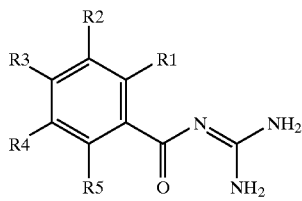

in which:

one of the radicals R(1), R(2), R(3) and R(5) is —CO—N=C(NH₂)₂;

and the other radicals R(1), R(2), R(3) and R(5) in each case are:

R(1) and R(5) independently of one another are hydrogen, alkyl having 1, 2, 3 or 4 carbon atoms, F, Cl, —OR(32), —NR(33)R(34) or CF₃;

R(32), R(33) and R(34) independently of one another are hydrogen or alkyl having 1, 2, 3 or 4 carbon atoms;

R(2) is hydrogen, F, Cl, Br, I, OH, —CN, CF₃, —CO—NH=C(NH₂)₂, alkyl having 1, 2, 3, 4, 5, 6, 7 or 8 carbon atoms, alkenyl having 2, 3, 4, 5, 6, 7 or 8 carbon atoms or —(CH₂)ₘR(14);

m is zero, 1 or 2;

R(14) is —(C₃–C₈)-cycloalkyl or phenyl, which is not substituted or is substituted by 1–3 substituents selected from the group consisting of F and Cl, —CF₃, methyl, methoxy and —NR(15)R(16);

R(15) and R(16) independently of one another are hydrogen or —CH₃;

or

R(2) is R(22)—SO₂—, R(23)R(24)N—CO—, R(28)—CO— or R(29)R(30)N—SO₂;

R(22) and R(28) independently of one another are methyl or —CF₃;

R(23), R(24), R(29) and R(30) independently of one another are hydrogen or methyl;

or

R(2) is —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which one CH₂ group can be replaced by oxygen, —S—, —NH—, —NCH₃ or —N-benzyl;

(R3) is hydrogen, —SR(25), —OR(25), —NR(25)R26), —CR(25)R(26)R(27);

R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF₃, CH₃, methoxy, hydroxyl, amino, methylamino and dimethylamino;

or

R(25) is —(C₁–C₉)-heteroaryl, which is unsubstituted or substituted by 1–3 substituents selected from the group consisting of F, Cl, CF₃, CH₃, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is CF₃, alkyl having 1, 2, 3, 4, 5, 6, 7 or 8 carbon atoms, alkenyl having 2, 3, 4, 5, 6, 7 or 8 carbon atoms, —(C₃–C₈)-cycloalkyl or —(CH₂)ₘR(14);

m is 1 or 2;

R(14) is —(C₃–C₈)-cycloalkyl or phenyl, which is not substituted or is substituted by 1–3 substituents selected from the group consisting of F and Cl, —CF₃, methyl, methoxy and —NR(15)R(16); R(15) and R(16) independently of one another are hydrogen or —CH₃;

or

R(4) is phenyl, which is substituted by 2, 3, 4 or five substituents selected from the group consisting of F, Cl, CF₃, methyl, methoxy and —NR(15)R(16);

R(15) and R(16) independently of one another are hydrogen or CH₃;

and their pharmaceutically tolerable salts;

(HOE 96/F 013)

as) diaryldicarboxylic acid diguanidides of the formula I

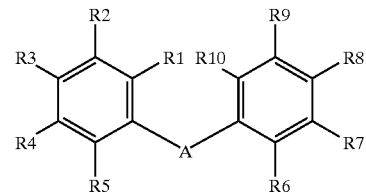

in which:

one of the radicals R(1), R(2), R(3), R(4) and R(5) is —CO—N=C(NH₂)₂;

the other radicals R(1) and R(5) in each case independently of one another are hydrogen, alkyl having 1, 2, 3 or 4 carbon atoms, F, Cl, —OR(32), —NR(33)R(34) or CF₃;

R(32), R(33) and R(34) independently of one another are hydrogen or alkyl having 1, 2, 3 or 4 carbon atoms;

the other radicals R(2) and R(4) in each case independently of one another are hydrogen, F, Cl, Br, I, OH, —CN, CF₃, —CO—N=C(NH₂)₂, alkyl having 1, 2, 3, 4, 5, 6, 7 or 8 carbon atoms, alkenyl having 2, 3, 4, 5, 6, 7 or 8 carbon atoms or —(CH₂)ₘR(14);

m is zero, 1 or 2;

R(14) is —(C₃–C₈)-cycloalkyl or phenyl, which is not substituted or is substituted by 1–3 substituents selected from the group consisting of F and Cl, —CF₃, methyl, methoxy and —NR(15)R(16);

R(15) and R(16) are hydrogen or —CH₃;

or the other radicals R(2) and R(4) in each case independently of one another are pyrrol-1-yl, pyrrol-2-yl or pyrrol-3-yl, which is not substituted or is substituted by 1–4 substituents selected from the group consisting of F, Cl, Br, I, —CN, $(C_2-C_8)$-alkanoyl, $(C_2-C_8)$-alkoxycarbonyl, formyl, carboxyl, —$CF_3$, methyl, methoxy;

or the other radicals R(2) and R(4) in each case are R(22)—$SO_2$—, R(23)R(24)N—CO—, R(28)—CO— or R(29)R(30)N—$SO_2$;

R(22) and R(28) independently of one another are methyl or —$CF_3$;

R(23), R(24), R(29) and R(30) independently of one another are hydrogen or methyl;

or the other radicals R(2) and R(4) in each case independently of one another are —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which one $CH_2$ group can be replaced by oxygen, —S—, —NH—, —$NCH_3$ or —N-benzyl;

the other radical R(3) in each case is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino;

or

R(25) is —$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

one of the radicals R(6), R(7), R(8), R(9) and R(10) is —CO—N=$C(NH_2)_2$;

the other radicals R(6) and R(10) in each case independently of one another are hydrogen, alkyl having 1, 2, 3 or 4 carbon atoms, F, Cl, —OR(132), —NR(133)R(134) or $CF_3$;

R(132), R(133) and R(134) independently of one another are hydrogen or alkyl having 1, 2, 3 or 4 carbon atoms;

the other radicals R(7) and R(9) in each case independently of one another are hydrogen, F, Cl, Br, I, OH, —CN, $CF_3$, —CO—N=$C(NH_2)_2$, alkyl having 1, 2, 3, 4, 5, 6, 7 or 8 carbon atoms, alkenyl having 2, 3, 4, 5, 6, 7 or 8 carbon atoms or —$(CH_2)_{mm}$R(114);

mm is zero, 1 or 2;

R(114) is —$(C_3-C_8)$-cycloalkyl or phenyl, which is not substituted or is substituted by 1–3 substituents selected from the group consisting of F and Cl, —$CF_3$, methyl, methoxy and —NR(115)R(116);

R(115) and R(116) are hydrogen or —$CH_3$;

or the other radicals R(7) and R(9) in each case independently of one another are pyrrol-1-yl, pyrrol-2-yl or pyrrol-3-yl, which is not substituted or is substituted by 1–4 substituents selected from the group consisting of F, Cl, Br, I, —CN, $(C_2-C_8)$-alkanoyl, $(C_2-C_8)$-alkoxycarbonyl, formyl, carboxyl, —$CF_3$, methyl and methoxy;

or the other radicals R(7) and R(9) in each case are R(122)—$SO_2$—, R(123)R(124)N—CO—, R(128)—CO— or R(129)R(130)N—$SO_2$;

R(122) and R(128) independently of one another are methyl or —$CF_3$;

R(123), R(124), R(129) and R(130) independently of one another are hydrogen or methyl;

or the other radicals R(7) and R(9) in each case independently of one another are —OR(135) or —NR(135)R(136);

R(135) and R(136) independently of one another are hydrogen or alkyl having 1, 2, 3, 4, 5 or 6 carbon atoms;

or

R(135) and R(136) together are 4–7 methylene groups, of which one $CH_2$ groups can be replaced by oxygen, —S—, —NH—, —$NCH_3$ or —N-benzyl;

the other radical R(8) in each case is hydrogen, —SR(125), —OR(125), —NR(125)R(126) or —CR(125)R(126)R(127);

R(125) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino;

or

R(125) is —$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

R(126) and R(127) independently of one another are defined as R(125) or are hydrogen or alkyl having 1, 2, 3, 4, 5, 6, 7 or 8 carbon atoms;

A is absent or is —NR(11)—CO—, —NR(12)—CO—NR(13)—, —NR(17)—CO—NR(18)—$SO_2$—, —NR(19)—$SO_2$—, —$SO_2$—NR(19)—$SO_2$—, —$SO_2$—NR(19)—CO—, —O—CO—NR(19)—$SO_2$— or —CR(20)=CR(21)—;

R(11), R(12), R(13), R(17), R(18), R(19), R(20) and R(21) independently of one another are hydrogen or alkyl having 1, 2, 3, 4, 5, 6, 7 or 8 carbon atoms and their pharmaceutically tolerable salts;

(HOE 96/F 026)

at) substituted thiophenylalkenylcarboxylic acid guanidides of the formula I

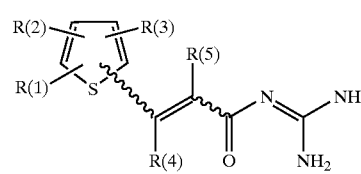

in which:

at least one of the substituents R(1), R(2) and R(3) is —$O_p$—$(CH_2)_s$—$C_qF_{2q+1}$, R(40)CO— or R(31)$SO_k$—;

p is zero or 1;

s is zero, 1, 2, 3 or 4;

q is 1, 2, 3, 4, 5, 6, 7 or 8;

k is zero, 1 or 2;

R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl and methoxy;

R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, CF$_3$, methyl or methoxy;

or

R(31) is NR(41)R(42);

R(41) and R(42) independently of one another are hydrogen, alkyl having 1, 2, 3 or 4 carbon atoms, perfluoroalkyl having 1, 2, 3 or 4 carbon atoms, or R(41) and R(42) together are 4 or 5 methylene groups, of which one CH$_2$ group can be replaced by oxygen, S, NH, N—CH$_3$ or N-benzyl;

and the other substituents R(1), R(2) and R(3) in each case independently of one another are H, F, Cl, Br, I, CN, —O$_{na}$—C$_{ma}$H$_{2ma+1}$ or —O$_{ga}$C$_{ra}$H$_{2ra}$R(10);

na is zero or 1;

ma is zero, 1, 2, 3, 4, 5, 6, 7 or 8;

ga is zero or 1;

ra is zero, 1, 2, 3 or 4;

R(10) is cycloalkyl having 3, 4, 5, 6, 7 or 8 carbon atoms or phenyl, Where the phenyl is not substituted or is substituted by 1–3 substituents selected from the group consisting of F, Cl, CF$_3$, methyl and methoxy;

R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl, which is not substituted or is substituted by 1–3 substituents selected from the group consisting of F, Cl, CF$_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;

(HOE 96/F 032)

au) ortho-substituted benzoylguanidines of the formula I

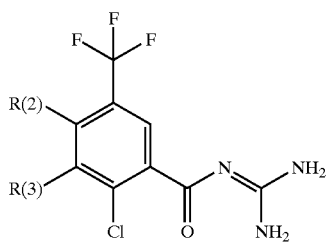

in which:

R(2) and R(3) independently of one another are hydrogen, Cl, Br, I, (C$_1$–C$_8$)-alkyl, (C$_3$–C$_8$)-cycloalkyl or —OR(5);

R(5) is (C$_1$–C$_8$)-alkyl or —C$_d$H$_{2d}$—(C$_3$–C$_8$)-cycloalkyl;

d is zero, 1 or 2;

where one of the two substituents R(2) and R(3) is always hydrogen but both substituents R(2) and R(3) are not simultaneously hydrogen, and their pharmaceutically tolerable salts;

(HOE 96/F 042)

av) benzoylguanidines of the formula I

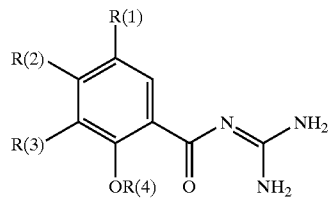

in which:

R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;

X is oxygen, S, NR(5), a is zero or 1;

b is zero, 1 or 2;

c is zero, 1, 2 or 3;

R(5) is H, alkyl having 1, 2, 3 or 4 carbon atoms or —C$_d$H$_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);

R(7) and R(8) independently are H or alkyl having 1, 2, 3 or 4 carbon atoms;

or

R(1) is —SR(10), —OR(10) or —CR(10)R(11)R(12);

R(10) is —C$_f$H$_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10) or are hydrogen or alkyl having 1, 2, 3 or 4 carbon atoms;

or

R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_n$—R(24);

R(17) is hydrogen or methyl, g, h and i identically or differently are zero, 1, 2, 3 or 4;

j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

R(18) is phenyl, which is unsubstituted or substituted by 1–3 substituents selected from the group consisting of F, Cl, CF$_3$, methyl, methoxy and NR(25)R(26);

R(25) and R(26) are H or alkyl having 1, 2, 3 or 4 carbon atoms;

or

R(18) is heteroaryl having 1, 2, 3, 4, 5, 6, 7, 8 or 9 carbon atoms, which is unsubstituted or substituted as phenyl;

or

R(18) is alkyl having 1, 2, 3, 4, 5 or 6 carbon atoms, which is unsubstituted or substituted by 1–3 OH;

or

R(18) is cycloalkyl having 3, 4, 5, 6, 7 or 8 carbon atoms;

R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);

m is 1, 2, 3 or 4;

R(2) and R(3) are defined as R(1);

R(4) is alkyl having 1, 2, 3 or 4 carbon atoms;

and their pharmaceutically tolerable salts;

(HOE 96/F 043)

aw) ortho-substituted benzoylguanidines of the formula I

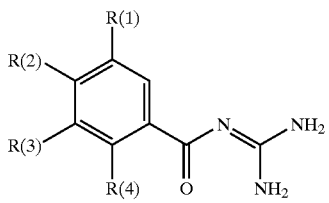

in which:

R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;

X is oxygen, S, NR(5), a is zero or 1;

b is zero, 1 or 2;

c is zero, 1, 2 or 3;

R(5) is H, alkyl having 1, 2, 3 or 4 carbon atoms or —C$_d$H$_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are unsubstituted or substituted by 1–3 substituents selected from the group consisting of F, Cl, CF$_3$, methyl, methoxy and NR(7)R(8);

R(7) and R(8) independently are H or alkyl having 1, 2, 3 or 4 carbon atoms;

or

R(1) is —SR(10), —OR(10) or —CR(10)R(11)R(12);

R(10) is —C$_f$H$_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10), or hydrogen or alkyl having 1, 2, 3 or 4 carbon atoms;

or

R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, CF$_3$, CH$_3$, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);

R(17) is hydrogen or methyl, g, h and i identically or differently are zero, 1, 2, 3 or 4;

j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

R(18) is phenyl, which is unsubstituted or substituted by 1–3 substituents selected from the group consisting of F, Cl, CF$_3$, methyl, methoxy and NR(25)R(26);

R(25) and R(26) are H or alkyl having 1, 2, 3 or 4 carbon atoms;

or

R(18) is heteroaryl having 1, 2, 3, 4, 5, 6, 7, 8 or 9 carbon atoms, which is unsubstituted or substituted as phenyl;

or

R(18) is alkyl having 1, 2, 3, 4, 5 or 6 carbon atoms, which is unsubstituted or substituted by 1–3 OH;

or

R(18) is cycloalkyl having 3, 4, 5, 6, 7 or 8 carbon atoms;

R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);

m is 1, 2, 3 or 4;

one of the two substituents R(2) and R(3) is hydroxyl;

and the other of the substituents R(2) and R(3) in each case is defined as R(1);

R(4) is alkyl having 1, 2, 3 or 4 carbon atoms; alkoxy having 1, 2, 3 or 4 carbon atoms, F, Cl, Br, I or —(CH$_2$)$_n$—(CF$_2$)$_o$—CF$_3$;

n is zero or 1;

o is zero or 1;

and their pharmaceutically tolerable salts;

(HOE 96/F 135)

ax) bis-ortho-substituted benzoylguanidines of the formula I

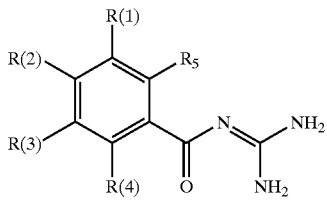

in which:

R(1), R(2) and R(3) independently of one another are R(10)—SO$_a$— or R(14)R(15)N—SO$_2$—;
  a is zero, 1 or 2,
  R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —C$_{ab}$H$_{2ab}$—R(16);
    ab is zero, 1, 2, 3 or 4;
    R(16) is cycloalkyl having 3, 4, 5, 6 or 7 carbon atoms, or phenyl, which is not substituted or is substituted by 1–3 substituents selected from the group consisting of F, Cl, CF$_3$, methyl, methoxy and NR(17)R(18);
      R(17) and R(18) independently of one another are hydrogen, CF$_3$ or alkyl having 1, 2, 3 or 4 carbon atoms;
    or
  R(14) and R(15) together are 4 or 5 methylene groups, of which one CH$_2$ group can be replaced by oxygen, sulfur, NH, N—CH$_3$ or N-benzyl;
    or
  R(14) and R(15) are hydrogen;
or
R(1), R(2) and R(3) independently of one another are SR(21), —OR(22), —NR(23)R(24) or —CR(25)R(26)R(27);
  R(21), R(22), R(23) and R(25) independently of one another are —C$_b$H$_{2b}$—(C$_1$-C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;
    b is zero, 1 or 2;
  R(24), R(26) and R(27) independently of one another are hydrogen, alkyl having 1, 2, 3 or 4 carbon atoms or perfluoroalkyl having 1, 2, 3 or 4 carbon atoms;
or
R(1), R(2) and R(3) independently of one another are hydrogen, F, Cl, Br, I, CN, —(Xa)$_{dg}$—C$_{da}$H$_{2da+1}$, —(Xb)$_{dh}$—(CH$_2$)$_{db}$—C$_{de}$F$_{2de+1}$, alkenyl having 3, 4, 5, 6, 7 or 8 carbon atoms or —C$_{df}$H$_{2df}$R(30);
  (Xa) is oxygen, sulfur or NR(33);
  R(33) is hydrogen, alkyl having 1, 2, 3 or 4 carbon atoms or perfluoroalkyl having 1, 2, 3 or 4 carbon atoms;
  dg is zero or 1;
  (Xb) is oxygen, sulfur or NR(34);
    R(34) is hydrogen, alkyl having 1, 2, 3 or 4 carbon atoms or perfluoroalkyl having 1, 2, 3 or 4 carbon atoms;
  dh is zero or 1;
  da is zero, 1, 2, 3, 4, 5, 6, 7 or 8;
  db is zero, 1, 2, 3 or 4;
  de is zero, 1, 2, 3, 4, 5, 6 or 7;
  df is zero, 1, 2, 3 or 4;
  R(30) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(31)R(32);
    R(31) and R(32) are hydrogen, alkyl having 1, 2, 3 or 4 carbon atoms or perfluoroalkyl having 1, 2, 3 or 4 carbon atoms;
R(1), R(2) and R(3) independently of one another are NR(40)R(41) or —(Xe)—(CH$_2$)$_{eb}$R(45);
  R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or (CH$_2$)$_e$—R(42);
    e is zero, 1, 2, 3 or 4;
    R(42) is cycloalkyl having 3, 4, 5, 6 or 7 carbon atoms or phenyl, which is not substituted or is substituted by 1–3 substituents selected from the group consisting of F, Cl, CF$_3$, methyl, methoxy and NR(43)R(44);
      R(43) and R(44) independently of one another are hydrogen, CF$_3$ or alkyl having 1, 2, 3 or 4 carbon atoms;
  or
  R(40) and R(41) together are 4 or 5 methylene groups, of which one CH$_2$ group can be replaced by oxygen, sulfur, NH, N—CH$_3$ or N-benzyl;
  (Xe) is oxygen, sulfur or NR(47);
    R(47) is hydrogen, alkyl having 1, 2, 3 or 4 carbon atoms or perfluoroalkyl having 1, 2, 3 or 4 carbon atoms;
  eb is zero, 1, 2, 3 or 4;
  R(45) is cycloalkyl having 3, 4, 5, 6 or 7 carbon atoms, or phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);
    Xfa is CH$_2$, oxygen, sulfur or NR(48);
    Xfb is oxygen, sulfur or NR(49);
      R(48), R(49), R(50) and R(51) independently of one another are hydrogen, alkyl having 1, 2, 3 or 4 carbon atoms or perfluoroalkyl having 1, 2, 3 or 4 carbon atoms;
    ed is 1, 2, 3 or 4;
    R(46) is hydrogen, alkyl having 1, 2, 3 or 4 carbon atoms or perfluoroalkyl having 1, 2, 3 or 4 carbon atoms;
or
R(1), R(2) and R(3) independently of one another are —CHR(52)R(53);
  R(52) is —(CH$_2$)$_g$—(CHOH)$_h$—(CH)$_i$—(CHOH)$_k$—R(54) or —(CH$_2$)$_g$—O—(CH$_2$—CH$_2$O)$_h$—R(54);
    R(54) is hydrogen or methyl;
    g, h, i identically or differently are zero, 1, 2, 3 or 4;
    k is 1, 2, 3 or 4;
  R(53) is hydrogen or alkyl having 1, 2, 3 or 4 carbon atoms;
or
R(1), R(2) and R(3) independently of one another are —C(OH)R(55)R(56);
  R(55) and R(56) identically or differently are hydrogen or alkyl having 1, 2, 3 or 4 carbon atoms;

or
R(55) and R(56) together are cycloalkyl having 3, 4, 5 or 6 carbon atoms;
or
R(55) is —CH$_2$OH;
and
R(4) and R(5) independently of one another are alkyl having 1, 2, 3 or 4 carbon atoms, alkoxy having 1, 2, 3 or 4 carbon atoms, OH, F, Cl, Br, I, CN, —O$_n$—(CH$_2$)$_o$—(CF$_2$)$_p$—CF$_3$;
n is zero or 1;
o is zero, 1 or 2;
p is zero, 1 or 2;
and their pharmaceutically tolerable salts;
(HOE 96/F 136)

ay) substituted 1-naphthoylguanidines of the formula I

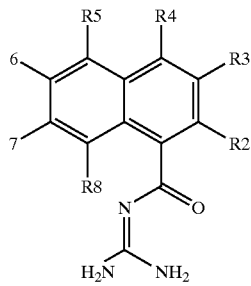

in which:
R2, R3, R4, R5, R6, R7 and R8 independently of one another are H, F, Cl, Br, I, CN, NO$_2$, CF$_3$, C$_2$F$_5$ or X$_a$Y$_b$Z;
X is O, S, NR(10), CR(11)R(12), C=O, C(=O)NR(10), C(=O)O, SO, SO$_2$, SO$_2$NR(10), OC=O, NR(10)C=O or NR(10)SO$_2$, where the linkage with the naphthalene ring in each case takes place via the left atom;
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
a is zero or 1;
Y is alkylene having 1, 2, 3, 4, 5, 6, 7 or 8 CH$_2$ groups, where one of these CH$_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
b is zero or 1;
Z is H, alkyl having 1, 2, 3, 4, 5, 6 or 7 carbon atoms, cycloalkyl having 3, 4, 5, 6 or 7 carbon atoms, C(=O)R(15), SO$_2$R(15), NR(16)R(17) or phenyl, which is not substituted or is substituted by 1–3 substituents selected from the group consisting of F, Cl, Br, CF$_3$, methyl, methoxy and NR(21)R(22);
R(21) and R(22) independently of one another are H or alkyl having 1, 2, 3 or 4 carbon atoms or perfluoroalkyl having 1, 2, 3 or 4 carbon atoms;
R(15) is N=C(NH$_2$)$_2$, NR(18)R(19), N(CH$_2$)$_c$NR(18)R(19) or OR(20);
c is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one CH$_2$ group can be replaced by oxygen, S, NH, N—CH$_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups, of which one CH$_2$ group can be replaced by oxygen, S, NH, N—CH$_3$, N-benzyl or N-(p-chlorophenyl);
or
Z is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(21)R(22);
but where, in the case where R(4) is an alkoxy radical, at least one of the substituents R(2), R(3), R(5), R(6), R(7) and R(8) is not hydrogen;
and their pharmaceutically tolerable salts;
(HOE 96/F 137)

az) substituted 2-naphthoylguanidines of the formula I

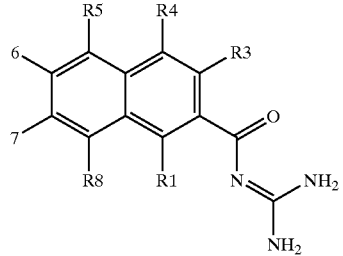

in which:
at least one of the substituents R1, R3, R4, R5, R6, R7 and R8 is XY$_a$WZ or X'Y$_a$WZ';
X is O, S, NR(10) or CR(11)R(12);
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Y is alkylene having 1, 2, 3, 4, 5, 6, 7 or 8 CH$_2$ groups, where one of these CH$_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
a is zero or 1;
W is CH$_2$, SO$_2$, S(=O)(=NH) or—if W does not immediately follow a heteroatom of the group XY$_a$—alternatively O or NR(14);
R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
Z is C(=O)R(15), SO$_2$R(15) or—if W is not O or NR(14)—alternatively NR(16)R(17);
R(15) is N=C(NH$_2$)$_2$, NR(18)R(19), N(CH$_2$)$_b$NR(18)R(19) or OR(20);
b is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms;

or
R(18) and R(19) together are 4 or 5 methylene groups, of which one CH$_2$ group can be replaced by oxygen, S, NH, N—CH$_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms;
or,
R(16) and R(17) together are 4 or 5 methylene groups, of which one CH$_2$ group can be replaced by oxygen, S, NH, N—CH$_3$, N-benzyl or N-(p-chlorophenyl);
X' is C=O, C(=O)NR(30), C(=O)O, SO, SO$_2$, SO$_2$NR(30), OC=O, NR(30)C=O or NR(30)SO$_2$, where the linkage with the naphthalene ring in each case takes place via the left atom;
R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
Z' is C(=O)R(15), SO$_2$R(15), an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(21)R(22);
R(21) and R(22) independently of one another are H, alkyl having 1, 2, 3 or 4 carbon atoms or perfluoroalkyl having 1, 2, 3 or 4 carbon atoms;
R(15) is N=C(NH$_2$)$_2$, NR(18)R(19), N(CH$_2$)$_b$NR(18)R(19) or OR(20);
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one CH$_2$ group can be replaced by oxygen, S, NH, N—CH$_3$, N-benzyl or N-(p-chlorophenyl);
b is 2 or 3;
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
or
Z' if W is not O or NR(14)—is NR(16)R(17);
R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups, of which one CH$_2$ group can be replaced by oxygen, S, NH, N—CH$_3$, N-benzyl or N-(p-chlorophenyl);
and the other substituents R1, R3, R4, R5, R6, R7 and R8 in each case, which are still not allocated by the definitions given above, independently of one another are H, F, Cl, Br, I, CN, NO$_2$, CF$_3$, C$_2$F$_5$ or V$_p$Q$_q$U;
V is O, S, SO, SO$_2$, NR(60), OC=O, C=O, C(=O)NR(60), C(=O)O or CR(66)R(67);
R(60), R(66) and R(67) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
p is zero or 1;
Q is alkylene having 1, 2, 3, 4, 5, 6, 7 or 8 CH$_2$ groups, where one of these CH$_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;
q is zero or 1;
U is H, alkyl having 1, 2, 3, 4, 5, 6 or 7 carbon atoms, cycloalkyl having 3, 4, 5, 6 or 7 carbon atoms, C(=O)R(65), SO$_2$R(65), NR(61)R(62) or phenyl, which is not substituted or is substituted by 1–3 substituents selected from the group consisting of F, Cl, Br, CF$_3$, methyl, methoxy and NR(63)R(64);
R(63) and R(64) independently of one another are H, alkyl having 1, 2, 3 or 4 carbon atoms or perfluoroalkyl having 1, 2, 3 or 4 carbon atoms;
R(65) is N=C(NH$_2$)$_2$, NR(61)R(62) or OR(60);
R(61) and R(62) independently of one another are H, alkyl having 1, 2, 3, 4, 5, 6, 7 or 8 carbon atoms or perfluoroalkyl having 1, 2, 3 or 4 carbon atoms;
or
R(61) and R(62) together are 4 or 5 methylene groups, of which one CH$_2$ group can be replaced by oxygen, S, NH, N—CH$_3$, N-benzyl or N-(p-chlorophenyl);
or
U is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(63)R(64);
but where at least one of the substituents R5, R6, R7 and R8 is not hydrogen; and their pharmaceutically tolerable salts;

(HOE 96/F 141)

ba) ortho-substituted benzoylguanidines of the formula I in which:

R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CH$_2$)$_c$—CF$_3$;
X is oxygen, sulfur or NR(9);
a is zero or 1:
b is zero, 1 or 2;
c is zero, 1, 2, or 3;
R(9) is H, alkyl having 1, 2, 3 or 4 carbon atoms or —C$_d$H$_{2d}$R(6);
d is zero, 1, 2, 3 or 4;
R(6) is cycloalkyl having 3, 4, 5, 6, 7 or 8 carbon atoms, phenyl, biphenyl or naphthyl, where the aromatics phenyl, biphenylyl or naphthyl are not substituted or are substituted by 1–3 substituents selected from the group consisting of F, Cl, CF$_3$, methyl, methoxy and NR(7R(8);
R(7) and R(8) are independently, H or alkyl having 1, 2, 3 or 4 carbon atoms;

or
R(1) is —SR(10), —OR(10) or —CR(10)R(11)R(12);
- R(10) is —$C_fH_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, $CF_3$, $CH_3$, methoxy, hydroxyl, amino, methylamino and dimethylamino;
  - f is zero, 1 or 2;
- R(11) and (R12), independently of each other, are defined as R(10) or are hydrogen or alkyl having 1, 2, 3 or 4 carbon atoms;

or
R(1) is phenyl, naphthyl, biphenylyl or heteroaryl having 1, 2, 3, 4, 5, 6, 7, 8 or 9 carbon atoms, the latter linked via a carbon or nitrogen atom of the ring, each of which is unsubstituted or is substituted by 1–3 substituents selected from the group consisting of F, Cl, $CF_3$, $CH_3$, methoxy, hydroxyl, amino, methylamino and dimethylamino, or
(R1) is —SR(13), —OR(13), —NHR(13), —NR(13)R(14), —CHR(13)R(15), —[R(15)R(16)]OH, —C≡CR(18), —C[R(19)]=CHR(18), —C[R(20)R(21)]$_k$—(CO)—[CR(22)R(23)]$_l$—R(24),
- k is zero, 1, 2, 3 or 4;
- l is zero, 1, 2, 3 or 4;
- R(13) and R(14), identically or differently, are —$(CH_2)_g$—$(CHOH)_{h-(CH2)_l}$—$(CHOH)_{kk}$—R(17) or —$(CH_2)_g$—O—$(CH_2-CH_2O)_n$—R(24);
  - R(17) is hydrogen or methyl g, h and l, identically or differently, are zero, 1, 2, 3 or 4;
  - kk is 1, 2, 3 or 4;
- R(15) and R(16), identically or differently, are hydrogen, alkyl having 1, 2, 3, 4, 5 or 6 carbon atoms, or, together with the carbon atom carring them, cycloalkyl having 3, 4, 5, 6, 7 or 8 carbon atoms;
- R(18) is phenyl, which is unsubstituted or is substituted by 1–3 substituents selected from the group consisting of F, Cl, $CF_3$, methyl, methoxy and NR(25)R(26);
  - R(25) and R(26) are H or alkyl having 1, 2, 3 or 4 carbon atoms;

or
- R(18) is heteroaryl having 1, 2, 3, 4, 5, 6, 7, 8 or 9 carbon atoms, which is unsubstituted or is substituted as phenyl;
- or R(18) is alkyl having 1, 2, 3, 4, 5 or 6 carbon atoms, which is unsubstituted or is substituted by 1–3 OH;

or
- R(18) is cycloalkyl having 3, 4, 5, 6, 7 or 8 carbon atoms;
- R(19), R(20), R(21), R(22) and R(23), identically or differently, are hydrogen or methyl;
- R(24) is H, alkyl having 1, 2, 3, 4, 5 or 6 carbon atoms, cycloalkyl having 3, 4, 5, 6, 7 or 8 carbon atoms or —$C_mH_{2m}$—R(18);
  - m is 1, 2, 3 or 4;
one of the two substituents R(2) and R(3) is —O—CO—R(27);
- R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl, where phenyl, biphenylyl, naphthyl, pyridyl or quinolyl are unsubstituted or substituted by 1–3 substituents selected from the group consisting of F, Cl, $CF_3$, methyl, methoxy and NR(7)R(8);
  - R(7) and R(8) independently of one another are hydrogen or alkyl having 1, 2, 3 or 4 carbon atoms;
where one of the substituents R(2) and R(3) is always defined as R(1);
R(4) and R(5) independently of one another are hydrogen, alkyl having 1, 2, 3 or 4 carbon atoms, alkoxy having 1, 2, 3 or 4 carbon atoms, F, Cl, Br, I, CN or —$(CH_2)_n$—$(CF_2)_o$—$CF_3$,
- n is zero or 1,
- o is zero or 1,
and their pharmaceutically tolerable salts;
(HOE 96/F 154)
bb) benzoylguanidines of the formula I

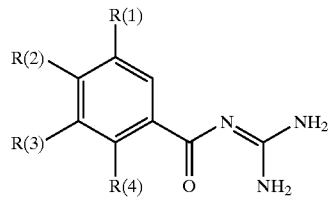

in which:
R(1) is R(13)—$SO_m$ or R(14)R(15)N—$SO_2$—;
- m is 1 or 2;
- R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(16),
  - n is zero, 1, 2, 3 or 4;
  - R(16) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, mehtyl, methoxy and NR(25)R(26);
    - R(25) and R(26) are, independently of each other, hydrogen, alkyl having 1, 2, 3 or 4 carbon atoms or perfluoroalkyl having 1, 2, 3 or 4 carbon atoms;
- R(14) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —$C_nH_{2n}$—R(27),
  - n is zero, 1, 2, 3 or 4;
  - R(27) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, $CF_3$, mehtyl, methoxy and NR(28)R(29);
    - R(28) and R(29) are, independently of each other, hydrogen, alkyl having 1, 2, 3 or 4 carbon atoms or perfluoroalkyl having 1, 2, 3 or 4 carbon atoms;
- R(15) is hydrogen, alkyl having 1, 2, 3 or 4 carbon atoms or perfluoroalkyl having 1, 2, 3 or 4 carbon atoms;

or
- R(14) and R(15) are, together, 4 or 5 methylene groups of which one $CH_2$ group can be replaced by oxygen, S, NH, N—$CH_3$ or N-benzyl;
one of the substituents R(2) and R(3) is hyrdogen;
and the other of the substituents R(2) and R(3) in each case is —CHR(30)R(31);
- R(30) is —$(CH_2)g$—$(CHOH)_h$—$(CH_2)_l$—R(32) or —$(CH_2)g$—O—$(CH_2CH_2O)_n$R(24);
  - R(24) and R(32) are, independently of each other, hydrogen or methyl;

g, h and i are, identically or differently, zero, 1, 2, 3 or 4;

k is 1, 2, 3 or 4;

or the other of the substituents R(2) and R(3) in each case is —C(OH)R(33)R(34) are, identically or differently, hydrogen or alkyl having 1, 2, 3 or 4 carbon atoms, or R(33) and R(34) are, together, cycloalkyl having 3, 4, 5 or 6 carbon atoms;

or

R(33) is —CH$_2$OH;

R(4) is alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;

n is zero or 1;

o is zero, 1 or 2;

and their pharmaceutically tolerable salts;

(HOE 96F 202)

bc) indanylidineacetylguanidines of the formula I

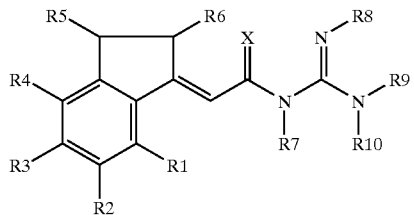

in which:

R1, R2, R3, R4, R1 and R1 independently of one another are H, C$_1$–C$_{10}$-alkyl; haloalkyl having 1–6 carbon atoms, O—C$_1$–C$_{10}$-alkyl, haloalkoxy having 1–6 carbon atoms, F, Cl, Br, I, aryl, substituted aryl, heteroaryl, substituted heteroaryl, Oh, O-lower alkyl, O-aryl, O-lower alkylaryl, O-substituted aryl, O-lower alkyl-substituted aryl, O—C(=O)—C$_1$–C$_4$-alkylaryl, O—C(=O)—NH—C$_1$–C$_4$-alkyl, O—C(=O)—N(C$_1$–C$_4$-alkyl)$_2$, NO$_2$, CN, CF$_3$, NH$_2$, NH—C(=O)—C$_1$–C$_4$-alkyl, NH—C(=O)—NH$_2$, COOH, C(=O)—O—C$_1$–C$_4$-alkyl, C(=O)—NH$_2$, C(=O)—NH—C$_1$–C$_4$-alkyl, C(=O)—N(C$_1$–C$_4$-alkyl)$_2$, C$_1$–C$_4$—COOH, C$_1$–C$_4$-alkyl-C(=O)—O—C$_1$–C$_4$-alkyl, SO$_3$H, SO$_2$-alkyl; SO$_2$-alkylaryl, SO$_2$—N-(alkyl)$_2$, SO$_2$—N(alkyl)(alkylaryl), C(=O)—R11, C$_1$–C$_{10}$-alkyl-C(=O)—R11 C$_2$–C$_{10}$alkenyl-C(=O)—R11, C$_2$–C$_{10}$-alkynyl-C(=O)—R11, NH—C(=O)—C$_1$–C$_{10}$-alkyl-C(=O)—R11 or O—C$_1$–C$_{11}$-alkyl-C(=)—R11;

R11 is C$_1$–C$_4$-alkyl, C$_1$–C$_4$-alkynyl, aryl, substituted aryl, NH$_2$, NH—C$_1$–C$_4$-alkyl, N—(C$_1$–C$_4$-alkyl)$_2$, SO$_3$H, SO$_2$-alkyl, SO$_2$-alkylaryl, SO$_2$N-(alkyl)$_2$ or SO$_2$—N(alkyl)(alylaryl);

X is O, S or NH;

R7, R8, R9 and R10 independently of one another are H, alkyl, cycloalkyl, aryl, alkylaryl, or R8 and R9 together are part of a 5-, 6- or 7-membered heterocyclic ring;

or their pharmaceutically acceptable salts;

(HOE 96/F 226)

bd) phenyl-substituted alkenylcarbosylic acid guanidides of the formula I

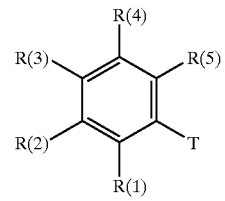

in which:

T is

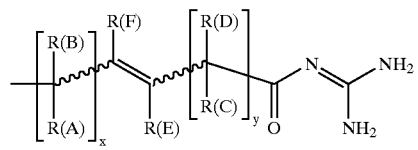

R(A) is hydrogen, F, Cl, Br, I, CN, OH, OR(6), (C$_1$–C$_4$)-alkyl, O$_r$(CH$_2$)$_a$C$_b$F$_{2b+1}$, (C$_3$–C$_8$)-cycloalkyl oder NR(7)R(8)

r is zero or 1;

a is zero, 1, 2, 3 or 4;

b is 1, 2, 3 or 4;

R(6) is (C$_1$–C$_4$)-alkyl, (C$_1$–C$_4$)-perfluoroalkyl, (C$_3$–C$_6$)-alkenyl, (C$_3$–C$_8$)-cycloalkyl, phenyl or benzyl; the phenyl nucleus not being substituted or being substituted by 1–3 substituents selected from the group consisting of F, Cl, CF$_3$, methyl, methoxy and NR(9)R(10);

R(9) and R(10) are H, (C$_1$–C$_4$)-alkyl or (C$_1$–C$_4$)-perfluoroalkyl,

R(7) and R(8) independently of one another are defined as R(6);

or

R(7) and R(8) together are 4 or 5 methylene groups, of which one CH$_2$ group can be replaced by oxygen, sulfur, NH, N—CH$_3$ or N-benzyl;

R(B), R(C) and R(D) independently are defined as R(A);

x is zero, 1 or 2;

y is zero, 1 or 2;

R(F) is hydrogen, F, Cl, Br, I, CN, OR(12), (C$_1$–C$_8$)-alkyl, O$_p$(CH$_2$)$_f$C$_g$F$_{2g+1}$, (C$_3$–C$_8$)-cycloalkyl or (C$_1$–C$_9$)-heteroaryl;

p is zero or 1;

f is zero, 1, 2, 3 or 4;

g is 1, 2, 3, 4, 5, 6, 7 or 8;

R(12) is (C$_1$–C$_8$)-alkyl, (C$_1$–C$_4$)-perfluoroalkyl, (C$_3$–C$_8$)-alkenyl, (C$_3$–C$_8$)-cycloalkyl, phenyl or benzyl, the phenyl nucleus not being substituted or being substituted by 1–3 substituents selected from the group consisting of F, Cl, CF$_3$, methyl, methoxy and NR(13)R(14);

R(13) and R(14) are H, (C$_1$–C$_4$)-alkyl or (C$_1$–C$_4$)-perfluoroalkyl;

R(E) is defined independently as R(F);

R(1) is defined independently as T;

or

R(1) is hydrogen, —O$_k$C$_m$H$_{2m+1}$, —O$_n$(CH$_2$)$_p$C$_q$F$_{2q+1}$, F, Cl, Br, I, CN, —(C=O)—N=C(NH$_2$)$_2$, —SO$_r$R(17), —SO$_{12}$NR(31)R(32), —O$_u$(CH$_2$)$_v$C$_6$H$_5$, —O$_{u2}$—(C$_1$–C$_9$)-heteroaryl or —S$_{u2}$—(C$_1$–C$_9$)-heteroaryl;

k is zero or 1;
m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1 or 2;
r2 is zero, 1 or 2;
R(31) and R(32) independently of one another are hydrogen, $(C_1-C_8)$-alkyl or $(C_1-C_8)$-perfluoroalkyl;
or
R(31) and R(32) are, together, 4 or 5 methylene groups of which one $CH_2$ group can be replaced by oxygen, S, NH, N—$CH_3$ or N-benzyl;
R(17) is $(C_1-C_8)$-alkyl;
u is zero or 1;
u2 is zero or 1;
v is zero, 1, 2, 3 or 4; where the phenyl nucleus is not substituted or is substituted by 1–3 substituents selected from the group consisting of F, Cl, $CF_3$, methyl, methoxy, —$(CH_2)_w$NR(21)R(22), NR(18)R(19) and $(C_1-C_9)$-heteroaryl;
R*18), R(19), R(21) and R(22) independently of one another are $(C_1-C_4)$-alkyl or $(C_1-C_4)$-perfluoroalkyl;
w is 1, 2, 3 or 4;
where the heterocycle of the $(C_1-C_9)$-heteroaryl is unsubstituted or substituted by 1–3 substituents selected from the group consisting of F, Cl, $CF_3$, methoxy or methoxy;
R(2), R(3), R(4) and R(5) independently of one another are defined as R(1),
or
R(1) and R(2) or R(2) and R(3) in each case together are —CH—CH═CH—CH—, which is not substituted or is substituted by 1–3 substituents selected from the group consisting of F, Cl, $CF_3$, methyl, methoxy, —$(CH_2)_{w2}$NR(24)R(25) and NR(26)R(27);
R(24), R(25), R(26) and R(27) are H, $(C_1-C_4)$-alkyl or $(C_1-C_4)$-perfluoroalkyl;
w2 is 1, 2, 3 or 4;
the radical T being present in the molecule at least twice, but only three times at most;
and their pharmaceutically tolerable salts;
(HOE 97/F 082)
be) benzoylguanidines of the formula I

I in which:
R(1) is $CF_3$;
one of the substituents R(2) and R(3) is hydrogen;
and the other substituent R(2) or R(3) in each case is —C(OH)($CH_3$)—$CH_2$OH, —CH($CH_3$)—$CH_2$OH or —C(OH)($CH_3$)$_2$;
R(4) is methyl, methoxy, Cl or $CF_3$;
and their pharmaceutically tolerable salts.
(DE 195 02 895, DE 44 30 212, EP 667 341, DE 44 04 183, EP 708 088, EP 723 963, EP 0 694 537, DE 44 21 495, EP 699 660, EP 699 663, EP 699 666, DE 43 37 611, EP 0719 766, WO 94/26709, WO 96 04 241, EP 726 254, U.S. Pat. No. 4,251,545, DE 35 02 629, WO 84/000875, Kumamoto et al,. Pham. Bull. [1966], 7–13; U.S. Pat. No. 3,780,027, JP 8225513; EP 743 301)

II. Also suitable are compounds of the formula in which:
W, Y and Z are a nitrogen atom or a carbon atom substituted by R(2) or R(3) or R(4);
R(1) is hydrogen, A, Hal, —$CF_3$, —$CF_2$F, —$CHF_2$, —$CH_2CF_3$, —$C_2F_5$, —CN, —$NO_2$, -ethynyl, or an X—R';
A is alkyl having 1 to 6 carbon atoms;
Hal is F, Cl, Br or I;
X is oxygen, S or NR";
R" is hydrogen, A or a cyclic methylene chain having 3 to 7 carbon atoms;
R' is H, A, HO—A—, HOOC—A—, $(C_3-C_7)$-cycloalkyl, $(C_6-C_8)$-cycloalkylalkyl, $CF_3$, $CH_2$F, $CHF_2$, $CH_2$—$CF_3$, Ph, —$CH_2$—Ph or Het;
Ph is phenyl, naphthyl or biphenylyl which is unsubstituted or mono-, di or trisbustituted by A, OA, NR'R", Hal, $CF_3$;
Het is a mono- or binuclear saturated, unsaturated or aromatic heterocycle having 1 to 4 nitrogen, oxygen and/or sulfur atoms, which is unsubstituted or mono-, di- or trisubstituted by Hal, $CF_3$, A, OH, OA, —X—R', —CN, —$NO_2$, and/or carbonyl oxygen, where Het is bonded via N or an alkylene chain $C_mH_{2m}$ where m=zero tp 6;
or
R' and R" together are alkylene having 4–5 carbon atoms, in which one $CH_2$ group can also be replaced by oxygen, S, NH, N—A, N—Ph and N—$CH_2$—Ph;
R(2) and R(3) independently of one another are hydrogen, Hal, A, HO—A—, X—R', —C(═N—OH)—A, A—O—CO—$(C_1-C_4)$-alkyl-, CN, $NO_2$, COOOH, halogen-substituted A, in particular $CF_3$, $CH_2$F, $CHF_2$, $C_2F_5$, $CH_2CF_3$, or S(O)$_n$R'";
R'" is A, Ph or —Het;
n is zero, 1 or 2;
or
R(2) and R(3) independently of one another are $SO_2$NR'R", Ph or —O—Ph, —O—$CH_2$—Ph, —CO—A, —CHO, —COOA, —CSNR'R", CONR'R", —CH═CH—COOH, —CH═CH—COOA, indenyl, indanyl, decahydronaphthyl, cyclopentenyl, dihydrothienyl, dihydrofuryl, heterobicyclyl, alkylthienyl, halothienyl, haloalkylthienyl, acylthienyl, halofuryl, haloalkylfuryl or pyrrolyl;
or
R(2) and R(3) independently of one another are R(5)—O—;
R(5) is hydrogen, A, $(C_1-C_6)$-alkenyl or $(C_3-C_7)$-cycloalkyl;
R(4) is Ph, Het, —O—Het; $CF_3$; S(O)$_n$R'", —$SO_2$NR'R", alk;

or two of the substituents R(1) to R(4) together are a group —O—CR(6)R(7)—CO—NR(8)—, where R(2) has the meaning indicated;
R(6), R(7), R(8) and R(9) independently of one another are H or A;
or
R(8) is (C$_5$–C$_7$)-cycloalkyl;
or
R(8) is cyano;
alk is straight-chain or branched (C$_1$–C$_8$)-alkyl or (C$_3$–C$_8$)-cycloalkyl, which is unsubstituted or mono-, di- or trisubstituted by A;
or
alk is an ethenyl or ethynyl radical which is substituted by H, A, Ph or Het.
[DE 41 27 026, DE 43 37 609, JP 07025766, Edward j. Cragoe, Jr., DIURETICS (Chemistry, Pharmacology and Medicine), J. Wiley & Sons (1983), 303–341]

III. Compounds of the formula in which
X is H, Hal, (Hal)$_3$C—, (C$_1$–C$_6$)-alkyl, (C$_3$–C$_6$)-cycloalkyl, substituted phenyl, (C$_1$–C$_5$)-alkyl-S— or (C$_1$–C$_5$)-alkyl-SO$_2$—;
Y is NH$_2$ or substituted amino;
or
X and Z together are a —(CH$_2$)$_4$— or a 1,3-butadienylene chain;
or
Z is H, Hal, OH, Hs, (C$_1$–C$_5$)-alkyl, (C$_3$–C$_6$)-cycloalkyl, substituted phenyl;
or
Z is an amino group —NR(1)R(2);
R(1) is H, straight- or branched-chain, optionally substituted (C$_1$–C$_8$)-alkyl, which can be interrupted by oxygen;
or
R(1) is (C$_3$–C$_8$)-alkenyl, (C$_3$–C$_8$)-alkynyl, (C$_3$–C$_7$)-cycloalkyl or OH-substituted phenyl or OH-substituted phenyl-(C$_1$–C$_4$)-alkyl or OH-substituted (C$_3$–C$_7$)-cycloalkyl;
R(2) is 1-morpholino, hydrogen or a straight or branched (C$_1$–C$_8$)-alkyl chain, which can be interrupted by oxygen or an amino group, which straight or branched (C$_1$–C$_8$)-alkyl chain is unsubstituted or substituted by a substituted or unsubstituted mono- or polynuclear heterocycle which contains nitrogen, oxygen or sulfur atoms;
or
which alkyl chin is substituted by phenyl, optionally mono- or polysubstituted by (C$_1$–C$_4$)-alkoxy, optionally substituted by OH, alkylamino, alkyl or phenyl;
or
by an aminocarbonyl group
or
by hydroxyl or (C$_1$–C$_4$)-alkoxy groups,
or
R(2) is phenyl, unsubstituted or substituted by alkyl, alkoxy, an amino group, which as substituents carries:
H, a mono- or polynuclear hetercycle which contains nitrogen, oxygen or sulfur atoms, which is unsubstituted or substituted by H, Hal or (C$_1$–C$_4$)-alkyl;
a phenyl radical, unsubstituted or substituted by a substituent selected from the group consisting of (C$_1$–C$_4$)-alkyl, (C$_1$–C$_4$)-alkoxy, Hal and OH;
or
R(2) is 1-piperidino, unsubstituted or substituted in the 4-position by an acyl radical of an aliphatic, alicyclic, aromatic or heteroaromatic carboxylic acid, (C$_1$–C$_8$)-alkyl, which for its part can be substituted by OH or (C$_1$–C$_4$)-alkoxy or a (C$_1$–C$_4$)-alkoxy-substituted phenyl radical;
or
R(2) is amidino, which is unsubstituted or substituted by phenyl, which is unsubstituted or substituted by Hal or alkyl;
or
R(2) is an acyl radical of an aliphatic, alicyclic, aromatic or heteroaromatic carboxylic acid,
or
R(2) is a (C$_1$–C$_8$)-alkyl chain, which can be substituted by a phenyl radical carring OH, alkoxy or alkyl radicals,
or
R(1) and R(2) together with the nitrogen atom to which they are bonded, are a piperazine ring, which is unsubstituted or via a (C$_1$–C$_6$)-methylene chain carries a mono- or polynuclear heterocycle, which contains nitrogen, oxygen or sulfur,
Hal is F, Cl, Br or I.
(EP 708 091, EP 622 356, JP 5-125085)

IV. Likewise suitable are indoloylguanidine derivatives of the formula in which
R(2) is hydrogen, unsubstituted or substituted (C$_1$–C$_8$)-alkyl, (C$_3$–C$_7$)-cycloalkyl, OH, (C$_1$–C$_6$)-alkyl-O—, an aromatic radical or a group —CH$_2$—R(20);
R(20) is (C$_2$–C$_6$)-alkenyl or (C$_2$–C$_6$)-alkynyl;
R(1) is 1 to 5 identical or different substituents, which are: hydrogen, unsubstituted or substituted (C$_1$–C$_8$)-alkyl, (C$_2$–C$_8$)-alkenyl, (C$_2$–C$_6$)-alkynyl, (C$_3$–C$_7$)-cycloalkyl, halogen, —NO$_2$, (C$_2$–C$_8$)-alkanoyl, arylalkanoyl having up to 10 carbon atoms, aroyl having upt to 11 carbon atoms, —COOH, ($C_2$–$C_6$)-alkoxycarbonyl, an aromatic group or one of the following mentioned groups: —OR (3), —NR(6)R(7) or —S(O)$_n$R(40);

R(3) is hydrogen, ($C_1$–$C_8$)-alkyl, substituted ($C_1$–$C_8$)-alkyl, ($C_3$–$C_7$)-cycloalkyl, an aromatic radical or a group —$CH_2$—R(30) R(30) is alkenyl ro alkynyl;

R(6) and R(7) independently of one another are hydrogen, unsubstituted or substituted ($C_1$–$C_8$)-alkyl, ($C_3$–$C_7$)-cycloalkyl, ($C_2$–$C_8$)-alkanoyl, an arylalkanoyl group having up to 10 carbon atoms, an aroyl group having up to 11 carbon atoms, an aromatic group or —$CH_2$—R (60);

R(60) is ($C_2$–$C_6$)-alkenyl or ($C_2$–$C_6$)-alkynyl;

or

R(6) and R(7) together with the nitrogen atom are a 5–7-membered cyclic amine, which can additionally contain further heteroatoms in the ring;

n is zero, 1 or 2;

R(40) is unsubstituted or substituted ($C_1$–$C_8$)-alkyl, or an aromatic group, or a group

A is oxygen, —S(O)$_n$— or —N(R50)—; R(50) is hydrogen or ($C_1$–$C_8$)-alkyl;

R' is hydrogen, unsubstituted or substituted ($C_1$–$C_8$)-alkyl, in which the ring represents a saturated 3–8membered heterocycle having a nitrogen atom, said substituted alkyl carries one or more groups selected from teh group consisting of halogen, —OH, ($C_1$–$C_6$)-alkoxy, —CN, —COOH, ($C_2$–$C_6$)-alkoxycarbonyl, ($C_2$–$C_6$)-alkanoyl, arylalkanoyl having upt to 10 carbon atoms, aroyl having up to 11 carbon atoms, an aromatic gorup, —CONR(4)R(5), R(4) and R(5) identically or differently are hydrogen or ($C_1$–$C_8$)-alkyl;

or

R(4) and R(5) are connected to one another and together form a 5–7-membered cyclic amine which can additionally contain further heteroatoms in the ring, or said substituted alkyl carries a group

in which:

E is a nitrogen atom or a CH group;

R" is hydrogen, ($C_1$–$C_8$)-alkyl which is unsubstituted or substituted by OH, ($C_1$–$C_6$)-alkoxy, —CN, —COOH, ($C_2$–$C_6$)-alkoxycarbonyl, ($C_2$–$C_6$)-alkanoyl, aralkanoyl having upt to 10 carbon atoms, aroyl having up to 11 carbon atoms, an aromatic group, —NR(6)R(7), —CONR(4)R(5);

R(4) and R(5) independently of one another are hydrogen or ($C_1$–$C_8$)-alkyl;

where the cyclic system of the formula

is a 3–8-membered saturated aliphatic or heterocyclic ring system having a nitrogen atom, and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl, and where the aryl radicals mentioned can be unsubstituted or substituted by unsubstituted ($C_1$–$C_8$)-alkyl or substituted ($C_1$–$C_8$)-alkyl, halogen, —$NO_2$, ($C_2$–$C_6$)-alkoxycarbonyl, COOH, —OR(3), NR(6)R(7), —CONR(4)R(5), —$SO_2$NR(6)R(7) or S(O)$_n$R(40), where R(1) and the guanidinocarbonyl radical can be in any desired position of the 5- or 6-membered ring of the indole system, and the appropriate pharmaceutically tolerable salts. (WO 95 04052)

V. Additionally suitable are heterocyclic guanidine derivatives of the formula

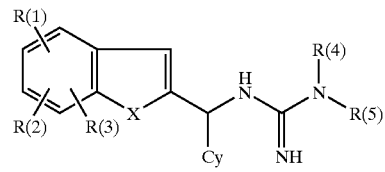

in which:

X is —O—, —S—, —NH—, —N[($C_1$–$C_4$)-alkyl]— or —N(phenyl)—;

R(1), R(2) and R(3) are hydrogen, halogen, ($C_1$–$C_4$)-alkyl, ($C_1$–$C_4$)-alkyl-O—, phenyl, benzyl;

or

R(4) and R(5) independently of one another are hydrogen, ($C_1$–$C_{12}$)-alkyl, benzhydryl, aralkyl, which is unsubstituted or substituted by one or more substituents from the groups halogen, ($C_1$–$C_4$)-alkyl, ($C_1$–$C_4$)-alkyl-O— or —$CF_3$, —$(CH_2)_m$—$CH_2$—T, m is zero to 3;

T is —CO—O—T(1);

T(1) is hydrogen or ($C_1$–$C_4$)-alkyl;

Cy is a benso-fused unsaturated or dihydro-5-membered ring heterocycle

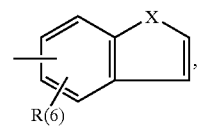

a pyrazole or imidazole ring of the formula

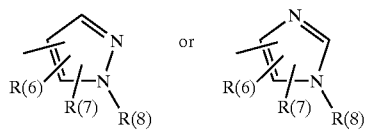

a naphthyl radical or a dihydro- or tetrahydronaphtyl radical

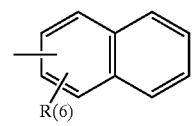

a 2-, 3- or 4-pyridyl radical

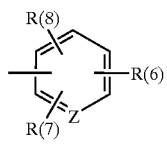

Z is N— or CH;

a thienyl radical

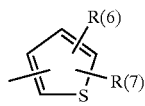

R(6) is hydrogen, halogen, hydroxyl, $(C_1-C_{10})$-alkyl, $(C_1-C_{10})$-alkyl-O—, phenoxy, $(C_1-C_{10})$-alkyloxymethyloxy- or $—(O)_nS—R(9)$;

R(9) is $(C_1-C_{10})$-alkyl, thienyl, pyridyl, thiazolyl, thiadiazolyl, imidazolyl, pyrazolyl or phenyl, each of which is unsubstituted or mono- or disubstituted y halogen, $(C_1-C_4)$-alkyl or $(C_1-C_4)$-alkyl-O—:

R(7) and R(8) is hydrogen, halogen, hydroxyl, $(C_1-C_{10})$-alkyl, $(C_1-C_{10})$-alkyl-O—, phenyl, phenoxy or $(C_1-C_{10})$-alkoxymethyloxy;

or

Cy is phenyl, which is unsubstituted or mono- or disubstituted by halogen, $(C_1-C_4)$-alkyl or $(C_1-C_4)$-alkyl-O—;

or

Cy is —Gr—Am;

Gr is $—R(13)—R(12)—(CH_2)_qC[W][W(1)]—(CH_2)_q—$; R(13)R(14)— or R(15)—;

R(12) is a single bond, —O—, $—(O)_nS—$, —CO— or —CONH—;

R(13) is a single bond, phenyl, thienyl, pyridyl, thiazolyl, thiadiazolyl, imidazolyl or pyrazolyl;

R(14) is a single bond or $SO_2—$;

R(15) is $(C_2-C_{10})$-alkenyl— or $(C_2-C_{10})$-alkynyl;

W and W(1) independently of one another are hydrogen, $(C_1-C_4)$-alkyl;

or

W and W(1) cyclically connected to one another are a $(C_3-C_8)$-hydrocarbon ring;

q and q' are zero to 9;

Am is —NR(10)R(11);

R(10) is hydrogen, $(C_1-C_4)$-alkyl or benzyl,

R(11) is $(C_1-C_4)$-alkyl, phenyl or benzyl;

or

R(10) and R(11) together are a $(C_3-C_{10})$-alkylene group, which is unsubstituted or substituted by —COOH, $(C_1-C_5)$-alkoxycarbonyl, $(C_2-C_4)$-hydroxyl-alkylene or benzyl;

or

Am is pyrrolyl, pyridyl, pyrazolyl, morpholinyl, dihydropyridyl, tetrahydropyridyl, quinuclidinyl, imidazolyl, 3-azabicyclo[3.2.1]octyl, shich is unsubstituted or substituted by $(C_1-C_4)$-alkyl, or Am is azabicyclo[3.2.1]nonyl;

or

Am is a piperazine group of the formula

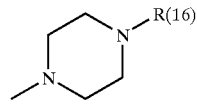

R(16) is hydrogen, $(C_1-C_4)$-alkyl, $(C_3-C_6)$-cycloalkyl, phenyl, tolyl, methoxyphenyl, halophenyl, halphenyl, diphenylmethylene, benzyl or pyridyl;

or

Am is an azido group $—(O)_t—(CH_2)q—C[W][W(1)]—(CH_2)q'—N_3$; t is zero or 1;

where W and W(1) have the previously indicated meaning;

and the optical enantiomers and the pharmacologically tolerable salts.

VI. Furtherore suitable are the guanidine compounds, as described in EP-743 301 (DE 195 17 848), EP 758 644 (DE 195 29 612), EP 760 365 (DE 195 31 138)

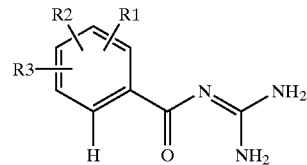

where R1=R2 is H, halo, alkyl, CN, $NO_2$, perlfuoroalkyl, $SO_nCF_3$; $R_3$ is $CH=CH_2$, $CH_2\_CH=CH_2$, $CH_2\_CH=CH_2$, cycloalkenyl, cycloalkenylalkyl;

R4 is alkyl, (substituted) phenyl, or as described in DE 195 48 708, WO 97 25 310, WO 97 27 183, DE 196 01 303, EP 787 728, JP 82 25 513, JP 090 59 245, JP 090 67 332, JP 090 67 340, WO 97 11 055 and EP 743 301.

Preference is given to the use of the following compounds:

I. (HOE 89/F 288-U.S. Pat. No. 5,292,755)

a) benzoylguanidines of the formula I

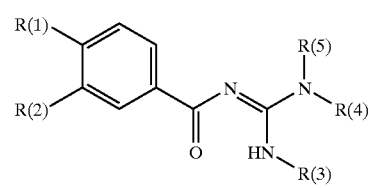

in which:

R(1) or R(2) is $R(6)—S(O)_3-$ or $R(7)R(8)N—O_2S—$;

and the other substituent R(1) or R(2) in each case is H, F, Cl, Br, $(C_1-C_4)$-alkyl, $(C_1-C_4)$-alkoxy or phenoxy, which is unsubstituted or substituted by 1–3 substituents selected from the group consisting of fluorine, chorine, methyl and mehtoxy;

or the other substituent $R(6)_n$ or R(7)R(8)N—;

n is zero, 1 or 2;

R(6) is $(C_1-C_6)$-cycloalkyl, cyclopentylmethyl, cyclohexylmethyl or phenyl, which is unsubstituted or substituted by 1–3 substituents selected from the group consisting of fluorine, chlorine, methyl and methoxy;

R(7) and R(8) identically or differently are H or $(C_1-C_6)$-alkyl;

or
R(7) is phenyl-$(CH_2)_m$;
m is 1–4;
or
R(7) is phenyl; which is unsubstituted or substituted by 1–2 substituents selected from the group consisting of fluorine, chlorine, methyl and methoxy;
or
R(7) and R(8) together are a straight-chain or branched $(C_4-C_7)$-chain, where the chain can additionally be interrupted by O, S or NR(9) is H or methyl;
or
R(7) and R(8) together with the nitrogen atom to which they are bonded, are a dihydroindole, tetrahydroquinoline or tetrahydroisoquinoline system;
R(3), R(4) and R(5) independently of one another are H or $(C_1-C_2)$-alkyl,
or
R(3) and R(4) together are a $(C_2-C_4)$-alkylene chain;
or
R(4) and R(5) together are a $(C_4-C_7)$-alkylene chain;
and their pharmaceutically tolerable salts;
(HOE 92/F 034 U.S. Pat. No. 5,373,924)
b) benzoylguanidines of the formula I

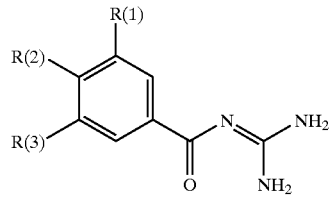

in which:
R(1) is $R(4)-SO_m$ or $R(5)R(6)N-SO_2-$;
m is zero, 1 or 2;
R(4) and R(5) are $C_1-C_8$-alkyl, $C_3-C_6$-alkenyl, or $-C_nH_{2n}-R(7)$;
n is zero, 1, 2, 3 or 4;
R(7) is $C_5-C_7$-cycloalkyl or phenyl, which is unsubstituted or substituted by 1–3 substituents selected from the group consisting of F, Cl, $CF_3$, methyl, methoxy and NR(8)R(9);
R(8) and R(9) are H or $C_1-C_4$-alkyl;
or
R(5) is H;
R(6) is H or $C_1-C_4$-alkyl,
or
R(5) and R(6) together are 4 or 5 methylene groups, of which one $CH_2$ group can be replaced by an O, S, NH, $N-CH_3$ or N-benzyl;
R(2) is hydrogen, F, Cl, Cr, $(C_1-C_4)$-alkyl-, $O-(CH_2)_m C_pF_{2p+1}$ or $-X-R(10)$;
m is zero or 1;
p is 1, 2, or 3;
X is O, S or NR(11);
R(10) is H, $C_1-C_6$-alkyl, $C_1-C_4$-cycloalkyl, cyclohexylmethyl, cyclopentylmethyl or $-C_nH_{2n}-R(12)$;
n is zero, 1, 2, 3 or 4;
R(12) is phenyl, which is unsubstituted or substituted by 1—3 substituents selected from the group consisting of F, Cl, $CF_3$, methyl, methoxy, und NR(8)R(9);
R(8) and R(9) are H or $C_1-C_4$-alkyl;
R(11) is hydrogen or $C_1-C_3$-alkyl;
or
R(10) and R(11) together are 4 or 5 methylene groups, of which one $CH_2$ group can be replaced by O, S, NH, $N-CH_3$ or N-benzyl;
R(3) is defined as R(1), or is $C_1-C_6$-alkyl, nitro, cyano, trifluoromethyl, F,
Cl, Br, I or $-X-R(10)$;
X is O, S or NR(11);
R(10) is H, $C_1-C_6$-alkyl, $C_5-C_7$-cycloalkyl, cyclohexylmethyl, cyclopentylmethyl or $-C_nH_{2n}-R(12)$;
n is zero to 4;
R(12) is phenyl, which is unsubstituted or substituted by 1–3 substituents selected from the group consisting of F, Cl, $CF_3$, methyl, methoxy and NR(8)R(9);
R(8) and R(9) are H or $C_1-C_4$-alkyl;
R(11) is $C_1-C_3$-alkyl,
or
R(10) and R(11) together are 4 or 5 methylene groups, of which one $CH_2$ group can be replaced by O, S, NH, $N-CH_3$ or N-benzyl;
and their pharmaceutically tolerable salts;
(HOE 92/F 035 EP-Offenlegungsschrift 556 673)
c) ortho-substituted benzoylguanidines of the formula I

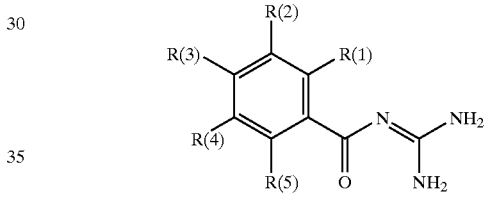

in which:
R(1) is F, Cl, Br, I, $C_1-C_6$-alkyl or $-X-R(6)$;
X is O, S, NR(7) or Y—ZO;
Y is O or NR(7);
Z is C or SO;
R(6) is H, $C_1-C_6$-alkyl, $C_5-C_7$-cycloalkyl, cyclohexylmethyl, cyclopentylmethyl, $-(CH_2) mC_pF_{2p+1}$ or $-C_nH_{2n}-R(8)$;
m is zero or 1;
p is 1–3;
n is zero to 4;
R(8) is phenyl, which is unsubstituted or substituted by 1–3 substituents selected from the group consisting of F, Cl, $CF_3$, methyl, methoxy and NR(9)R(10);
R(9) and R(10) are H or $C_1-C_4$-alkyl;
R(7) is H or $C_1-C_3$-alkyl;
or
R(6) and R(7) together are 4 or 5 methylene groups, of which one $CH_2$ group can be replaced by O, S, NH, $N-CH_3$ or N-benzyl;
R(3) is H or $-X-R(6)$;
X is O, S, NR(7) or Y—ZO;
R(7) is H or $C_1-C_3$-alkyl;
Y is O or NR(7); where Y is bonded to the phenyl radical of the formula I,
Z is C or SO;
R(6) is H, $C_1-C_6$-alkyl, $C_5-C_7$-cycloalkyl, cyclohexylmethyl, cyclopentylmethyl, $-(CH_2) mC_pF_{2p+1}$ or $-C_nH_{2n}-R(8)$;

m is zero or 1;
p is 1–3;
n is zero to 4;
R(8) is phenyl, which is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
or
R(6) and R(7) together are 4 or 5 methylene groups, of which one $CH_2$ group can be replaced by O, S, NH, N—$CH_3$ or N-benzyl;
R(2) and R(4) identically or differently are R(11)—$SO_q$— or R(12)R(13)N—$SO_2$—;
q is zero–2;
R(11) is $C_1$–$C_4$-alkyl, which is unsubstituted or carries phenyl as a substituent, where phenyl is unsubstituted or substituted by 1–3 substituents selected from the group consisting of F, Cl, $CF_3$, methyl, methoxy and NR(9)R(10);
R(9) and R(10) are H or $C_1$–$C_4$-alkyl;
R(12) and R(13) are defined as R(6) and R(7);
or
one of the two radicals R(2) or R(4) is hydrogen or is defined as R(1);
R(5) is H, methyl, F, Cl or methoxy,
and their pharmaceutically tolerable salts;
(HOE 92/F 036—U.S. Pat. No. 5,364,868)
d) benzoylguanidines of the formula I

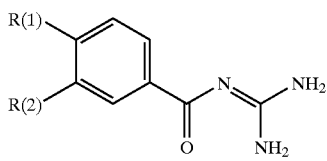

in which:
R(1) or R(2) is an amino group —NR(3)R(4);
R(3) and R(4) identically or differently are H, $C_1$–$C_6$-alkyl or $C_3$–$C_7$-cycloalkyl;
or
R(3) is phenyl-$(CH_2)_p$—;
p is 0, 1, 2, 3 or 4;
or
R(3) is phenyl, where the phenyl in each case is unsubstituted or carries one to two substituents selected from the group consisting of fluorine, chlorine, methyl and methoxy;
or
R(3) and R(4) together can be a straight-chain or branched $C_4$–$C_7$-methylene chain, where one —$CH_2$— member of the methylene chain can be replaced by oxygen, S or NR(5); R(5) is H or lower alkyl;
the other substituent R(1) or R(2) in each case is H, F, Cl, $C_1$–$C_4$-alkyl, $C_1$–$C_4$-alkoxy, $CF_3$, $C_mF_{2m+1}$—$CH_2$—, benzyl or phenoxy, where the respective phenyl radical is unsubstituted or carries one to two substituents selected from the group consisting of methyl, methoxy, fluorine and chlorine;
m is 1, 2 or 3;
and their pharmaceutically tolerable salts;
(92/F 197 K—NZ 248 013)
e) benzoylguanidines of the formula I

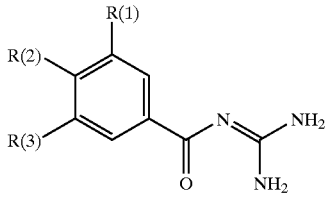

in which:
R(1) is R(4)—$SO_m$ or R(5)R(6)N—$SO_2$—;
m is zero, 1 or 2;
R(4) and R(5) are $C_1$–$C_8$-alkyl, $C_3$–$C_6$-alkenyl or —$C_nH_{2n}$—R(7);
n is zero, 1, 2, 3 or 4;
R(7) is $C_5$–$C_7$-cycloalkyl or phenyl, which is unsubstituted or substituted by 1–3 substituents selected from the group consisting of F, Cl, $CF_3$, methyl, methoxy and NR(8)R(9);
R(8) and R(9) are H or $C_1$–$C_4$-alkyl;
or
R(5) is H;
R(6) is H or $C_1$–$C_4$-alkyl;
or
R(5) and R(6) together are 4 or 5 methylene groups, of which one $CH_2$ group can be replaced by an O, S, NH, N—$CH_3$ or N-benzyl;
R(2) is hydrogen, straight-chain or branched $(C_5$–$C_8)$-alkyl, —CR(13)=CHR(12) or —C≡CR(12);
R(12) is phenyl, which is unsubstituted or substituted by 1–3 substituents selected from the group consisting of F, Cl, $CF_3$, methyl, methoxy and NR(14)R(15);
R(14) and R(15) are H or $(C_1$–$C_4)$-alkyl;
or
R(12) is $(C_1$–$C_9)$-heteroaryl, which is unsubstituted or substituted as phenyl,
or
R(12) is $(C_1$–$C_6)$-alkyl, which is unsubstituted or substituted by 1–3 OH,
or
R(12) is $(C_3$–$C_8)$-cycloalkyl;
R(13) is hydrogen or methyl,
or
R(12) is $(C_3$–$C_8)$-cycloalkyl, $(C_3$–$C_8)$-cycloalkyl-$(C_1$–$C_4)$-alkyl, phenyl, $C_6H_5$—$(C_1$–$C_4)$-alkyl, naphthyl, biphenylyl, 1,1-diphenyl-$(C_1$–$C_4)$-alkyl, cyclopentadienyl, pyridyl, pyrrolyl, furanyl, thienyl, thiazolyl, oxazolyl, indenyl, quinolyl, indolyl, benzofuranyl, benzothienyl, benzothiazolyl, benzoxazolyl, imidazolyl, pyrazolyl, triazolyl, tetrazolyl, isoxazolyl, isothiazolyl, pyrazinyl, pyrimidinyl, pyridazinyl, indazolyl, isoquinolyl, phthalazinyl, quinoxalinyl, quinazolinyl or cinnolinyl;
R(3) is defined as R(2);
and where the aromatic substituents R(2) and R(3) are unsubstituted or substituted by 1–3 substituents from the groups F, Cl, $CF_3$, $(C_1$–$C_4)$-alkyl or -alkoxy, or NR(10)R(11) with R(10) and R(11) being H or $(C_1$–$C_4)$-alkyl;
and their pharmaceutically tolerable salts;
(HOE 92/F 303 K—EP-Offenlegungsschrift 589 336, NZ 248 703)

f) benzoylguanidines of the formula I

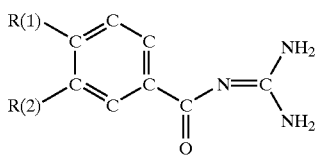

in which:
R(1) or R(2) is R(3)—S(O)$_n$— or R(4)R(5)N—SO$_2$—
the other substituent R(1) or R(2) in each case is H, OH, F, Cl, Br, I, C$_1$–C$_4$-alkyl, C$_1$–C$_4$-alkoxy, benzyloxy or phenoxy, which is unsubstituted or carries one to three substituents selected from the group consisting of fluorine, chlorine, methyl, methoxy, hydroxyl and benzyloxy, R(3)—S(O)$_n$, —NR(4)R(5) or 3,4-dehydropiperidine R(3) is C$_1$–C$_6$-alkyl, C$_5$–C$_7$-cycloalkyl, cyclopentylmethyl, cyclohexylmethyl or phenyl, which is unsubstituted or substituted by one to three substituents selected from the group consisting of fluorine, chlorine, methyl and methoxy;

R(4) and R(5) identically or differently, are H or C$_1$–C$_6$-alkyl;

or

R(4) is phenyl-(CH$_2$)$_m$—;
m is 1, 2, 3 or 4;

or

R(4) is phenyl, which is unsubstituted or carries on to two substituents selected from the group consisting of fluorine, chlorine, methyl and methoxy;

or

R(4) and R(5) together are a straight-chain or branched C$_4$–C$_7$-chain, where the chain can additionally be interrupted by O, S or NR(6), R(6) is H or methyl;

or

R(4) and R(5) together with the nitrogen atom to which they are bonded, are a dihydroindole, tetrahydroquinoline or tetrahydroisoquinoline system;

n is zero, 1 or 2;

and their pharmaceutically tolerable salts;
(92/F 304—U.S. Pat. No. 5,416,094)

g) isoquinolines of the formula I

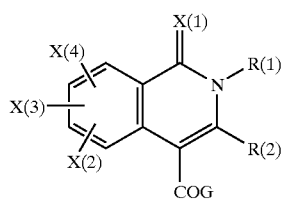

in which:
R(1) is hydrogen, alkyl, cycloalkyl, arylalkyl, alkenyl, substituted aminoalkyl or an aryl or heteroaryl ring; where the rings are unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, trifluoromethyl, R(2) is hydrogen, halogen, alkyl or aryl; which is unsubstituted or substituted by 1–3 groups selected from the group consisting of halogen, nitro, amino, mono(lower alkyl)amino, di(lower alkyl)amino, lower alkyl, lower alkoxy, benzyloxy, phenoxy, hydroxyl, G is —N=C{[NR(3)R(4)][NR(5)R(6)]}

X(2), X(3) and X(4) independently of one another are hydrogen, halogen, nitro, amino, alkyl, sulfonamide, mono)lower alkyl)amino, di(lower alkyl)amino, lower alkyl, benzyloxy, hydroxyl;

X(1) is hydrogen, oxygen, sulfur or NR(7);

R(7) is hydrogen, alkyl, cycloalkyl, arylalkyl, alkenyl, substituted aminoalkyl or an aryl or a heteroaryl ring; which rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl and trifluoromethyl; in which substituents each alkyl chain or alkenyl chain can be interrupted by oxygen, sulfur or NR(8);

R(8) is hydrogen, alkyl, cycloalkyl, arylalkyl, alkenyl, substituted aminoalkyl or an aryl or heteroaryl ring, which rings are unsubstituted or substituted by 1–3 groups selected from the group consisting of halogen, nitro, amino, mono(lower alkyl)amino, di(lower alkyl) amino, lower alkyl, lower alkoxy, benzyloxy, phenoxy, hydroxyl and trifluoromethyl;

and their pharmaceutically acceptable salts;
(92/F 404—EP 602 522, NZ 250 438)

h) compounds of the formula I

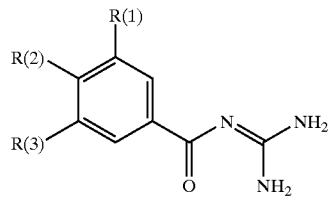

in which:
R(1) is hydrogen, F, Cl, Br, I, —NO$_2$, —C≡N, —CF$_3$, R(4)—SO$_m$ or R(5)R(6)N—SO$_2$—;

m is zero, 1 or 2;

R(4) and R(5) are (C$_1$–C$_8$)-alkyl, (C$_3$–C$_6$)-alkenyl, —C$_n$H$_{2n}$—R(7) or CF$_3$;

n is zero, 1, 2, 3 or 4;

R(7) is (C$_3$–C$_7$)-cycloalkyl or phenyl, which is not substituted or is substituted by 1–3 substituents selected from the group consisting of F, Cl, CF$_3$, methyl, methoxy and NR(8)R(9);

R(8) and R(9) are H or C$_1$–C$_4$-alkyl;

or

R(5) is H;

R(6) is H or (C$_1$–C$_4$)-alkyl;

or

R(5) and R(6) together are 4 or 5 methylene groups, of which one CH$_2$ group can be replaced by oxygen, S, NH, N—CH$_3$ or N-benzyl;

R(2) is —SR(10), —OR(10), —NHR(10), —NR(10)R(11), —CHR(10)R(12),
—[CR(12)R(13)OR(13')], —{C—[CH$_2$—OR(13')]R(12)(R(13)} or —[CR(18)R(17)]$_p$—(C))—[CR(19)R(20)]$_q$—R(14); R(10) and R(11) identically or differently are —[CHR(16)]$_s$—(CH$_2$)$_p$—(CHOH)$_q$—(CH$_2$)$_r$—(CHOH)$_r$—R(21) or —(CH$_2$)$_p$—O—(CH$_2$—CH$_2$O)$_q$—R(21), R(21) is hydrogen, methyl,
p, q, r identically or differently are zero, 1, 2, 3 or 4;
s is zero or 1;
t is 1, 2, 3 or 4;
R(12) and R(13) identically or differently are hydrogen, $(C_1-C_6)$-alkyl or, together with the carbon atom carrying them, are a $(C_3-C_8)$-cycloalkyl,
R(13') is hydrogen or $(C_1-C_4)$-alkyl;
R(14) is H, $(C_1-C_6)$-alkyl, $(C_3-C_8)$-cycloalkyl or $-C_aH_{2a}-R(15)$;
a is zero, 1, 2, 3 or 4;
R(15) is phenyl, which is unsubstituted or substituted by 1–3 substituents selected from the group consisting of F, Cl, $CF_3$, methyl, methoxy and NR(8)R(9); R(8) and R(9) are H or $(C_1-C_4)$-alkyl;
or
R(15) is $(C_1-C_9)$-heteroaryl, which is unsubstituted or substituted as phenyl,
or
R(15) is $(C_1-C_6)$-alkyl, which is unsubstituted or substituted by 1–3 OH;
R(16), R(17), R(18), R(19) and R(20) are hydrogen or $(C_1-C_3)$-alkyl;
R(3) is defined as R(1),
or
R(3) is $(C_1-C_6)$-alkyl or $-X-R(22)$;
X is oxygen, S or NR(16); R(16) is H or $(C_1-C_3)$-alkyl;
or
R(22) and R(16) together are 4 or 5 methylene groups, of which one $CH_2$ group can be replaced by oxygen, S, NH, N—$CH_3$ or N-benzyl;
R(22) is defined as R(14);
and their pharmaceutically tolerable salts;
(HOE 92/F 405—EP 602 523, NZ 250 437)
i) benzoylguanidines of the formula I

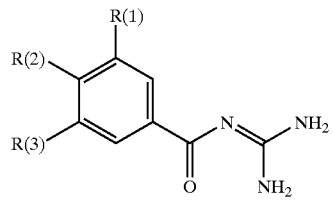

in which:
R(1) is hydrogen, F, Cl, Br, I, $-NO_2$, $-C\equiv N$, R(16)—$C_pH_{2p}-O_q$, R(4)—$SO_m$ or R(5)R(6)N—$SO_2-$;
m is zero, 1 or 2;
p is zero or 1;
q is zero, 1, 2 or 3;
R(16) is $C_rF_{2r+1}$;
r is 1, 2 or 3;
R(4) and R(5) are $(C_1-C_8)$-alkyl, $(C_3-C_6)$-alkenyl, $-C_nH_{2n}-R(7)$ or $CF_3$;
n is zero, 1, 2, 3 or 4;
R(7) is $(C_3-C_7)$-cycloalkyl or phenyl, which is not substituted or is substituted by 1–3 substituents selected from the group consisting of F, Cl, $CF_3$, methyl, methoxy and NR(8)R(9);
R(8) and R(9) are H or $C_1-C_4$-alkyl;
or
R(5) is H;
R(6) is H or $(C_1-C_4)$-alkyl;

or
R(5) and R(6) together are 4 or 5 methylene groups, of which one $CH_2$ group can be replaced by oxygen, S, NH, N—$CH_3$ or N-benzyl,
R(2) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;
or
R(2) is $-SR(10)$, $-OR(10)$, $-NR(10)R(11)$, $-CR(10)R(11)R(12)$;
R(10) is $-C_aH_{2a}-(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;
a is zero, 1 or 2;
R(11) and R(12) independently of one another are defined as R(10) or are hydrogen or $(C_1-C_4)$-alkyl;
R(3) is defined as R(1), or is $(C_1-C_6)$-alkyl or $-X-R(13)$;
X is oxygen, S, or NR(14);
R(14) is H or $(C_1-C_3)$-alkyl;
R(13) is H, $(C_1-C_6)$-alkyl, $(C_3-C_8)$-cycloalkyl or $-C_bH_{2b}-R(15)$;
b is zero, 1, 2, 3 or 4;
or
R(13) and R(14) together are 4 or 5 methylene groups, of which one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(8)R(9); R(8) and R(9) are H or $(C_1-C_4)$-alkyl;
and their pharmaceutically tolerable salts;
(HOE 92/F 411—NZ 250 450, EP 603 650)
k) benzoylguanidines of the formula I

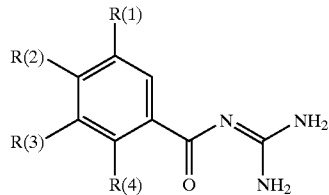

in which:
one of the substituents R(1), R(2), R(3) or R(4) is an amino group $-NR(5)[C_nH_{2n}-R(6)]$;
R(5) is hydrogen or $C_{(1-6)}$-alkyl;
n is zero, 1, 2, 3 or 4;
R(6) is H or $C_{(1-4)}$-alkyl;
in which one $CH_2$ group can be replaced by 1 sulfur atom or a group NR(7);
R(7) is hydrogen, methyl or ethyl;
or
R(6) is $C_{(3-8)}$-cycloalkyl or phenyl, which is unsubstituted or carries 1, 2 or 3 substituents selected from the group consisting of F, Cl, Br, methyl, methoxy, $-NR(8)R(9)$;
R(8) and R(9) are H, methyl or ethyl;

or
R(5) and R(6) together with the nitrogen atom are a 5-, 6- or 7-membered ring, in which 1 carbon atom can be replaced by oxygen, S or NR(10);
R(10) is H, $C_{(1-3)}$-alkyl or benzyl;
and the other substituents R(1), R(2), R(3), R(4) in each case are:
hydrogen, F, Cl, Br, I, CN, $CF_3$, $NO_2$, $CF_3$—O—, $C_mF_{2m+1}$—$CH_2$—O— or
R(11)—$C_qH_{2q}$—$X_p$—;
m is 1, 2 or 3;
q is zero, 1, 2, 3 or 4;
p is zero or 1;
X is oxygen or NR(12);
R(12) is H or $C_{(1-3)}$-alkyl;
R(11) is hydrogen, $C_{(1-6)}$-alkyl, $C_{(3-8)}$-cycloalkyl or phenyl, which is unsubstituted or substituted by 1, 2 or 3 substituents selected from the group consisting of F, Cl, $CH_3$, $CH_3$—O— and NR(13)R(14);
R(13), R(14) are H, methyl or ethyl;
and their pharmaceutically tolerable salts;
(HOE 92/F 422—EP 604 852)

l) benzoylguanidines of the formula I

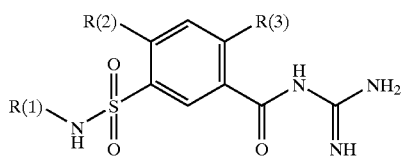

I in which:
R(1) is R(4)R(5)N—C(X)—;
X is oxygen, S or N—R(6);
R(4) and R(5) identically or differently, are H, $(C_1-C_8)$-alkyl, $(C_3-C_6)$-alkenyl or —$C_nH_{2n}$—R(7);
n is zero, 1, 2, 3 or 4;
R(7) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl;
or
R(4) and R(5) together are 4 or 5 methylene groups, of which one $CH_2$ group can be replaced by oxygen, S, NH, N—$CH_3$ or N-benzyl; R(6) is defined as R(4) or is amidine;
R(2) is H, F, Cl, Br, I, $(C_1-C_8)$-alkyl, 1-alkenyl or 1-alkynyl, $(C_3-C_8)$-cycloalkyl, $(C_3-C_8)$-cycloalkyl-$(C_1-C_4)$-alkyl, phenyl, $C_8H_5$—$(C_1-C_4)$-alkyl, naphthyl, biphenylyl, 1,1-diphenyl-$(C_1-C_4)$-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);
W is oxygen, S or NR(9);
R(8) is H, $(C_1-C_6)$-alkyl, $(C_5-C_7)$-cycloalkyl, cyclohexylmethyl, cyclopentylmethyl, —$(CH_2)_mC_pF_{2p+1}$ or —$C_qH_{2q}$—R(10);
m is zero or 1;
p is 1, 2 or 3;
q is zero, 1, 2, 3 or 4;
R(10) is phenyl, which is unsubstituted or substituted by 1–3 substituents selected from the group consisting of F, Cl, $CF_3$, methyl, methoxy and NR(11)R(12);
R(11) and R(12) are H or $(C_1-C_4)$-alkyl;
R(9) is H or $(C_1-C_3)$-alkyl;
or
R(8) and R(9) together are 4 or 5 methylene groups, of which one $CH_2$ group can be replaced by oxygen, S, NH, N—$CH_3$ or N-benzyl;
R(3) is H, F, Cl, Br, I, $(C_1-C_6)$-alkyl or —W—R(8) as defined for R(2),
and their pharmaceutically acceptable salts;
(93/F 054—NZ 250 919, EP-Offenlegungsschrift 612 723)

m) benzoylguanidines of the formula I

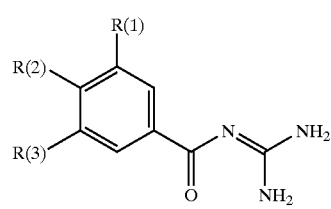

(I)

in which:
R(1), R(2), R(3) are hydrogen, F, Cl, Br, I or $(C_1-C_{12})$-alkyl;
one of the substituents R(1), R(2) or R(3) is $N_3$, CN, OH or $(C_1-C_{10})$-alkyloxy, if at least one of the remaining substituents R(1), R(2) or R(3) is a sufficiently lipophilic alkyl radical having 3 to 12 carbon atoms;
or
one of the substituents R(1), R(2) and R(3) is R(4)—$C_nH_{2n}$—$O_m$—;
m is zero or 1;
n is zero, 1, 2 or 3;
R(4) is $C_pF_{2p+1}$;
p is 1, 2 or 3, if n is zero or 1;
or
R(4) is $(C_3-C_{12})$-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or $(C_1-C_4)$-alkyl;
or one of the substituents R(1), R(2) and R(3) is —C≡CR(5) or —C[R(6)]=CR(5);
R(5) is phenyl, which is unsubstituted or substituted by 1–3 substituents selected from the group consisting of F, Cl, $CF_3$, methyl, methoxy, hydroxyl, amino, methylamino and dimethylamino, $(C_1-C_9)$-heteroaryl, which is unsubstituted or substituted as phenyl,
or
R(5) is $(C_1-C_6)$-alkyl, which is unsubstituted or substituted by 1–3 OH;
or
R(5) is $(C_3-C_8)$-cycloalkyl,
R(6) is hydrogen or methyl;
and their pharmacologically acceptable salts;

(93/F 153—EP-Offenlegungsschrift 627 413, NZ 260 660)
o) benzoylguanidines of the formula I

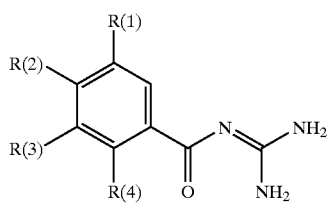

in which:
R(1) is hydrogen, F, Cl, Br, I, —NO$_2$, —C≡N, X$_o$—(CH$_2$)$_p$—(CF$_2$)$_q$—CF$_3$, R(5)—SO$_m$, R(6)—CO— or R(6)R(7)N—SO$_2$—, where
X is oxygen, S or NR(14);
m is zero, 1 or 2;
o is zero or 1;
p is zero, 1 or 2;
q is zero, 1, 2, 3, 4, 5 or 6;
R(5) and R(6) are (C$_1$–C$_8$)-alkyl, (C$_3$–C$_6$)-alkenyl, —C$_n$H$_{2n}$—R(8) or CF$_3$;
n is zero, 1, 2, 3 or 4;
R(8) is (C$_3$–C$_7$)-cycloalkyl or phenyl, which is not substituted or is substituted by 1–3 substituents selected from the group consisting of F, Cl, CF$_3$, methyl, methoxy and NR(9)R(10);
R(9) and R(10) are H or C$_1$–C$_4$-alkyl;
or
R(6) is H;
R(7) is H or (C$_1$–C$_4$)-alkyl;
or
R(6) and R(7) together are 4 or 5 methylene groups, of which one CH$_2$ group can be replaced by oxygen, S, NH, N—CH$_3$ or N-benzyl;

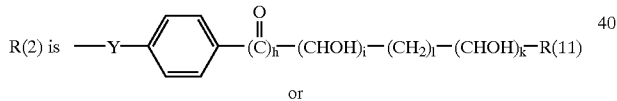

or

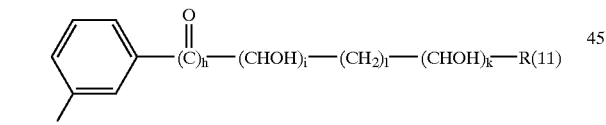

or

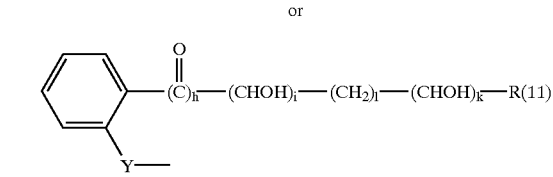

Y is oxygen, —S— or —NR(12)—;
R(11) and R(12) are hydrogen or (C$_1$–C$_3$)-alkyl;
h is zero or 1;
i, j and k independently are zero, 1, 2, 3 or 4;
but where h, i and k are not simultaneously zero,
R(3) is defined as R(1), or is (C$_1$–C$_6$)-alkyl or —X—R(13);
X is oxygen, S or NR(14);
R(14) is H or (C$_1$–C$_3$)-alkyl;
R(13) is H, (C$_1$–C$_6$)-alkyl, (C$_3$–C$_8$)-cycloalkyl or —C$_b$H$_{2b}$—R(15);

b is zero, 1, 2, 3 or 4;
or
R(13) and R(14) together are 4 or 5 methylene groups, where one CH$_2$ group can be replaced by oxygen, S, NH, N—CH$_3$ or N-benzyl;
R(15) is phenyl, which is unsubstituted or substituted by 1–3 substituents selected from the group consisting of F, Cl, CF$_3$, methyl, methoxy and NR(9)R(10);
R(9) and R(10) are H or (C$_1$–C$_4$)-alkyl;
R(4) is hydrogen, —OR(16) or —NR(16)R(17);
R(16) and R(17) independently are hydrogen or (C$_1$–C$_3$)-alkyl;
and their pharmaceutically tolerable salts;
(HOE 93/F 154—EP-Offenlegungsschrift 628 543, NZ 260 681)
p) benzoylguanidines of the formula I

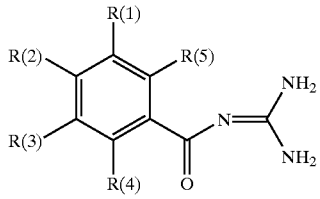

in which:
R(1) is R(6)—CO or R(7)R(8)N—CO;
R(6) is (C$_1$–C$_8$)-alkyl, (C$_1$–C$_8$)-perfluoroalkyl, (C$_3$–C$_8$)-alkenyl or —C$_n$H$_{2n}$—R(9);
n is zero, 1, 2, 3 or 4;
R(9) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11);
R(10) and R(11) are H, (C$_1$–C$_4$)-alkyl or (C$_1$–C$_4$)-perfluoroalkyl;
R(7) is H, (C$_1$–C$_8$)-alkyl, (C$_1$–C$_8$)-perfluoroalkyl, (C$_3$–C$_8$)-alkenyl or —C$_n$H$_{2n}$—R(12);
n is zero, 1, 2, 3 or 4;
R(12) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);
R(13) and R(14) are H, (C$_1$–C$_4$)-alkyl or (C$_1$–C$_4$)-perfluoroalkyl;
R(8) is H, (C$_1$–C$_4$)-alkyl or (C$_1$–C$_4$)-perfluoroalkyl;
or
R(7) and R(8) together are 4 or 5 methylene groups, of which one CH$_2$ group can be replaced by oxygen, S, NH, N—CH$_3$ or N-benzyl;
R(2) is defined as R(1), or is H, F, Cl, Br, I, CN, NO$_2$, (C$_1$–C$_8$)-alkyl, (C$_1$–C$_8$)-perfluoroalkyl, (C$_3$–C$_8$)-alkenyl or —C$_n$H$_{2n}$R(15);
n is zero 1, 2, 3, 4;
R(15) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(16)R(17);
R(16) and R(17) are H, (C$_1$–C$_4$)-alkyl or (C$_1$–C$_4$)-perfluoroalkyl;

or

R(2) is ($C_1$–$C_9$)-heteroaryl, which is linked via C or N and which is unsubstituted or substituted by 1–3 substituents selected from the group consisting of F, Cl, $CF_3$, $CH_3$, methoxy, hydroxyl, amino methylamino and dimethylamino;

or

R(2) is SR(18), —OR(18), —NR(18)R(19), —CR(18)R(19)R(20);

R(18) is —$C_aH_{2a}$—($C_1$–$C_9$)-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(19) and R(20) independently of one another are defined as R(18) or are hydrogen, ($C_1$–$C_4$)-alkyl or ($C_1$–$C_4$)-perfluoroalkyl;

or

R(2) is R(21)—$SO_m$ or R(22)R(23)N—$SO_2$—;

m is 1 or 2;

R(21) is ($C_1$–$C_8$)-alkyl, ($C_1$–$C_8$)-perfluoroalkyl, ($C_3$–$C_8$)-alkenyl, —$C_nH_{2n}$—R(24), n is zero, 1, 2, 3 or 4;

R(24) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28) are H, ($C_1$–$C_4$)-alkyl or ($C_1$–$C_4$)-perfluoroalkyl;

R(22) is H, ($C_1$–$C_8$)-alkyl, ($C_1$–$C_8$)-perfluoroalkyl, ($C_3$–$C_8$)-alkenyl, —$C_nH_{2n}$—R(29);

n is zero, 1, 2, 3 or 4;

R(29) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);

R(30) and R(31) are H, ($C_1$–$C_4$)-alkyl or ($C_1$–$C_4$)-perfluoroalkyl;

R(23) is H, ($C_1$–$C_4$)-alkyl or ($C_1$–$C_4$)-perfluoroalkyl;

or

R(22) and R(23) together are 4 or 5 methylene groups, of which one $CH_2$ group can be replaced by oxygen, S, NH, N—$CH_3$ or N-benzyl;

or

R(2) is R(33)X—;

X is oxygen, S, NR(34), (D=O)A—, NR(34)C=$MN^{(*)}$R(35)—;

M is oxygen or S;

A is oxygen or NR(34);

D is C or SO;

R(33) is ($C_1$–$C_8$)-alkyl, ($C_3$–$C_8$)-alkenyl, $(CH_2)_bC_dF_{2d+1}$, —$C_nH_{2n}$—R(36), b is zero or 1;

d is 1, 2, 3, 4, 5, 6 or 7;

n is zero, 1, 2, 3 or 4;

R(36) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);

R(37) and R(38) are H, ($C_1$–$C_4$)-alkyl or ($C_1$–$C_4$)-perfluoroalkyl;

R(34) is H, ($C_1$–$C_4$)-alkyl or ($C_1$–$C_4$)-perfluoroalkyl;

R(35) is defined as R(33);

or

R(33) and R(34) together are 4 or 5 methylene groups, of which one $CH_2$ group can be replaced by oxygen, S, NH, N—$CH_3$ or N-benzyl; where A and $N^{(*)}$ are bonded to the phenyl nucleus of the benzoylguanidine parent structure;

or

R(2) is —SR(40), —OR(40), —NHR(40)R(41), —CHR(40)R(42), —C[R(42)R(43)OH], —C≡CR(45), —CR(46)=CHR(45), —[CR(47)R(48)]$_u$—(CO)—[CR49)R(50)]$_v$—R(44);

R(40), R(41) identically or differently are —$(CH_2)_p$—$(CHOH)_q$—$(CH_2)_r$—$(CHOH)_t$—R(51) or —$(CH_2)_p$—O—$(CH_2$—$CH_2O)_q$—R(51);

R(51) is hydrogen or methyl;

u is 1, 2, 3 or 4;

v is zero, 1, 2, 3 or 4;

p, q, r identically or differently are zero, 1, 2, 3 or 4;

t is 1, 2, 3 or 4;

R(42) and R(43) identically or differently are hydrogen or ($C_1$–$C_6$)-alkyl;

or

R(42) and R(43) together with the carbon atom carrying them form a ($C_3$–$C_8$)-cycloalkyl;

R(44) is H, ($C_1$–$C_6$)-alkyl, ($C_3$–$C_8$)-cycloalkyl or —$C_eH_{2e}$—R(45);

e is zero, 1, 2, 3 or 4;

R(45) is phenyl, which is unsubstituted or substituted by 1–3 substituents from the group consisting of F, Cl, $CF_3$, methyl, methoxy and NR(52)R(53) where R(52) and R(53) are H or ($C_1$–$C_4$)-alkyl, or R(45) is ($C_1$–$C_9$)-heteroaryl, which is unsubstituted or substituted as phenyl;

or

R(45) is ($C_1$–$C_6$)-alkyl, which is unsubstituted or substituted by 1–3 OH;

R(46), R(47), R(48), R(49) and R(50) are hydrogen or methyl;

or

R(2) is R(55)—NH—$SO_2$—;

R(55) is R(56)R(57)N—C(=Y)—;

Y is oxygen, S or N—R(58);

R(56) and R(57) identically or differently are H, ($C_1$–$C_8$)-alkyl, ($C_3$–$C_6$)-alkenyl or —$C_fH_{2f}$—R(59);

f is zero, 1, 2, 3 or 4;

R(59) is ($C_5$–$C_7$)-cycloalkyl or phenyl, which is unsubstituted or substituted by 1–3 substituents selected from the group consisting of F, Cl, $CF_3$, methoxy and ($C_1$–$C_4$)-alkyl;

or

R(56) and R(57) together are 4 or 5 methylene groups, of which one $CH_2$ group can be replaced by oxygen, S, NH, N—$CH_3$ or N-benzyl;

R(58) is defined as R(56) or is amidine;

R(3), R(4) and R(5) independently of one another are defined as R(1) or R(2);

and their pharmaceutically tolerable salts;

(HOE 93/F 220-EP-Offenlegungsschrift 640 593, NZ 264 117)

q) benzoylguanidines of the formula I

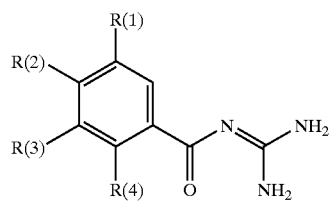

in which:
R(1) is hydrogen, F, Cl, Br, I, —$NO_2$, —C≡N, —$X_o$—$(CH_2)_p$—$(CF_2)_q$—$CF_3$,
R(5)—$SO_m$—, R(6)—CO—, R(6)R(7)N—CO— or R(6)R(7)N—$SO_2$—;
X is oxygen, —S— or NR(14);
m is zero, 1 or 2;
o is zero or 1;
p is zero, 1 or 2;
q is zero, 1, 2, 3, 4, 5 or 6;
R(5) and R(6) are ($C_1$–$C_8$)-alkyl, ($C_3$–$C_6$)-alkenyl, —$C_nH_{2n}$—R(8) or $CF_3$;
n is zero, 1, 2, 3 or 4;
R(8) is ($C_3$–$C_7$)-cycloalkyl, phenyl, which is not substituted or is substituted by 1 to 3 substituents selected from the group consisting of F, Cl, $CF_3$, methyl, methoxy and NR(9)R(10);
R(9) and R(10) are H or ($C_1$–$C_4$)-alkyl;
or
R(6) is hydrogen,
R(7) is hydrogen or ($C_1$–$C_4$)-alkyl;
or
R(6) and R(7) together are 4 or 5 methylene groups, of which one $CH_2$ group can be replaced by oxygen, S, NH, N—$CH_3$ or N-benzyl;
R(2) is

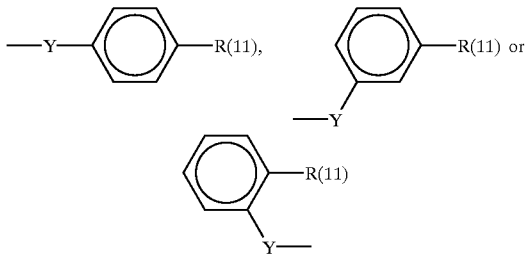

R(11) is ($C_1$–$C_9$)-heteroaryl, which is linked via C or N and which is unsubstituted or substituted by 1 to 3 substituents selected from the group consisting of F, Cl, $CF_3$, $CH_3$, methoxy, hydroxyl, amino, methylamino, dimethylamino and benzyl;
Y is oxygen, —S— or NR(12);
R(12) is H or ($C_1$–$C_4$)-alkyl;
R(3) is defined as R(1);
or
R(3) is ($C_1$–$C_6$)-alkyl or —X—R(13);
X is oxygen, —S— or NR(14);
R(14) is H or ($C_1$–$C_3$)-alkyl;
R(13) is H, ($C_1$–$C_6$)-alkyl, ($C_3$–$C_8$)-cycloalkyl or —$C_bH_{2b}$—R(15);
b is zero, 1, 2, 3 or 4;

or
R(13) and R(14) together are 4 or 5 methylene groups, of which one $CH_2$ group can be replaced by oxygen, S, NH, N—$CH_3$ or N-benzyl;
R(15) is phenyl, which is unsubstituted or substituted by 1–3 substituents selected from the group consisting of F, Cl, $CF_3$, methyl, methoxy and NR(9)R(10);
R(9) and R(10) are H or ($C_1$–$C_4$)-alkyl;
R(4) is hydrogen, —OR(16), —NR(16)R(17) or $C_rF_{2r+1}$,
R(16) and R(17) independently are hydrogen or ($C_1$–$C_3$)-alkyl;
r is 1, 2, 3 or 4;
and their pharmaceutically tolerable salts;
(HOE 93/F 223 K-EP 639 573, NZ 264 130)

r) benzo-fused 5-membered ring heterocycles of the formula I

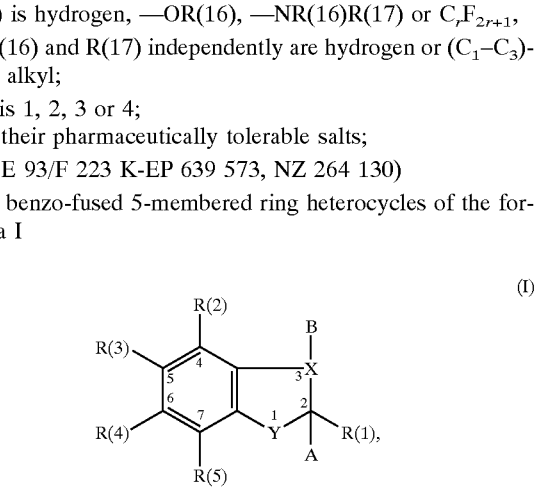

in which:
X is N or CR(6);
Y is oxygen, S or NR(7);
A, B together are a bond
or
A, B are both hydrogen, if X is simultaneously CR(6) and Y is NR(7);
one of the substituents R(1) to R(6) is a —CO—N═C$(NH_2)_2$ group;
the other substituents R(1) to R(6) in each case are hydrogen, F, Cl, Br, I or ($C_1$–$C_6$)-alkyl;
up to two of the other substituents R(1) to R(6) are CN, $NO_2$, $N_3$, ($C_1$–$C_4$)-alkyloxy or $CF_3$;
up to one of the other substituents is R(8)—$C_nH_{2n}$—Z—;
n is zero to 10; where the alkylene chain —$C_nH_{2n}$— is straight-chain or branched and where one carbon atom can be replaced by an oxygen or sulfur atom or by a nitrogen atom;
R(8) is hydrogen, ($C_2$–$C_6$)-alkenyl or ($C_3$–$C_{10}$)-cycloalkyl, which is unsubstituted or substituted by 1 to 4 methyl groups or an OH group, or can contain an ethylene group —CH═CH—, and in which one methylene group can be replaced by an oxygen or sulfur atom or by a nitrogen atom;
or
R(8) is phenyl, which is unsubstituted or substituted by 1 to 3 substituents selected from the group consisting of F, Cl, Br, I, $CF_3$, $CH_3$—S(O)$_s$— or R(9)—$W_y$—;
s is zero, 1 or 2;
R(9) is H, methyl, ethyl,
W is oxygen or NR(10);
R(10) is H or methyl;
y is zero of 1;
or
R(8) is $C_mF_{2m+1}$;
m is 1 to 3;

or

R(8) is 1- or 2-naphthyl, pyridyl, quinolyl or isoquinolyl;
Z is —CO—, —CH$_2$— or [CR(11)(OH)]$_q$—;
q is 1, 2 or 3;
R(11) is H or methyl;
or
Z is oxygen or —NR(12)—;
R(12) is H or methyl;
or
Z is —S(O)$_s$—;
s is zero, 1 or 2;
or
Z is —SO$_2$—NR(13)—;
R(13) is H or (C$_1$–C$_4$)-alkyl;
R(7) is hydrogen, (C$_1$–C$_{10}$)-alkyl, (C$_2$–C$_{10}$)-alkenyl or R(8)-C$_n$N$_{2n}$—;
and their pharmaceutically tolerable salts;
(HOE 93/F 236-EP-Offenlegungsschrift 638 548, NZ 264 216)

s) benzoylguanidines of the formula I

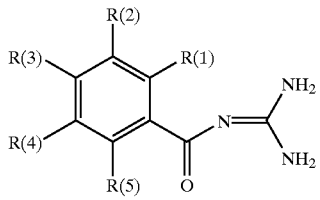

(I)

in which:
R(1), R(3) or R(4) is —NR(6)C=XNR(7)R(8);
X is oxygen or S;
R(6) is hydrogen, (C$_1$–C$_8$)-alkyl, (C$_1$–C$_8$)-perfluoroalkyl, (C$_3$–C$_8$)-alkenyl or —C$_n$H$_{2n}$—R(9);
n is zero, 1, 2, 3 or 4;
R(9) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(10)R(11);
R(10) and R(11) are H, (C$_1$–C$_4$)-alkyl or (C$_1$–C$_4$)-prefluoroalkyl;
R(7) is hydrogen, (C$_1$–C$_8$)-alkyl, (C$_1$–C$_8$)-perfluoroalkyl, (C$_3$–C$_8$)-alkenyl or —C$_o$H$_{2o}$—R(12);
o is zero, 1, 2, 3 or 4;
R(12) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(13)R(14);
R(13) and R(14) are H, (C$_1$–C$_4$)-alkyl or (C$_1$–C$_4$)-perfluoroalkyl;
R(8) is defined as R(7);
or
R(7) and R(8) together are 4 or 5 methylene groups, of which one CH$_2$ group can be replaced by oxygen, S, NH N—CH$_3$ or N-benzyl;
the remaining substituents R(2), R(3), R(4), R(5) or R(1), R(2), R(4), R(5) or R(1), R(2), R(3), R(5) in each case independently of one another are hydrogen, F, Cl, Br, I, —O$_{ta}$(C$_1$–C$_8$)-alkyl, —O$_{tb}$(C$_3$–C$_8$)-alkenyl, —O$_{tc}$(CH$_2$)$_b$C$_d$F$_{2d+1}$, —O$_{td}$C$_p$H$_{2p}$R(18), or up to 2 groups CN, NO$_2$, NR(16)R(17), b is zero or 1;
d is 1, 2, 3, 4, 5, 6 or 7;
ta is zero or 1;
tb is zero or 1;
tc is zero or 1;
td is zero or 1;
p is zero, 1, 2, 3 or 4;
R(18) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(19)R(20);
R(19) and R(20) are hydrogen or (C$_1$–C$_4$)-alkyl or (C$_1$–C$_4$)-perfluoroalkyl;
R(16) is hydrogen, (C$_1$–C$_8$)-alkyl, (C$_1$–C$_8$)-perfluoroalkyl, (C$_3$–C$_8$)-alkenyl, —C$_q$H$_{2q}$—R(21),
q is zero, 1, 2, 3 or 4;
R(21) is (C$_3$–C$_8$)-cycloalkyl, phenyl, biphenylyl or naphthyl, where the aromatics are not substituted or are substituted by 1–3 substituents from the group F, Cl, CF$_3$, methyl, methoxy or NR(22)R(23), R(22) and R(23) are hydrogen, (C$_1$–C$_4$)-alkyl or (C$_1$–C$_4$)-perfluoroalkyl;
R(17) is hydrogen, (C$_1$–C$_8$)-alkyl, (C$_1$–C$_8$)-perfluoroalkyl, (C$_3$–C$_8$)-alkenyl, —C$_r$H$_{2r}$—R(24);
r is zero, 1, 2, 3 or 4;
R(24) is (C$_3$–C$_8$)-cycloalkyl, phenyl, biphenylyl or naphthyl, where the aromatics are not substituted or are substituted by 1–3 substituents selected from the group consisting of F, Cl, CF$_3$, methyl, methoxy and NR(25)R(26);
R(25) and R(26) are hydrogen, (C$_1$–C$_4$)-alkyl or (C$_1$–C$_4$)-perfluoroalkyl;
or
R(16) and R(17) together are 4 or 5 methylene groups, of which one CH$_2$ group can be replaced by oxygen, S, NH, N—CH$_3$ or N-benzyl;
and their pharmaceutically tolerable salts;
(HOE 93/F 249-EP-Offenlegungsschrift 640 587, NZ 264 282)

t) diacyl-substituted guanidines of the formula I

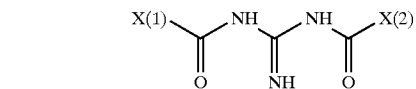

I in which:
X(1) and X(2) are

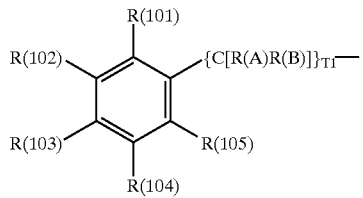

T1 is zero, 1, 2, 3 or 4;
R(A) and R(B) independently of one another are hydrogen, F, Cl, Br, I, CN, OR(106), (C$_1$–C$_8$)-alkyl, (C$_3$–C$_8$)-cycloalkyl, O$_{zk}$(CH$_2$)$_{zi}$C$_{zm}$F$_{2zm+1}$, NR(107)R(108), phenyl or benzyl, where the aromatics are not substituted or are substituted by 1–3 substituents selected from the group consisting of F, Cl, $CF_3$, methyl, methoxy and NR(109)R(110);

R(109) and R(110) are hydrogen, $(C_1-C_4)$-alkyl or $(C_1-C_4)$-perfluoroalkyl;

zl is zero, 1, 2, 3 or 4;

zk is zero or 1;

zm is 1, 2, 3, 4, 5, 6, 7 or 8;

R(106) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl methoxy and NR(111) and R(112) are hydrogen, $(C_1-C_4)$-alkyl or $(C_1-C_4)$-perfluoroalkyl;

R(107) and R(108) independently of one another are defined as R(106), or

R(107) and R(108) together are 4 or 5 methylene groups, of which one $CH_2$ group can be replaced by oxygen, S, NH, N—$CH_3$ or N-benzyl;

or

X(1) and X(2) are

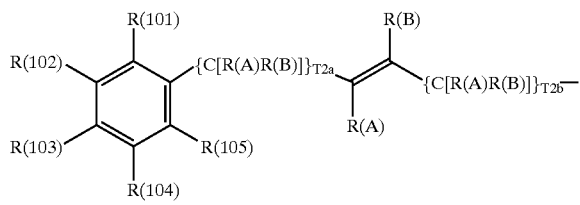

T2a and T2b independently of one another are zero, 1 or 2; where the double bond can have the (E)- or (Z)- configuration;

or

X(1) and X(2) are

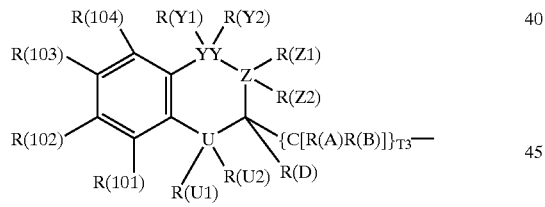

T3 is zero, 1 or 2;

U, YY and Z independently of one another are C or N, where U, YY, Z can carry the following number of substituents:

| U, YY or Z | Bonded in the ring to a double bond | Number of permitted substituents |
|---|---|---|
| C | yes | 1 |
| C | no | 2 |
| N | yes | 0 |
| N | no | 1 |

R(D) is hydrogen, $(C_1-C_8)$-alkyl or $(C_1-C_8)$-prefluoroalkyl,

R(U1), R(U2), R(Y1), R(Y2), R(Z1), R(Z2) independently of one another are hydrogen, F, Cl, Br, I, CN, OR(114), $(C_1-C_8)$-alkyl, $(C_3-C_8)$-cycloalkyl, $O_{zka(CH2)}{}_{zla}(CH_2)_{zla}C_{zma}F_{2zma+1}$, NR(115)R(116), phenyl or benzyl, where the aromatics are not substituted or are substituted by 1–3 substituents selected from the group consisting of F, Cl, $CF_3$, methyl, methoxy, NR(117)R(118), R(117) and R(118) are hydrogen, $(C_1-C_4)$-alkyl or $(C_1-C_4)$-perfluoroalkyl, zka is zero or 1;

zla is zero, 1, 2, 3 or 4;

zma is 1, 2, 3, 4, 5, 6, 7 or 8;

R(114) is hydrogen, $(C_1-C_8)$-alkyl, $(C_1-C_8)$-perfluoroalkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(119)R(120);

R(119) and R(120) are hydrogen, $(C_1-C_4)$-alkyl or $(C_1-C_4)$-perfluoroalkyl;

R(115) and R(116) independently of one another are defined as R(114);

or

R(115) and R(116) together are 4 or 5 methylene groups, of which one $CH_2$ group can be replaced by oxygen, S, NH, N—$CH_3$ or N-benzyl; but where the constitution of U is nitrogen (N), YY is nitrogen (N) and Z is carbon (C) is excluded, R(101), R(102), R(103), R(104) and R(105) independently of one another are hydrogen, F, Cl, Br, I, —C≡N, $X_{zoa}$—$(CH_2)_{zpa}$—$(C_{zqa}F_{2zqa+1})$, R(110a)—$SO_{zbm}$, R(110b)R(110c)N—CO, R(111a)—CO— or R(112a)R(113a)N—$SO_2$—, where the perfluoroalkyl group is straight-chain or branched, X is oxygen, S or NR(114a);

R(114a) is H or $(C_1-C_3)$-alkyl;

zoa is zero or 1;

zbm is zero, 1 or 2;

zpa is zero, 1, 2, 3 or 4;

zqa is 1, 2, 3, 4, 5, 6, 7 or 8;

R(110a), R(110b), R(111a) and R(112a) independently of one another are $(C_1-C_8)$-alkyl, $(C_3-C_8)$-alkenyl, —$C_{zn}H_{2zn}$—R(115a) or $(C_1-C_8)$-perfluoroalkyl;

zn is zero, 1, 2, 3 or 4;

R(115a) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(116a)R(117a);

R(116a) and R(117a) are hydrogen, $(C_1-C_4)$-perfluoroalkyl or $(C_1-C_4)$;

or

R(110b), R(111a) and R(112a) are hydrogen;

R(110c) and R(113a) independently are hydrogen, $(C_1-C_4)$-perfluoroalkyl or $(C_1-C_4)$-alkyl;

or

R(110b) and R(110c) and R(112a) and R(113a) together are 4 or 5 methylene groups, of which one $CH_2$ group can be replaced by oxygen, sulfur, NH, N—$CH_3$ or N-benzyl;

or

R(101), R(102), R(103), R(104), R(105) independently of one another are $(C_1-C_8)$-alkyl, —$C_{zal}H_{2zal}$R(118a) or $(C_3-C_8)$-alkenyl, zal is zero, 1, 2, 3 or 4;

R(118a) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy or NR(119a) and R(119b);

R(119a) and R(119b) are hydrogen, $(C_1-C_4)$-alkyl or $(C_1-C_4)$-perfluoroalkyl;

or

R(101), R(102), R(103), R(104), R(105) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino and dimethylamino;

or

R(101), R(102), R(103), R(104), R(105) independently of one another are —C≡C—R(193);

R(193) is phenyl which is not substituted or is substituted by 1–3 substituents from the group consisting of F, Cl, $CF_3$, methyl, methoxy or NR(194)R(195);

R(194) and R(195) are hydrogen or $CH_3$;

or

R(101), R(102), R(103), R(104), R(105) independently of one another are

—Y-para-$C_6H_4$—$(CO)_{zh}$—$(CHOH)_{zi}$—$(CH_2)_{zj}$—$(CHOH)_{zk}$—R(123),

—Y-meta-$C_6H_4$—$(CO)_{zad}$—$(CHOH)_{zae}$—$(CH_2)_{zaf}$—$(CHOH)_{zag}$—R(124)

or

—Y-ortho-$C_6H_4$—$(CO)_{zah}$—$(CHOH)_{zao}$—$(CH_2)_{zap}$—$(CHOH)_{zak}$—R(125);

Y is oxygen, —S— or —NR(122d)—;

zh, zad, zah independently are zero or 1;

zi, zj, zk, zae, zaf, zag, zao, zap and zak independently are zero, 1, 2, 3 or 4;

but where in each case zh, zi and zk are not simultaneously zero, zad, zae and zag are not simultaneously zero, and zah, zao and zak are not simultaneously zero, R(123), R(124), R(125) and R(122d) independently are hydrogen or $(C_1-C_3)$-alkyl;

or

R(101), R(102), R(103), R(104) and R(105) independently of one another are SR(129), —OR(130), —NR(131)R(132) or —CR(133)R(134)R(135);

R(129), R(130), R(131) and R(133) independently are —$C_{zab}H_{2zab}$—$(C_1-C_9)$-heteroaryl, which is unsubstituted or substituted by 1–3 substituents from the group consisting of F, Cl, $CF_3$, $CH_3$, methoxy, hydroxyl, amino, methylamino and dimethylamino;

zab is zero, 1 or 2;

R(132), R(134) and R(135) independently are defined as R(129) or are hydrogen, $(C_1-C_4)$-alkyl or $(C_1-C_4)$-perfluoroalkyl;

or

R(101), R(102), R(103), R(104) and R(105) independently of one another are —W-para-$(C_6H_4)$—R(196), —W-meta-$(C_6H_4)$-R(197) or —W-ortho-$(C_6H_4)$—R(198);

R(196), R(197) and R(198) independently of one another are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino. dimethylamino and benzyl;

W is oxygen, S or NR(136)—;

R(136) is hydrogen or $(C_1-C_4)$-alkyl;

or

R(101), R(102), R(103), R(104) and R(105) independently of one another are R(146)X(1a)-;

X(1a) is oxygen, S, NR(147), (D=O)A—, NR(148)C=MN$^{(*)}$R(149)-;

M is oxygen or sulfur;

A is oxygen or NR(150);

D is C or SO;

R(146) is $(C_1-C_8)$-alkyl, $(C_3-C_8)$-alkenyl, $(CH_2)_{zbz}C_{zdz}F_{2zdz+1}$ or —$C_{zxa}H_{2zxa}$—R(151);

zbz is zero or 1;

zdz is 1, 2, 3, 4, 5, 6 or 7;

zxa is zero, 1, 2, 3 or 4;

R(151) is $(C_3-C_8)$-cycloalkyl, phenyl, biphenylyl or naphthyl, where the aromatics are not substituted or are substituted by 1–3 substituents from the group consisting of F, Cl, $CF_3$, methyl, methoxy and NR(152)R(153);

R(152) and R(153) are hydrogen, $(C_1-C_4)$-alkyl or $(C_1-C_4)$-perfluoroalkyl;

R(147), R(148) and R(150) independently are hydrogen, $(C_1-C_4)$-alkyl, $(C_1-C_4)$-perfluoroalkyl;

R(149) is defined as R(146), or

R(146) and R(147), or R(146) and R(148) together are 4 or 5 methylene groups, of which one $CH_2$ group can be replaced by oxygen, sulfur, NH, N—$CH_3$ or N-benzyl;

where A and N$^{(*)}$ are bonded to the phenyl nucleus of the alkanoyl parent structure;

or

R(101), R(102), R(103), R(104) and R(105) independently of one another are —SR(164), —OR(165), —NHR(166), —NR(167)R(168), —CHR(169)R(170), —CR(154)R(155)OH, —C≡CR(156), —CR(158)=CR(157) or —[CR(159)R(160)]$_{zu}$—(C=O)—[CR(161)R(162)]$_{zv}$—R(163);

R(164), R(165), R(166), R(167), R(169) identically or differently are —$(CH_2)_{zy}$—$(CHOH)_{zz}$—$(CH_2)_{zaa}$—$(CHOH)_{zt}$—R(171) or —$(CH_2)_{zab}$—O—$(CH_2$—$CH_2O)_{zac}$—R(172);

R(171) and R(172) are hydrogen or methyl;

zu is 1, 2, 3 or 4;

zv is zero, 1, 2, 3 or 4;

zy, zz, zaa, zab, zac identically or differently are zero, 1, 2, 3 or 4;

zt is 1, 2, 3 or 4;

R(168), R(170), R(154), R(155) identically or differently are hydrogen or $(C_1-C_6)$-alkyl, or R(169) and R(170), or R(154) and R(155) together with the carbon atom carrying them are a $(C_3-C_8)$-cycloalkyl;

R(163) is hydrogen, $(C_1-C_6)$-alkyl, $(C_3-C_8)$-cycloalkyl or —$C_{zeb}H_{2zeb}$—R(173);

zeb is zero, 1, 2, 3 or 4;

R(156), R(157) and R(173) independently are phenyl which is unsubstituted or is substituted by 1–3 substituents from the group consisting of F, Cl, $CF_3$, methyl, methoxy and NR(174)R(175);

R(174) and R(175) are hydrogen or $(C_1-C_4)$-alkyl;

or

R(156), R(157) and R(173) independently are $(C_1-C_9)$-heteroaryl, which is unsubstituted or substituted as phenyl;

R(158), R(159), R(160), R(161) and R(162) are hydrogen or methyl, or

R(101), R(102), R(103), R(104), R(105) independently of one another are R(176)—NH—$SO_2$—;

R(176) is R(177)R(178)N—(C=Y')—;
Y' is oxygen, S or N—R(179);
R(177) and R(178) identically or differently are hydrogen, $(C_1-C_8)$-alkyl, $(C_3-C_6)$-alkenyl or —$C_{zfa}R_{2zfa}$—R(180);
zfa is zero, 1, 2, 3 or 4;
R(180) is $(C_5-C_7)$-cycloalkyl or phenyl, which is unsubstituted or substituted by 1–3 substituents selected from the group consisting of F, Cl, $CF_3$, methoxy or $(C_1-C_4)$-alkyl;
or
R(177) and R(178) together are 4 or 5 methylene groups, of which one $CH_2$ group can be replaced by oxygen, sulfur, NH, N—$CH_3$ or N-benzyl;
R(179) is defined as R(177) or is amidine,
or
R(101), R(102), R(103), R(104), R(105) independently of one another are NR(184a)R(185), OR(184b,) SR(184c) or —$C_{znx}H_{2znx}$—R(184b);
znx is zero, 1, 2, 3 or 4;
R(184d) is $(C_3-C_7)$-cycloalkyl or phenyl, which is not substituted or substituted by 1–3 substituents from the group consisting of F, Cl, $CF_3$, methyl, methoxy and NR(116k)R(117k);
R(116k) and R(117k) are hydrogen or $(C_1-C_4)$-alkyl;
R(184a), R(184b,) R(184c), R(185) independently of one another are hydrogen, $(C_1-C_8)$-alkyl, $(C_1-C_8)$-perfluoroalkyl or $(CH_2)_{zao}$—R(184g);
zao if zero, 1, 2, 3 or 4;
R(184g) is $(C_3-C_7)$-cycloalkyl or phenyl, which is not substituted or substituted by 1–3 substituents from the group consisting of F, Cl, $CF_3$, methyl, methoxy and NR(184u)R(184v);
R(184u) and R(184v) are hydrogen or $(C_1-C_4)$-alkyl;
or
R(184a) and R(185) together are 4 or 5 methylene groups, of which one $CH_2$ group can be replaced by oxygen, sulfur, NH, N—$CH_3$ or N-benzyl;
and their pharmaceutically tolerable salts;
(HOE 93/F 254-EP-Offenlegungsschrift 640 588, NZ 264 307)
u) benzoylguanidines of the formula I

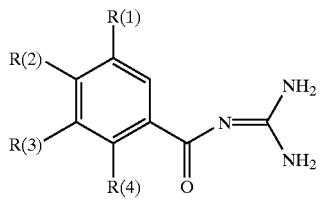

in which:
R(1) is H, F, Cl, Br, I, CN, $NO_2$, $(C_1-C_8)$-alkyl, $(C_3-C_8)$-cycloalkyl or $X_a$—$(CH_2)_b$—$(CF_2)_c$—$CF_3$;
X is oxygen, S or NR(5);
a is zero or 1;
b is zero, 1 or 2;
c is zero, 1, 2 or 3;
R(5) is H, $(C_1-C_4)$-alkyl or —$C_dH_{2d}$R(6);
d is zero, 1, 2, 3 or 4;
R(6) is $(C_3-C_8)$-cycloalkyl, phenyl, biphenylyl or naphthyl, where the aromatics are not substituted or are the substituted by 1 to 3 substituents selected from the group consisting of F, Cl, $CF_3$, methyl, methoxy and NR(7)R(8);

R(7) and R(8) independently are H or $(C_1-C_4)$-alkyl;
or
R(1) is —SR(10), —OR(10) or —CR(10)R(11)R(12);
R(10) is —$C_fH_{2f}$—$(C_3-C_8)$-cycloalkyl, —$(C_1-C_9)$-heteroaryl or phenyl, where the aromatic systems are unsubstituted or substituted by one to 3 substituents selected from the group consisting of F, Cl, $CF_3$, $CH_3$, methoxy, hydroxyl, amino, methylamino and dimethylamino;
f is zero, 1 or 2;
R(11) and R(12) independently of one another are defined as R(10) or are hydrogen or $(C_1-C_4)$-alkyl;
or
R(1) is phenyl, naphthyl, biphenylyl or $(C_1-C_9)$-heteroaryl, the latter linked via C or N, and which are unsubstituted or substituted by 1 to 3 substituents selected from the group consisting of F, Cl, $CF_3$, $CH_3$, methoxy, hydroxyl, amino, methylamino and dimethylamino;
or
R(1) is SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)-[CR(22)R(23)R(24)]$_l$;
R(13) and R(14) identically or differently are —$(CH_2)_g$—$(CHOH)_h$—$(CH_2)_i$—$(CHOH)_j$—R(17),
R(17) is hydrogen or methyl;
—$(CH_2)_g$—O—$(CH_2$—$CH_2O)_h$—R(24),
g, h, i identically or differently are zero, 1, 2, 3 or 4;
j is 1, 2, 3 or 4;
R(15) and R(16) identically or differently are hydrogen, $(C_1-C_6)$-alkyl or together with the carbon atom carrying them are a $(C_3-C_8)$-cycloalkyl;
R(18) is phenyl, which is unsubstituted or substituted by 1 to 3 substituents selected from the group consisting of F, Cl, $CF_3$, methyl, methoxy and NR(25)R(26);
R(25) and R(26) are H or $(C_1-C_4)$-alkyl;
or
R(18) is $(C_1-C_9)$-heteroaryl, which is unsubstituted or substituted as phenyl;
or
R(18) is $(C_1-C_6)$-alkyl, which is unsubstituted or substituted by 1 to 3 OH;
or
R(18) is $(C_3-C_8)$-cycloalkyl;
R(19), R(20), R(21), R(22) and R(23) are hydrogen or methyl;
k is zero, 1, 2, 3 or 4;
l is zero, 1, 2, 3 or 4;
R(24) is H, $(C_1-C_6)$-alkyl, $(C_3-C_8)$-cycloalkyl or —$C_mH_{2m}$—R(18);
m is 1, 2, 3 or 4;
R(2) and R(3) independently of one another are defined as R(1);
R(4) is $(C_1-C_3)$-alkyl, F, Cl, Br, I, CN or —$(CH_2)_n$—$(CF_2)_o$—$CF_3$;
n is zero or 1;
o is zero, 1 or 2;
and their pharmaceutically tolerable salts;

HOE 93/F 436-EP-Offenlegungsschrift 659 748, NZ 270 264)

v) acylguanidines of the formula I

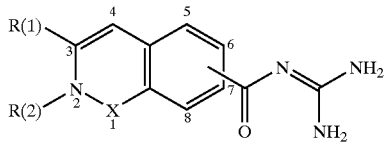

in which:

X is carbonyl, sulfonyl,

R(1) is H, $(C_1-C_8)$-alkyl, unsubstituted or substituted by hydroxyl,
  $(C_3-C_8)$-cycloalkyl, phenyl, which is unsubstituted or substituted by 1–3 substituents from the group, F, Cl, $CF_3$, $CH_3$, methoxy, hydroxyl, amino, methylamino or dimethylamino, R(2) is H, $(C_1-C_4)$-alkyl, and their pharmaceutically tolerable salts;

(HOE 94/F 014 K-EP-Offenlegungsschrift 666 252, NZ 270 370)

w) phenyl-substituted alkycarboxylic guanidides, carrying perfluoroalkyl groups, of the formula I

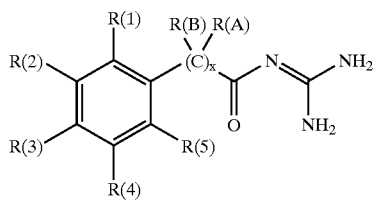

in which:

R(A) is hydrogen, F, Cl, Br, I, CN, OR(6), $(C_1-C_8)$-alkyl, $(C_3-C_8)$-cycloalkyl, $O_r(CH_2)_aC_bF_{2b+1}$ or NR(7)R(8);
  r is zero or 1;
  a is zero, 1, 2, 3 or 4;
  b is 1, 2, 3, 4, 5, 6, 7 or 8;
  R(6) is hydrogen, $(C_1-C_8)$-alkyl, $(C_3-C_8)$-alkenyl, $(C_3-C_8)$-cycloalkyl, phenyl or benzyl, where the aromatics are not substituted or are substituted by 1–3 substituents selected from the group consisting of F, Cl, $CF_3$, methyl, methoxy and NR(9)R(10);
    R(9) and R(10) are H, $(C_1-C_4)$-alkyl or $(C_1-C_4)$-perfluoroalkyl;
  R(7) and R(8) independently of one another are defined as R(6);

R(B) independently is defined as R(A);

X is 1, 2 or 3;

R(1) is hydrogen, $(C_1-C_8)$-alkyl, $(C_3-C_8)$-cycloalkyl, $-O_t(CH_2)_dC_eF_{2e+1}$, F, Cl, Br, I or CN;
  t is zero or 1;
  d is zero, 1, 2, 3 or 4;
  e is 1, 2, 3, 4, 5, 6, 7 or 8;

R(2), R(3), R(4) and R(5) independently of one another are defined as R(1);

but with the condition that at least one of the substituents R(1), R(2), R(3), R(4), R(5), R(A) and R(B) is an $-O_t(CH_2)_dC_eF_{2e+1}$ or an $O_r(CH_2)_aC_bF_{2b+1}$ group, and their pharmaceutically tolerable salts;

(HOE 94/F 094-EP-Offenlegungsschrift 676 395, NZ 270 894)

x) heteroaroylguanidines of the formula I

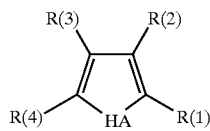

in which:

HA is $SO_m$, O or NR(5);
  m is zero, 1 or 2;
  R(5) is hydrogen, $(C_1-C_8)$-alkyl or $-C_{am}H_{2am}R(81)$;
    am is zero, 1 or 2;
    R(81) is $(C_3-C_8)$-cycloalkyl or phenyl, which is not substituted or is substituted by 1–3 substituents selected from the group consisting of F, Cl, $CF_3$, methyl, methoxy and NR(82)R(83);
      R(82) and R(83) Is H or $CH_3$;
    or
    R(81) is $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

one of the two substituents R(1) and R(2) is $-CO-N=C(NH_2)_2$;

and the other in each case is hydrogen, F, Cl, Br, I, $(C_1-C_3)$-alkyl, $-OR(6)$, $C_rF_{2r+1}$, $-CO-N=C(NH_2)_2$ or $-NR(6)R(7)$;
  R(6) and R(7) independently are hydrogen or $(C_1-C_3)$-alkyl;
  r is 1, 2, 3 or 4;

R(3) and R(4) independently of one another are hydrogen, F, Cl, Br, I, $-C\equiv N$, $X-(CH_2)_p-(C_q-F_{2q+1})$, R(8)—$SO_{bm}$, R(9)R(10)N—CO, R(11)—CO— or R(12)R(13)N—$SO_2$—, where the perfluoroalkyl group is straight-chain or branched,
  X is oxygen, S or NR(14);
  R(14) is H or $(C_1-C_3)$-alkyl;
  bm is zero, 1 or 2;
  p is zero, 1 or 2;
  q is zero, 1, 2, 3, 4, 5 or 6;
  R(8), R(9), R(11) and R(12) independently are $(C_1-C_8)$-alkyl, $(C_3-C_6)$-alkenyl, $-C_nH_{2n}-R(15)$, $CF_3$;
    n is zero, 1, 2, 3 or 4;
    R(15) is $(C_3-C_7)$-cycloalkyl or phenyl; which is not substituted or is substituted by 1–3 substituents selected from the group consisting of F, Cl, $CF_3$, methyl, methoxy or NR(16)R(17);
      R(16) and R(17) are H or $(C_1-C_4)$-alkyl;
  or
  R(9), R(11) and R(12) are H;
  R(10) and R(13) independently are H or $(C_1-C_4)$-alkyl;
  or
  R(9) and R(10), and R(12) and R(13) together are 4 or 5 methylene groups, of which one $CH_2$ group can be replaced by oxygen, S, NH, N—$CH_3$ or N-benzyl,
or R(3) and R(4) independently of one another are $(C_1-C_8)$-alkyl or $-C_{al}H_{2al}R(18)$;
  al is zero, 1 or 2;
  R(18) is $(C_1-C_8)$-cycloalkyl or phenyl; which is not substituted or is substituted by 1–3 substituents selected from the group consisting of F, Cl, $CF_3$, methyl, methoxy and NR(19)R(20);

R(19) and R(20) are H or $CH_3$;

or

R(3) and R(4) independently of one another are $(C_1-C_9)$-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;

or

R(3) and R(4) independently of one another are

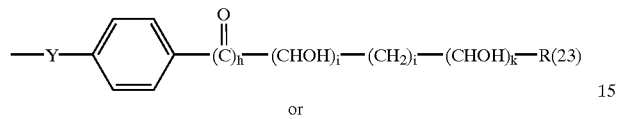

or

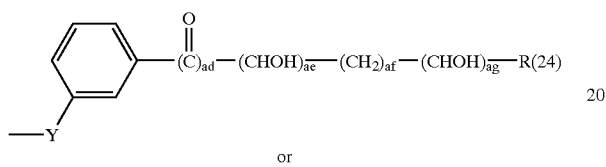

or

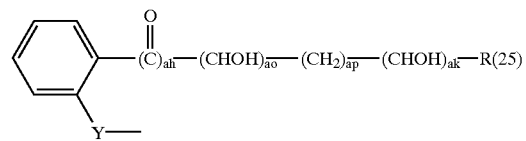

Y is oxygen, —S— or —NR(22)—;

h, ad, ah independently are zero or 1;

i, j, k, ae, af, ag, ao, ap and ak independently are zero, 1, 2, 3, 4, but where in each case h, i and k are not simultaneously zero, ad, ae and ag are not simultaneously zero, ah, ao and ak are not simultaneously zero, R(23), R(24) R(25) and R(22) independently are hydrogen of $(C_1-C_8)$-alkyl;

or

R(3) and R(4) independently are hydrogen, F, Cl, Br, I, CN, $(C_1-C_8)$-alkyl, $(C_1-C_8)$-perfluoroalkyl, $(C_3-C_8)$-alkenyl or —$C_gH_{2g}$R(26);

g is zero, 1, 2, 3 or 4;

R(26) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);

R(27) and R(28); are H, $(C_1-C_4)$-alkyl or $(C_1-C_4)$-perfluoroalkyl;

or

R(3) and R(4) independently of one another are SR(29), —OR(30), —NR(31)R(32) or —CR(33)R(34)R(35);

R(29), R(30), R(31) and R(33) independently of one another are —$C_aH_{2a}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl;

or

R(3) and R(4) independently of one another are

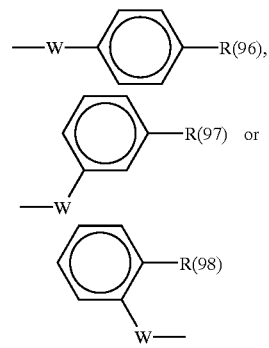

R(96), R(97) and R(98) independently of one another are $(C_1-C_9)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—;

R(36) is H or $(C_1-C_4)$-alkyl;

R(3) and R(4) independently of one another are R(37)—$SO_{cm}$ or R(38)R(39)N—$SO_2$—;

cm is 1 or 2;

R(37) is $(C_1-C_8)$-alkyl, $(C_1-C_8)$-perfluoroalkyl, $(C_3-C_8)$-alkenyl or —$C_sH_{2s}$R(40);

s is zero, 1, 2, 3 or 4;

R(40) is $(C_1-C_8)$-cycloalkyl, phenyl, biphenylyl or naphthyl, where the aromatic are not substituted or are substituted by 1–3 substituents selected from the group consisting of F, Cl, $CF_3$, methyl, methoxy and NR(41)R(42);

R(41) and R(42) are H, $(C_1-C_4)$-alkyl or $(C_1-C_4)$-perfluoroalkyl;

R(38) is H, $(C_1-C_8)$-alkyl, $(C_1-C_8)$-perfluoroalkyl, $(C_3-C_8)$-alkenyl or —$C_wH_{2w}$—R(43);

w is zero, 1, 2, 3 or 4;

R(43) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(44)R(45);

R(44) and R(45) are H, $(C_1-C_4)$-alkyl or $(C_1-C_4)$-perfluoroalkyl;

R(39) is H, $(C_1-C_4)$-alkyl or $(C_1-C_4)$-perfluoroalkyl;

or

R(38) and R(39) together are 4 or 5 methylene groups, of which one $CH_2$ group can be replaced by oxygen, S, NH, N—$CH_3$ or N-benzyl;

or

R(3) and R(4) independently of one another are R(46)X(1)—;

X(1) is oxygen, S, NR(47), (D=O)A—, NR(48)C=MN$^{(*)}$R(49)—,

M is oxygen or S;

A is oxygen or NR(50);

D is C or SO;

R(46) is $(C_1-C_8)$-alkyl, $(C_3-C_8)$-alkenyl, $(CH_2)_bC_dF_{2d+1}$ or —$C_xH_{2x}$—R(51);

b is zero or 1;

d is 1, 2, 3, 4, 5, 6 or 7;

x is zero, 1, 2, 3 or 4;

R(51) is (C$_3$–C$_8$)-cycloalkyl, phenyl, biphenylyl or naphthyl, where the aromatics are not substituted or are substituted by 1–3 substituents selected from the group consisting of F, G, CF$_3$, methyl, methoxy and NR(52)R(53);

R(52) and R(53) are H, (C$_1$–C$_4$)-alkyl or (C$_1$–C$_4$)-perfluoroalkyl;

R(47), R(48) and R(50) independently are hydrogen, (C$_1$–C$_4$)-alkyl or (C$_1$–C$_4$)-perfluoroalkyl, R(49) is defined as R(46);

or

R(48) and R(47), or R(46) and R(48) together are 4 or 5 methylene groups, of which one CH$_2$ group can be replaced by oxygen, S, NH, N—CH$_3$ or N-benzyl, where A and N(*) are bonded to the phenyl nucleus of the benzoylguanidine parent structure;

or

R(3) and R(4) independently of one another are —SR(64), —OR(65), —NHR(66), —NR(67)R(68), —CHR(69)R(70), —C(OH)R(54)R(55), —C≡CR(56), —CR(58)=CHR(57), —[CR(59)R(60)]$_u$—(CO)—[CR(61)R(62)]$_v$—R(63);

R(64), R(65), R(66), R(67) and R(69) identically or differently are —(CH$_2$)$_y$—(CHOH)$_z$(CH$_2$)$_{aa}$—(CH$_2$OH)$_t$—R(71) or —(CH$_2$)$_{ab}$—O—(CH$_2$—CH$_2$O)$_{ac}$—R(72), R(71) and R(72) are hydrogen or methyl;

u is 1, 2, 3, or 4;

v is zero, 1, 2, 3 or 4;

y, z, aa identically or differently are zero, 1, 2, 3 or 4;

t is 1, 2, 3 or 4;

R(68), R(70), R(54) and R(55) identically or differently are hydrogen, (C$_1$–C$_6$)-alkyl;

or

R(69) end R(70), or R(54) and R(55) together with the carbon atom carrying them are a (C$_1$–C$_8$)-cycloalkyl;

R(63) is H, (C$_1$–C$_6$)-alkyl, (C$_3$–C$_8$)-cycloalkyl or —C$_e$H$_{2e}$—R(73);

e is zero, 1, 2, 3 or 4;

R(56), R(57) and R(73) independently are phenyl, which are unsubstituted or substituted by 1–3 substituents selected from the group consisting of F, Cl, CF$_3$, methyl, methoxy and NR(74)R(75);

R(74) and R(75) are H or (C$_1$–C$_4$)-alkyl;

or

R(56), R(57) and R(73) independently are (C$_1$–C$_9$)-heteroaryl, which is unsubstituted or substituted as phenyl;

R(58), R(59), R(60), R(61) and R(62) are hydrogen or methyl, or

R(3) and R(4) independently of one another are R(78)—NH—SO$_2$—;

R(76) is R(77)R(78)N—(C=Y')—;

Y' is oxygen, S or N—R(79);

R(77) and R(78) identically or differently are H, (C$_1$–C$_8$)-alkyl, (C$_3$–C$_6$)-alkenyl, —C$_f$H$_{2f}$—R(80);

f is zero, 1, 2, 3 or 4;

R(80) is (C$_5$–C$_7$)-cycloalkyl or phenyl, which is unsubstituted or substituted by 1–3 substituents selected from the group consisting of F, Cl, CF$_3$, methoxy and (C$_1$–C$_4$)-alkyl;

or

R(77) and R(78) together are 4 or 5 methylene groups, of which one CH$_2$ group can be replaced by oxygen, S, NH, N—CH, or N-benzyl, R(79) is defined as R(77) or is amidine;

or

R(3) and R(4) independently of one another are NR(84)R(85);

R(84) and R(85) independently of one another are H, (C$_1$–C$_4$)-alkyl, or together are 4 or 5 methylene groups, of which one CH$_2$ group can be replaced by oxygen, S, NH, N—CH$_3$ or N-benzyl; or of which one or two CH$_2$ groups can be replaced by CH—C$_{dm}$H$_{2dm+1}$, and their pharmaceutically tolerable salts;

(HOE 94/F 123-EP-Offenlegungsschrift 682 017, NZ 272 058)

Y) bycyclic heteroaroylguanidines of the formula I

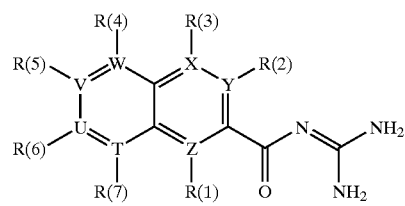

in which

T, U, V, W, X, Y and Z independently of one another are nitrogen or carbon; but with the restriction that x and z are not simultaneously nitrogen, and that T, U, V, W, X, Y, and Z carry no substituents if they are nitrogen, and that no more than four of them are simultaneously nitrogen, R(1) and R(2) independently d one another are hydrogen, F, Cl, Br, I, (C$_1$–C$_3$)-alkyl, (C$_1$–C$_3$)-perfluoroalkyl, OR(8). NR(8)R(9) or C(=O)N=C(NH$_2$)$_2$;

R(8) and R(9) independently of one another are hydrogen or (C$_1$–C$_3$)-alkyl;

or

R(8) and R(9) together are 4 or 5 methylene groups of which one CH$_2$ group can De replaced by oxygen, S, NH, N—CH$_3$ or N-benzyl;

R(3), R(4), R(5), R(6) end R(7) independently d one another are hydrogen, F, Cl, Br, I, —C≡N, X$_k$—(CH$_2$)$_p$—(C$_q$F$_{2q+1}$), R(10a)—SO$_{bm}$, R(10b)R(10c)N—CO, R(11)—CO— or R(12)R(13)N—SO$_2$—, where the perfluoroalkyl group is straight-chain or branched;

X is oxygen, S or NR(14);

R(14) is H of (C$_1$–C$_3$)-alkyl;

bm is zero, 1 or 2;

p is zero, 1 or 2;

k is zero or 1;

q 1, 2, 3, 4, 5 or 6;

R(10a), R(10b), R(11) and R(12) independently of one another are (C$_1$–C$_8$)-alkyl, (C$_3$–C$_8$)-alkenyl, —C$_n$H$_{2n}$—R(15) or (C$_1$–C$_8$)-perfluoroalkyl;

n is zero, 1, 2, 3 or 4;

R(15) is (C$_3$–C$_7$)-cycloalkyl or phenyl, is not substituted or is substituted by 1–3 substituents selected from the group consisting of F, Cl CF$_3$, methyl, methoxy and NR(16)R(17);

R(16) and R(17) are H or C$_1$–C$_4$-alkyl;

or

R(10b), R(11) and R(12) are hydrogen;

R(10c) and R(13) independently are hydrogen or (C$_1$–C$_4$)-alkyl, or

R(10b), and R(10c) and R(12) and R(13) together are 4 or 5 methylene groups, of which one CH$_2$ group can be replaced by oxygen, sulfur, NH, N—CH$_3$ or N-benzyl;

or

R(3), R(4), R(5), R(6) and R(7) independently of one another are $(C_1-C_8)$-alkyl, $-C_{al}H_{2al}R(18)$ or $(C_3-C_8)$-alkenyl, al is zero, 1 or 2;

R(18) is $(C_3-C_8)$-cycloalkyl, phenyl, biphenylyl or naphthyl, where the aromatics are not substituted or are substituted by 1–3 substituents selected from the group consisting of F, Cl, $CF_3$ methyl, methoxy and NR(19a) R(19b);

R(19a) and R(19b) are hydrogen, $(C_1-C_4)$-alkyl or $(C_1-C_4)$-perfluoroalkyl;

or

R(3), R(4), R(5), R(8) and R(7) independently of one another are $(C_1-C_9)$-heteroaryl, which is linked via C or N and which is unsubstituted or substituted by 1–3 substituents from the group consisting of F, Cl, $CF_3$, $CH_3$, methoxy, hydroxyl, amino, methylamino or dimethylamino;

or

R(3), R(4), R(5), R(6) and R(7) independently of one another are

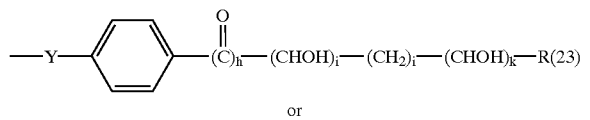

or

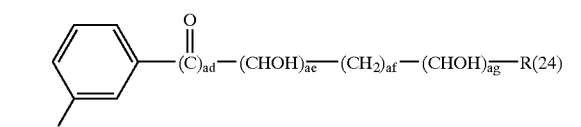

or

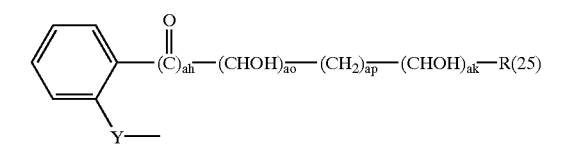

Y is oxygen, —S— or —NR(22)—;

h, ad, ah independently of one another are zero or 1;

i, j, k, ae, af, ag, ao, ap and ak independently of one another are zero, 1, 2, 3 or 4;

but where in each case h, i and k are not simultaneously zero, ad, ae and ag are not simultaneously zero, and ah, ao and ak are not simultaneously zero, R(23), R(24) R(25) and R(22) independently of one another are hydrogen or $(C_1-C_3)$-alkyl;

or

R(3), R(4), R(5), R(6) and R(7) independently of one another are SR(29), —OR(30), —NR(31)R(32) or —CR (33)R(34)R(35);

R(29), R(30), R(31) and R(33) independently of one another are $-C_aH_{2a}-(C_1-C_9)$-heteroaryl, which is unsubstituted or substituted by 1–3 substituents selected from the group consisting of F, Cl, $CF_3$, $CH_3$ methoxy, hydroxyl, amino, methylamino and dimethylamino;

a is zero, 1 or 2;

R(32), R(34) and R(35) independently of one another are defined as R(29) or are hydrogen, $(C_1-C_4)$-alkyl or $(C_1-C_4)$-perfluoroalkyl;

or

R(3), R(4), R(5), R(6) and R(7) independently of one another are

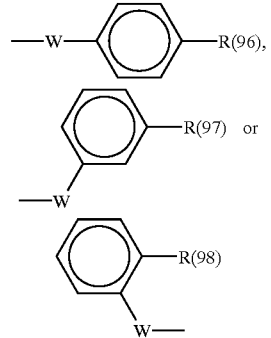

R(96), R(97) and R(98) independently of one another are $(C_1-C_8)$-heteroaryl, which is linked via C or N and which is unsubstituted or substituted by 1 to 3 substituents from the group consisting of F, Cl, $CF_3$, $CH_3$, methoxy, hydroxyl, amino, methylamino, dimethylamino or benzyl;

W is oxygen, S or NR(36)—; R(36) is H or $(C_1-C_4)$-alkyl;

or

R(3), R(4), R(5), R(6) and R(7) independently of one another are R(46)X(1)—;

X(1) is oxygen, S, NR(47), (D=O)A— or NR(48) C=MN$^{(*)}$R(49)—;

M is oxygen or sulfur,

A is oxygen or NR(50);

D is C or SO;

R(46) is $(C_1-C_8)$-alkyl, $(C_3-C_8)$-alkenyl, $(CH_2)_bC_dF_{2d+1}$ or $-C_xH_{2x}-R(51)$;

b is zero or 1;

d is 1, 2, 3, 4, 5, 6 or 7;

x is zero, 1, 2, 3 or 4;

R(52) is $(C_3-C_8)$-cycloalkyl, phenyl, biphenylyl or naphthyl, where the aromatics are not substituted or are substituted by 1–3 substituents selected from the group consisting of F, Cl, $CF_3$, methyl, methoxy and NR(52)R(53);

R(52) and R(53) are hydrogen, $(C_1-C_4)$-alkyl or $(C_1-C_4)$-perfluoroalkyl;

R(47), R(48) and R(50) independently are hydrogen, $(C_1-C_4)$-alkyl or $(C_1-C_4)$-perfluoroalkyl;

R(49) is defined as R(46);

or

R(46) and R(47), or R(46) and R(48) together are 4 or 5 methylene groups, of which one $CH_2$ groups can be replaced by oxygen, sulfur, NH, N—$CH_3$ or N-benzyl;

where A and N$^{(*)}$ are bonded to the phenyl nucleus of the heteroaroylguanidine parent structure;

or

R(3), R(4), R(5), R(8) and R(7) independently of one another are —SR(64), —OR(65), —NHR(66), —NR(67) R(68), —CHR(69)R(70) or —CR(54)R(55)OH, —C≡CR(56), —CR(58)=CR(57) or —[(CR(59)R (60)]$_u$ —CO—[CR(61)R(62)]$_v$—R(63);

R(64), R(65), R(66), R(67) and R(69) identically or differently are —$(CH_2)_y$—$(CHOH)_z(CH_2)_{aa}$—$(CHOH)_t$—R(71) or —$(CH_2)_{ab}$—O—$(CH_2$—$CH_2O)_{ac}$—R(72)

R(71) and R(72) independently of one another are hydrogen or methyl;

u is 1, 2, 3 or 4;

v is zero, 1, 2, 3 or 4;

y, z, as identically or different are zero, 1, 2, 3 or 4;

t is 1, 2, 3 or 4;

R(68), R(70), R(54) and R(55) identically or differently are hydrogen or $(C_1-C_6)$-alkyl;

or

R(69) and R(70), or R(54) and R(55) together with the carbon atom carrying them are $(C_3-C_8)$-cycloalkyl;

R(63) is hydrogen, $(C_1-C_6)$-alkyl, $(C_3-C_8)$-cycloalkyl or $-C_eH_{2e}-R(73)$;

e is zero, 1, 2, 3 or 4;

R(56), R(57) and R(73) independently are phenyl, which is unsubstituted or substituted by 1–3 substituents selected from the group consisting of F, Cl, $CF_3$, methyl, methoxy and NR(74)R(75);

R(74) and R(75) are hydrogen or $(C_1-C_4)$-alkyl;

or

R(56), R(57) and R(73) independently are $(C_1-C_9)$-heteroaryl, which is unsubstituted or substituted as phenyl;

R(58), R(59), R(60), R(61) and R(62) are hydrogen or methyl;

or

R(3), R(4), R(5), R(6) and R(7) independently of one another are R(76)—NH—$SO_2$—;

R(76) is R(77)R(78)N—(C=Y')—;

Y' is oxygen, S or N—R(79);

R(77) and R(78) identically or differently are hydrogen, $(C_1-C_8)$-alkyl, $(C_3-C_6)$-alkenyl or —$C_fH_{2f}$—R(80);

f is zero, 1, 2, 3 or 4;

R(80) is $(C_5-C_7)$-cycloalkyl or phenyl, which is unsubstituted or substituted by 1–3 substituents selected from the group consisting of F, Cl, $CF_3$, methoxy and $(C_1-C_4)$-alkyl;

or

R(77) and R(78) together are 4 or 5 methylene groups, of which one $CH_2$ group can be replaced by oxygen, sulfur, NH, N—$CH_3$ or N-benzyl;

R(79) is defined as R(77) or is amidine;

or

R(3), R(4), R(5), R(6) and R(7) Independently of one another are NR(84a)R(85), OR(84b), SR(84c)

n is zero, 1, 2, 3 or 4;

R(84d) is $(C_3-C_7)$-cycloalkyl or phenyl, which is not substituted or is substituted by 1–3 substituents from the group consisting of F, Cl, $CF_3$, methyl, methoxy and NR(16)R(17);

R(16) and R(17) are hydrogen or $C_1-C_4$-alkyl;

R(84a), R(84b), R(84c) and R(85) independently of one another are hydrogen, $(C_1-C_8)$-alkyl, $(C_1-C_8)$-perfluoroalkyl or $(CH_2)_{ax}$—R(84g);

ax is zero, 1, 2, 3 or 4;

R(84g) is $(C_3-C_7)$-cycloalkyl or phenyl, which is not substituted or is substituted by 1—3 substituents selected from the group consisting of F, Cl, $CF_3$, methyl, methoxy and NR(84u)R(84v);

R(84u) and R(84v) are hydrogen or $C_1-C_4$-alkyl;

or

R(84a) and R(85) together are 4 or 5 methylene groups, of which one $CH_2$ group can be replaced by oxygen, sulfur, NH, N—$CH_3$ or N-benzyl, and their pharmaceutically tolerable salts;

(HOE 94/F 134-EP-Offenlegungsschrift 686 627, NZ 272 103)

z) benzoylguanidines of the formula I

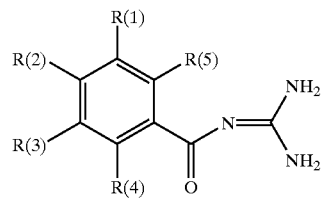

in which:

R(1) is R(6)—$SO_m$;

m is zero, 1 or 2;

R(6) is perfluoroalkyl having 1, 2, 3, 4, 5 or 6 carbon atoms, which is straight-chain or branched;

R(2) and R(3) independently of one another are hydrogen, F, Cl, Br, I, alkyl having 1, 2, 3 or 4 carbon atoms, alkoxy having 1, 2, 3 or 4 carbon atoms or phenoxy, which is unsubstituted or substituted by 1–3 substituents selected from the group consisting of F, Cl, methyl and methoxy;

or

R(2) and R(3) independently of one another are pyrrol-1-yl, pyrrol-2-yl or pyrrol-3-yl, which is not substituted or is substituted by 1 to 4 substituents selected from the group consisting of F, Cl, Br, I, CN, alkanoyl having 2, 3, 4, 5, 6, 7 or 8 carbon atoms, alkoxycarbonyl having 2, 3, 4, 5, 6, 7 or 8 carbon atoms, formyl, carboxyl, $CF_3$, methyl and methoxy;

R(4) and R(5) independently of one another are hydrogen, alkyl having 1, 2 or 3 carbon atoms, F, G, Br, I, CN, OR(7), NR(8)R(9) or —$(CH_2)_n$—$(CF_2)_o$—$CF_3$;

R(7), R(8) and R(9) independently of one another are hydrogen or alkyl having 1, 2, 3 or 4 carbon atoms;

n is zero or 1;

o is zero, 1 or 2;

and their pharmacologically acceptable salts;

(HOE 94/F 168-EP-Offenlegungsschrift 690 048, NZ 272 373)

aa) Phenyl-substituted alkenylcarboxylic acid guanidides, carrying perfluoroalkyl groups, of the formula I

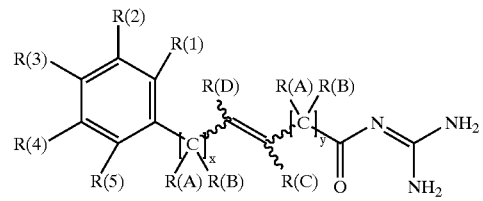

in which:

R(A) is hydrogen, F, Cl, Br, I, CN, OH, OR(6), $(C_1-C_8)$-alkyl, $O_r(CH_2)_aC_bF_{2b+1}$, $(C_3-C_8)$-cycloalkyl or NR(7)R(B);

r is zero or 1;

a is zero, 1, 2, 3 or 4;

b is 1, 2, 3, 4, 5, 6, 7 or 8;

R(6) is $(C_1-C_8)$-alkyl, $(C_1-C_4)$-perfluoroalkyl $(C_3-C_8)$-alkenyl, $(C_3-C_8)$-[ ]cycloalkyl, phenyl or benzyl: where the aromatics are not substituted or are substituted by 1–3 substituents from the group consisting of F, Cl, $CF_3$, methyl, methoxy and NR(9)R(10):

R(9) and R(10) are H, $(C_1-C_4)$-alkyl or $(C_1-C_4)$-perfluoroalkyl;

R(7) and R(8) independently of one another are defined as R(6);

or

R(7) and R(8) together are 4 or 5 methylene groups, of which one $CH_2$ group can be replaced by oxygen, sulfur NH, N—$CH_3$ or N-benzyl;

R(B) independently is defined as R(A);

x is zero, 1 or 2;

y is zero, 1 or 2;

R(C) is hydrogen, F, Cl, Br, I, CN, OR(12), $(C_1-C_8)$-alkyl, $O_p(CH_2)_f C_g F_{2g+1}$ or $(C_3-C_8)$-cycloalkyl;

p is zero or 1;

f is zero, 1, 2, 3 or 4;

g is 1, 2, 3, 4, 5, 6, 7 or 8;

R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl; where the aromatics phenyl or benzyl are not substituted or are substituted by 1–3 substituents from the group consisting of F, Cl, $CF_3$, methyl, methoxy and NR(13)R(14);

R(13) and R(14) independently of one another ere H, $(C_1-C_4)$-alkyl or $(C_1-C_4)$-perfluoroalkyl;

R(D) independently is defined as R(C),

R(1) is hydrogen, $(C_1-C_8)$-alkyl, —$O_t(CH_2)_d C_e F_{2e+1}$, $(C_3-C_8)$-cycloalkyl, F, Cl, Br, I or CN;

t is zero or 1;

d is zero, 1, 2, 3 or 4;

e is 1, 2, 3, 4, 5, 6, 7 or 8;

R(2), R(3), R(4) and R(5) independently of one another are defined as R(1);

but with the condition that at least one of the substituents R(A), R(B), R(C), R(D), R(1), R(2), R(4) or R(5) is a $O_t(CH_2)_a C_b F_{2b+1}$, or $O_t(CH_2)_d C_e F_{2e+1}$ group and R(3) is not a $O_t(CH_2)_d C_e F_{2e+1}$ group;

and their pharmaceutically tolerable salts;

(HOE 94/F 182-EP-Offenlegungsschrift 690 048, NZ 272 449)

ab) ortho-amino-substituted benzoylguanidines of the formula I

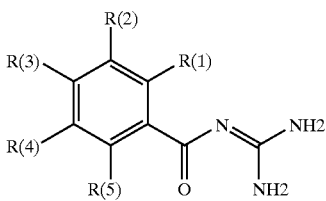

I in which:

R(1) is NR(50)R(6), R(50) and R(6) independently of one another are hydrogen, $(C_1-C_8)$-alkyl or $(C_1-C_8)$-perfluoroalkyl;

R(2), R(3), R(4) and R(5) independently of one another ere R(10)—$SO_a$—; , R(11)R(12)N—CO—, R(13)—CO— or R(14)R(15)N—$SO_2$—;

a is zero, 1 or 2,

R(10), R(11), R(12), R(13), R(14) and R(15) independently of one another are $(C_1-C_8)$-alkyl, $(C_1-C_8)$-perfluoroalkyl, $(C_3-C_6)$-alkenyl, or —$C_{ab}H_{2ab}$—R(16);

ab is zero, 1, 2, 3 or 4;

R(16) is $(C_3-C_7)$-cycloalkyl, phenyl, which is not substituted or is substituted by 1–3 substituents selected from the group consisting of F, Cl, $CF_3$, methyl, methoxy and NR(17)R(18);

R(17) and R(18) independently of one another are H, $CF_3$ or $(C_1-C_4)$-alkyl;

or

R(11), R(12), and also R(14) and R(15) together are 4 or 5 methylene groups, of which one $CH_2$ group can be replaced by oxygen, S, NH, N—$CH_3$ or N-benzyl, or R(11), R(12), R(14) and R(15) independently of one another are hydrogen;

or

R(2), R(3), R(4) and R(5) independently of one another are SR(21), —OR(b 2), —NR(23)R(24) or —CR(25)R(26)R(27);

R(21), R(22), R(23) and R(25) independently of one another are —$C_b H_{2b}$—$(C_1-C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

b is zero, 1 or 2;

R(24), R(26) and R(27) independently of one another are hydrogen, $(C_1-C_4)$-alkyl or $(C_1-C_4)$-perfluoroalkyl;

or

R(2), R(3), R(4) and R(5) independently of one another are hydrogen, F, Cl, Br, I, CN, —$(Xa)_{dg}$—$C_{da}H_{2da+1}$, —$(Xb)_{dh}$—$(CH_2)_{db}$—$C_{de}F_{2de+1}$, $(C_3-C_8)$-alkenyl or —$C_{df}H_{2df}$R(30);

(Xa) is O, S or NR(33);

R(33) is H, $(C_1-C_4)$-alkyl or $(C_1-C_4)$-perfluoroalkyl;

dg is zero or 1;

(Xb) is O, S or NR(34);

R(34) is H, $(C_1-C_4)$-alkyl, or $(C_1-C_4)$-perfluoroalkyl;

dh is zero or 1;

da is zero, 1, 2, 3, 4, 5, 6, 7, 8;

db is zero, 1, 2, 3, 4;

de is zero, 1, 2, 3, 4, 5, 6, 7;

df is zero, 1, 2, 3, 4;

R(30) is $(C_3-C_8)$-cycloalkyl, phenyl, biphenyl or naphthyl, where the aromatics phenyl, biphenylyl or naphthyl are not substituted or are substituted by 1–3 substituents selected from the group consisting of F, Cl, $CF_3$, methyl, methoxy and NR(31)R(32);

R(31) and R(32) are H, $(C_1-C_4)$-alkyl or $(C_1-C_4)$-perfluoroalkyl;

or

R(2), R(3), R(4) and R(5) independently of one another are NR(40)R(41) or —(Xe)—$(CH_2)_{eb}$R(45);

R(40) and R(41); independently of one another are hydrogen, $(C_1-C_8)$-alkyl, $(C_1-C_8)$-perfluoroalkyl or $(CH_2)$; R(42);

e is zero, 1, 2, 3 or 4;

R(42) is $(C_3-C_7)$-cycloalkyl, phenyl, which is not substituted or is substituted by 1–3 substituents selected from the group consisting of F, Cl, $CF_3$, methyl methoxy and NR(43)R(44);

R(43) and R(44) independently of one another are H, $CF_3$ or $(C_1-C_4)$-alkyl;

or

R(40) and R(41) together are 4 or 5 methylene groups, of which one $CH_2$ group can be replaced by oxygen, sulfur, NH, N—$CH_3$ or N-benzyl;

(Xe) is O, S or NR(47);

R(47) is H, $(C_1-C_4)$-alkyl or $(C_1-C_4)$-perfluoroalkyl;

eb is zero, 1, 2, 3 or 4;

R(45) is ($C_3$–$C_7$)-cycloalkyl, phenyl, which is not substituted or is substituted by 1–3 substituents selected from the group consisting of F, Cl, $CF_3$, methyl, methoxy, NR(50)R(51) and —(Xfa)—$(CH_2)_{ed}$—(Xfb)R(46);

Xfa is $CH_2$ O, S or NR(48);

Xfb is O, S or NR(49);

ed is 1, 2, 3 or 4;

R(46) is H, ($C_1$–$C_4$)-alkyl or ($C_1$–$C_4$)-perfluoroalkyl;

R(48), R(49), R(50) and R(51) independently of one another are H or ($C_1$–$C_4$)-alkyl or ($C_1$–$C_4$)-perfluoroalkyl;

where R(3) and R(4), however, cannot be hydrogen, and their pharmaceutically tolerable salts;

(HOE 94/E 265-NZ 272 948, EP-Offenlegungsschrift 700 904)

ac) benzoylguanidines of the formula I

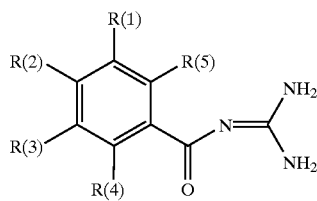

I in which:

one of the three substituents R(1), R(2) and R(3) is ($C_1$–$C_9$)-heteroaryl-N-oxide, which is inked via C or N and which is unsubstituted or substituted by 1–3 substituents selected from the group consisting of F, Cl, $CF_3$, $CH_3$, methoxy, hydroxyl, amino methylamino and dimethylamino;

or one of the three substituents R(1), R(2) and R(3) is —SR(10), —OR(10), —NR(10)R(11) of —CR(10))R(11)R(12);

R(10) is —$C_aF_{2a}$—($C_1$–$C_9$)-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;

a is zero, 1, or 2;

R(11) and R(12) independently of one another are defined as R(10), are hydrogen or ($C_1$–$C_4$)-alkyl;

and the other substituents R(1), R(2) and R(3) in each case independently of one another are ($C_1$–$C_8$)-alkyl, ($C_2$–$C_8$)-alkyl; or —$C_mH_{2m}$R(14);

m is zero, 1 or 2;

R(14) is ($C_3$–$C_8$)-cycloalkyl or phenyl, which is not substituted or is substituted by 1–3 substituents selected from the group consisting of F, Cl, $CF_3$, methyl, methoxy and NR(15)R(16), R(15) and R(16) are hydrogen or $CH_3$;

or the other substituents R(1), R(2) and R(3) in each case independently of one another are hydrogen, F, Cl, Br, I, —C≡N, X—$(CH_2)_p$—$(C_qF_{2q+1})$, R(22)—$SO_u$, R(23)R(24)N—CO, R(25)—CO—or R(26)R(27)N—$SO_2$—, where the perfluoroalkyl group is straighten or branched;

X is a bond, oxygen, S or NR(28);

u is zero, 1 or 2;

p is zero, 1 or 2;

q is zero, 1, 2, 3, 4, 5 or 8;

R(22), R(23), R(25) and R(26) independently are ($C_1$–$C_8$)-alkyl, ($C_2$–$C_8$)-alkenyl, —$C_nH_{2n}$—R(29) or $CF_3$;

n is zero, 1, 2, 3 or 4;

R(28) is hydrogen or ($C_1$–$C_3$)-alkyl;

R(29) is ($C_3$–$C_7$)-cycloalkyl or phenyl; which is not substituted or is substituted by 1–3 substituents selected from the group consisting of F, Cl, $CF_3$, methyl, methoxy and NR(30)R(31);

R(30) and R(31) are hydrogen or $C_1$–$C_4$alkyl, or

R(23), R(25) and R(26) are also hydrogen;

R(24) and R(27) independently of one another are hydrogen or ($C_1$–$C_4$)-alkyl;

or

R(23) and R(24), and also R(26) and R(27) together are 4 or 5 methylene groups, of which one $CH_2$ group can be replaced by oxygen, S, NH, N—$CH_3$ or N-benzyl;

or the other substituents R(1), R(2) and R(3) in each case independently of one another are OR(35) or NR(35)R(36); R(35) and R(38) independently of one another are hydrogen or ($C_1$–$C_6$)-alkyl;

or

R(35) and R(36) together are 4–7 methylene groups, of which one $CH_2$ group can be replaced by oxygen, S, NH, N—$CH_3$ or N-benzyl, R(4) and R(5) independently of one another are hydrogen, ($C_1$–$C_4$)-alkyl, F, Cl, R(32), R(33) and R(34) independently of one another are hydrogen or ($C_1$–$C_3$)-alkyl;

r is 1, 2, 3 or 4;

and their pharmaceutically tolerable salts;

(HOE 94/E 266-EP-Offenlegungsschrift 702 001, NZ 272 948)

ad) benzoylguanidines of the formula I

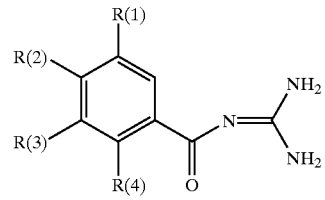

I in which:

R(1) is hydrogen, F, Cl, Br, I, CN, $NO_2$, OH, ($C_1$–$C_8$)-alkyl, ($C_3$–$C_8$)-cycloalkyl, $O_a$—$(CH_2)_b$—$(CF_2)_c$—$CF_3$;

a is zero or 1;

b is zero, 1 or 2;

c is zero, 1, 2 or 3;

or

R(1) is R(5)—$SO_m$ or R(6)R(7)N—$SO_2$—;

m is zero, 1 or 2;

R(5) and R(6) independently of one another are ($C_1$–$C_8$)-alkyl, ($C_3$–$C_6$)-alkenyl, $CF_3$ or —$C_nH_{2n}$—R(8);

n is zero, 1, 2, 3 or 4;

R(7) is hydrogen or ($C_1$–$C_4$)-alkyl;

R(8) a ($C_3$–$C_7$)-cycloalkyl or phenyl, which is not substituted or is substituted by 1–3 substituents selected from the group consisting of F, Cl, $CF_3$, methyl, methoxy and NR(9)R(10);

R(9) and R(10) independently of one another are hydrogen or ($C_1$–$C_4$)-alkyl;

or

R(6) is H;

or R(6) and R(7) together are 4 or 5 methylene groups, of which one $CH_2$ group can be replaced by oxygen, S, NH, N—$CH_3$ or N-benzyl, or R(1) is —SR(11), —OR(11) or —CR(11)R(12)R(13);

R(11) is —$C_pH_{2p}$—($C_3$–$C_8$)-cycloalkyl, —($C_1$–$C_9$)-heteroaryl or phenyl, where the aromatic systems are unsubstituted or substituted by 1–3 substituents selected from the group consisting of F, Cl, $CF_3$, $CH_3$, methoxy, hydroxyl, amino, methylamino and dimethylamino;

R(12), R(13) independently of one another are defined as R(11) or are hydrogen or ($C_1$–$C_4$)-alkyl;

p is zero, 1 or 2;

or

R(1) is phenyl, naphthyl, biphenylyl or ($C_1$–$C_9$)-heteroaryl, the latter linked via C or N, which are unsubstituted or substituted by 1–3 substituents selected from the group consisting of F, Cl, $CF_3$, $CH_3$, methoxy, hydroxyl, amino, methylamino and dimethylamino;

R(2) is —$CF_2$R(14), —CF[R(15)][R(16)], —CF[($CF_2$)$_q$—$CF_3$)][R(15)], —C[($CF_2$)$_r$—$CF_3$]=CR(15)R(16);

R(14) is ($C_1$–$C_4$)-alkyl or ($C_3$–$C_6$)-cycloalkyl;

R(15) and R(16) independently of one another are hydrogen or ($C_1$–$C_4$)-alkyl;

q is zero, 1 or 2;

r is zero, 1 or 2;

R(3) is defined as R(1);

R(4) is hydrogen, ($C_1$–$C_3$)-alkyl, F, Cl, Br, I, CN, —($CH_2$)$_s$—($CF_2$)$_t$—$CF_3$;

s is zero or 1;

t is zero, 1 or 2;

and their pharmaceutically tolerable salts;

(HOE 94/F 267—EP-Offenlegungsschrift 700 899, NZ 272 947)

ae) benzoylguanidines of the formula I

I in which:

one of the three substituents R(1), R(2) and R(3) is

—Y—4—[($CH_2$)$_k$—CHR(7)—(C=O)R(8)]-phenyl,

—Y—3—($CH_2$)$_k$—CHR(7)—(C=O)R(8)]-phenyl or

—Y—2—[$CH_2$]$_k$—CHR(7)—(C=O)R(8)]-phenyl, where the phenyl in each case is unsubstituted or substituted by 1–2 substituents from the group F, Cl, —$CF_3$, methyl, hydroxyl, methoxy, or —NR(37)R(38);

R(37) and R(38) independently of one another are hydrogen or —$CH_3$;

Y is a bond, oxygen, —S— or —NR(9);

R(9) is hydrogen or —($C_1$–$C_4$)-alkyl;

R(7) is —OR(10) or —NR(10)R(11);

R(10) and R(11) independently of one another are hydrogen, —($C_1$–$C_8$)-alkyl, —($C_1$–$C_8$)-alkanoyl, —($C_1$–$C_8$)-alkoxycarbonyl, benzyl, benzyloxycarbonyl;

or

R(10) is trityl;

R(8) is —OR(12) or —NR(12)R(13);

R(12) and R(13) independently of one another are hydrogen, —($C_1$–$C_8$)-alkyl or benzyl;

k is zero, 1, 2, 3 or 4;

and the other radicals R(1), R(2) and R(3) in each case independently of one another are —($C_1$–$C_8$)-alkyl, —$C_2$–$C_8$)-alkenyl or —($CH_2$)$_m$R(14);

m is zero, 1 or 2;

R(14) is —($C_3$–$C_8$)-cycloalkyl or phenyl, which is not substituted or is substituted by 1–3 substituents selected from the group consisting of F, Cl, —$CF_3$, methyl, methoxy and —NR(14)R(16);

R(15) and R(16) are hydrogen or —$CH_3$;

or the other radicals R(1), R(2) and R(3) in each case independently of one another are R(18)R(19)N—(C=Y')—NH—$SO_2$—; Y' is oxygen, —S— or —N—R(20);

R(18) and R(19) independently of one another are hydrogen, —($C_1$–$C_8$)-alkyl, —($C_3$–$C_6$)-alkenyl or —($CH_2$)$_t$—R(21);

t is zero, 1, 2, 3 or 4;

R(21) is —($C_5$–$C_7$)-cycloalkyl or phenyl, which is unsubstituted or substituted by 1–3 substituents selected from the group consisting of F, Cl, —$CF_3$, methoxy and —($C_1$–$C_4$)-alkyl;

or

R(18) and R(19) together are 4 or 5 methylene groups, of which one $CH_2$ group can be replaced by oxygen, —S—, —NH—, —N—$CH_3$ or —N-benzyl;

R(20) is defined as R(18) or is amidine;

or the other radicals R(1), R(2) and R(3) in each case independently of one another are hydrogen, F, Cl, Br, I, —C≡N, X—($CH_2$)$_p$—($C_qF_{2q+1}$), R(22)—$SO_u$—, R(23)R(24)N—CO—, R(25)—CO— or R(26)R(27)N—$SO_2$—, where the perfluoroalkyl group is straight-chain or branched;

X is a bond, oxygen, —S— or —NR(28);

u is zero, 1 or 2;

p is zero, 1 or 2;

q is 1, 2, 3, 4, 5 or 6;

R(22), R(23), R(25) and R(26) independently of one another are —($C_1$–$C_8$)-alkyl, —($C_3$–$C_6$)-alkenyl, —($CH_2$)$_n$—R(29) or —$CF_3$;

n is zero, 1, 2, 3 or 4;

R(28) is hydrogen or —($C_1$–$C_3$)-alkyl;

R(29) is —($C_3$–$C_7$)-cycloalkyl or phenyl, which is not substituted or is substituted by 1–3 substituents selected from the group consisting of F, Cl, —$CF_3$, methyl, methoxy and —NR(30)R(31);

R(30) and R(31) are hydrogen or —($C_1$–$C_4$)-alkyl;

or

R(23), R(25) and R(26) are hydrogen;

R(24) and R(27) independently of one another are hydrogen or —($C_1$–$C_4$)-alkyl;

or

R(23) and R(24), and also R(26) and R(27) together are 4 or 5 methylene groups, of which one $CH_2$ group can be replaced by oxygen, —S—, —NH—, —N—$CH_3$ or —N-benzyl;

or the other radicals R(1), R(2) and R(3) in each case independently of one another are —OR(35) or —NR(35)R(36);

R(35) and R(36) independently of one another are hydrogen or —($C_1$–$C_6$)-alkyl;
or
R(35) and R(36) together are 4–7 methylene groups, of which one $CH_2$ group can be replaced by oxygen, —S—, —NH—, —N—$CH_3$ or —N-benzyl;
R(4) and R(5) independently of one another are hydrogen, —($C_1$–$C_4$)-alkyl, F, Cl, —OR(32), —NR(33)R(34) or —$C_rF_{2r+1}$;
R(32), R(33) and R(34) independently of one another are hydrogen or —($C_1$–$C_3$)-alkyl;
r is 1, 2, 3 or 4;
and their pharmaceutically tolerable salts;
(HOE 94/F 352—EP-Offenlegungsschrift 713 684, NZ 280 517)
af) benzoylguanidines of the formula I

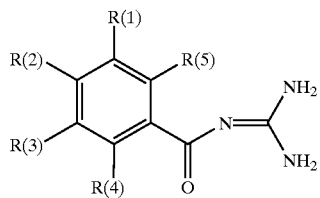

in which:
R(1) is R(6)—CO or R(7)R(8)N—CO;
R(6) is ($C_1$–$C_8$)-alkyl, ($C_1$–$C_8$)-perfluoroalkyl, ($C_3$–$C_8$)-alkenyl or —$C_nH_{2n}$—R(9),
n, is zero, 1, 2, 3 or 4;
R(9) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(10)R(11),
R(10) and R(11) are H, ($C_1$–$C_4$)-alkyl or ($C_1$–$C_4$)-perfluoroalkyl;
R(7) is H, ($C_1$–$C_8$)-alkyl, ($C_1$–$C_8$)-perfluoroalkyl, ($C_3$–$C_8$)-alkenyl or —$C_nH_{2n}$—R(12);
n is zero, 1, 2, 3 or 4;
R(12) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(13)R(14);
R(13) and R(14) are H, ($C_1$–$C_4$)-alkyl or ($C_1$–$C_4$)-perfluoroalkyl;
R(8) is H, ($C_1$–$C_4$)-alkyl or ($C_1$–$C_4$)-perfluoroalkyl;
or
R(7) and R(8) together are 4 or 5 methylene groups, of which one $CH_2$ group can be replaced by oxygen, S, NH, N—$CH_3$ or N-benzyl;
R(2) is defined as R(1), or is H, OH, F, Cl, Br, I, CN, $NO_2$, ($C_1$–$C_8$)-alkyl, ($C_1$–$C_8$)-perfluoroalkyl, ($C_3$–$C_8$)-alkenyl or —$C_nH_{2n}$R(15);
n is zero, 1, 2, 3 or 4;
R(15) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(16)R(17);
R(16) and R(17) are H, ($C_1$–$C_4$)-alkyl or ($C_1$–$C_4$)-perfluoroalkyl;

or
R(2) is ($C_1$–$C_9$)-heteroaryl, which is linked via C or N and which is unsubstituted or substituted by 1–3 substituents selected from the group consisting of F, Cl, $CF_3$, $CH_3$, methoxy, hydroxyl, amino, methylamino and dimethylamino;
or
R(2) is SR(18), —OR(18), —NR(18)R(19) or —CR(18)R(19)R(20);
R(18) is $C_aH_{2a}$—($C_1$–$C_9$)-heteroaryl, which is unsubstituted or substituted by 1–3 substituents selected from the group consisting of F, Cl, $CF_3$, $CH_3$, methoxy, hydroxyl, amino, methylamino, dimethylamino;
a is zero, 1 or 2;
R(19) and R(20) independently of one another are defined as R(18) or are hydrogen, ($C_1$–$C_4$)-alkyl or ($C_1$–$C_4$)-perfluoroalkyl;
or
R(2) is R(21)—$SO_m$ or R(22)R(23)N—$SO_2$—;
m is 1 or 2;
R(21) is ($C_1$–$C_8$)-alkyl, ($C_1$–$C_8$)-perfluoroalkyl, ($C_3$–$C_8$)-alkenyl or —$C_nH_{2n}$—R(24);
n is zero, 1, 2, 3 or 4;
R(24) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(27)R(28);
R(27) and R(28) are H, ($C_1$–$C_4$)-alkyl or ($C_1$–$C_4$)-perfluoroalkyl;
R(22) is H, ($C_1$–$C_8$)-alkyl, ($C_1$–$C_8$)-perfluoroalkyl, ($C_3$–$C_8$)-alkenyl or —$C_nH_{2n}$—R(29);
n is zero, 1, 2, 3 or 4;
R(29) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(30)R(31);
R(30) and R(31) are H, ($C_1$–$C_4$)-alkyl or ($C_1$–$C_4$)-perfluoroalkyl;
R(23) is hydrogen, ($C_1$–$C_4$)-alkyl or ($C_1$–$C_4$)-perfluoroalkyl;
or
R(22) and R(23) together are 4 or 5 methylene groups, of which one $CH_2$ group can be replaced by oxygen, S, NH, N—$CH_3$ or N-benzyl;
or
R(2) is R(33)X—;
X is oxygen, S, NR(34), (D=O)A- or NR(34)C=MN[(*)]R(35)—;
M is oxygen or S;
A is oxygen or NR(34);
D is C or SO;
R(33) is ($C_1$–$C_8$)-alkyl, ($C_3$–$C_8$)-alkenyl, ($CH_2$)$_bC_dF_{2d+1}$ or —$C_nH_{2n}$—R(36);
b is zero or 1;
d is 1, 2, 3, 4, 5, 6 or 7;
n is zero, 1, 2, 3, or 4;
R(36) is ($C_3$–$C_8$)-cycloalkyl, phenyl, biphenylyl or naphthyl, where the aromatics are not substituted or are substituted by 1–3 substituents selected from the group consisting of F, Cl, $CF_3$, methyl, methoxy and NR(37)R(38);
R(37) and R(38) are H, ($C_1$–$C_4$)-alkyl or ($C_1$–$C_4$)-perfluoroalkyl;
R(34) is hydrogen, ($C_1$–$C_4$)-alkyl or ($C_1$–$C_4$)-perfluoroalkyl;

R(35) is defined as R(33);
or
R(33) and R(34) together are 4 or 5 methylene groups, of which one CH$_2$ group can be replaced by oxygen, S, NH, N—CH$_3$ or N-benzyl;
where A and N$^{(*)}$ are bonded to the phenyl nucleus of the benzoylguanidine parent structure;
or
R(2) —SR(40), —OR(40), —NHR(40), —NR(40)R(41), —CHR(40)R(42), —CR(42)R(43)OH, —C≡CR(45), —CR(46)=CR(45) or —[CR(47)R(48)]$_u$—CO—[C(R49)R(50)]$_v$—R(44);
R(40) and R(41) independently of one another are —(CH$_2$)$_p$—(CHOH)$_q$—(CH$_2$)$_r$—(CHOH)$_t$—R(51) or —(CH$_2$)$_p$—O—(CH$_2$—CH$_2$O)$_q$—R(51);
R(51) is hydrogen or methyl;
u is 1, 2, 3 or 4;
v is zero, 1, 2, 3 or 4;
p, q and r independently of one another are zero, 1, 2, 3 or 4;
t is 1, 2, 3 or 4;
R(42) and R(43) independently of one another are hydrogen or (C$_1$–C$_6$)-alkyl;
or
R(42) and R(43) together with the carbon atom carrying them are a (C$_3$–C$_8$)-cycloalkyl;
R(44) is hydrogen, (C$_1$–C$_6$)-alkyl, (C$_3$–C$_8$)-cycloalkyl, —C$_e$H$_{2e}$—R(45); e is zero, 1, 2, 3 or 4;
R(45) is phenyl, which is unsubstituted or substituted by 1–3 substituents selected from the group consisting of F, Cl, CF$_3$, methyl, methoxy and NR(52)R(53);
R(52) and R(53) are H or (C$_1$–C$_4$)-alkyl;
or
R(45) is (C$_1$–C$_9$)-heteroaryl, which is unsubstituted or substituted as phenyl;
or
R(45) is (C$_1$–C$_6$)-alkyl, which is unsubstituted or substituted by 1–3 OH;
R(46), R(47), R(48), R(49) and R(50) independently of one another are hydrogen or methyl;
or R(2) is R(55)—NH—SO$_2$—;
R(55) is R(56)R(57)N—(C=Y)—;
Y is oxygen, S or N—R(58);
R(56) and R(57) independently of one another are hydrogen, (C$_1$–C$_8$)-alkyl, (C$_3$–C$_6$)-alkenyl or —C$_f$H$_{2f}$—R(59);
f is zero, 1, 2, 3 or 4;
R(59) is (C$_5$–C$_7$)-cycloalkyl, phenyl, which is unsubstituted or substituted by 1–3 substituents selected from the group consisting of F, Cl, CF$_3$, methoxy and (C$_1$–C$_4$)-alkyl;
or
R(56) and R(57) together are 4 or 5 methylene groups, of which one CH$_2$ group can be replaced by oxygen, S, NH, N—CH$_3$ or N-benzyl;
R(58) is defined as R(56) or is amidine;
R(3), R(4) and R(5) are independently of one another defined as R(1) or R(2), but where at least one of the substituents R(2), R(3), R(4) and R(5) must be OH;
and their pharmaceutically tolerable salts;
(HOE 95/F 0076 K—EP-Offenlegungsschrift 723 956, NZ 280 887)

ag) benzoylguanidines of the formula I

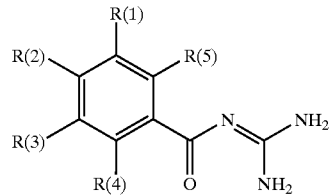

in which:
one of the three substituents R(1), R(2) and R(3) is R(6)-A-B-D-;
R(6) is a basic protonatable radical, i.e. an amino group —NR(7)R(8), an amidino group R(7)R(8)N—C[=N—R(9)]— or a guanidino group

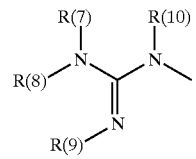

R(7), R(8), R(9) and R(10) independently of one another are hydrogen or alkyl having 1, 2, 3 or 4 carbon atoms;
or
R(7) and R(8) together are C$_a$H$_{2a}$;
a is 4, 5, 6 or 7; where if a=5, 6 or 7 a methylene group of the group C$_a$H$_{2a}$ can be replaced by a heteroatom group O, SO$_m$ or NR(11),
or
R(8) and R(9) or R(9) and R(10) or R(7) and R(10) are a group C$_a$H$_{2a}$;
a is 2, 3, 4 or 5; where if a=3, 4, or 5 a methylene group of the group C$_a$H$_{2a}$ can be replaced by a heteroatom group O, SO$_m$ or NR(11);
m is zero, 1 or 2;
R(11) is hydrogen or methyl;
or
R(6) is a basic heteroaromatic ring system having 1–9 carbon atoms;
A is C$_b$H$_{2b}$;
b is 1, 2, 3, 4, 5, 6, 7, 8, 9 or 10; where in the group C$_b$H$_{2b}$ one or two methylene groups can be replaced by one of the groupings selected from the group consisting of —O—, —CO—, —CH[OR(20)]—, —SO$_m$—, —NR(20)—, —NR(20)—CO—, —NR(20)—CO—NH—, —NR(20)—CO—NH—SO$_2$—

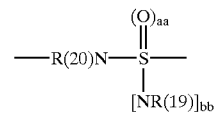

and —SO$_{aa}$[NR(29)]$_{bb}$—;
and where in the group C$_b$H$_{2b}$ a methylene group can be replaced by —CH—R(99), where R(99) together with R(7) forms a pyrrolidine or piperidine ring;
aa is 1 or 2;
bb is 0 or 1;
aa+bb=2;

R(19) is hydrogen or alkyl having 1, 2, 3 or 4 carbon atoms;

R(20) is hydrogen or methyl;

B is a phenylene or naphthylene radical

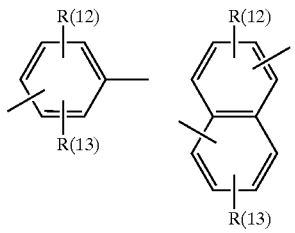

R(12) and R(13) independently of one another are hydrogen, methyl, F, Cl, Br, I, $CF_3$ or —$SO_w$—R (14);

R(14) is methyl or NR(15)R(16);

R(15) and R(16) independently of one another are hydrogen or alkyl having 1, 2, 3 or 4 carbon atoms;

w is zero, 1 or 2;

D is —$C_dH_{2d}$—$X_f$—;

d is zero, 1, 2, 3 or 4;

X is —O—, —CO—, —CH[OR(21)]—, —$SO_m$— or —NR(21)—;

f is zero or 1;

R(21) is hydrogen or methyl;

m is zero, 1 or 2;

and the other substituents R(1) and R(2) and R(3) in each case independently of one another are hydrogen, F, Cl, Br, I, —CN, —($C_1$-$C_8$)-alkyl, —($C_2$-$C_8$)-alkenyl, —NR(35)R(36) or R(17)—$C_gH_{2g}$—$Z_h$—;

g is zero, 1, 2, 3 or 4;

h is zero or 1;

R(35) and R(36) independently of one another are hydrogen or alkyl having 1, 2, 3, 4, 5 or 6 carbon atoms; or R(35) and R(36) together are 4–7 methylene groups, of which one $CH_2$ group can be replaced by oxygen, —S—, —NH—, —$NCH_3$ or —N-benzyl;

Z is —O—, —CO—, —$SO_v$—, —NR(18)—, —NR(18)—CO—, —NR(17)—CO—NH— or —NR(18)—$SO_2$—;

R(18) is hydrogen or methyl;

v is zero, 1 or 2;

R(17) is hydrogen, cycloalkyl having 3, 5 or 6 carbon atoms or $C_kF_{2k+1}$—;

k is 1, 2 or 3, or

R(17) is pyrrol-1-yl, pyrrol-2-yl or pyrrol-3-yl, which is not substituted or is substituted by 1–4 substituents selected from the group consisting of F, Cl, Br, I, —CN, ($C_2$-$C_8$)-alkanoyl, ($C_2$-$C_8$)-alkoxycarbonyl, formyl, carboxyl, —$CF_3$, methyl and methoxy; or R(17) -is ($C_3$-$C_8$)-cycloalkyl or phenyl, which is not substituted or is substituted by 1–3 substituents selected from the group consisting of F and Cl, —$CF_3$, methyl, hydroxyl, methoxy, —NR(37)R(38), $CH_3SO_2$— and $H_2NO_2S$—;

R(37) and R(38) are hydrogen or —$CH_3$;

R(4) and R(5) independently of one another are hydrogen, alkyl having 1, 2, 3 or 4 carbon atoms, F, Cl, —OR(32), —NR(33)R(34) or —$C_rF_{2r+1}$;

R(32), R(33) and R(34) independently of one another are hydrogen or alkyl having 1, 2 or 3 carbon atoms;

r is 1, 2, 3 or 4;

and their pharmacologically tolerable salts;

(HOE 95/F 072—EP-Offenlegungsschrift 738 712, NZ 286 380)

ah) indenoylguanidines of the formula I

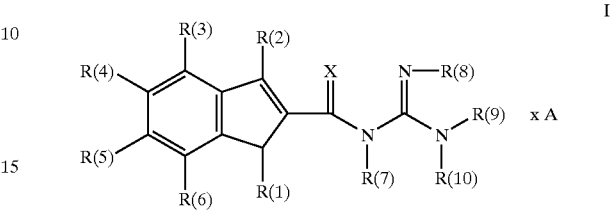

in which:

R(1) and R(2) independently of one another are hydrogen, alkyl having 1, 2, 3, 4, 5, 6, 7, 8, 9 or 10 carbon atoms, cycloalkyl having 3, 4, 5 or 6 carbon atoms, O-alkyl having 1, 2, 3 or 4 carbon atoms, O—C(=O)-alkyl having 1, 2, 3 or 4 carbon atoms or $C_mH_{2m}$—NR(12)R(13);

R(12) and R(13) independently of one another are hydrogen or alkyl having 1, 2, 3 or 4 carbon atoms;

m is zero, 1, 2, 3 or 4;

NH—C(=O)—$NH_2$, C(=O)—O-alkyl having 1, 2, 3 or 4 carbon atoms, C(=O)—$NH_2$, C(=O)—NH-alkyl having 1, 2, 3 or 4 carbon atoms, C(=O)—N(alkyl)$_2$ having 1, 2, 3 or 4 carbon atoms in each alkyl group, alkenyl having 2, 3, 4, 5, 6, 7, 8, 9 or 10 carbon atoms, alkynyl having 2, 3, 4, 5, 6, 7, 8, 9 or 10 carbon atoms, alkylaryl having 1, 2, 3 or 4 carbon atoms in the alkyl group, alkenylaryl having 2, 3, 4, 5, 6, 7, 8, 9 or 10 carbon atoms in the alkenyl group, alkynylaryl having 2, 3, 4, 5, 6, 7, 8, 9 or 10 carbon atoms in the alkynyl group, $C_1$-$C_4$-alkyl-substituted aryl, $C_1$-$C_4$-alkylheteroaryl, $C_1$-$C_4$-alkenylheteroaryl, aminoalkylaryl having 1, 2, 3 or 4 carbon atoms in the alkyl group, substituted aryl, heteroaryl and substituted heteroaryl;

R(3), R(4), R(5) and R(6) independently of one another are hydrogen, alkyl having 1, 2, 3, 4, 5, 6, 7, 8, 9 or 10 carbon atoms, O-alkyl having 1, 2, 3, 4, 5, 6, 7, 8, 9 or 10 carbon atoms, halogen, (such as F, Cl, Br, I), OH, aryl, substituted aryl, heteroaryl, substituted heteroaryl, O-lower alkyl, O-aryl, O-lower alkylaryl, O-substituted aryl, O-lower alkyl-substituted aryl, O—C(=O)—$C_1$-$C_4$-alkylaryl, O—C(=O)—NH—$C_1$-$C_4$-alkyl, O—C(=O)—N($C_1$-$C_4$-alkyl)$_2$, $NO_2$, CN, $CF_3$, $NH_2$, NH—C(=O)—$C_1$-$C_4$-alkyl, NH—C(=O)—$NH_2$, COOH, C(=O)—O—$C_1$-$C_4$-alkyl, C(=O)—$NH_2$, C(=O)—NH—$C_1$-$C_4$-alkyl, C(=O)—N($C_1$-$C_4$-alkyl)$_2$, $C_1$-$C_4$—COOH, $C_1$-$C_4$-alkyl-C(=O)—O—$C_1$-$C_4$-alkyl, $SO_3H$, $SO_2$-alkyl, $SO_2$-alkylaryl, $SO_2$—N-(alkyl)$_2$, $SO_2$—N(alkyl)(alkylaryl), C(=O)—R(11), $C_1$-$C_{10}$-alkyl-C(=O)—R(11), $C_2$-$C_{10}$-alkenyl-C(=O)—R(11), $C_2$-$C_{10}$-alkynyl-C(=O)—R(11), NH—C(=O)—$C_1$-$C_{10}$-alkyl-C(=O)—R(11), O—$C_1$-$C_{11}$-alkyl-C(=O)—R(11);

R(11) is $C_1$-$C_4$-alkyl, $C_1$-$C_4$-alkynyl, aryl, substituted aryl, $NH_2$, NH—$C_1$-$C_4$-alkyl, N—($C_1$-$C_4$-alkyl)$_2$, $SO_3H$, $SO_2$-alkyl, $SO_2$-alkylaryl, $SO_2$—N-(alkyl)$_2$, $SO_2$—N(alkyl)(alkylaryl);

X is O, S or NH;

R(7), R(8), R(9) and R(10) independently of one another are hydrogen, alkyl, cycloalkyl, aryl, alkylaryl;

or

R(8) and R(9) together are part of a 5, 6 or 7-membered heterocyclic ring;

A is absent or is a nontoxic organic or inorganic acid;

(HOE 95/F 109—EP 748 795, NZ 286 583)

ai) benzyloxycarbonylguanidines of the formula I

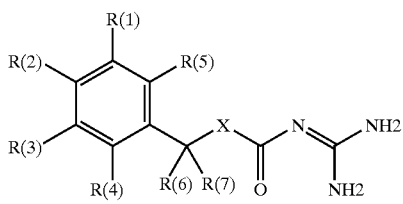

I in which:

R(1), R(2) and R(3) independently of one another are —Y-[4-R(8)-phenyl], —Y-[3-R(8)-phenyl] or —Y-[2-R(8)-phenyl], where the phenyl is in each case unsubstituted or substituted by 1–2 substituents from the group consisting of F, Cl, —$CF_3$, methyl, hydroxyl, methoxy and —NR(96)R(97); R(96) and R(97) independently of one another are hydrogen or —$CH_3$;

Y is a bond, $CH_2$, oxygen, —S— or —NR(9);
  R(9) is hydrogen or alkyl having 1, 2, 3 or 4 carbon atoms;

R(8) is $SO_a$[NR(98)]$_b$NR(99)R(10);
  a is 1 or 2;
  b is 0 or 1;
  a+b=2;
  R(98), R(99) and R(10) independently of one another are hydrogen, —($C_1$-$C_8$)-alkyl, benzyl, —($C_2$-$C_8$)-alkylene-NR(11)R(12), ($C_2$-$C_8$)-alkylene-NR(13)—($C_2$-$C_8$)-alkylene-NR(37)R(38) or ($C_0$-$C_8$)-alkylene-CR(39)R(40)CR(41)R(42)($C_0$-$C_8$)-alkylene-NR(43)R(44);
  R(11), R(12), R(13), R(37), R(38), R(43) and R(44) independently of one another are hydrogen, —($C_1$-$C_8$)-alkyl or benzyl;
  R(39), R(40), R(41) and R(42) independently of one another are hydrogen, —($C_1$-$C_8$)-alkyl or —($C_0$-$C_3$)-alkylenephenyl, where the phenyl is not substituted or is substituted by 1–3 substituents selected from the group consisting of F, Cl, —$CF_3$, methyl and methoxy;
  or
  R(99) and R(10) together are 4–6 methylene groups, or which one $CH_2$ group can be replaced by oxygen, —S—, —NH—, —N—$CH_3$ or —N-benzyl;
or
R(8) is $SO_a$[NR(98)]$_b$NR(95)—C[=N—R(94)]—NR(93)R(92); R(92), R(93), R(94) and R(95) independently of one another are hydrogen or alkyl having 1, 2, 3 or 4 carbon atoms;
or
R(1), R(2) and R(3) independently of one another are pyrrol-1-yl, pyrrol-2-yl or pyrrol-3-yl, which is not substituted or is substituted by 1–4 substituents selected from the group consisting of F, Cl, Br, I, —CN, ($C_2$-$C_8$)-alkanoyl, ($C_2$-$C_8$)-alkoxycarbonyl, formyl, carboxyl, —$CF_3$, methyl, methoxy;

or

R(1), R(2) and R(3) independently of one another are hydrogen, —($C_1$-$C_8$)-alkyl, —($C_2$-$C_8$)-alkenyl or —($CH_2$)$_m$R(14);
  m is zero, 1 or 2;
  R(14) is —($C_3$-$C_8$)-cycloalkyl or phenyl, which is not substituted or is substituted by 1–3 substituents selected from the group consisting of F and —Cl, —$CF_3$, methyl, methoxy and —NR(15)R(16);
  R(15) and R(16) are hydrogen or —$CH_3$;
or
R(1), R(2) and R(3) independently of one another are -Q-4-[($CH_2$)$_k$—CHR(17)—(C=O)R(20)]-phenyl, -Q-3-($CH_2$)$_k$—CHR(17)—(C=O)R(20)]-phenyl or -Q-2-[($CH_2$)$_k$—CHR(17)—(C=O)R(20)]-phenyl, where the phenyl in each case is unsubstituted or substituted by 1–2 substituents from the group F, Cl, —$CF_3$, methyl, hydroxyl, methoxy and —NR(35)R(36); R(35) and R(36) independently of one another are hydrogen or —$CH_3$;
  Q is a bond, oxygen, —S— or —NR(18);
  R(18) is hydrogen or —($C_1$-$C_4$)-alkyl;
  R(17) is —OR(21) or —NR(21)R(22);
  R(21) and R(22) independently of one another are hydrogen, —($C_1$-$C_8$)-alkyl, —($C_1$-$C_8$)-alkanoyl, —($C_1$-$C_8$)-alkoxycarbonyl, benzyl, benzyloxycarbonyl;
  or
  R(21) is trityl;
  R(20) is —OR(23) or —NR(23)R(24);
  R(23), R(24) independently or one another are hydrogen, —($C_1$-$C_8$)-alkyl or benzyl;
  k is zero, 1, 2, 3 or 4;
or
R(1), R(2) and R(3) independently of one another are ($C_1$-$C_9$)-heteroaryl, which is linked via C or N and which is unsubstituted or substituted by 1–3 substituents from the group F, Cl, $CF_3$, $CH_3$, methoxy, hydroxyl, amino, methylamino and dimethylamino;
or
R(1), R(2) and R(3) are —SR(25), —OR(25), —NR(25)R(26), —CR(25)R(26)R(27);
  R(25) is —$C_fH_{2f}$—($C_1$-$C_9$)-heteroaryl, which is unsubstituted or substituted by 1–3 substituents from the group F, Cl, $CF_3$, $CH_3$, methoxy, hydroxyl, amino, methylamino and dimethylamino;
  f is zero, 1 or 2;
  R(26) and R(27) independently of one another are defined as R(25) or are hydrogen or ($C_1$-$C_4$)-alkyl,
or
R(1), R(2) and R(3) independently of one another are ($C_1$-$C_9$)-heteroaryl-N-oxide, which is linked via C or N and which is unsubstituted or substituted by 1–3 substituents selected from the group consisting of F, Cl, $CF_3$, $CH_3$, methoxy, hydroxyl, amino, methylamino and dimethylamino;
or
R(1), R(2) and R(3) independently of one another are —SR(28), —OR(28), —NR(28)R(29) or —CR(28)R(29)R(30);
  R(28) is —$C_gH_{2g}$—($C_1$-$C_9$)-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;
  g is zero, 1 or 2;
  R(29), R(30) independently of one another are defined as R(28), hydrogen or ($C_1$-$C_4$)-alkyl;

or

R(1), R(2) and R(3) independently of one another are hydrogen, F, Cl, Br, I, —C≡N, T-(CH$_2$)$_h$—(C$_i$F$_{2i+1}$), R(31)SO$_l$—, R(32)R(33)N—CO—, R(34)—CO— or R(45)R(46)N—SO$_2$, where the perfluoroalkyl group is straight-chain or branched;

T is a bond, oxygen, —S— or —NR(47);

l is zero, 1 or 2;

h is zero, 1 or 2;

i is 1, 2, 3, 4, 5 or 6;

R(31), R(32), R(34) and R(45) independently of one another are —(C$_1$–C$_8$)-alkyl, —(C$_3$–C$_6$)-alkenyl; (CH$_2$)$_n$R(48) or —CF$_3$;

n is zero, 1, 2, 3 or 4;

R(47) is hydrogen or alkyl with 1, 2 or 3 carbon atoms;

R(48) is —(C$_3$–C$_7$)-cycloalkyl or phenyl, which is not substituted or is substituted by 1–3 substituents selected from the group consisting of F, Cl, —CF$_3$, methyl, methoxy and —NR(49)R(50);

R(49) and R(50) are hydrogen or alkyl having 1, 2, 3 or 4 carbon atoms;

or

R(32), R(34) and R(45) are hydrogen;

R(33) and R(46) independently of one another are hydrogen or alkyl having 1, 2, 3 or 4 carbon atoms;

or

R(32) and R(33), and R(45) and R(46) together are 5 or 6 methylene groups, of which one CH$_2$ group can be replaced by oxygen, —S—, —NH—, —NCH$_3$ or —N-benzyl;

or

R(1), R(2) and R(3) independently of one another are R(51)-A-G-D-;

R(51) is a basic protonatable radical, i.e. an amino group —NR(52)R(53), an amidino group R(52)R(53)N—C[=N—R(54)]— or a guanidino group R(52)R(53)N—C[=N—R(54)]—NR(55)—;

R(52), R(53), R(54) and R(55) independently of one another are hydrogen or alkyl having 1, 2, 3 or 4 carbon atoms;

or

R(52) and R(53) are a group C$_\alpha$H$_{2\alpha}$;

α is 4, 5, 6 or 7;

where if α=5, 6 or 7 a carbon atom of the group C$_\alpha$H$_{2\alpha}$ can be replaced by a heteroatom group O, SO$_d$ or NR(56), or R(53) and R(54) or R(54) and R(55) or R(52) and R(55) are a group C$_\gamma$H$_{2\gamma}$;

γ is 2, 3, 4 or 5;

where if γ=3, 4 or 5 a carbon atom of the group C$_\gamma$H$_{2\gamma}$ can be replaced by a heteroatom group O, SO$_d$ or NR(56);

d is zero, 1 or 2;

R(56) is hydrogen or methyl;

or

R(51) is a basic heteroaromatic ring system having 1–9 carbon atoms;

A is a group C$_e$H$_{2e}$;

e is zero, 1, 2, 3, 4, 5, 6, 7, 8, 9 or 10; where in the group C$_e$H$_{2e}$ a carbon atom can be replaced by one of the groupings —O—, —CO—, —CH[OR(57)]—, —SO$_r$—, —NR(57)—, —NR(57)—CO—, —NR(57)—CO—NH—, —NR(57)—CO—NH—SO$_2$— or —NR(57)—SO$_2$—;

r is zero, 1 or 2;

G is a phenylene radical

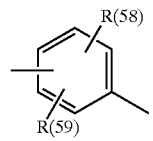

R(58) and R(59) independently of one another are hydrogen, methyl, methoxy, F, Cl, Br, I, CF$_3$ or —SO$_s$—R(60);

R(60) is methyl or NR(61)R(62);

R(61) and R(62) independently of one another are hydrogen or alkyl having 1, 2, 3 or 4 carbon atoms;

D is —C$_v$H$_{2v}$-E$_w$-;

v is zero, 1, 2, 3 or 4;

E is —O—, —CO—, —CH[OR(63)]—, —SO$_{aa}$— or —NR(63)—;

w is zero or 1;

aa is zero, 1 or 2

R(63) is hydrogen or methyl, or

R(1), R(2) and R(3) independently of one another are —CF$_2$R(64), —CF[R(65)][R(66)], —CF[(CF$_2$)$_q$—CF$_3$][R(65)], —C[(CF$_2$)$_p$—CF$_3$]=CR(65)R(66);

R(64) is alkyl having 1, 2, 3 or 4 carbon atoms or cycloalkyl having 3, 4, 5, 6 or 7 carbon atoms;

R(65) and R(66) independently of one another are hydrogen or alkyl having 1, 2, 3 or 4 carbon atoms;

q is zero, 1 or 2;

p is zero, 1 or 2;

or

R(1), R(2) and R(3) independently of one another are —OR(67) or —NR(67)R(68);

R(67) and R(68) independently of one another are hydrogen or alkyl having 1, 2, 3, 4, 5 or 6 carbon atoms;

or

R(67) and R(68) together are 4, 5, 6 or 7 methylene groups, of which one CH$_2$ group can be replaced by oxygen, —S—, SO$_2$, —NH—, —NCH$_3$ or —N-benzyl;

R(4) and R(5) independently of one another are hydrogen, alkyl having 1, 2, 3 or 4 carbon atoms, F, Cl, —OR(69), —NR(70)R(71) or —C$_z$F$_{2z+1}$;

R(69), R(70) and R(71) independently of one another are hydrogen or alkyl having 1, 2 or 3 carbon atoms;

z is 1, 2, 3 or 4;

R(6) and R(7) independently of one another are hydrogen or alkyl having 1, 2, 3 or 4 carbon atoms;

X is oxygen or NR(72);

R(72) is hydrogen or alkyl having 1, 2, 3 or 4 carbon atoms;

and their pharmaceutically tolerable salts;

(HOE 95/F 115—DP 744 397, NZ 286 622)

ak) alkenylcarboxylic acid guanidines, carrying fluorophenyl groups, of the formula I

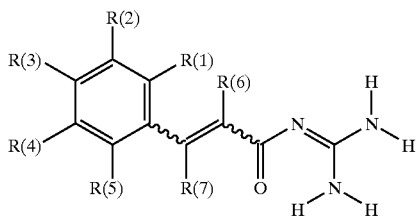

in which:

R(6) is hydrogen, $(C_1-C_8)$-alkyl, $(C_3-C_8)$-cycloalkyl or phenyl, where the phenyl group is not substituted or is substituted by 1–3 substituents selected from the group consisting of F, Cl, $CF_3$, methyl, methoxy and NR(9)R(10);

R(9) and R(10) are hydrogen, $(C_1-C_4)$-alkyl or $(C_1-C_4)$-perfluoroalkyl;

R(7) independently is defined as R(6);

R(1), R(2), R(3), R(4) and R(5) independently of one another are hydrogen or F; where, however, at least one of the radicals R(1), R(2), R(3), R(4) and R(5) must be fluorine;

and their pharmaceutically tolerable salts;

HOE 95/F 167—NZ 299 015)

al) benzoylguanidines of the formula I

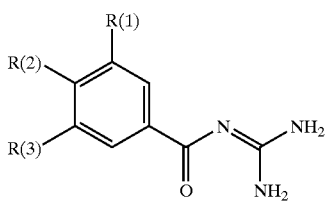

in which:

R(1) is R(4)—$SO_m$ or R(5)R(6)N—$SO_2$—;

m is 1 or 2;

R(4) and R(5) independently of one another are alkyl having 1, 2, 3, 4, 5, 6, 7 or 8 carbon atoms, alkenyl having 3, 4, 5 or 6 carbon atoms, $CF_3$ or —$C_nH_{2n}$—R(7);

n is zero, 1, 2, 3 or 4;

R(6) is H or alkyl having 1, 2, 3 or 4 carbon atoms;

R(7) is cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(8)R(9);

R(8) and R(9) are H or alkyl having 1, 2, 3 or 4 carbon atoms;

or

R(5) is also hydrogen;

or

R(5) and R(6) together are 4 or 5 methylene groups, of which a $CH_2$ group can be replaced by oxygen, S, NH, N—$CH_3$ or N-benzyl;

or

R(1) is —$O_p$—$(CH_2)_q$—$(CF_2)_r$—$CF_3$;

p is zero or 1;

q is zero, 1 or 2;

r is zero, 1, 2 or 3;

or

R(1) is —SR(10), —OR(10) or —CR(10)R(11)R(12);

R(10), R(11) and R(12) independently of one another are hydrogen, alkyl having 1, 2, 3, 4, 5, 6, 7 or 8 carbon atoms, —$C_sH_{2s}$—$(C_3-C_8)$-cycloalkyl or an aromatic system selected from the group consisting of pyridyl, pyrrolyl, quinolyl, isoquinolyl, imidazolyl or phenyl;

s is zero, 1 or 2; where the aromatic systems pyridyl, pyrrolyl, quinolyl, isoquinolyl, imidazolyl and phenyl are unsubstituted or substituted by 1–3 substituents selected from the group consisting of F, Cl, $CF_3$, $CH_3$, methoxy, hydroxyl, amino, methylamino and dimethylamino;

R(2) is —$(CH_2)_u$—$(CF_2)_t$—$CF_3$;

t is zero, 1, 2 or 3;

u is zero or 1;

R(3) is hydrogen or independently is defined as R(1);

and their pharmaceutically tolerable salts;

(HOE 95/F 173—NX 299 052)

am) substituted cinnamic acid guanidides of the formula I

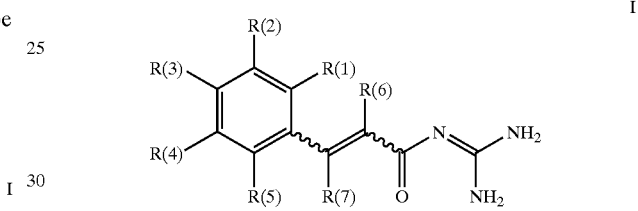

in which:

at least one of the substituents R(1), R(2), R(3), R(4) and R(5) is —$X_a$—$Y_b$—$L_n$—U;

X is CR(16)R(17), O, S or NR(18);

R(16), R(17) and R(18) independently of one another are H, alkyl having 1, 2, 3 or 4 carbon atoms or perfluoroalkyl having 1, 2, 3 or 4 carbon atoms;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T, T-alkylene having 1, 2, 3, 4, 5, 6, 7 or 8 carbon atoms in the alkylene group, T is NR(20), O, S or phenylene, where the phenylene is not substituted or is substituted by 1–3 substituents selected from the group consisting of F, Cl, $CF_3$, methyl, methoxy and NR(21)R(22);

R(20), R(21) and R(22) independently of one another are H, alkyl having 1, 2, 3 or 4 carbon atoms or perfluoroalkyl having 1, 2, 3 or 4 carbon atoms;

b is zero or 1;

L is O, S, NR(23) or $C_kH_{2k}$;

k is 1, 2, 3, 4, 5, 6, 7, 8;

n is zero or 1;

U is NR(24)R(25) or an N-containing heterocycle having 1, 2, 3, 4, 5, 6, 7, 8 or 9 carbon atoms;

R(24) and R(25) independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;

or

R(24) and R(25) together are 4 or 5 methylene groups, of which one $CH_2$ group can be replaced by oxygen, S, NH, N—$CH_3$ or N-benzyl;

where the N-containing heterocycles are N- or C-bridged and are not substituted or are substituted by 1–3 substituents selected from the group consisting of F, Cl, CF$_3$, methyl, methoxy and NR(27)R(28);

R(23), R(27) and R(28) independently of one another are H, alkyl having 1, 2, 3 or 4 carbon atoms or perfluoroalkyl having 1, 2, 3 or 4 carbon atoms;

and the other substituents R(1), R(2), R(3), R(4) and R(5) in each case independently of one another are H, F, Cl, Br, I, Cn, —O$_n$—C$_m$H$_{2m+1}$, —O$_p$—(CH$_2$)$_s$—C$_q$F$_{2q+1}$ or —C$_r$H$_{2r}$R(10);

n is zero or 1;

m is zero 1, 2, 3, 4, 5, 6, 7 or 8;

p is zero or 1;

q is 1, 2, 3, 4, 5, 6, 7 or 8;

s is zero, 1, 2, 3 or 4;

r is zero, 1, 2, 3 or 4;

R(10) is cycloalkyl having 3, 4, 5, 6, 7 or 8 carbon atoms, or phenyl, where the phenyl is not substituted or is substituted by 1–3 substitutents selected from the group consisting of F, Cl, CF$_3$, methyl, methoxy and NR(11)R(12);

R(11) and R(12) independently of one another are H, alkyl having 1, 2, 3, or 4 carbon atoms or perfluoroalkyl having 1, 2, 3 or 4 carbon atoms;

R(6) and R(7) independently of one another are hydrogen, F, Cl, Br, I, Cn, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, CF$_3$, methyl, methoxy and NR(14)R(15);

R(14) and R(15) independently of one another are H, alkyl having 1, 2, 3 or 4 carbon atoms or perfluoroalkyl having 1, 2, 3, or 4 carbon atoms;

and their pharmaceutically tolerable salts;

(HOE 95/F 220—NZ 299 052) an) benzoylguanidines of the formula I

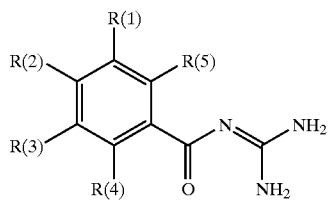

in which:

at least one of the substituents R(1), R(2) and R(3) is R(6—C(OH)$_2$—;

R(6) is perfluoroalkyl having 1, 2 or 3 carbon atoms, which is straight-chain or branched;

and the other substituents R(1), R(2) and R(3) independently of one another are hydrogen, OH, F, Cl, Br, I, alkyl having 1, 2, 3, 4, 5 or 6 carbon atoms, cycloalkyl with 3, 4, 5 or 6 carbon atoms, alkoxy having 1, 2, 3 or 4 carbon atoms or phenoxy, which is unsubstituted or is substituted by 1–3 substituents selected from the group consisting of F, Cl, methyl and methoxy;

or the other substituents R(1), R(2) and R(3) independently of one another are alkyl-SO$_x$, —CR(7)=CR(8)R(9) or —C≡CR(9);

x is zero, 1 or 2;

R(7) is hydrogen or methyl;

R(8) and R(9) independently of one another are hydrogen, alkyl having 1, 2, 3 or 4 carbon atoms, cycloalkyl having 3, 4, 5, 6, 7 or 8 carbon atoms or phenyl, which is unsubstituted or is substituted by 1–3 substituents selected from the group consisting of F, Cl, CF$_3$, methyl and methoxy;

or the other substituents R(1), R(2) and R(3) independently of one another are phenyl, C$_6$H$_5$—(C$_1$–C$_4$)-alkyl, naphthyl, biphenylyl, quinolinyl, isoquinolinyl or imidazolyl, where quinolinyl, isoquinolinyl or imidazolyl are bonded via C or N and where phenyl, C$_6$H$_5$-(C$_1$–C$_4$)-alkyl, naphthyl, biphenylyl, quinolinyl, isoquinolinyl and imidazolyl are unsubstituted or are substituted by 1–3 substituents selected from the group consisting of F, Cl, CF$_3$, CH$_3$, methoxy, hydroxyl, amino, methylamino and dimethylamino;

or the other substituents R(1), R(2) and R(3) independently of one another are SR(10), —OR(10), —CR(10)R(11)R(12);

R(10) is —C$_f$H$_{2f}$-(C$_3$–C$_8$)-cycloalkyl, quniolinyl, isoquinolinyl, pyridinyl, imidazolyl or phenyl, where the aromatic systems quinolinyl, isoquinolinyl, pyridinyl, imidazolyl and phenyl are unsubstituted or are substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12) independently of one another are defined as R(10), hydrogen or alkyl having 1, 2, 3 or 4 carbon atoms;

R(4) and R(5) independently of one another are hydrogen, alkyl having 1, 2 or 3 carbon atoms, F, Cl, Br, I, CN, OR(13), NR(14)R(15), —(CH$_2$)$_n$—(CF$_2$)$_o$—CF$_3$;

R(13), R(14) and R(15) independently of one another are hydrogen or alkyl having 1, 2, 3 or 4 carbon atoms;

n is zero or 1;

o is zero, 1 or 2;

and their pharmacologically acceptable salts;

(HOE 95/F 253—NZ 299 682) ao) sulfonimidamides of the formula I

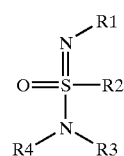

in which:

at least one of the three substituents R(1), R(2) and R(3) is a benzoylguanidine, which is unsubstituted or substituted in the phenyl moiety by 1—4 radicals selected from the group consisting of alkyl having 1, 2, 3, 4, 5, 6, 7 or 8 carbon atoms, alkenyl having 2, 3, 4, 5, 6, 7 or 8 carbon atoms, —(CH$_2$)$_m$—R(14), F, Cl, Br, I, —C≡N, CF$_3$, R(22)SO$_2$—, R(23)R(24)N—CO—, R(25)—CO—, R(26)R(27)N—SO$_2$, —OR(35), —SR(35) or —NR(35)R(36);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

R(22), R(23), R(25) and R(26) independently of one another are alkyl having 1, 2, 3, 4, 5, 6, 7 or 8 carbon atoms, alkenyl having 2, 3, 4, 5, 6, 7 or 8 carbon atoms, (CH$_2$)$_n$R(29) or —CF$_3$;

n is zero, 1, 2, 3 or 4;

R(29) is —(C$_3$–C$_7$)-cycloalkyl or phenyl, which is not substituted or is substituted by 1–3 substituents selected from the group consisting of F, Cl, —CF$_3$, methyl, methoxy and —NR(30)R(31);

R(30) and R(31) are hydrogen or alkyl having 1, 2, 3 or 4 carbon atoms;

or

R(23), R(25) and R(26) are hydrogen;

R(24) and R(27) independently of one another are hydrogen or alkyl having 1, 2, 3 or 4 carbon atoms;

or

R(23) and R(24), and also R(26) and R(27) together are 5 or 6 methylene groups, of which one CH$_2$ group can be replaced by oxygen, —S—, —NH—, —NCH$_3$ or —N-benzyl;

R(35) and R(36) independently of one another are hydrogen or alkyl having 1, 2, 3, 4, 5 or 6 carbon atoms;

or

R(35) and R(36) together are 4–7 methylene groups, of which one CH$_2$ group can be replaced by oxygen, —S—, —NH—, —NCH$_3$ or —N-benzyl;

or

R(35) is phenyl, which is not substituted or is substituted by 1–3 substituents selected from the group consisting of F, Cl, —CF$_3$, methyl, methoxy, SO$_2$R(5), SO$_2$NR(6)R(7) and —NR(32)R(33);

R(5) is alkyl having 1, 2, 3, 4, 5 or 6 carbon atoms

R(6) and R(7) independently of one another are hydrogen or alkyl having 1, 2, 3 or 4 carbon atoms;

R(32) and R(33) independently of one another are hydrogen or alkyl having 1, 2, 3 or 4 carbon atoms;

or

R(35) is C$_1$–C$_9$-heteroaryl, which is unsubstituted or substituted by 1–3 substituents selected from the group consisting of F, Cl, CF$_3$, CH$_3$, methoxy, hydroxyl, amino, methylamino and dimethylamino;

and the other substituents R(1), R(2) and R(3) in each case independently of one another are alkyl having 1, 2, 3, 4, 5, 6, 7 or 8 carbon atoms, (CH$_2$)$_p$R(10)

p is zero, 1, 2, 3 or 4;

R(10) is phenyl, which is not substituted or is substituted by 1–3 substituents selected from the group consisting of F, Cl, —CF$_3$, methyl, methoxy, —SO$_2$NR(17)R(8) and —SO$_2$R(9);

R(17) and R(8) independently of one another are hydrogen or alkyl having 1, 2, 3 or 4 carbon atoms;

R(9) is alkyl having 1, 2, 3 or 4 carbon atoms;

or the other radicals R(1) and R(3) in each case are hydrogen, R(4) is hydrogen or alkyl having 1, 2, 3 or 4 carbon atoms; and their pharmaceutically tolerable salts;

(HOE 95/F 265—NZ 299 739)

ap) benzoylguanidines of the formula I

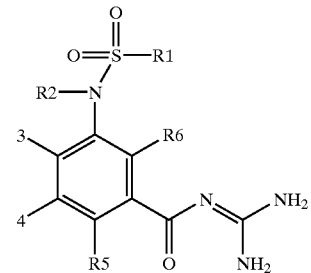

in which:

R(1) is alkyl having 1, 2, 3, 4, 5, 6, 7 or 8 carbon atoms or NR(7)R(8);

R(7) and R(8) independently of one another are hydrogen or alkyl having 1, 2, 3, 4, 5, 6, 7 or 8 carbon atoms;

R(2) is hydrogen, alkyl having 1, 2, 3, 4, 5, 6, 7 or 8 carbon atoms or —SO$_2$R(9);

R(9) independently is defined as R(1);

R(3) is hydrogen, —SR(25), —OR(25), —NR(25)R(26) or —CR(25)R(26)R(27);

R(25) is hydrogen, alkyl having 1, 2, 3, 4, 5, 6, 7 or 8 carbon atoms, or phenyl, which is unsubstituted or substituted by 1–3 substituents selected from the group consisting of F, Cl, CF$_3$, CH$_3$, methoxy, hydroxyl, amino, methylamino and dimethylamino;

or

R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is hydrogen, F, Cl, Br, I, OH, —C≡N, CF$_3$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);

R(15) and R(16) independently of one another are hydrogen or —CH$_3$;

R(5) and R(6) independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

and their pharmaceutically tolerable salts;

(HOE 95/F 269 K)

aq) benzenedicarboxylic acid diguanidides of the formula I

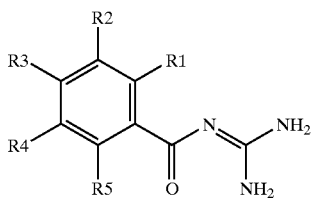

in which:
one of the radicals R(1), R(2), R(3) and R(4) is —CO—N═C(NH$_2$)$_2$;
and the other radicals R(1), R(2), R(3) and R(4) in each case are:
R(1) is hydrogen, alkyl having 1, 2, 3 or 4 carbon atoms, F, Cl, Br, I, —OR(32), —NR(33)R(34) or CF$_3$;
R(32), R(33) and R(34) independently of one another are hydrogen or alkyl having 1, 2, 3 or 4 carbon atoms;
R(2) and R(4) independently of one another are hydrogen, F, Cl, Br, I, OH, —CH, CF$_3$, —CO—N═C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) are hydrogen or —CH$_3$;
or
R(2) and R(4) independently of one another are pyrrol-1-yl, pyrrol-2-yl or pyrrol-3-yl, not which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl, methoxy;
or
R(2) and R(4) independently of one another are R(22)—SO$_2$—, R(23)R(24)N—CO—, R(28)—CO— or R(29)R(30)N—SO$_2$;
R(22) and R(28) independently of one another are methyl or —CF$_3$;
R(23), R(24), R(29) and R(30) independently of one another are hydrogen or methyl;
or
R(2) and R(4) independently of one another are —OR(35) or —NR(35)R(36);
R(35) and R(36) independently of one another are hydrogen or alkyl having 1, 2, 3, 4, 5 or 6 carbon atoms;
or
R(35) and R(36) together are 4–7 methylene groups, of which one CH$_2$ group can be replaced by oxygen, —S—, —NH—, —NCH$_3$ or —N-benzyl;
R(3) is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino;
or
R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;
R(5) is alkyl having 1, 2, 3 or 4 carbon atoms, F, Cl, Br, I, X—(CH$_2$)$_y$—CF$_3$ or phenyl, which is not substituted or is substituted by 1–3 substituents selected from the group consisting of F and Cl, —CF$_3$, methyl, methoxy and —NR(6)R(7);
R(6) and R(7) independently of one another are hydrogen or —CH$_3$;
X is a bond or oxygen;
y is zero, 1 or 2;
and their pharmaceutically tolerable salts;
(HOE 95/F 269 BK)
ar) benzenedicarboxylic acid diguanidides of the formula I

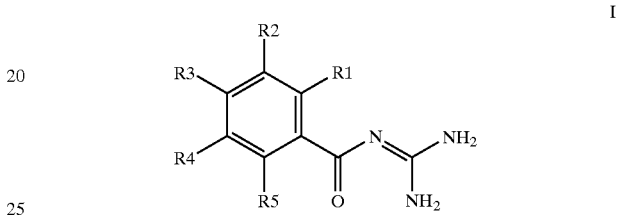

in which:
one of the radicals R(1), R(2), R(3) and R(5) is —CO—N═C(NH$_2$)$_2$;
and the other radicals R(1), R(2), R(3) and R(5) in each case are:
R(1) and R(5) independently of one another are hydrogen, alkyl having 1, 2, 3 or 4 carbon atoms, F, Cl, —OR(32), —NR(33)R(34) or CF$_3$;
R(32), R(33) and R(34) independently of one another are hydrogen or alkyl having 1, 2, 3 or 4 carbon atoms;
R(2) is hydrogen, F, Cl, Br, I, OH, —CN, CF$_3$, —CO—N═C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);
m is zero, 1 or 2;
R(14) is —(C$_3$–C$_8$)-cycloalkyl or phenyl, which is not substituted or is substituted by 1–3 substituents selected from the group consisting of F and Cl, —CF$_3$, methyl, methoxy and —NR(15)R(16);
R(15) and R(16) independently of one another are hydrogen or —CH$_3$;
or
R(2) is R(22)—SO$_2$—, R(23)R(24)N—CO—, R(28)—CO— or R(29)R(30)N—SO$_2$;
R(22) and R(28) independently of one another are methyl or —CF$_3$;
R(23), R(24), R(29) and R(30) independently of one another are hydrogen or methyl;
or
R(2) is —OR(35) or —NR(35)R(36);
R(35) and R(36) independently of one another are hydrogen or alkyl having 1, 2, 3, 4, 5 or 6 carbon atoms;
or
R(35) and R(36) together are 4–7 methylene groups, of which one CH$_2$ group can be replaced by oxygen, —S—, —NH—, —NCH$_3$ or —N-benzyl;
R(3) is hydrogen, —SR(25), —OR(25), —NR(25)R(26), —CR(25)R(26)R(27);
R(25) is hydrogen, alkyl having 1, 2, 3, 4, 5, 6, 7 or 8 carbon atoms or phenyl, which is unsubstituted or substituted by 1–3 substituents selected from the group consisting of F, Cl, $CF_3$, $CH_3$, methoxy, hydroxyl, amino, methylamino and dimethylamino;

or

R(25) is —$(C_1$–$C_9)$-heteroaryl, which is unsubstituted or substituted by 1–3 substituents selected from the group consisting of F, Cl, $CF_3$, $CH_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is $CF_3$, alkyl having 1, 2, 3, 4, 5, 6, 7 or 8 carbon atoms, alkenyl having 2, 3, 4, 5, 6, 7 or 8 carbon atoms, —$(C_3$–$C_8)$-cycloalkyl or —$(CH_2)_m R(14)$;

m is 1 or 2;

R(14) is —$(C_3$–$C_8)$-cycloalkyl or phenyl, which is not substituted or is substituted by 1–3 substituents selected from the group consisting of F and Cl, —$CF_3$, methyl, methoxy and —NR(15)R(16);

R(15) and R(16) independently of one another are hydrogen or —$CH_3$;

or

R(4) is phenyl, which is substituted by 2, 3, 4 or five substituents selected from the group consisting of F, Cl, $CF_3$, methyl, methoxy and —NR(15)R(16);

R(15) and R(16) independently of one another ar hydrogen or $CH_3$;

and their pharmaceutically tolerable salts;

(HOE 96/F 026)

at) substituted thiophenylalkenylcarboxylic acid guanidides of the formula I

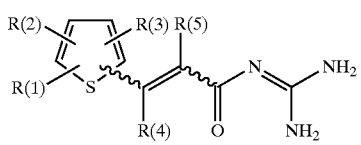

in which:

at least one of the substituents R(1), R(2) and R(3) is —$O_p$—$(CH_2)_s$—$C_q F_{2q+1}$, R(40)CO— or R(31)$SO_k$—;

p is zero or 1;

s is zero, 1, 2, 3 or 4;

q is 1, 2, 3, 4, 5, 6, 7 or 8;

k is zero, 1 or 2;

R(40) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl and methoxy;

R(31) is alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is not substituted or is substituted by 1–3 substituents selected from the group consisting of F, Cl, $CF_3$, methyl or methoxy;

or

R(31) is NR(41)R(42);

R(41) and R(42) independently of one another are hydrogen, alkyl having 1, 2, 3 or 4 carbon atoms, perfluoroalkyl having 1, 2, 3 or 4 carbon atoms, or R(41) and R(42) together are 4 or 5 methylene groups, of which one $CH_2$ group can be replaced by oxygen, S, NH, N—$CH_3$ or N-benzyl;

and the other substituents R(1), R(2) and R(3) in each case independently of one another are H, F, Cl, Br, I, CN, —$O_{na}$—$C_{ma}H_{2ma+1}$ or —$O_{ga}C_{ra}H_{2ra}R(10)$;

na is zero or 1;

ma is zero, 1, 2, 3, 4, 5, 6, 7 or 8;

ga is zero or 1;

ra is zero, 1, 2, 3, or 4;

R(10) is cycloalkyl having 3, 4, 5, 6, 7 or 8 carbon atoms or phenyl, Where the phenyl is not substituted or is substituted by 1–3 substituents selected from the group consisting of F, Cl, $CF_3$, methyl and methoxy;

R(4) and R(5) independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms or phenyl, which is not substituted or is substituted by 1–3 substituents selected from the group consisting of F, Cl, $CF_3$, methyl, methoxy and NR(14)R(15);

R(14) and R(15) independently of one another are H, alkyl having 1, 2, 3 or 4 carbon atoms or perfluoroalkyl having 1, 2, 3 or 4 carbon atoms;

and their pharmaceutically tolerable salts;

(HOE 96/F 032)

au) ortho-substituted benzoylguanidines of the formula I

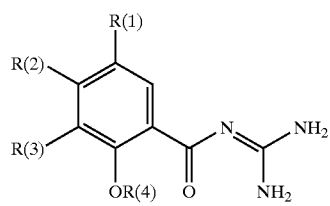

in which:

R(2) and R(3) independently of one another are hydrogen, Cl, Br, I, $(C_1$–$C_8)$-alkyl, $(C_3$–$C_8)$-cycloalkyl or —OR(5);

R(5) is $(C_1$–$C_8)$-alkyl or —$C_d H_{2d}$—$(C_3$–$C_8)$-cycloalkyl;

d is zero, 1 or 2;

where one of the two substituents R(2) and R(3) is always hydrogen but both substituents R(2) and R(3) are not simultaneously hydrogen, and their pharmaceutically tolerable salts;

(HOE 96/F 042)

av) benzoylguanidines of the formula I in which:

R(1) is H, F, Cl, Br, I, CN, $NO_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or $X_a$—$(CH_2)_b$—$(CF_2)_c$—$CF_3$;

X is oxygen, S, NR(5),
a is zero or 1;
b is zero, 1 or 2;
c is zero, 1, 2 or 3;
  R(5) is H, alkyl having 1, 2, 3 or 4 carbon atoms or —$C_dH_{2d}$R(6);
  d is zero, 1, 2, 3 or 4;
    R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, $CF_3$, methyl, methoxy and NR(7)R(8);
      R(7) and R(8) independently are H or alkyl having 1, 2, 3 or 4 carbon atoms;

or
R(1) is —SR(10), —OR(10) or —CR(10)R(11)R(12);
  R(10) is —$C_fH_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, $CF_3$, $CH_3$, methoxy, hydroxyl, amino, methylamino and dimethylamino;
  f is zero, 1 or 2;
  R(11) and R(12) independently of one another are defined as R(10) or are hydrogen or alkyl having 1, 2, 3 or 4 carbon atoms;

or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, $CF_3$, $CH_3$, methoxy, hydroxyl, amino, methylamino and dimethylamino, or
R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24),
  k is zero, 1, 2, 3 or 4;
  l is zero, 1, 2, 3 or 4;
  R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24);
  R(17) is hydrogen or methyl,
  g, h and i identically or differently are zero, 1, 2, 3 or 4;
  j is 1, 2, 3 or 4;
  R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;
  R(18) is phenyl, which is unsubstituted or substituted by 1–3 substituents selected from the group consisting of F, Cl, $CF_3$, methyl, methoxy and NR(25)R(26);
    R(25) and R(26) are H or alkyl having 1, 2, 3 or 4 carbon atoms;
  or
  R(18) is heteroaryl having 1, 2, 3, 4, 5, 6, 7, 8 or 9 carbon atoms, which is unsubstituted or substituted as phenyl;

or
  R(18) is alkyl having 1, 2, 3, 4, 5 or 6 carbon atoms, which is unsubstituted or substituted by 1–3 OH;
or
  R(18) is cycloalkyl having 3, 4, 5, 6, 7 or 8 carbon atoms;
  R(19), R(20), R(21), R(22) and R(23) identically or differently are hydrogen or methyl;
  R(24) is H, alkyl having 1, 2, 3, 4, 5 or 6 carbon atoms, cycloalkyl having 3, 4, 5, 6, 7 or 8 carbon atoms or —$C_mH_{2m}$—R(18);
  m is 1, 2, 3 or 4;
R(2) and R(3) are defined as R(1);
R(4) is alkyl having 1, 2, 3 or 4 carbon atoms;
and their pharmaceutically tolerable salts;
(HOE 96/F 043)
  aw) ortho-substituted benzoylguanidines of the formula I

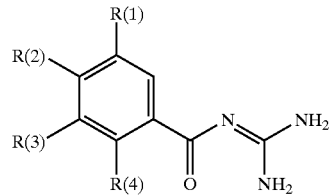

in which:
R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;
X is oxygen, S, NR(5),
a is zero or 1;
b is zero, 1 or 2;
c is zero, 1, 2 or 3;
  R(5) is H, alkyl having 1, 2, 3 or 4 carbon atoms or —$C_dH_{2d}$R(6);
  d is zero, 1, 2, 3 or 4;
    R(6) is cycloalkyl having 3, 4, 5, 6, 7 or 8 carbon atoms, phenyl, biphenylyl or naphthyl, where the aromatics phenyl, biphenylyl or naphthyl are unsubstituted or substituted by 1–3 substituents selected from the group consisting of F, Cl, $CF_3$, methyl, methoxy and NR(7)R(8);
      R(7) and R(8) independently are H or alkyl having 1, 2, 3 or 4 carbon atoms;

or
R(1) is —SR(10), —OR(10) or —CR(10)R(11)R(12);
  R(10) is —$C_fH_{2f}$-cycloalkyl having 3, 4, 5, 6, 7 or 8 carbon atoms in the cycloalkyl ring, or phenyl, where phenyl is unsubstituted or substituted by 1–3 substituents selected from the group consisting of F, Cl, $CF_3$, $CH_3$, methoxy, hydroxyl, amino, methylamino and dimethylamino;
  f is zero, 1 or 2;
  R(11) and R(12) independently of one another are defined as R(10), or hydrogen or alkyl having 1, 2, 3 or 4 carbon atoms;

or
R(1) is phenyl, naphthyl, biphenylyl or heteroaryl having 1, 2, 3, 4, 5, 6, 7, 8 or 9 carbon atoms, with the latter being linked via a carbon atom or a nitrogen atom of the ring, which are in each case unsubstituted or substituted by 1–3 substituents selected from the group consisting of F, Cl, $CF_3$, $CH_3$, methoxy, hydroxyl, amino, methylamino and dimethylamino, or R(1) is —SR(13), —OR(13), —NHR(13), —NR(13)R(14), —CHR(13)R(15), —C[R(15)R(16)OH], —C≡CR(18), —C[R(19)]=CHR(18), —C[R(20)R(21)]$_k$—(CO)—[CR(22)R(23)]$_l$—R(24), k is zero, 1, 2, 3 or 4;

l is zero, 1, 2, 3 or 4;

R(13) and R(14) identically or differently are —(CH$_2$)$_g$—(CHOH)$_h$—(CH$_2$)$_i$—(CHOH)$_j$—R(17) or —(CH$_2$)$_g$—O—(CH$_2$—CH$_2$O)$_h$—R(24); R(17) is hydrogen or methyl, g, h and i identically or differently are zero, 1, 2, 3 or 4;

j is 1, 2, 3 or 4;

R(15) and R(16) identically or differently are hydrogen, alkyl having 1, 2, 3, 4, 5 or 6 carbon atoms or, together with the carbon atom carrying them, are cycloalkyl having 3, 4, 5, 6, 7 or 8 carbon atoms;

R(18) is phenyl, which is unsubstituted or substituted by 1–3 substituents selected from the group consisting of F, Cl, CF$_3$, methyl, methoxy and NR(25)R(26);

R(25) and R(26) are H or alkyl having 1, 2, 3 or 4 carbon atoms;

or

R(18) is heteroaryl having 1, 2, 3, 4, 5, 6, 7, 8 or 9 carbon atoms, which is unsubstituted or substituted by 1–3 OH;

or

R(18) is cycloalkyl having 3, 4, 5, 6, 7 or 8 carbon atoms;

R(19), R(20), R(21), R(22) and R(23) identically or differently are hydrogen or methyl;

R(24) is H, alkyl having 1, 2, 3, 4, 5 or 6 carbon atoms, cycloalkyl having 3, 4, 5, 6, 7 or 8 carbon atoms or —C$_m$H$_{2m}$—R(18);

m is 1, 2, 3 or 4;

one of the two substituents R(2) and R(3) is hydroxyl; and the other of the substituents R(2) and R(3) in each case is defined as R(1);

R(4) is alkyl having 1, 2, 3 or 4 carbon atoms; alkoxy having 1, 2, 3 or 4 carbon atoms, F, Cl, Br, I or —(CH$_2$)$_n$—(CF$_2$)$_o$—CF$_3$;

n is zero or 1;

o is zero or 1;

and their pharmaceutically tolerable salts;

(HOE 96/F 135)

ax) bis-ortho-substituted benzoylguanidines of the formula I

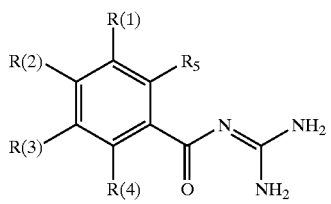

in which:

R(1), R(2) and R(3) independently of one another are R(10)-SO$_a$— or R(14)R(15)N—SO$_2$—;

a is zero, 1 or 2,

R(10), R(14) and R(15) independently of one another are alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5 or 6 carbon atoms or —CH$_{ab}$H$_{2ab}$—R(16);

ab is zero, 1, 2, 3 or 4;

R(16) is cycloalkyl having 3, 4, 5, 6 or 7 carbon atoms, or phenyl, which is not substituted or is substituted by 1–3 substituents selected from the group consisting of F, Cl, CF$_3$, methyl, methoxy and NR(17)R(18);

R(17) and R(18) independently of one another are hydrogen, CF$_3$ or alkyl having 1, 2, 3 or 4 carbon atoms;

or

R(14) and R(15) together are 4 or 5 methylene groups, of which one CH$_2$ group can be replaced by oxygen, sulfur, NH, N—CH$_3$ or N-benzyl;

or

R(14) and R(15) are hydrogen;

or

R(1), R(2) and R(3) independently of one another are SR(21), —OR(22), —NR(23)R(24) or —CR(25)R(26)R(27);

R(21), R(22), R(23) and R(25) independently of one another are —C$_b$H$_{2b}$—(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

b is zero, 1 or 2;

R(24), R(26) and R(27) independently of one another are hydrogen, alkyl having 1, 2, 3 or 4 carbon atoms or perfluoroalkyl having 1, 2, 3 or 4 carbon atoms;

or

R(1), R(2) and R(3) independently of one another are hydrogen, F, Cl, Br, I, CN, —(Xa)$_{dg}$—C$_{da}$H$_{2da+1}$, —(Xb)$_{dh}$—(CH$_2$)$_{db}$—C$_{de}$F$_{2de+1}$, alkenyl having 3, 4, 5, 6, 7 or 8 carbon atoms or —C$_{df}$H$_{2df}$R(30);

(Xa) is oxygen, sulfur or NR(33)

R(33) is hydrogen, alkyl having 1, 2, 3 or 4, carbon atoms or perfluoroalkyl having 1, 2, 3 or 4 carbon atoms;

dg is zero or 1;

(Xb) is oxygen, sulfur or NR(34);

R(34) is hydrogen, alkyl having 1, 2, 3 or 4 carbon atoms or perfluoroalkyl having 1, 2, 3 or 4 carbon atoms;

dh is zero or 1;

da is zero, 1, 2, 3, 4, 5, 6, 7 or 8;

db is zero, 1, 2, 3 or 4;

de is zero, 1, 2, 3, 4, 5, 6 or 7;

df is zero, 1, 2, 3 or 4;

R(30) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(31)R(32);

R(31) and R(32) are hydrogen, alkyl having 1, 2, 3 or 4 carbon atoms or perfluoroalkyl having 1, 2, 3 or 4 carbon atoms;

or

R(1), R(2) and R(3) independently of one another are NR(40)R(41) or —(Xe)—(CH$_2$)$_{eb}$R(45);

R(40) and R(41) independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms or (CH$_2$)$_e$—R(42);

e is zero, 1, 2, 3 or 4;

R(42) is cycloalkyl having 3, 4, 5, 6 or 7 carbon atoms or phenyl, which is not substituted or is substituted by 1–3 substituents selected from the group consisting of F, Cl, CF$_3$, methyl, methoxy and NR(43)R(44);

R(43) and R(44) independently of one another are hydrogen, CF$_3$ or alkyl having 1, 2, 3 or 4 carbon atoms;

or

R(40) and R(41) together are 4 or 5 methylene groups, of which one CH$_2$ group can be replaced by oxygen, sulfur, NH, N—CH$_3$ or N-benzyl;

(Xe) is oxygen, sulfur or NR(47);

R(47) is hydrogen, alkyl having 1, 2, 3 or 4 carbon atoms or perfluoroalkyl having 1, 2, 3 or 4 carbon atoms;

eb is zero, 1, 2, 3 or 4;

R(45) is cycloalkyl having 3, 4, 5, 6 or 7 carbon atoms, or phenyl, which is not substituted or is substituted by 1–3 substituents selected from the group consisting of F, Cl, CF$_3$, methyl, methoxy, NR(50)R(51) and —(Xfa)—(CH$_2$)$_{ed}$—(Xfb)R(46);

Xfa is CH$_2$, oxygen, sulfur or NR(48);

Xb is oxygen, sulfur or NR(49);

R(48), R(49), R(50) and R(51) independently of one another are hydrogen, alkyl having 1, 2, 3 or 4 carbon atoms or perfluoroalkyl having 1, 2, 3 or 4 carbon atoms;

ed is 1, 2, 3 or 4;

R(46) is hydrogen, alkyl having 1, 2, 3 or 4 carbon atoms or perfluoroalkyl having 1, 2, 3 or 4 carbon atoms;

or

R(1), R(2) and R(3) independently of one another are —CHR(52)R(53);

R(52) is —(CH$_2$)$_g$—(CHOH)$_h$—(CH)$_i$—(CHOH)$_k$—R(54) or —(CH$_2$)$_g$—O—(CH$_2$—CH$_2$O)$_h$—R(54);

R(54) is hydrogen or methyl;

g, h, i identically or differently are zero, 1, 2, 3 or 4;

k is 1, 2, 3 or 4;

R(53) is hydrogen or alkyl having 1, 2, 3 or 4 carbon atoms;

or

R(1), R(2) and R(3) independently of one another are —C(OH)R(55)R(56);

R(55) and R(56) identically or differently are hydrogen or alkyl having 1, 2, 3 or 4 carbon atoms;

or

R(55) and R(56) together are cycloalkyl having 3, 4, 5 or 6 carbon atoms;

or

R(55) is —CH$_2$OH;

and

R(4) and R(5) independently of one another are alkyl having 1, 2, 3 or 4 carbon atoms, alkoxy having 1, 2, 3 or 4 carbon atoms, OH, F, Cl, Br, I, CN, —O$_n$—(CH$_2$)$_o$—(CF$_2$)$_p$—CF$_3$;

n is zero or 1;

o is zero, 1 or 2;

p is zero, 1 or 2;

and their pharmaceutically tolerable salts;

(HOE 96/F 136)

ay) substituted 1-naphthoylguanidines of the formula I

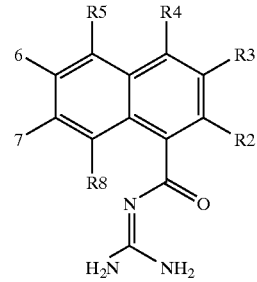

in which:

R2, R3, R4, R5, R6, R7 and R8 independently of one another are H, F, Cl, Br, I, CN, NO$_2$, CF$_3$, C$_2$F$_5$ or X$_a$Y$_b$Z;

X is O, S, NR(10), CR(11)R(12), C=O, C(=O)NR(10), C(=O)O, SO, SO$_2$, SO$_2$NR(10), OC=O, NR(10)C=O or NR(10)SO$_2$, where the linkage with the naphthalene ring in each case takes place via the left atom;

R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

a is zero or 1;

Y is alkylene having 1, 2, 3, 4, 5, 6, 7 or 8 CH$_2$ groups, where one of these CH$_2$ groups can be replaced by O, S, NR(13) or o-, p- or m-phenylene;

R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

b is zero or 1;

Z is H, alkyl having 1, 2, 3, 4, 5, 6 or 7 carbon atoms, cycloalkyl having 3, 4, 5, 6 or 7 carbon atoms, C(=O)R(15), SO$_2$R(15), NR(16)R(17) or phenyl, which is not substituted or is substituted by 1–3 substituents selected from the group consisting of F, Cl, Br, CF$_3$, methyl, methoxy and NR(21)R(22);

R(21) and R(22) independently of one another are H or alkyl having 1, 2, 3 or 4 carbon atoms or perfluoroalkyl having 1, 2, 3 or 4 carbon atoms;

R(15) is N=C(NH$_2$)$_2$, NR(18)R(19), N(CH$_2$)$_c$NR(18)R(19) or OR(20);

c is 2 or 3;

R(18) and R(19) independently of one another are H, alkyl having 1, 2, 3, 4, 5, 6, 7 or 8 carbon atoms or perfluoroalkyl having 1, 2, 3 or 4 carbon atoms;

or

R(18) and R(19) together are 4 or 5 methylene groups, of which one CH$_2$ group can be replaced by oxygen, S, NH, N—CH$_3$, N-benzyl or N-(p-chlorophenyl);

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms;

or

R(16) and R(16) together are 4 or 5 methylene groups, of which one CH$_2$ group can be replaced by oxygen, S, NH, N—CH$_3$, N-benzyl or N-(p-chlorophenyl);

or

Z is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(21)R(22);

but where, in the case where R(4) is an alkoxy radical, at least one of the substituents R(2), R(3), R(5), R(6), R(7) and R(8) is not hydrogen;

and their pharmaceutically tolerable salts;

(HOE 96/F 137)

az) substituted 2-naphthoylguanidines of the formula I

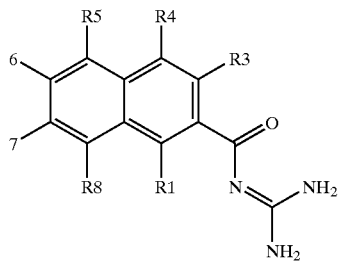

I in which:

at least one of the substituents R1, R3, R4, R5, R6, R7 and R8 is XY$_a$WZ or X'Y$_a$WZ';

X is O, S, NR(10) or CR(11)R(12);
R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

Y is alkylene having 1, 2, 3, 4, 5, 6, 7 or 8 CH$_2$ groups, where one of these CH$_2$ groups can be replaced by O, S, NR(13) or o-, p- or m-phenylene;
R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

a is zero or 1;

W is CH$_2$, SO$_2$, S(=O)(=NH) or—if W does not immediately follow a heteroatom of the group XY$_a$—alternatively O or NR(14);
R(14) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

Z is C(=O)R(15), SO$_2$R(15) or—if W is not O or NR(14)—alternatively NR(16)R(17);
R(15) is N=C(NH$_2$)$_2$, NR(18)R(19), N(CH$_2$)$_b$NR(18)R(19) or OR(2);
b is 2 or 3;
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one CH$_2$ group can be replaced by oxygen, S, NH, N—CH$_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms;
or,
R(16) and R(17) together are 4 or 5 methylene groups, of which one CH$_2$ group can be replaced by oxygen, S, NH, N—CH$_3$, N-benzyl or N-(p-chlorophenyl);

X' is C=O, C(=O)NR(30), C(=O)O, SO, SO$_2$, SO$_2$NR(30), OC=O, NR(30)C=O or NR(30)SO$_2$, where the linkage with the naphthalene ring in each case takes place via the left atom;
R(30) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

Z' is C(=O)R(15), SO$_2$R(15), an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(21)R(22);
R(21) and R(22) independently of one another are H, alkyl having 1, 2, 3 or 4 carbon atoms or perfluoroalkyl having 1, 2, 3 or 4 carbon atoms;
R(15) is N'C(NH$_2$)$_2$, NR(18)R(19), N(CH$_2$)$_b$NR(18)R(19) or OR(20);
R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups, of which one CH$_2$ group can be replaced by oxygen, S, NH, N—CH$_3$, N-benzyl or N-(p-chlorophenyl);
b is 2 or 3;
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
or
Z'—if W is not O or NR(14)—is NR(16)R(17);
R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups, of which one CH$_2$ group can be replaced by oxygen, S, NH, N—CH$_3$, N-benzyl or N-(p-chlorophenyl);

and the other substituents R1, R3, R4, R5, R6, R7 and R8 in each case, which are still not allocated by the definitions given above, independently of one another are H, F, Cl, Br, I, CN, NO$_2$, CF$_3$, C$_2$F$_5$ or V$_p$Q$_q$U;

V is O, S, SO, SO$_2$, NR(60), OC=O, C=O, C(=O)NR(60), C(=O)O or CR(66)R(67);
R(60), R(66) and R(67) independently of one another are H, alkyl having 1, 2, 3, 4, 5, or 6 carbon atoms, perfluoroalkyl having 1, 2, 3 or 4 carbon atoms or cycloalkyl having 3, 4, 5, 6 or 7 carbon atoms;

p is zero or 1;

Q is alkylene having 1, 2, 3, 4, 5, 6, 7 or 8 CH$_2$ groups, where one of these CH$_2$ groups can be replaced by O, S, NR(68) or o-, p- or m-phenylene;
R(68) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

q is zero or 1;

U is H, alkyl having 1, 2, 3, 4, 5, 6 or 7 carbon atoms, cycloalkyl having 3, 4, 5, 6 or 7 carbon atoms, C(=O)R(65), SO$_2$R(65), NR(61)R(62) or phenyl, which is not substituted or is substituted by 1–3 substituents selected from the group consisting of F, Cl, Br, CF$_3$, methyl, methoxy and NR(63)R(64);
R(63) and R(64) independently of one another are H, alkyl having 1, 2, 3 or 4 carbon atoms or perfluoroalkyl having 1, 2, 3 or 4 carbon atoms;

R(65) is N=C(NH$_2$)$_2$, NR(61)R(62) or OR(60);

R(61) and R(62) independently of one another are H, alkyl having 1, 2, 3, 4, 5, 6, 7 or 8 carbon atoms or perfluoroalkyl having 1, 2, 3 or 4 carbon atoms;

or

R(61) and R(62) together are 4 or 5 methylene groups, of which one CH$_2$ group can be replaced by oxygen, S, NH, N—CH$_3$, N-benzyl or N-(p-chlorophenyl);

or

U is an N-containing heterocycle having 1, 2, 3, 4, 5, 6, 7, 8 or 9 carbon atoms, where the N-containing heterocycle is linked via N or C and is not substituted or is substituted by 1–3 substituents selected from the group consisting of F, Cl, Br, CF$_3$, methyl, methoxy and NR(63)R(64);

but where at least one of the substituents R5, R6, R7 and R8 is not hydrogen; and their pharmaceutically tolerable salts;

(HOE 96/F 141)

ba) ortho-substituted benzoylguanidines of the formula I

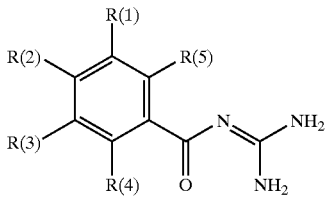

in which:

R(1) is H, F, Cl, Br, I, CN, NO$_2$, alkyl having 1, 2, 3, 4, 5, 6, 7 or 8 carbon atoms, alkoxy having 1, 2, 3, 4, 5, 6, 7 or 8 carbon atoms, cycloalkyl having 3, 4, 5, 6, 7 or 8 carbon atoms, cycloalkoxy having 3, 4, 5, 6, 7 or 8 carbon atoms or X$_a$—(CH$_2$)$_b$—(CF$_2$)$_c$—CF$_3$;

X is oxygen, sulfur or NR(9);

a is zero or 1;

b is zero, 1 or 2;

c is zero, 1, 2, or 3;

R(9) is H, alkyl having 1, 2, 3 or 4 carbon atoms or —C$_d$H$_{2d}$R(6);

d is zero, 1, 2, 3 or 4;

R(6) is cycloalkyl having 3, 4, 5, 6, 7 or 8 carbon atoms, phenyl, biphenylyl or naphthyl, where the aromatics phenyl, biphenylyl or naphthyl are not substituted or are substituted by 1–3 substituents selected from the group consisting of F, Cl, CF$_3$, methyl, methoxy and NR(7)R(8);

R(7) and R(8) are independently H or alkyl having 1, 2, 3 or 4 carbon atoms;

or

R(1) is —SR(10), —OR(10) or —CR(10)R(11)R(12);

R(10) is —C$_f$H$_{2f}$-cycloalkyl having 3, 4, 5, 6, 7 or 8 carbon atoms in the cycloalkyl ring, heteroaryl having 1, 2, 3, 4, 5, 6, 7, 8 or 9 carbon atoms or phenyl, where heteroaryl and phenyl are unsubstituted or are substituted by 1–3 substituents selected from the group consisting of F, Cl, CF$_3$, CH$_3$, methoxy, hydroxyl, amino, methylamino and dimethylamino;

f is zero, 1 or 2;

R(11) and R(12), independently of each other, are defined as R(10) or are hydrogen or alkyl having 1, 2, 3 or 4 carbon atoms;

or

R(1) is phenyl, naphthyl, biphenylyl or heteroaryl having 1, 2, 3, 4, 5, 6, 7, 8 or 9 carbon atoms, the latter linked via carbon or nitrogen atom of the ring, each of which is unsubstituted or is substituted by 1–3 substituents selected from the group consisting of F, Cl, CF$_3$, CH$_3$, methoxy, hydroxyl, amino, methylamino and dimethylamino, or R(1) is —SR(13), —OR(13), —NHR(13), —NR(13)R(14), —CHR(13)R(15), —C[R(15)R(16)]OH, —C≡CR(18), —C[R(19)]=CHR(18), —C[R(20)R(21)]$_k$—(CO)—[CR(22)R(23)]$_i$—R(24), k is zero, 1, 2, 3 or 4;

i is zero, 1, 2, 3 or 4;

R(13) and R(14), identically or differently, are —(CH$_2$)$_g$—(CHOH)$_h$—(CH$_2$)$_i$—(CHOH)$_{kk}$—R(17) or —(CH$_2$)$_g$—O—(CH$_2$—CH$_2$O)$_n$—R(24);

R(17) is hydrogen or methyl, g, h and i, identically or differently, are zero, 1, 2, 3 or 4;

kk is 1, 2, 3 or 4;

R(15) and R(16), identically or differently, are hydrogen, alkyl having 1, 2, 3, 4, 5 or 6 carbon atoms, or, together with the carbon atom carrying them, cycloalkyl having 3, 4, 5, 6, 7 or 8 carbon atoms;

R(18) is phenyl, which is unsubstituted or is substituted by 1–3 substituents selected from the group consisting of F, Cl, CF$_3$, methyl, methoxy and NR(25)R(26);

R(25) and R(26) are H or alkyl having 1, 2, 3 or 4 carbon atoms;

or

R(18) is heteroaryl having 1, 2, 3, 4, 5, 6, 7, 8 or 9 carbon atoms, which is unsubstituted or is substituted as phenyl;

or

R(18) is alkyl having 1, 2, 3, 4, 5 or 6 carbon atoms, which is unsubstituted or is substituted by 1–3 OH;

or

R(18) is cycloalkyl having 3, 4, 5, 6, 7 or 8 carbon atoms;

R(19), R(20), R(21), R(22) and R(23), identically or differently, are hydrogen or methyl;

R(24) is H, alkyl having 1, 2, 3, 4, 5 or 6 carbon atoms, cycloalkyl having 3, 4, 5, 6, 7 or 8 carbon atoms or —C$_{m2m}$—R(18);

m is 1, 2, 3 or 4;

one of the two substituents R(2) and R(3) is —O—CO—R(27);

R(27) is alkyl having 1, 2, 3, 4, 5, 6, 7 or 8 carbon atoms, cycloalkyl having 3, 4, 5, 6, 7 or 8 carbon atoms, phenyl, biphenylyl, naphthyl, pyridyl or quinolinyl, where phenyl, biphenylyl, naphthyl, pyridyl or quinolyl are unsubstituted or substituted by 1–3 substituents selected from the group consisting of F, Cl, CF$_3$, methyl, methoxy and NR(7)R(8);

R(7) and R(8) independently of one another are hydrogen or alkyl having 1, 2, 3 or 4 carbon atoms;

where one of the substituents R(2) and R(3) is always defined as R(1);

R(4) and R(5) independently of one another are hydrogen, alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;

n is zero or 1, o is zero or 1, and their pharmaceutically tolerable salts;

(HOE 96/F 154)

bb) benzoylguanidines of the formula I

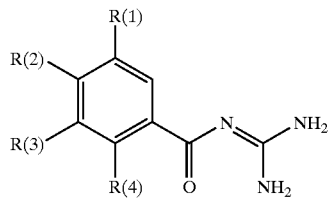

in which:

R(1) is R(13)—SO$_m$ or R(14)R(15)N—SO$_2$—;
  m is 1 or 2;
  R(13) is alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(16), n is zero, 1, 2, 3 or 4;
    R(16) is cycloalkyl having 3, 4, 5, 6, 7 or 8 carbon atoms, phenyl, biphenylyl or naphthyl, where phenyl, biphenylyl and naphthyl are not substituted or are substituted by 1–3 substituents selected from the group consisting of F, Cl, CF$_3$, methyl, methoxy and NR(25)R(26);
      R(25) and R(26) are, independently of each other, hydrogen, alkyl having 1, 2, 3 or 4 carbon atoms or perfluoroalkyl having 1, 2, 3 or 4 carbon atoms;
  R(24) is hydrogen, alkyl having 1, 2, 3, 4, 5, 6, 7 or 8 carbon atoms, perfluoroalkyl having 1, 2, 3, 4, 5, 6, 7 or 8 carbon atoms, alkenyl having 3, 4, 5, 6, 7 or 8 carbon atoms or —C$_n$H$_{2n}$—R(27), n is zero, 1, 2, 3 or 4;
    R(27) is cycloalkyl having 3, 4, 5, 6, 7 or 8 carbon atoms, phenyl, biphenyl or naphthyl, where phenyl, biphenylyl and naphthyl are not substituted or are substituted by 1–3 substituents selected from the group consisting of F, Cl, CF$_3$, methyl, methoxy and NR(28)R(29);
      R(28) and R(29) are, independently of each other, hydrogen, alkyl having 1, 2, 3 or 4 carbon atoms or perfluoroalkyl having 1, 2, 3 or 4 carbon atoms;
  R(15) is hydrogen, alkyl having 1, 2, 3 or 4 carbon atoms or perfluoroalkyl having 1, 2, 3 or 4 carbon atoms;

or

R(14) and R(15) are, together, 4 or 5 methylene groups of which one CH$_2$ group can be replaced by oxygen, S, NH, N—CH$_3$ or N-benzyl;
one of the substituents R(2) and R(3) is hydrogen;
and the other of the substituents R(2) and R(3) in each case is —CHR(30)R(31);
  R(30) is —(CH$_2$)$_g$—(CHOH)$_h$—(CH$_2$)$_i$—(CHOH)$_k$—R(32) or —(CH$_2$)$_g$—O—(CH$_2$—CH$_2$O)$_h$—R(24);
    R(24) and R(32) are, independently of each other, hydrogen or methyl;
    g, h and i are, identically or differently, zero, 1, 2, 3 or 4;
    k is 1, 2, 3 or 4;
or the other of the substituents R(2) and R(3) in each case is —C(OH)R(33)R(34);
  R(31), R(33) and R(34) are, identically or differently, hydrogen or alkyl having 1, 2, 3 or 4 carbon atoms, or
  R(33) and R(34) are, together, cycloalkyl having 3, 4, 5 or 6 carbon atoms;
or
  R(33) is —CH$_2$OH;
R(4) is alkyl having 1, 2, 3 or 4 carbon atoms, alkoxy having 1, 2, 3 or 4 carbon atoms, F, Cl, Br, I, CN or —(CH$_2$)$_n$—(CF$_2$)$_o$—CF$_3$;
  n is zero or 1;
  o is zero, 1 or 2;
and their pharmaceutically tolerable salts;
(HOE 96/F 226)
bd) phenyl-substituted alkenylcarboxylic acid guanidides of the formula I

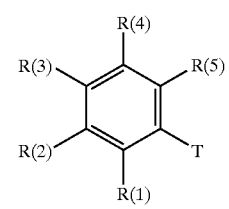

in which:
T is

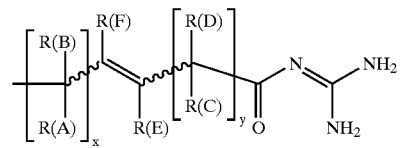

R(A) is hydrogen, F, Cl, Br, I, CN, OH, OR(6), (C$_1$–C$_4$)-alkyl, O$_r$(CH$_2$)$_a$C$_b$F$_{2b+1}$, (C$_3$–C$_8$)-cycloalkyl oder NR(7)R(8)
r is zero or 1;
  a is zero, 1, 2, 3 or 4;
  b is 1, 2, 3 or 4;
  R(6) is (C$_1$–C$_4$)-alkyl, (C$_1$–C$_4$)-perfluoroalkyl, (C$_3$–C$_6$)-alkenyl, (C$_3$–C$_8$)-cycloalkyl, phenyl or benzyl, the phenyl nucleus not being substituted or being substituted by 1–3 substituents selected from the group consisting of F, Cl, CF$_3$, methyl, methoxy and NR(9)R(10);
    R(9) and R(10) are H, (C$_1$–C$_4$)-alkyl or (C$_1$–C$_4$)-perfluoroalkyl;
  R(7) and R(8) independently of one another are defined as R(6);
or
  R(7) and R(8) together are 4 or 5 methylene groups, of which one CH$_2$ group can be replaced by oxygen, sulfur, NH, N—CH$_3$ or N-benzyl;
R(B), R(C) and R(D) independently are defined as R(A);
x is zero, 1 or 2;
y is zero, 1 or 2;
R(F) is hydrogen, F, Cl, Br, I, CN, OR(12), (C$_1$–C$_8$)-alkyl, O$_p$(CH$_2$)$_f$C$_g$F$_{2g+1}$, (C$_3$–C$_8$)-cycloalkyl or (C$_1$–C$_9$)-heteroaryl;
  p is zero or 1;
  f is zero, 1, 2, 3 or 4;
  g is 1, 2, 3, 4, 5, 6, 7 or 8;
  R(12) is (C$_1$–C$_8$)-alkenyl, (C$_1$–C$_4$)-perfluoroalkyl, (C$_3$–C$_8$)-alkenyl, (C$_3$–C$_8$)-cycloalkyl, phenyl or benzyl, the phenyl nucleus not being substituted or being substituted by 1–3 substituents selected from the group consisting of F, Cl, CF$_3$, methyl, methoxy and NR(13)R(14);

R(13) and R(14) are H, (C$_1$–C$_4$)-alkyl or (C$_1$–C$_4$)-perfluoroalkyl;

R(E) is defined independently as R(F);
R(1) is defined independently as T;

or

R(1) is hydrogen, —O$_k$C$_m$H$_{2m+1}$, —O$_n$(CH$_2$)$_p$C$_q$F$_{2q+1}$, F, Cl, Br, I, CN, —(C=O)—N=C(NH$_2$)$_2$, —SO$_r$R(17), —SO$_{r2}$NR(31)R(32), —O$_u$(CH$_2$)$_v$C$_6$H$_5$, —O$_{u2}$—(C$_1$–C$_9$)-heteroaryl or —S$_{u2}$—(C$_1$–C$_9$)-heteroaryl;

k is zero or 1;

m is zero, 1, 2, 3, 4, 5, 6, 7 or 8;

n is zero or 1;

p is zero, 1, 2, 3 or 4;

q is 1, 2, 3, 4, 5, 6, 7 or 8;

r is zero, 1 or 2;

r2 is zero, 1 or 2;

R(31) and R(32) independently of one another are hydrogen, (C$_1$–C$_8$)-alkyl or (C$_1$–C$_8$)-perfluoroalkyl;

or

R(31) and R(32) are, together, 4 or 5 methylene groups of which one CH$_2$ group can be replaced by oxygen, S, NH, N—CH$_3$ or N-benzyl;

R(17) is (C$_1$–C$_8$)-alkyl;

u is zero or 1;

u2 is zero or 1;

v is zero, 1, 2, 3 or 4; where the phenyl nucleus is not substituted or is substituted by 1–3 substituents selected from the group consisting of F, Cl, CF$_3$, methyl, methoxy, —(CH$_2$)$_w$NR(21)R(22), NR(18)R(19) and (C$_1$–C$_9$)-heteroaryl; R(18), R(19), R(21) and R(22) independently of one another are (C$_1$–C$_4$)-alkyl or (C$_1$–C$_4$)-perfluoroalkyl;

w is 1, 2, 3 or 4;

where the heterocycle of the (C$_1$–C$_9$)-heteroaryl is unsubstituted or substituted by 1–3 substituents selected from the group consisting of F, Cl, CF$_3$, methyl or methoxy;

R(2), R(3), R(4) and R(5) independently of one another are defined as R(1), or

R(1) and R(2) or R(2) and R(3) in each case together are —CH—CH=CH—CH—, which is not substituted or is substituted by 1–3 substituents selected from the group consisting of F, Cl, CF$_3$, methyl, methoxy, —(CH$_2$)$_{w2}$NR(24)R(25) and NR(26)R(27);

R(24), R(25), R(26) and R(27) are H, (C$_1$–C$_4$)-alkyl or (C$_1$–C$_4$)-perfluoroalkyl;

w2 is 1, 2, 3 or 4;

the radical T being present in the molecule at least twice, but only three times at most;

and their pharmaceutically tolerable salts;

(HOE 97/F 082)
be) benzoylguanidines of the formula I

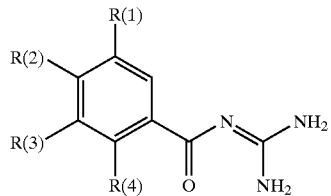

in which:
R(1) is CF$_3$;
one of the substituents R(2) and R(3) is hydrogen;
and the other substituent R(2) or R(3) in each case is —C(OH)(CH$_3$)—CH$_2$OH, —CH(CH$_3$)—CH$_2$OH or —C(OH)(CH$_3$)$_2$;
R(4) is methyl, methoxy, Cl or CF$_3$;
and their pharmaceutically tolerable salts;
(DE 195 02 895, DE 44 30 212, EP 667 341, DE 44 04 183, EP 708 088, EP 723 963, EP 0 694 537, DE 44 21 495, EP 699 660, EP 699 663, EP 699, 666, DE 43 37 611, EP 0719 766, WO 94/26709, WO 96 04 241, EP 726 254, U.S. Pat. No 4,251,545, DE 35 02 629, WO 84/00875, Kumamoto et al., Pharm. Bull. [1966], 7–13; U.S. Pat. No. 3,780,027, JP 8225513; EP 743 301) and also
II. compounds of the formula

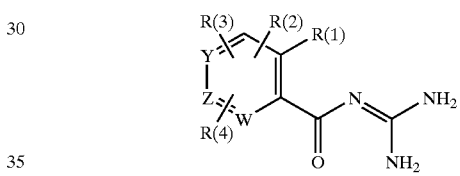

in which:
W, Y and Z are a nitrogen atom or a carbon atom substituted by R(2) or R(3) or R(4);
R(1) is hydrogen, A, Hal, —CF$_3$—, —CH$_2$F, —CHF$_2$, —CH$_2$CF$_3$, —C$_2$F$_5$, —CN, —NO$_2$, -ethynyl, or an X—R';
A is alkyl having 1 to 6 carbon atoms;
Hal is F, Cl, Br or I;
X is oxygen, S or NR";
R" is hydrogen, A or a cyclic methylene chain having 3 to 7 carbon atoms;
R' is H, A, HO—A—, HOOC—A—, (C$_3$–C$_7$)-cycloalkyl, (C$_6$–C$_8$)-cycloalkylalyl, CF$_3$, CH$_2$F, CHF$_2$, CH$_2$—CF$_3$, Ph, —CH$_2$—Ph or Het;
Ph is phenyl, naphthyl or biphenylyl which is unsubstituted or mono, di or trisubstituted by A, OA, NR'R", Hal, CF$_3$;
Het is a mono- or binuclear saturated, unsaturated or aromatic heterocycle having 1 to 4 nitrogen, oxygen and/or sulfur atoms, which is substituted or mono-, di- or trisubstituted by Hal, CF$_3$, A, OH, OA, —X—R', —CN, —NO$_2$, and/or carbonyl oxygen, where Het is bonded via N or an alkylene chain C$_m$H$_{2m}$ where m=zero to 6;
or
R' and R" together are alkylene having 4–5 carbon atoms, in which one CH$_2$ group can also be replaced by oxygen, S, NH, N—A, N—Ph and N—CH$_2$—Ph;
R(2) and R(3) independently of one another are hydrogen, Hal, A, HO—A—, X—R', —C(=N—OH)—A, A—O—

CO—($C_1$–$C_4$)-alkyl—, CN, $NO_2$, COOH, halogen-substituted A, in particular $CF_3$, $CH_2F$, $CHF_2$, $C_2F_5$, $CH_2CF_3$, or $S(O)_nR'''$;

R''' is A, Ph or -Het;

n is zero, 1 or 2;

or

R(2) and R(3) independently of one another are $SO_2NR'R''$, Ph or —O—Ph, —O—$CH_2$—Ph, —CO—A, —CHO, —COOA, —CSNR'R'', CONR'R'', —CH═CH—COOH, —CH═CH—COOA, indenyl, indanyl, decahydronaphthyl, cyclopentenyl, dihydrothienyl, dihydrofuryl, heterobicyclyl, alkylthienyl, halothienyl, haloalkylthienyl, actylthienyl, halofuryl, haloalkylfuryl or pyrrolyl;

or

R(2) and R(3) independently of one another are R(5)—O—;

R(5) is hydrogen, A, ($C_1$–$C_6$)-alkenyl or ($C_3$–$C_7$)-cycloalkyl;

R(4) is Ph, Het, —O—Het; $CF_3$, $S(O)_nR'''$, —$SO_2NR'R''$, alk;

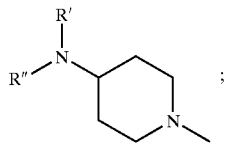

or two of the substituents R(1) to R(4) together are a group of —O—CR(6)R(7)—CO—NR(8)—,

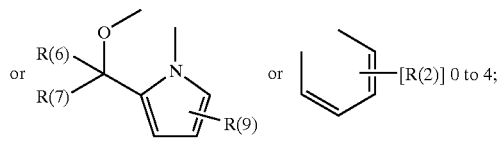

where R(2) has the meaning indicated;

R(6), R(7), R(8) and R(9) independently of one another are H or A;

or

R(8) is ($C_5$–$C_7$)-cycloalkyl;

or

R(9) is cyano;

alk is straight-chain or branched ($C_1$–$C_8$)-alkyl or ($C_3$–$C_8$)-cycloalkyl, which is unsubstituted or mono, di- or trisubstituted by A;

or alk is an ethenyl or ethynyl radical which is substituted by H, A, Ph or Het;

and also

IV. indoloylguanidine derivatives of the formula

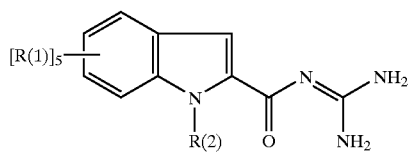

in which

R(2) is hydrogen, unsubstituted or substituted ($C_1$–$C_8$)-alkyl, ($C_3$–$C_7$)-cycloalkyl, OH, ($C_1$–$C_6$)-alkyl-O—, an aromatic radical or a group —$CH_2$—R(20);

R(20) is ($C_2$–$C_6$)-alkenyl or ($C_2$–$C_6$)-alkynyl;

R(1) is 1 to 5 identical or different substituents, which are: hydrogen, unsubstituted or substituted ($C_1$–$C_8$)-alkyl, ($C_2$–$C_6$)-alkenyl, ($C_2$–$C_6$)-alkynyl, ($C_3$–$C_7$)-cycloalkyl, halogen, —$NO_2$, ($C_2$–$C_8$)-alkanoyl, arylalkanoyl having up to 10 carbon atoms, aroyl having up to 11 carbon atoms, —COOH, ($C_2$–$C_6$)-alkoxylcarbonyl, an aromatic group or one of the following mentioned groups: —OR(3), —NR(6)R(7) or —$S(O)_nR(40)$;

R(3) is hydrogen, ($C_1$–$C_8$)-alkyl, substituted ($C_1$–$C_8$)-alkyl, ($C_3$–$C_7$)-cycloalkyl, an aromatic radical or a group —$CH_2$—R(30) R(30) is alkenyl or alkynyl;

R(6) and R(7) independently of one another are hydrogen, unsubstituted or substituted ($C_1$–$C_8$)-alkyl, ($C_3$–$C_7$)-cycloalkyl, ($C_2$–$C_8$)-alkanoyl, an arylalkanoyl group having up to 10 carbon atoms, an aroyl group having up to 11 carbon atoms, an aromatic group or —$CH_2$—R(60);

R(60) is ($C_2$–$C_6$)-alkenyl, or ($C_2$–$C_6$)-alkynyl;

or

R(6) and R(7) together with the nitrogen atom are a 5–7-membered cyclic amine, which can additionally contain further heteroatoms in the ring;

n is zero, 1 or 2;

R(40) is unsubstituted or substituted ($C_1$–$C_8$)-alkyl, or an aromatic group, or a group

A is oxygen, —$S(O)_n$— or —N(R50)—;

R(50) is hydrogen or ($C_1$–$C_8$)-alkyl;

R' is hydrogen unsubstituted or substituted ($C_1$–$C_8$)-alkyl, in which the ring represents a saturated 3–8-membered heterocycle having a nitrogen atom, said substituted alkyl carries one or more groups selected from the group consisting of halogen, —OH, ($C_1$–$C_6$)-alkoxy, —CN, —COOH, ($C_2$–$C_6$)-alkoxycarbonyl, ($C_2$–$C_8$)-alkanoyl, arylalkanoyl having up to 10 carbon atoms, aroyl having up to 11 carbon atoms, an aromatic group, —CONR(4)R(5), R(4) and R(5) identically or differently are hydrogen or ($C_1$–$C_8$)-alkyl;

or

R(4) and R(5) are connected to one another and together form a 5–7-membered cyclic amine which can additionally contain further heteroatoms in the ring, or said substituted alkyl carries a group

in which:

E is a nitrogen atom or a CH group;

R'' is hydrogen, ($C_1$–$C_8$)-alkyl which is unsubstituted or substituted by OH, ($C_1$–$C_6$)-alkoxy, —CN, —COOH, ($C_2$–$C_6$)-alkoxycarbonyl, ($C_2$–$C_8$)-alkanoyl, aralkanoyl having up to 10 carbon atoms, aroyl having up to 11 carbon atoms, an aromatic group, —NR(6)R(7), —CONR(4)R(5);

R(4) and R(5) independently of one another are hydrogen or $(C_1-C_8)$-alkyl, where the cyclic system of the formula

is a 3–8-membered saturated aliphatic or heterocyclic ring system having a nitrogen atom, and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl, and where and aryl radicals mentioned can be unsubstituted or substituted by unsubstituted $(C_1-C_8)$-alkyl or substituted $(C_1-C_8)$-alkyl, halogen, —$NO_2$, $(C_2-C_6)$-alkoxycarbonyl, COOH, —OR(3), NR(6)R(7), —CONR(4)R(5), —SO2NR(6)R(7) or $S(O)_nR(40)$, where R(1) and the guanidinocarbonyl radical can be in any desired position of the 5- or 6-membered ring of the indole system, and the appropriate pharmaceutically tolerable salts; and also VI. the guanidine compound, as described in EP-743 301 (DE 195 17 848), EP 758 644 (DE 195 29 612), EP 760 365 (DE 195 31 138)

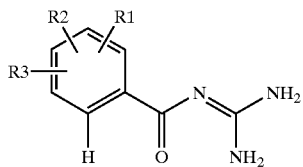

where R1=R2 is H, halo, alkyl, CN, $NO_2$, perfluoroalkyl, $SO_nCF_3$; $R_3$ is CH=$CH_2$, $CH_2$—CH=$CH_2$, $CH_2$—$CH_2$—CH=$CH_2$, cycloalkenyl, cycloalkenylalkyl; R4 is alkyl, (substituted) phenyl, or as described in DE 195 48 708, WO 97 25 310, WO 97 27 183, DE 196 01 303, EP 787 728, JP 82 25 513, JP 090 59 245, JP 090 67 332, JP 090 67 340, WO 97 11 055 and EP 743 301.

and the appropriate pharmaceutically tolerable salts; and also

VI. The guanidine compounds, as described in EP-743 301 (DE 195 17 848), EP 758 644 (DE 195 29 612), EP 760 365 (DE 195 31 138)

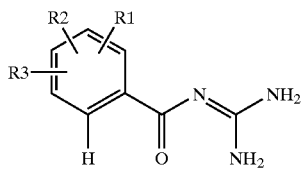

where R1=R2 is H, halo, alky, CN, $NO_2$, perfluoroalkyl, $SO_nCF_3$; $R_3$ is CH=$CH_2$, $CH_2$—CH=$CH_2$, $CH_2$—CH=$CH_2$, cycloalkenyl, cycloalkenylalkyl; R4 is alkyl, (substituted) phenyl, or as described in DE 195 48 708, WO 97 25 310, WO 97 27 183, DE 196 01 303, EP 787 728, JP 82 25 513, JP 090 59 245, JP 090 67 332, JP 090 67 340, WO 97 11 055 and EP 743 301.

The use of the following compounds is particularly preferred:

I. (HOE 89/F 288-U.S. Pat. No. 5,292,755)

a) benzoylguanidines of the formula I

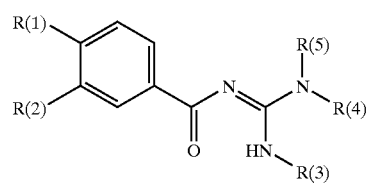

I in which:

R(1) or R(2) is R(6)—$S(O)_n$— or R(7)R(8)N—$O_2S$—;

and the other substituent R(1) or R(2) in each case is H, F, Cl, Br, $(C_1-C_4)$-alkyl, $(C_1-C_4)$-alkoxy or phenoxy, which is unsubstituted or substituted by 1–3 substituents selected from the group consisting of fluorine, chorine, methyl and methoxy;

or the other substituent R(1) or R(2) in each case is R(6)—$S(O)_n$ or R(7)R(8)N—;

n is zero, 1 or 2;

R(6) is $(C_1-C_6)$-alkyl, $(C_5-C_7)$-cycloalkyl, cyclopentylmethyl, cyclohexylmethyl or phenyl, which is unsubstituted or substituted by 1–3 substituents selected from the group consisting of fluorine, chlorine, methyl and methoxy;

R(7) and R(8) identically or differently are H or $(C_1-C_6)$-alkyl, or

R(7) is phenyl-$(CH_2)_m$;

m is 1–4;

or

R(7) is phenyl, which is unsubstituted or substituted by 1–2 substituents selected from the group consisting of fluorine, chlorine, methyl and methoxy;

or

R(7) and R(8) together are a straight-chain or branched $(C_4-C_7)$-chain, where the chain can additionally be interrupted by O, S or NR(9);

R(9) is H or methyl;

or

R(7) and R(8) together with the nitrogen atom to which they are bonded, are a dihydroindole, tetrahydroquinoline or tetrahydroisoquinoline system;

R(3), R(4) and R(5) independently of one another are H or $(C_1-C_2)$-alkyl, or

R(3) and R(4) together are a $(C_2-C_4)$-alkylene, chain;

or

R(4) and R(5) together are a $(C_4-C_7)$-alkylene chain;

and their pharmaceutically tolerable salts;

(HOE 92/F 034-U.S. Pat. No. 5,373,924)

b) benzoylguanidines of the formula I

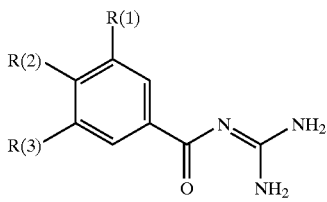

in which:

R(1) is R(40)—SO$_m$ or R(5)R(6)N—SO$_2$—;

m is zero, 1 or 2;

R(4) and R(5) are C$_1$–C$_8$-alkyl, C$_3$–C$_6$-alkenyl or —C$_n$H$_{2n}$—R(7);

n is zero, 1, 2, 3 or 4;

R(7) is C$_5$–C$_7$-cycloalkyl or phenyl, which is unsubstituted or substituted by 1–3 substituents selected from the group consisting of F, Cl, CF$_3$, methyl, methoxy and NR(8)R(9);

R(8) and R(9) are H or C$_1$–C$_4$-alkyl;

R(5) is H;

R(6) is H or C$_1$–C$_4$-alkyl, or

R(5) and R(6) together are 4 or 5 methylene groups, of which one CH$_2$ group can be replaced by an O, S, NH, N—CH$_3$ or N-benzyl;

R(2) is hydrogen, F, Cl, Br, (C$_1$–C$_4$)-alkyl—, O—(CH$_2$)$_m$C$_p$F$_{2p+1}$ or —X—R(10);

m is zero or 1;

p is 1, 2 or 3;

X is O, S or NR(11);

R(10) is H, C$_1$–C$_6$-alkyl, C$_5$–C$_7$-cycloalkyl, cyclohexylmethyl, cyclopentylmethyl or —C$_n$H$_{2n}$—R(12);

n is zero, 1, 2, 3 or 4;

R(12) is phenyl, which is unsubstituted or substituted by 1–3 substituents selected from the group consisting of F, Cl, CF$_3$, methyl, methoxy und NR(8)R(9);

R(8) and R(9) are H or C$_1$–C$_4$-alkyl;

R(11) is hydrogen or C$_1$–C$_3$-alkyl;

or

R(10) and R(11) together are 4 or 5 methylene groups, of which one CH$_2$ group can be replaced by O, S, NH, N—CH$_3$ or N-benzyl;

R(3) is defined as R(1), or is C$_1$–C$_6$-alkyl, nitro, cyano, trifluoromethyl, F, Cl, Br, I or —X—R(10);

X is O, S or NR(11);

R(10) is H, C$_1$–C$_6$-alkyl, C$_5$–C$_7$-cycloalkyl, cyclohexylmethyl, cyclopentylmethyl or —C$_n$H$_{2n}$—R(12);

n is zero to 4;

R(12) is phenyl, which is unsubstituted or substituted by 1–3 substituents selected from the group consisting of F, Cl, CF$_3$, methyl, methoxy and NR(8)R(9);

R(8) and R(9) are H or C$_1$–C$_4$-alkyl;

R(11) is C$_1$–C$_3$-alkyl, or

R(10) and R(11) together are 4 or 5 methylene groups, of which one CH$_2$ group can be replaced by O, S, NH, N—CH$_3$ or N-benzyl;

and their pharmaceutically tolerable salts;

(HOE 92/F 035 EP-Offenlegungsschrift 556 673)

c) ortho-substituted benzoylguanidines of the formula I

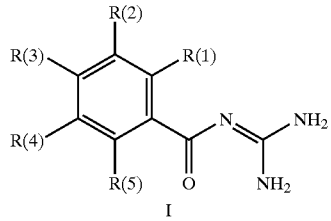

in which:

R(1) is F, Cl, Br, I, C$_1$–C$_6$-alkyl or —X—R(6);

X is O, S, NR(7) or Y—ZO;

Y is O or NR(7);

Z is C or SO;

R(6) is H, C$_1$–C$_6$-alkyl, C$_5$–C$_7$-cycloalkyl, cyclohexylmethyl, cyclopentylmethyl, —(CH$_2$)$_m$C$_p$F$_{2p+1}$ or —C$_n$H$_{2n}$—R(8);

m is zero or 1;

p is 1–3;

n is zero to 4;

R(8) is phenyl, which is unsubstituted or substituted by 1–3 substituents selected from the group consisting of F, Cl, CF$_3$, methyl, methoxy and NR(9)R(10);

R(9) and R(10) are H or C$_1$–C$_4$-alkyl;

R(7) is H or C$_1$–C$_3$-alkyl;

or

R(6) and R(7) together are 4 or 5 methylene groups, of which one CH$_2$ group can be replaced by O, S, NH, N—CH$_3$ or N-benzyl;

R(3) is H or —X—R(6);

X is O, S, NR(7) or Y—ZO;

R(7) is H or C$_1$–C$_3$-alkyl;

Y is O or NR(7); where Y is bonded to the phenyl radical of the formula I,

Z is C or SO;

R(6) is H, C$_1$–C$_6$-alkyl, C$_5$–C$_7$-cycloalkyl, cyclohexylmethyl, cyclopentylmethyl, —(CH$_2$)$_m$C$_p$F$_{2p+1}$ or —C$_n$H$_{2n}$—R(8);

m is zero or 1;

p is 1–3;

n is zero to 4;

R(8) is phenyl, which is unsubstituted or substituted by 1–3 substituents selected from the group consisting of F, Cl, CF$_3$, methyl, methoxy and NR(9)R(10);

R(9) and R(10) are H or C$_1$–C$_4$-alkyl;

or

R(6) and R(7) together are 4 or 5 methylene groups, of which one CH$_2$ group can be replaced by O, S, NH, N—CH$_3$ or N-benzyl;

R(2) and R(4) identically or differently are R(11)—SO$_q$— or R(12)R(13)N—SO$_2$—;

q is zero-2;

R(11) is C$_1$–C$_4$-alkyl, which is unsubstituted or carries phenyl as a substituent, where phenyl is unsubstituted or substituted by 1–3 substituents selected from the group consisting of F, Cl, $CF_3$, methyl, methoxy and NR(9)R(10);

R(9) and R(10) are H or $C_1$–$C_4$-alkyl;

R(12) and R(13) are defined as R(6) and R(7);

or one of the two radicals R(2) or R(4) is hydrogen or is defined as R(1);

R(5) is H, methyl, F, Cl or methoxy, and their pharmaceutically tolerable salts;

(HOE 92/F 303 K-EP-Offenlegungsschrift 589 336, NZ 248 703)

f) benzoylguanidines of the formula I

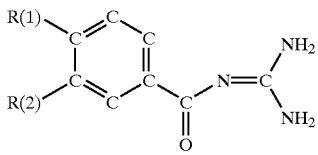

in which:

R(1) or R(2) is R(3)—S(O)$_n$— or R(4)R(5)N—SO$_2$— the other substituent R(1) or R(2) in each case is H, OH, F, Cl, Br, I, $C_1$–$C_4$-alkyl, $C_1$–$C_4$-alkoxy, benzyloxy or phenoxy, which is unsubstituted or carries one to three substituents selected from the group consisting of fluorine, chlorine, methyl, methoxy, hydroxyl and benzyloxy, R(3)—S(O)$_n$, —NR(4)R(5) or 3,4-dehydropiperidine R(3) is $C_1$–$C_6$-alkyl, $C_5$–$C_7$-cycloalkyl, cyclopentylmethyl, cyclohexylmethyl or phenyl, which is unsubstituted or substituted by one to three substituents selected from the group consisting of fluorine, chlorine, methyl and methoxy;

R(4) and R(5) identically or differently, are H or $C_1$–$C_6$-alkyl;

or

R(4) is phenyl-(CH$_2$)$_m$—;

m is 1, 2, 3 or 4;

or

R(4) is phenyl, which is unsubstituted or carries one to two substituents selected from the group consisting of fluorine, chlorine, methyl and methoxy;

or

R(4) and R(5) together are a straight-chain or branched $C_4$–$C_7$-chain, where the chain can additionally be interrupted by O, S or NR(6), R(6) is H or methyl;

or

R(4) and R(5) together with the nitrogen atom to which they are bonded, are a dihydroindole, tetrahydroquinoline or tetrahydroisoquinoline system;

n is zero, 1 or 2;

and their pharmaceutically tolerable salts;

(HOE 92/F 422-EP 604 852)

l) benzoylguanidines of the formula I

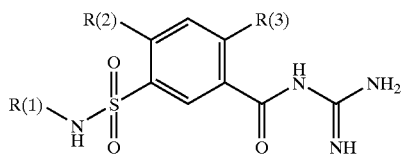

in which:

R(1) is R(4)R(5)N—C(X)—;

X is oxygen, S or N—R(6);

R(4) and R(5) identically or differently, are H, ($C_1$–$C_8$)-alkyl, ($C_3$–$C_6$)-alkenyl or —$C_nH_{2n}$—R(7);

n is zero, 1, 2, 3 or 4;

R(7) is ($C_5$–$C_7$)-cycloalkyl or phenyl, which is unsubstituted or substituted by 1–3 substituents selected from the group consisting of F, Cl, $CF_3$, methoxy and ($C_1$–$C_4$)-alkyl;

or

R(4) and R(5) together are 4 or 5 methylene groups, of which one $CH_2$ group can be replaced by oxygen, S, NH, N—$CH_3$ or N-benzyl; R(6) is defined as R(4) or is amidine;

R(2) is H, F, Cl, Br, I, ($C_1$–$C_8$)-alkyl, 1-alkenyl or 1-alkynyl, ($C_3$–$C_8$)-cycloalkyl, ($C_3$–$C_8$)-cycloalkyl-($C_1$–$C_4$)-alkyl, phenyl, $C_6H_5$-($C_1$–$C_4$)-alkyl, naphthyl, biphenylyl, 1,1-diphenyl-($C_1$–$C_4$)-alkyl, cyclopentadienyl, pyridyl, thiopyridyl, pyrrolyl, furanyl, thienyl, thiazolyl, oxazolyl, indenyl, quinolyl, indolyl, benzofuranyl, benzothienyl, benzothiazolyl, benzoxazolyl or —W—R(8);

W is oxygen, S or NR(9);

R(8) is H, ($C_1$–$C_6$)-alkyl, ($C_5$–$C_7$)-cycloalkyl, cyclohexylmethyl, cyclopentylmethyl, —(CH$_2$)$_m$C$_pF_{2p+1}$ or —$C_qH_{2q}$—R(10);

m is zero or 1;

p is 1, 2 or 3;

q is zero, 1, 2, 3 or 4;

R(10) is phenyl, which is unsubstituted or substituted by 1–3 substituents selected from the group consisting of F, Cl, $CF_3$, methyl, methoxy and NR(11)R(12);

R(11) and R(12) are H or ($C_1$–$C_4$)-alkyl;

R(9) is H or ($C_1$–$C_3$)-alkyl;

or

R(8) and R(9) together are 4 or 5 methylene groups, of which one $CH_2$ group can be replaced by oxygen, S, NH, N—$CH_3$ or N-benzyl;

R(3) is H, F, Cl, Br, I, ($C_1$–$C_6$)-alkyl or —W—R(8) as defined for R(2), and their pharmaceutically acceptable salts;

(93/F 054-NZ 250 919, EP-Offenlegungsschrift 612 723)

m) benzoylguanidines of the formula I

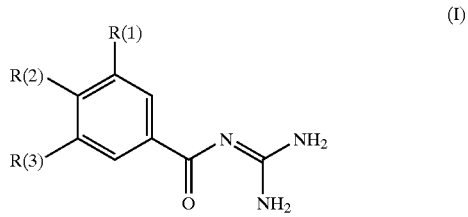

in which:

R(1), R(2), R(3) are hydrogen, F, Cl, Br, I or ($C_1$–$C_{12}$)-alkyl; one of the substituents R(1), R(2) or R(3) is $N_3$, CN, OH or ($C_1$–$C_{10}$)-alkyloxy, if at least one of the remaining substituents R(1), R(2) or R(3) is a sufficiently lipophilic alkyl radical having 3 to 12 carbon atoms;

or one of the substituents R(1), R(2) and R(3) is R(4)—$C_nH_{2n}O_m$—;

m is zero or 1;

n is zero, 1, 2 or 3;

R(4) is $C_pF_{2p+1}$;
p is 1, 2 or 3, if n is zero or 1;
or
R(4) is $(C_3-C_{12})$-cycloalkyl, phenyl, pyridyl, quinolyl or isoquinolyl, where the aromatic and heteroaromatic ring systems are unsubstituted or substituted by a substituent selected from the group consisting of F, Cl, $CF_3$, methyl, methoxy and NR(5)R(6);
R(5) and R(6) are hydrogen or $(C_1-C_4)$-alkyl;
or one of the substituents R(1), R(2) and R(3) is —C≡CR(5) or —C[R(6)]=CR(5);
R(5) is phenyl, which is unsubstituted or substituted by 1–3 substituents selected from the group consisting of F, Cl, $CF_3$, methyl, methoxy, hydroxyl, amino, methylamino and dimethylamino, $(C_1-C_9)$-heteroaryl, which is unsubstituted or substituted as phenyl,
or
R(5) is $(C_1-C_6)$-cycloalkyl, which is unsubstituted or substituted by 1–3 OH;
or
R(5) is $(C_3-C_8)$-cycloalkyl,
R(6) is hydrogen or methyl;
and their pharmacologically acceptable salts;
(HOE 93/F 254-EP-Offenlegungsschrift 640 588, NZ 264 307)
u) benzoylguanidines of the formula I

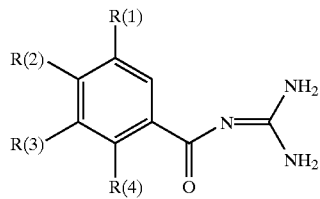

in which:
R(1) is H, F, Cl, Br, I, CN, $NO_2$, $(C_1-C_8)$-alkyl, $(C_3-C_8)$-cycloalkyl or $X_a$—$(CH_2)_b$—$(CF_2)_c$—$CF_3$;
X is oxygen, S or NR(5);
a is zero or 1;
b is zero, 1 or 2;
c is zero, 1, 2 or 3;
R(5) is H, $(C_1-C_4)$-alkyl or —$C_dH_{2d}R(6)$;
d is zero, 1, 2, 3 or 4;
R(6) is $(C_3-C_8)$-cycloalkyl, phenyl, biphenylyl or naphthyl, where the aromatics are not substituted or are substituted by 1 to 3 substituents selected from the group consistng of F, Cl, $CF_3$, methyl, methoxy and NR(7)R(8);
R(7) and R(8) independently are H or $(C_1-C_4)$-alkyl;
or
R(1) is —SR(10), —OR(10) or —CR(10)R(11)R(12);
R(10) is —$C_fH_{2f}$—$(C_3-C_8)$-cycloalkyl, —$(C_1-C_9)$-heteroaryl or phenyl, where the aromatic systems are unsubstituted or substituted by 1 to 3 substituents selected from the group consisting of F, Cl, $CF_3$, $CH_3$, methoxy, hydroxyl, amino, methylamino and dimethylamino;
f is zero, 1 or 2;
R(11) and R(12) independently of one another are defined as R(10) or are hydrogen or $(C_1-C_4)$-alkyl;
or
R(1) is phenyl, naphthyl, biphenylyl or $(C_1-C_9)$-heteroaryl, the latter linked via C or N, and which are unsubstituted or substituted by 1 to 3 substituents selected from the group consisting of F, Cl, $CF_3$, $CH_3$, methoxy, hydroxyl, amino, methylamino and dimethylamino;
or
R(1) is —SR(13), —OR(13), —NHR(13), —NR(13)R(14), —CHR(13)R(15), —C[R(15)R(16)]OH, —C≡CR(18), —C[R(19)]=CR(18), —[CR(20)R(21)]$_k$—(CO)—[CR(22)R(23)R(24)]$_l$;
R(13) and R(14) identically or differently are —$(CH_2)_g$—$(CHOH)_h$—$(CH_2)_i$—$(CHOH)_j$—R(17),
R(17) is hydrogen or methyl;
—$(CH_2)_g$—O—$(CH_2$—$CH_2O)_h$—R(24),
g, h, i identically or differently are zero, 1, 2, 3 or 4;
j is 1, 2, 3 or 4;
R(15) and R(16) identically or differently are hydrogen, $(C_1-C_6)$-alkyl or together with the carbon atom carrying them are a $(C_3-C_8)$-cycloalkyl;
R(18) is phenyl, which is undsubstituted or substituted by 1 to 3 substituents selected from the group consisting of F, Cl, $CF_3$, methyl, methoxy and NR(25)R(26);
R(25) and R(26) are H or $(C_1-C_4)$-alkyl;
or
R(18) is $(C_1-C_9)$-heteroaryl, which is unsubstituted or substituted as phenyl;
or
R(18) is $(C_1-C_6)$-alkyl, which is unsubstituted or substituted by 1 to 3 OH;
or
R(18) is $(C_3-C_8)$-cycloalkyl;
R(19), R(20), R(22) and R(23) are hydrogen or methyl;
k is zero, 1, 2, 3 or 4;
l is zero, 1, 2, 3 or 4;
R(24) is H, $(C_1-C_6)$-alkyl, $(C_3-C_8)$-cycloalkyl or —$C_mH_{2m}$—R(18);
m is 1, 2, 3 or 4;
R(2) and R(3) independently of one another area defined as R(1);
R(4) is $(C_1-C_3)$-alkyl, F, Cl, Br, I, CN or —$(CH_2)_n$—$(CF_2)_o$—$CF_3$;
n is zero or 1;
o is zero, 1 or 2;
and their pharmaceutically tolerable salts;
(HOE 94/F 168-EP-Offenlegungsschrift 690 048, NZ 272 373)
ab) Phenyl-substituted alkenylcarboxylic acid guanidides, carrying perfluoroalkyl groups, of the formula I

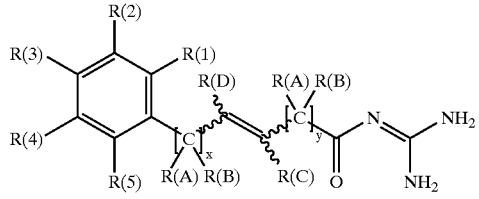

in which:
R(A) is hydrogen, F, Cl, Br, I, CN, OH, OR(6), $(C_1-C_8)$-alkyl, $O_r(CH_2)_aC_bF_{2b+1}$, $(C_3-C_8)$-cycloalkyl or NR(7)R(8);
r is zero or 1;
a is zero, 1, 2, 3 or 4;
b is 1, 2, 3, 4, 5, 6, 7 or 8;
R(6) is $(C_1-C_8)$-alkyl, $(C_1-C_4)$-perfluoroalkyl, $(C_3-C_8)$-alkenyl, $(C_3-C_8)$-cycloalkyl, phenyl or benzyl; where the aromatics are not substituted or are substituted by 1–3 substituents from the group consisting of F, Cl, $CF_3$, methyl, methoxy and NR(9) and R(10)

R(9) and R(10) are H, $(C_1-C_4)$-alkyl or $(C_1-C_4)$-perfluoroalkyl;

R(7) and R(8) independently of one another are defined as R(6);

or

R(7) and R(8) together are 4 or 5 methylene groups, of which one $CH_2$ group can be replaced by oxygen, sulfur, NH, N—$CH_3$ or N-benzyl;

R(B) independenlty is defined as R(A);

x is zero, 1 or 2;

y is zero, 1 or 2;

R(C) is hydrogen, F, Cl, Br, I, CN, OR(12), $(C_1-C_8)$-alkyl, $O_p(CH_2)_f C_g F_{2g+1}$ or $(C_3-C_8)$-cycloalkyl;

p is zero or 1;

f is zero, 1, 2, 3 or 4;

g is 1, 2, 3, 4, 5, 6, 7 or 8;

R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl; where the aromatics phenyl or benzyl are not substituted or are substituted by 1–3 substituents from the group consisting of F, Cl, $CF_3$, methyl, methoxy and NR(13)R(14);

R(13) and R(14) independently of one another are H, $(C_1-C_4)$-alkyl or $(C_1-C_4)$-perfluoroalkyl;

R(D) independently is defined as R(C),

R(1) is hydrogen, $(C_1-C_8)$-alkyl, $-O_t(CH_2)_d C_e F_{2e+1}$, $(C_3-C_8)$-cycloalkyl, F, Cl, Br, I or CN;

t is zero or 1;

d is zero, 1, 2, 3 or 4;

e is 1, 2, 3, 4, 5, 6, 7 or 8;

R(2), R(3), R(4) and R(5) independently of one another are defined as R(1); but with the condition that a least one of the substituents R(A), R(B), R(C), R(D), R(1), R(2), R(4) or R(5) is an $O_t(CH_2)_a C_b F_{2b+1}$, $O_p(CH_2)_f C_g F_{2g+1}$ or $O_t(CH_2)_d C_e F_{2e+1}$ group and R(3) is not an $O_t(CH_2)_d C_{2e+1}$ group;

and their pharmaceutically tolerable salts;

(HOE 94/F 265-NZ 272 946, EP-Offenlegungsschrift 700 904)

ad) benzoylguanidines of the formula I

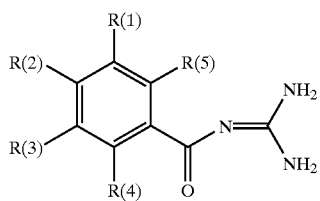

I in which:

one of the three substituents R(1), R(2) and R(3) is $(C_1-C_9)$-heteroary-N-oxide, which is linked via C or N and which is unsubstituted or substituted by 1–3 substituents selected from the group consisting of F, Cl, $CF_3$, methoxy, hydroxyl, amino, methylamino and dimethylamino;

or one of the three substituents R(1), R(2) and R(3) is —SR (10), —OR(10), —NR(10)R(11) or —CR(10)R(11)R(12);

R(10) is —$C_a H_{2a}$—$(C_1-C_9)$-heteroaryl-N-oxide, which is unsubstituted or substituted by 1–3 substituents selected from the group consisting of F, Cl, $CF_3$, $CH_3$, methoxy, hydroxyl, amino, methylamino and dimethylamino;

a is zero, 1 or 2;

R(11) and R(12) independently of one another are defined as R(10), are hydrogen or $(C_1-C_4)$-alkyl;

and the other substituents R(1), R(2) and R(3) in each case independently of one another are $(C_1-C_8)$-alkyl, $(C_2-C_8)$-alkenyl or —$C_m H_{2m} R(14)$;

m is zero, 1 or 2;

R(14) is $(C_3-C_8)$-cycloalkyl or phenyl, which is not substituted or is substituted by 1–3 substituents selected from the group consisting of F, Cl, $CF_3$, methyl, methoxy and NR(15)R(16), R(15) and R(16) are hydrogen or $CH_3$;

or the other substituents R(1), R(2) and R(3) in each case independently of one another are hydrogen, F, Cl, Br, I, —C≡N, X—$(CH_2)_p$—$(C_q F_{2q+1})$, R(22)—$SO_u$, R(23)R(24)N—CO, R(25)—CO— or R(26)R(27)N—$SO_2$—, where the perfluoroalkyl group is straight-chain or branched;

X is a bond, oxygen, S or NR(28);

u is zero, 1 or 2;

p is zero, 1 or 2;

q is zero, 1, 2, 3, 4, 5 or 6;

R(22), R(23), R(25) and R(26) independently are $(C_1-C_8)$-alkyl, $(C_2-C_6)$-alkenyl, —$C_n H_{2n}$—R(29) or $CF_3$;

n is zero, 1, 2, 3 or 4;

R(28) is hydrogen or $(C_1-C_3)$-alkyl;

R(29) is $(C_3-C_7)$-cycloalkyl or phenyl; which is not substituted or is substituted by 1–3 substituents selected from the group consisting of F, Cl, $CF_3$, methyl, methoxy and NR(30)R(31);

R(30) and R(31) are hydrogen or $C_1-C_4$-alkyl,

R(23), R(25) and R(26) are also hydrogen;

R(24) and R(27) independently of one another are hydrogen or $(C_1-C_4)$-alkyl;

or

R(23) and R(24), and also R(26) and R(27) together are 4 or 5 methylene groups, of which one $CH_2$ group can be replaced by oxygen, S, NH, N—$CH_3$ N-benzyl;

or the other substituents R(1), R(2) and R(3) in each case independently of one another are OR(35) or NR(35)R(36);

R(35) and R(36) independently of one another are hydrogen or $(C_1-C_6)$-alkyl;

or

R(35) and R(36) together are 4–7 methylene groups, of which one $CH_2$ group can be replaced by oxygen, S, NH, N—$CH_3$ or N-benzyl, R(4) and R(5) independently of one another are hydrogen, $(C_1-C_4)$-alkyl, F, Cl, —OR(32), —NR(33)R(34) or $C_r F_{2r+1}$;

R(32), R(33) and R(34) independently of one another are hydrogen or $(C_1-C_3)$-alkyl;

r is 1, 2, 3 or 4;

and their pharmaceutically tolerable salts;

(HOE 95/F 007 K-EP-Offenlegungsschrift 723 956, NZ 280 887)

ag) benzoylguanidines of the formula I

[Structure I: benzene ring with substituents R(1), R(2), R(3), R(4), R(5) and a C(=O)-N=C(NH$_2$)(NH$_2$) group]

in which:
one of the three substituents R(1), R(2) and R(3) is R(6)—A—B—D—;
R(6) is a basic protonatable radical i.e. an amino group —NR(7)R(8), an amidino group R(7)R(8)N—C[=N—R(9)]— or a guanidino group

[Structure: guanidino group with R(7), R(8), R(9), R(10)]

R(7), R(8), R(9) and R(10) independently of one another are hydrogen or alkyl having 1, 2, 3 or 4 carbon atoms;
or
R(7) and R(8) together are $C_aH_{2a}$;
a is 4, 5, 6 or 7; where if a=5, 6 or 7 methylene group of the group $C_aH_{2a}$ can be replaced by a heteroatom group O, $SO_m$ or NR(11),
or
R(8) and R(9) or R(9) and R(10) or R(7) and R(10) are a group $C_aH_{2a}$;
a is 2, 3, 4 or 5; where if a=3, 4 or 5 a methylene group of the group $C_aH_{2a}$ can be replaced by a heteroatom group O, $SO_m$ or NR(11);
m is zero 1 or 2;
R(11) is hydrogen or methyl;
or
R(6) is a basic heteroaromatic ring system having 1–9 carbon atoms;
A is $C_bH_{2b}$;
b is 1, 2, 3, 4, 5, 6, 7, 8, 9 or 10; where in the group $C_bH_{2b}$ one or two methylene groups can be replaced by one of the groupings selected from the group consisting of —O—, —CO—, —CH[OR(20)]—, —$SO_m$—, —NR(20)—, —NR(20)—CO—, —NR(20)—CO—NH—, —NR(20)—CO—NH—$SO_2$—

[Structure: —R(20)N—S(=O)$_{aa}$[NR(19)]$_{bb}$—]

and —$SO_{aa}$[NR(19)]$_{bb}$—; and where in the group $C_bH_{2b}$ a methylene group can be replaced by —CH—R(99), where R(99) together with R(7) forms a pyrrolidine or piperidine ring;
aa is 1 or 2;
bb is 0 or 1;
aa+bb=2;

R(19) is hydrogen or alkyl having 1, 2, 3 or 4 carbon atoms;
R(20) is hydrogen or methyl;
B is a phenylene or naphthylene radical

[Structures: phenylene with R(12), R(13); naphthylene with R(12), R(13)]

R(12) and R(13) independently of one another are hydrogen, methyl, F, Cl, Br, I, CF$_3$ or —SO$_w$—R(14);
R(14) is methyl or NR(15)R(16);
R(15) and R(16) independently of one another are hydrogen or alkyl having 1, 2, 3 or 4 carbon atoms;
w is zero, 1 or 2;
D is —$C_dH_{2d}X_f$—;
d is zero, 1, 2, 3 or 4;
X is —O—, —CO—, —CH[OR(21)]—, —SO$_m$— or —NR(21)—;
f is zero or 1;
R(21) is hydrogen or methyl;
m is zero, 1 or 2;
and the other substituents R(1) and R(2) and R(3) in each case independently of one another are hydrogen, F, Cl, Br, I, —CN, —(C$_1$–C$_8$)-alkyl, —(C$_2$–C$_8$)-alkenyl, NR(35)R(36) or R(17)—C$_g$H$_{2g}$—Z$_h$—;
g is zero, 1, 2, 3 or 4;
h is zero or 1;
R(35) and R(36) independently of one another are hydrogen or alkyl having 1, 2, 3, 4, 5 or 6 carbon atoms;
or
R(35) and R(36) together are 4–7 methylene groups, of which one CH$_2$ group can be replaced by oxygen, —S—, —NH—, —NCH$_3$ or —N-benzyl;
Z is —O—, —CO—, —SO$_v$—, —NR(18)—, —NR(18)—CO—, —NR(18)—CO—NH— or —NR(18)—SO$_2$—;
R(18) is hydrogen or methyl;
v is zero, 1 or 2;
R(17) is hydrogen, cycloalkyl having 3, 5 or 6 carbon atoms or C$_k$F$_{2k+1}$—;
k is 1, 2 or 3,
or
R(17) is pyrrol-1-yl, pyrrol-2-yl or pyrrol-3-yl, which is not substituted or is substituted by 1–4 substituents selected from the group consisting of F, Cl, Br, I, —CN, (C$_2$–C$_8$)-alkanoyl, (C$_2$–C$_8$)-alkoxycarbonyl, formyl, carboxyl, —CF$_3$, methyl and methoxy;
or
R(17) is (C$_3$–C$_8$)-cycloalkyl or phenyl, which is not substituted or is substituted by 1–3 substituents selected from the group consisting of F and Cl, —CF$_3$, methyl, hydroxyl, methoxy, —NR(37)R(38), CH$_3$SO$_2$— and H$_2$NO$_2$S—;
R(37) and R(38) are hydrogen or —CH$_3$;
R(4) and R(5) independently of one another are hydrogen, alkyl having 1, 2, 3 or 4 carbon atoms, F, Cl, —OR(32), —NR(33)R(34) or —C$_r$F$_{2r+1}$;

R(32), R(33) and R(34) independently of one another are hydrogen or alkyl having 1, 2 or 3 carbon atoms;
r is 1, 2, 3 or 4;
and their pharmacologically tolerable salts;
(HOE 96/F 032)
au) ortho-substituted benzoylguanidines of the formula I

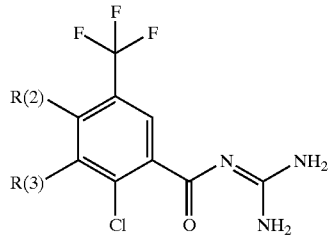

in which:
R(2) and R(3) independently of one another are hydrogen, Cl, Br, I, $(C_1-C_8)$-alkyl, $(C_3-C_8)$-cycloalkyl or —OR(5);
R(5) is $(C_1-C_8)$-alkyl or —$C_dH_{2d}$—$(C_3-C_8)$-cycloalkyl;
d is zero, 1 or 2;
where one of the two substituents R(2) and R(3) is always hydrogen but both substituents R(2) and R(3) are not simultaneously hydrogen, and their pharmaceutically tolerable salts;
and also
IV. indoloylguanidine derivatives of the formula

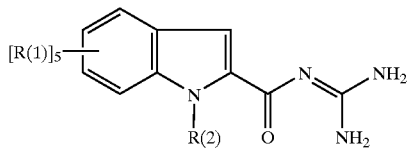

in which
R(2) is hydrogen, unsubstituted or substituted $(C_1-C_8)$-alkyl, $(C_3-C_7)$-cycloalkyl, OH, $(C_1-C_6)$-alkyl-O—, an aromatic radical or a group —$CH_2$—R(20);
R(20) is $(C_2-C_6)$-alkenyl or $(C_2-C_6)$-alkynyl;
R(1) is 1 to 5 identical or different substituents, which are: hydrogen, unsubstituted or substituted $(C_1-C_8)$-alkyl, $(C_2-C_6)$-alkenyl, $(C_2-C_6)$-alkynyl, $(C_3-C_7)$-cycloalkyl, halogen, —$NO_2$, $(C_2-C_8)$-alkanoyl, arylalkanoyl having up to 10 carbon atoms, aroyl having up to 11 carbon atoms, —COOH, $(C_2-C_6)$-alkoxycarbonyl, an aromatic group or one of the following mentioned groups: —OR(3), —NR(6)R(7) or —$S(O)_nR(40)$;
R(3) is hydrogen, $(C_1-C_8)$-alkyl, substituted $(C_1-C_8)$-alkyl, $(C_3-C_7)$-cycloalkyl, an aromatic radical or a group —$CH_2$—R(30) R(30) is alkenyl or alkynyl;
R(6) and R(7) independently of one another are hydrogen, unsubstituted or substituted $(C_1-C_8)$-alkyl, $(C_3-C_7)$-cycloalkyl, $(C_2-C_8)$-alkanoyl, an arylalkanoyl group having up to 10 carbon atoms, an aroyl group having up to 11 carbon atoms, an aromatic group or —$CH_2$—R(60);
R(60) is $(C_2-C_6)$-alkenyl or $(C_2-C_6)$-alkynyl;
or
R(6) and R(7) together with the nitrogen atom are a 5–7 membered cyclic amine, which can additionally contain further heteroatoms in the ring;
n is zero, 1 or 2;
R(40) is unsubstituted or substituted $(C_1-C_8)$-alkyl, or an aromatic group, or a group

A is oxygen, —$S(O)_n$— or —N(R50)—;
R(50) is hydrogen or $(C_1-C_8)$-alkyl;
R' is hydrogen, unsubstituted or substituted $(C_1-C_8)$-alkyl,
in which the ring represents a saturated 3–8-membered heterocycle having a nitrogen atom,
said substituted alkyl carries one or more groups selected from the group consisting of halogen, —OH, $(C_1-C_6)$-alkoxy, —CN, —COOH, $(C_2-C_6)$-alkoxycarbonyl, $(C_2-C_8)$-alkanoyl, arylalkanoyl having up to 10 carbon atoms, aroyl having up to 11 carbon atoms, an aromatic group, —CONR(4)R(5),
R(4) and R(5) identically or differently are hydrogen or $(C_1-C_8)$-alkyl;
or
R(4) and R(5) are connected to one another and together form a 5–7-membered cyclic amine which can additionally contain further heteroatoms in the ring,
or said substituted alkyl carries a group

in which:
E is a nitrogen atom or a CH group;
R" is hydrogen, $(C_1-C_8)$-alkyl which is unsubstituted or substituted by OH or substituted $(C_1-C_8)$-alkyl, $(C_1-C_6)$-alkoxy, —CN, —COOH, $(C_2-C_6)$-alkoxycarbonyl, $(C_2-C_8)$-alkanoyl, aralkanoyl having up to 10 carbon atoms, aroyl having up to 11 carbon atoms, an aromatic group, —NR(6)R(7), —CONR(4)R(5);
R(4) and R(5) independently of one another are hydrogen or $(C_1-C_8)$-alkyl;
where the cyclic system of the formula

is a 3–8-membered saturated aliphatic or heterocyclic ring system having a nitrogen atom,
and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl, and where the aryl radicals mentioned can be unsubstituted or substituted by unsubstituted $(C_1-C_8)$-alkyl or substituted $(C_1-C_8)$-alkyl, halogen, —$NO_2$, $(C_2-C_6)$-alkoxycarbonyl, COOH, —OR(3), NR(6)R(7), —CONR(4)R(5), —$SO_2NR(6)R(7)$ or $S(O)_nR(40)$, where R(1) and the guanidinocarbonyl radical can be in any desired position of the 5- or 6-membered ring of the indole system, and the appropriate pharmaceutically tolerable salts;
The use of 4-isopropyl-3-methylsulfonylbenzoylguanidine methylsulfonate is very particularly preferred.
As described in the patent publications, NHE inhibitors have a high antiarrhythmic potential against arrhythmias which are caused by anoxia and ischemia in the heart.

It was therefore surprising that those arrhythmias are also inhibited which are not induced by ischemias, but by pharmaceuticals having arrhythmogenic potential. Thus NHE inhibitors, as individual preparations or in a fixed combination, open up, for numerous valuable pharmaceuticals whose administration can be restricted by side effects on the heart, the possibility of being used in therapy with a lower risk or free of the risk of side effects.

Pharmaceutical groups with arrhythmogenic activity of this type have acquired growing importance, in particular during the last decade, in the sciences, in clinics and medical practices and with the health authorities because of these side effects, which in some cases are slight, but in some cases also life-threatening. Classes of active compound of this type having arrhythmogenic potential include, for example, antihistaminics (e.g. terfenadine), potentiating agents for man (e.g. Viagra), phosphodiesterase inhibitors such as, for example, milrinone or amrinone, adenylate cyclase activators such as, for example, forskolin and its derivatives (e.g. NK H477), neuroleptics such as, for example, chlorpromazine, and numerous other classes of pharmaceutical and their individual representatives.

As wide-based clinical studies in past years have shown, antiarrhythmics of class 1 and 3 also have a significant arrhythmia-producing potential. These arrhythmias cannot be decreased or suppressed by combined administration with another antiarrhythmic. The inhibition of this type of arrhythmias induced by antiarrhythmics by NHE inhibitors therefore represents a surprising use form of the NHE inhibitors.

How the adverse effect on heart function, which can be triggered by pharmaceuticals having undesired side effects on the heart and can cause heart damage due to chronic or acute absorption into the body, can be decreased or abolished by NHE inhibitors as exemplified by cariporide (Hoe 642) is described by the following experiments on isolated functioning rat heart:

All investigations were carried out using hearts of Wistar-Kyoto rats (300–400 g body weight, BW). The rats were kept on a standard diet and had free access to water.

The rats were anesthetized with pentobartital (60 mg/kg, i.p.), heparinized (500 I.U./100 g BW i.p.) and respirated with room air via a cannula which was inserted into the trachea. The thorax was then opened, and the heart was removed and placed in a 4° C. physiological solution. After cannulation of the aorta, the hearts were suspended in the unit and perfused in a retrograde manner according to the Langendorff method with an oxygenated (95% $O_2$, 5% $CO_2$), noncirculating Tyrode solution (in mmol/l: NaCl 124.6; KCl 4.0; $CaCl_2$ 2.2; $MgCl_2$ 1.1; $NaHCO_3$ 24.9; $NaH_2PO_4$ 0.3; glucose 11.1) using a perfusion pressure of 51 mm Hg. The pulmonary artery and the left auricle were then cannulated and all pulmonary veins were ligated close to the auricle. After an equilibration phase of 15 minutes, the retrograde perfusion was changed into an anterograde perfusion (working-heart mode). At the same time, the filling pressure was adjusted to 11 mm Hg and the afterload to 51 mm Hg. The hearts were paced during the entire experiment at a frequency of 5 Hz. After 15 minutes in the working mode, the coronary flow was reduced by 90% in order to include a global low flow ischemia. The aortic pressure drops from 51 to 11 mm Hg in the course of this. This situation represents an angina pectoris attack in the patient. The low flow ischemia lasted 30 minutes. The hearts were then reperfused for 15 minutes in the Langendorff mode and for a further 15 minutes in the working mode.

All animals received oral Rulide (macrolide, 20 mg/kg) dissolved in 1 ml of olive oil, or only 1 ml of olive oil (control), before the experiments. The $Na^+/H^+$ exchange inhibitor cariporide (1 $\mu$mol/l) and its vehicle (Tyrode solution) were added directly to the perfusion solution, i.e. immediately before the latter flows into the heart. The computer-controlled infusion of cariporide and the vehicle solution was begun 15 minutes before low flow ischemia and lasted for the entire experiment. The infusion quantity was 1:100th of the heart minute volume. The following parameters were measured 15 minutes before ischemia and at the end of the reperfusion phase: left ventricular pressure (LVP), left auricle pressure (LAP), aortic pressure (AP), heart-time volume (HTV), coronary flow (CF), aortic flow (AF), heart rate (HR), contractility ($dP/dt_{max}$), left ventricular pressure increase (LVPI) and the external heart work (EHW). From these values, the recovery (values after reperfusion based on the starting values before ischemia in %) was calculated. Moreover, the ECG was recorded during the entire experiment and the sum of the individual arrhythmia intervals (ventricular tachycardias and ventricular fibrillations) over the entire experimental period was formed.

Results:

None of the substances used themselves had an effect on any of the measured parameters.

Ischemia and reperfusion led to a 20–50% decrease of the recovery in all parameters (Table 1). The incidence of ventricular arrhythmias was 33% with a mean period of 34 seconds during ischemia and 100% with a period of 797 seconds during reperfusion.

Pretreatment with Rulide (macrolide) led to a further impairment of recovery and to an increase in the incidence and the duration of ventricular arrhythmias compared with the control group (Table 1+2). This points to the cardiotoxic action of macrolides during myocardial ischemia and reperfusion.

Pretreatment of the heart with cariporide (HOE 642) completely prevented the cardiotoxic effect of the macrolide (Table 1+2). Thus the hearts in the groups under cariporide treatment recovered almost completely after ischemia and reperfusion (recovery of all parameters with HOE 642 around 90%) and it was also possible to reduce the incidence of ventricular fibrillation during the reperfusion phase from 100% in the macrolide group to 38% by means of cariporide. Moreover, the length of ventricular arrhythmias during the reperfusion phase was reduced from 1709 seconds in the macrolide group to 198 seconds by means of cariporide treatment. Cariporide, on the other hand, had no effect on the arrhythmias during ischemia.

TABLE 1

Recovery of the coronary flow (CF), heart-time volume (HTV), aortic flow (AF), contractility ($dP/dt_{max}$), the left-ventricular pressure increase (LVPI) and the external heart work (EHW) (in %) after low flow ischemia and reperfusion in the isolated functioning rat heart

| | LVPI % | $dP/dt_{max}$ % | CF % | AF % | HTV % | EHW % |
|---|---|---|---|---|---|---|
| Vehicle [olive oil or Tyrode solution] | 76 ± 8 | 80 ± 10 | 66 ± 9 | 52 ± 10 | 56 ± 10 | 46 ± 10 |
| Cariporide (HOE642) | 89 ± 2 | 88 ± 3 | 81 ± 2 | 85 ± 3 | 84 ± 2 | 79 ± 4 |
| Rulide | 31 ± 14 | 33 ± 15 | 32 ± 4 | 8 ± 6 | 14 ± 8 | 10 ± 7 |
| Rulide + HOE642 | 99 ± 2 | 100 ± 3 | 95 ± 2 | 83 ± 2 | 85 ± 2 | 87 ± 4 |

TABLE 2

Indicence and mean duration of ventricular tachycardias (VT) and ventricular fibrillations (VF) during and after ischemia/reperfusion on the isolated functioning rat heart

| | Ischemia | | Reperfusion | | |
|---|---|---|---|---|---|
| | VF % | VF sec | VT % | VF % | VT + VF sec |
| Vehicle | 33 | 34 ± 30 | 100 | 100 | 797 ± 183 |
| Cariporide (HOE642) | 33 | 38 ± 26 | 100 | 0 | 204 ± 32 |
| Rulide | 100 | 181 ± 79 | 100 | 100 | 1709 ± 319 |
| Rulide + HOE642 | 100 | 194 ± 28 | 100 | 14 | 198 ± 27 |

The results on the isolated functioning rat heart show that the Na$^+$/H$^+$ exchange inhibitor cariporide (HOE 642) completely inhibits the cardiotoxic and proarrhythmogenic effect of macrolides during ischemia and reperfusion.

What is claimed is:

1. A pharmaceutical composition comprising:
   (A) at least one therapeutic agent having a cardiotoxic component or an adverse side effect on the heart; and
   (B) a cardioprotective amount of an inhibitor of the Na+/H+ exchanger for the at least one therapeutic agent having a cardiotoxic component or adverse side effect on the heart.

2. A pharmaceutical composition according to claim 1, wherein the Na+/H+ exchange inhibitor is selected from:
   a) benzoylguanidines of the formula I

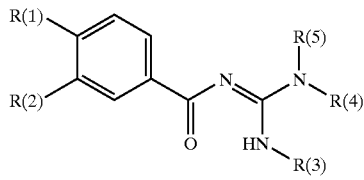

in which:
R(1) or R(2) is R(6)—S(O)$_n$— or R(7)R(8)N—O$_2$S—;
and the other substituent R(1) or R(2) in each case is chosen from H, F, Cl, Br, (C$_1$–C$_4$)-alkyl, (C$_1$–C$_4$)-alkoxy or phenoxy, which is unsubstituted or substituted by 1–3 substituents selected form fluorine, chlorine, methyl and methoxy;
or the other substituent R(1) or R(2) in each case is R(6)—S(O)$_n$ or R(7)R(8)N—;
n is zero, 1 or 2;
R(6) is chosen from (C$_1$–C$_6$)-alkyl, (C$_5$–C$_7$)-cycloalkyl, cyclopentylmethyl, cyclohexylmethyl or phenyl,
which is unsubstituted or substituted by 1–3 substituents selected from fluorine, chlorine, methyl and methoxy;
R(7) and R(8) identically or differently are H or (C$_1$–C$_6$)-alkyl; or
R(7) is phenyl-(CH$_2$)$_m$;
m is 1–4; or
R(7) is phenyl,
which is unsubstituted or substituted by 1–2 substituents selected from fluorine, chlorine, methyl and methoxy; or
R(7) and R(8) together are a straight-chain or branched (C$_4$–C$_7$)-chain, where the chain can additionally be interrupted by O, S or NR(9);
R(9) is H or methyl; or
R(7) and R(8) together with the nitrogen atom to which they are bonded, are a dihydroindole, tetrahydroquinoline or tetrahydroisoquinoline system;
R(3), R(4) and R(5) independently of one another are H or (C$_1$–C$_2$)-alkyl, or
R(3) and R(4) together are a (C$_2$–C$_4$)-alkylene chain; or
R(4) and R(5) together are a (C$_4$–C$_7$)-alkylene chain;
and their pharmaceutically tolerable salts;
compounds of the formula

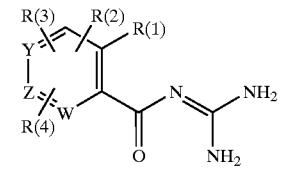

in which:
W, Y and Z are selected from a nitrogen atom or a carbon atom substituted by R(2) or R(3) or R(4);
R(1) is hydrogen, A, Hal, —CF$_3$, —CH$_2$F, —CHF$_2$, —CH$_2$CF$_3$, —C$_2$F$_5$, —CN, —NO$_2$, -ethynyl, or an X—R';
A is alkyl having 1 to 6 carbon atoms;
Hal is F, Cl, Br or I;
X is oxygen, S or NR";
R" is hydrogen, A or a cyclic methylene chain having 3 to 7 carbon atoms;
R' is H, A, HO—A—, HOOC—A—, (C$_3$–C$_7$)-cycloalkyl, (C$_6$–C$_8$)-cycloalkylalkyl, CF$_3$, CH$_2$F, CHF$_2$, CH$_2$—CF$_3$, Ph, —CH$_2$—Ph or Het;
Ph is phenyl, naphthyl or biphenylyl, which is unsubstituted or mono-, di- or trisubstituted by A, OA, NR'R", Hal, CF$_3$;
Het is mono- or binuclear saturated, unsaturated or aromatic heterocycle having 1 to 4 nitrogen, oxygen and/or sulfur atoms, which is unsubstituted or mono-, di- or trisubstituted by Hal, CF$_3$, A, OH, OA, —X—R', —CN, —NO$_2$, and/or carbonyl oxygen,
where Het is bonded via N or an alkylene chain C$_m$H$_{2m}$ where m=zero to 6; or
R' and R'' together are alkylene having 4–5 carbon atoms, in which one CH$_2$ group can also be replaced by oxygen, S, NH, N—A, N—Ph and N—CH$_2$—Ph;

R(2) and R(3) independently of one another are hydrogen, Hal, A, HO—A—, X—R', —C(=N—OH)—A, A—O—CO—(C$_1$–C$_4$)-alkyl-, CN, NO$_2$, COOH, halogen-substituted A, CF$_3$, CH$_2$F, CHF$_2$, C$_2$F$_5$, CH$_2$CF$_3$, or S(O)$_n$R'''; 
R''' is A, Ph or —Het;
n is zero, 1 or 2; or R(2) and R(3) independently of one another are SO$_2$NR'R'', Ph or —O—Ph, —O—CH$_2$—Ph, —CO—A, —CHO, —COOA, —CSNR'R'', CONR'R'', —CH=CH—COOH, —CH=CH—COOA, indenyl, indanyl, decahydronaphthyl, cyclopentenyl, dihydrothienyl, dihydrofuryl, heterobicyclyl, alkylthienyl, halothienyl, haloalkylthienyl, acylthienyl, halofuryl, haloalkylfuryl or pyrrolyl; or R(2) and R(3) independently of one another are R(5)—O—;
R(5) is hydrogen, A, (C$_1$–C$_6$)-alkenyl or (C$_3$–C$_7$)-cycloalkyl;

R(4) is Ph, Het, —O—Het; CF$_3$, S(O)$_n$R''', —SO$_2$NR'R'', alk;

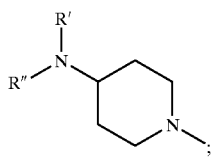

or two of the substituents R(1) to R(4) together are a group —O—CR(6)R(7)—CO—NR(8)—, or

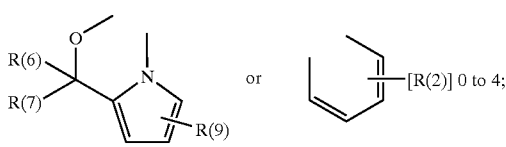

where
R(2) has the meaning indicated;
R(6), R(7), R(8) and R(9) independently of one another are H or A; or
R(8) is (C$_5$–C$_7$)-cycloalkyl; or
R(9) is cyano;
alk is straight-chain or branched (C$_1$–C$_8$)-alkyl or (C$_3$–C$_8$)-cycloalkyl, which is unsubstituted or mono-, di- or trisubstituted by A; or alk is an ethenyl or ethynyl radical which is substituted by H, A, Ph or Het;
indoloylguanidines of the formula

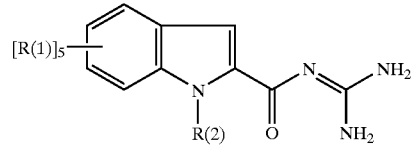

in which
R(2) is hydrogen, unsubstituted or substituted (C$_1$–C$_8$)-alkyl, (C$_3$–C$_7$)-cycloalkyl, OH, (C$_1$–C$_6$)-alkyl-O—, an aromatic radical or a group —CH$_2$—R(20);
R(20) is (C$_2$–C$_6$)-alkenyl or (C$_2$–C$_6$)-alkynyl;
R(1) is 1 to 5 identical or different substituents, which are: hydrogen, unsubstituted or substituted (C$_1$–C$_8$)-alkyl, (C$_2$–C$_6$)-alkenyl, (C$_2$–C$_6$)-alkynyl, (C$_3$–C$_7$)-cycloalkyl, halogen, —NO$_2$, (C$_2$–C$_8$)-alkanoyl, arylalkanoyl having up to 10 carbon atoms, aroyl having up to 11 carbon atoms, —COOH, (C$_2$–C$_6$)-alkoxycarbonyl, an aromatic group or one of the following groups: —OR(3), —NR(6)R(7) or —S(O)$_n$R(40);
R(3) is hydrogen, (C$_1$–C$_8$)-alkyl, substituted (C$_1$–C$_8$)-alkyl, (C$_3$–C$_7$)-cycloalkyl, an aromatic radical or a group —CH$_2$—R(30)
R(30) is alkenyl or alkynyl;
R(6) and R(7) independently of one another are hydrogen, unsubstituted or substituted (C$_1$–C$_8$)-alkyl, (C$_3$–C$_7$)-cycloalkyl, (C$_2$–C$_8$)-alkanoyl, an arylalkanoyl group having up to 10 carbon atoms, an aroyl group having up to 11 carbon atoms, an aromatic group or —CH$_2$—R(60);
R(60) is (C$_2$–C$_6$)-alkenyl or (C$_2$–C$_6$)-alkynyl; or
R(6) and R(7) together with the nitrogen atom are a 5–7-membered cyclic amine, which can additionally contain further heteroatoms in the ring;
n is zero, 1 or 2;
R(40) is unsubstituted or substituted (C$_1$–C$_8$)-alkyl, or an aromatic group, or a group

A is oxygen, —S(O)$_n$— or —N(R50)—;
R(50) is hydrogen or (C$_1$–C$_8$)-alkyl;
R' is hydrogen, unsubstituted or substituted (C$_1$–C$_8$)-alkyl, in which the ring represents a saturated 3–8-membered heterocycle having a nitrogen atom,
said substituted alkyl carries one or more groups selected from halogen, —OH, (C$_1$–C$_6$)-alkoxy, —CN, —COOH, (C$_2$–C$_6$)-alkoxycarbonyl, (C$_2$–C$_8$)-alkanoyl, arylalkanoyl having up to 10 carbon atoms, aroyl having up to 11 carbon atoms, an aromatic group, —CONR(4)R(5);
R(4) and R(5) identically or differently are hydrogen or (C$_1$–C$_8$)-alkyl; or
R(4) and R(5) are connected to one another and together form a 5–7-membered cyclic amine which can additionally contain further heteroatoms in the ring, or said substituted alkyl carries a group

in which:
E is a nitrogen atom or a CH group;
R″ is hydrogen, ($C_1$–$C_8$)-alkyl which is unsubstituted or substituted by OH, ($C_1$–$C_6$)-alkoxy, —CN, —COOH, ($C_2$–$C_6$)-alkoxycarbonyl, ($C_2$–$C_8$)-alkanoyl, aralkanoyl having up to 10 carbon atoms, aroyl having up to 11 carbon atoms, an aromatic group, —NR(6)R(7), —CONR(4)R(5);
R(4) and R(5) independently of one another are hydrogen or ($C_1$–$C_8$)-alkyl;
where the cyclic system of the formula

is a 3–8-membered saturated aliphatic or heterocyclic ring system having a nitrogen atom,
and where the aromatic groups mentioned are an aryl radical having up to 10 carbon atoms, a 5- or 6-membered heteroaryl radical having 1–4 nitrogen atoms, a 5- or 6-membered heteroaryl group containing 1 or 2 nitrogen atoms and a heteroatom which is oxygen or sulfur, or furyl,
and where the aryl radicals mentioned can be unsubstituted or substituted by unsubstituted ($C_1$–$C_8$)-alkyl or substituted ($C_1$–$C_8$)-alkyl, halogen, —$NO_2$, ($C_2$–$C_6$)-alkoxycarbonyl, COOH, —OR(3), NR(6)R(7), —CONR(4)R(5), —$SO_2$NR(6)R(7) or S(O)$_n$R(40),
where R(1) and the guanidinocarbonyl radical can be in any desired position of the 5- or 6-membered ring of the indole system,
and pharmaceutically acceptable salts of any of the foregoing.

3. A pharmaceutical composition according to claim 1, wherein the Na+/H+ exchange inhibitor is a benzoylguanidine of the formula

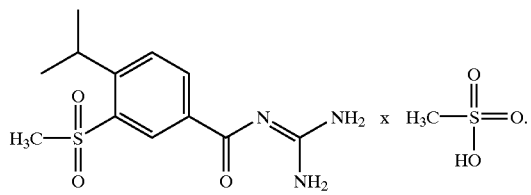

4. A pharmaceutical composition comprising:
(A) at least one therapeutic agent having arrhythmogenic potential; and
(B) an antiarrhythmia-effective amount of an inhibitor of the Na+/H+ exchanger.

5. A pharmaceutical composition according to claim 4, wherein said at least one therapeutic agent having arrhythmogenic potential is a thyroid hormone, an anticholinesterolemic derived from an antihistamine, a male potentiating agent, a phosphodiesterase inhibitor, an adenylate cyclase inhibitor, a neuroleptic, or a combination thereof.

6. A pharmaceutical composition for the treatment of cancer, comprising:
(A) at least one cytotoxic or cytostatic agent; and
(B) a cardioprotective amount of an inhibitor of the Na+/H+ exchanger.

7. A pharmaceutical composition according to claim 6, wherein said cytotoxic or cytostatic agent is a quinone-like therapeutic.

8. A pharmaceutical composition according to claim 7, wherein said quinone-like therapeutic is adriamycin, 4′-epidoxorubicin, daunorubicin, carubicin, aclarubicin, dactinomycin, mitoxantrone, amentantrone, bisanthrene, amsacrine, nitacrine, mitomycin, or a combination thereof.

9. A method for treating or preventing at least one cardiotoxic effect or adverse cardiac side effect of a substance, comprising administering simultaneously or sequentially with said substance a cardioprotective amount of an inhibitor of the Na+/H+ exchanger to a patient effective to protect the patient against at least one cardiotoxic effect or adverse side effect of the substance.

10. A method for treating or preventing at least one cardiotoxic effect or adverse cardiac side effect of a substance, comprising administering simultaneously or sequentially with said substance a cardioprotective amount of an inhibitor of the Na+/H+ exchanger according to claim 2 to a patient in need thereof.

11. A method for treating or preventing at least one cardiotoxic effect or adverse cardiac side effect of a substance, comprising administering simultaneously or sequentially with said substance a cardioprotective amount of an inhibitor of the Na+/H+ exchanger according to claim 3 to a patient in need thereof.

12. A method for treating or preventing at least one cardiotoxic effect or adverse cardiac side effect of a natural or synthetic toxin, comprising administering simultaneously or sequentially with said toxin a cardioprotective amount of an inhibitor of the Na+/H+ exchanger according to claim 2 to a patient in need thereof.

13. A method according to claim 12, wherein said natural toxin is selected from a snake venom, a fish toxin, a marine jellyfish sting toxin, a spider toxin, and a scorpion toxin.

14. A method for treating cancer, comprising administering at least one cytostatic or cytotoxic agent having a cardiotoxic component or an adverse side effect on the heart either simultaneously or sequentially with a cardioprotective amount of an inhibitor of the Na+/H+ exchanger to a patient in need thereof.

15. A method for the administration of at least one cytostatic or cytotoxic agent having a cardiotoxic component or an adverse side effect on the heart, comprising administering simultaneously or sequentially with said agent a cardioprotective amount of an inhibitor of the Na+/H+ exchanger to a patient in need thereof.

16. A method according to claim 15, wherein the cytostatic or cytotoxic agent is adriamycin.

17. A method for treating or preventing arrhythmias induced by a therapeutic agent having arrhythmogenic potential, comprising administering either simultaneously or sequentially with the therapeutic agent an antiarrhythmia-effective amount of an inhibitor of the Na+/H+ exchanger to a patient in need thereof.

18. A method for treating or preventing at least one cardiotoxic effect or adverse cardiac side effect of an antibiotic, comprising administering either simultaneously or sequentially with said antibiotic a cardioprotective amount of an inhibitor of the Na+/H+ exchanger to a patient in need thereof.

19. A method according to claim 18, wherein the antibiotic is a ketolide or macrolide.

20. A product comprising:
(A) at least one therapeutic agent having a cardiotoxic component or an adverse side effect on the heart; and
(B) a cardioprotective amount of an inhibitor of the Na+/H+ exchanger, wherein (A) and (B) are capable of either simultaneous or sequential administration.

* * * * *